US007364877B2

(12) United States Patent
Julien et al.

(10) Patent No.: US 7,364,877 B2
(45) Date of Patent: Apr. 29, 2008

(54) POLYNUCLEOTIDES ENCODING DISORAZOLE POLYKETIDE SYNTHASE POLYPEPTIDES

(75) Inventors: Bryan Julien, Oakland, CA (US); Ralph C. Reid, San Rafael, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 271 days.

(21) Appl. No.: 10/729,802

(22) Filed: Dec. 5, 2003

(65) Prior Publication Data

US 2005/0032184 A1 Feb. 10, 2005

Related U.S. Application Data

(60) Provisional application No. 60/512,892, filed on Oct. 20, 2003, provisional application No. 60/484,934, filed on Jul. 2, 2003, provisional application No. 60/473,311, filed on May 22, 2003, provisional application No. 60/465,038, filed on Apr. 23, 2003, provisional application No. 60/455,521, filed on Mar. 17, 2003, provisional application No. 60/431,272, filed on Dec. 6, 2002.

(51) Int. Cl.
*C12P 21/06* (2006.01)

(52) U.S. Cl. .................. 435/69.1; 435/320.1; 435/252; 435/325; 530/350; 530/300; 536/23.1

(58) Field of Classification Search ..................... None
See application file for complete search history.

(56) References Cited

U.S. PATENT DOCUMENTS

| | | | |
|---|---|---|---|
| 4,874,748 | A | 10/1989 | Katz et al. |
| 5,063,155 | A | 11/1991 | Cox et al. |
| 5,098,837 | A | 3/1992 | Beckmann et al. |
| 5,149,639 | A | 9/1992 | Katz et al. |
| 5,672,491 | A | 9/1997 | Khosla et al. |
| 5,686,295 | A | 11/1997 | Jaoua et al. |
| 5,712,146 | A | 1/1998 | Khosla et al. |
| 5,830,750 | A | 11/1998 | Khosla et al. |
| 5,843,718 | A | 12/1998 | Khosla et al. |
| 6,410,301 | B1 | 6/2002 | Julien et al. |
| 6,509,455 | B1 | 1/2003 | Ashley et al. |

FOREIGN PATENT DOCUMENTS

| | | |
|---|---|---|
| WO | WO 93/13663 | 7/1993 |
| WO | WO 95/08548 | 3/1995 |
| WO | WO 97/02358 | 1/1997 |
| WO | WO 98/27203 | 6/1998 |

OTHER PUBLICATIONS

Wells, Biochemistry, vol. 29, pp. 8509-8517, 1990.*

Seffernick et al. ,J. Bacteriology, vol. 183, pp. 2405-2410, 2001.*

Guo et al.,PNAS, vol. 101, No. 25, pp. 9205-9210, 2004.*

Cheng, Y.-Q. et al. (2002). "Identification and Localization of the Gene Cluster Encoding Biosynthesis of the Antitumor Macrolactam Leinamycin in *Streptomyces atroolivaceus* S-140," *Journal of Bacteriology* 184(24):7013-7024.

Cheng, Y.-Q et al., (2003). "Type I Polyketide Synthase Requiring a Discrete Acyltransferase for Polyketide Biosynthesis," *PNAS* 100(6):3149-3154.

Elnakady, Y. A. et al. (2004). "Disorazol $A_1$, A Highly Effective Antimitotic Agent Acting on Tubulin Polymerization and Inducing Apoptosis in Mammalian Cells," *Biochemical Pharmacology* 67:927-935.

Hartung, I.V. et al. (2002). "Toward the Total Synthesis of Disorazole $A_1$ and $C_1$: Asymmetric Synthesis of a Masked Southern Segment," *Organic Letters* 4(19):3239-3242.

Irschik, H. et al. (1995). "Disorazol A, an Efficient Inhibitor of Eukaryotic Organisms Isolated from Myxobacteria," *The Journal of Antibiotics* 48(1):31-35.

Jansen, R. et al. (1994). "Disorazoles, Highly Cytotoxic Metabolites from the Sorangicin-Producing Bacterium *Sorangium cellulosum*, Strain So ce12," *Liebigs Ann. Chem.* 759-773.

Piel, J. (2002). "A Polyketide Synthase-Peptide Synthetase Gene Cluster from an Uncultured Bacterial Symbiont of *Paederus* Beetles," *PNAS USA* 99(22):14002-14007.

Tang, G-L et al. (2004). "Leinamycin Biosynthesis Revealing Unprecedented Architectural Complexity For a Hybrid Polyketide Synthetase and Nonribosomal Peptide Synthetase," *Chemistry and Biology* 11:33-45.

* cited by examiner

*Primary Examiner*—Hope Robinson
(74) *Attorney, Agent, or Firm*—Townsend and Townsend and Crew LLP

(57) ABSTRACT

The sequence of the disorazole polyketide synthase protein gene is disclosed. Domains of disorazole polyketide synthase and polynucleotides encoding them are provided. Methods to prepare disorazoles in pharmaceutically useful quantities are described, as are methods to prepare disorazole analogs and other polyketides using the polynucleotides encoding disorazole polyketide synthase domains or modifying enzymes.

13 Claims, 7 Drawing Sheets

FIGURE 1. Chemical structures of Disorazoles A, B, C, D, E, F, G, H and I.
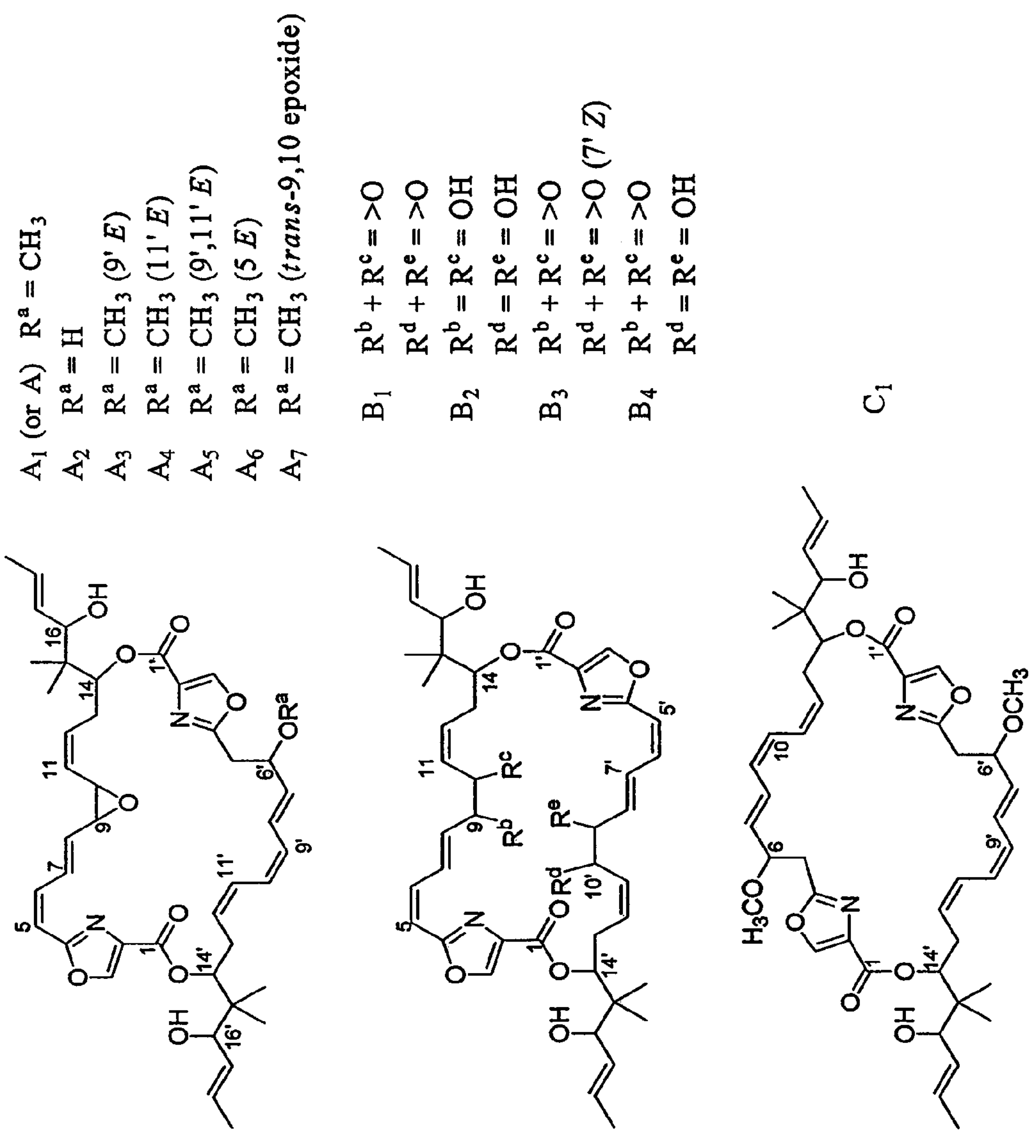

F1 Rg = CH3
F2 Rg = H
F3 Rg = CH3 (9,11 E)
G1
G2
OH
OR9
OCH3
5
9
11
14
1'
6'
7'
9'
11'
14'
16
16'
1

$G_3$

H

I

SEQUENCE LISTING

```
<160> NUMBER OF SEQ ID NOS: 9

<210> SEQ ID NO 1
<211> LENGTH: 77294
<212> TYPE: DNA
<213> ORGANISM: Sorangium cellulosum

<400> SEQUENCE: 1

tgggtatccc gagccgctgg cgccgttccc acaaggcctt gcggctgatg ccgagccgac      60

gggcaatctc ggtctccgtc agctcgtcct ggtgctccag cacgaagcgg cggaaatagc     120

cctcgagcga gtccgaaggc ggcgccccgt cgcgcagcga tgcggaggag acgggcggag     180

gcggccgcgg cgggtcgtcg agcccgaggt gggccctctc gatcgcgctg cccccggcga     240

gcaccacggc gcggtgaacg gcgttctcca gctcccggac gttgcccggc cacggcgccg     300

ccgcgatggc cgcgcgcgcc tccgccgaca gcgcgagcgg cgcctgcccc atcacccgcg     360

tccgtcgctt cagcagcgac tcggcgatgc gcaccgcgtc cccgggccgc tcccgcagcg     420

gcggcagccg gatctccagc acccgcagcc ggaaatacag gtcgctccgg aagctcccct     480

cgcgcaccat cgccccgaga tcccggtgcg tcgccgcgat cagccgcacg tccgcccgcc     540

gggcgcgcgt cgaccccacc cgccgcactt cgcccgtctg caaaaaacgc agcaggcgcc     600

cctgcacctt catcggcagc tcgccgacct cgtcgagcag cagcgtcccg ccctccgccg     660

cctcgcacag ccccgcccgc gccgcgagcg cgcccgcggc cgcgccggcc tcgtacccga     720

acagctcgcc ctcgatctgc gcatcgggga tcgccgcgca ctgcacgagc acgaacggct     780

gctgccgccg cgggctcagc cggtgcaccg cgcgcgccag cgtctccttg cccgtgcccc     840

cctcgcccac caccagcagc gtcgcctcgc tcggcgccac cttgcgcacc tgcgcgaaca     900

cctctcgcat cgccgcagag ccgcccacca tcccctcgag ctcgtcgccg tccggcgccg     960

gcggcgcggg cggcgcggcc agaggcgcgg gcggcgcggc ctcggggcgc acgctggcga    1020

ggtggcgctc gacaagcgcg acgagctcgt cgtgatcgaa cggcttcgag aggtaatccg    1080

ccgcgccccg cttcacggcc tccaccgccg ccttcacggt cgcatagctc gtcatcagca    1140

ccaccggcgc gctcccgcac cgccccacga gctccgtccc cggcgcgccg ggcaagcgca    1200

cgtccgccag caccagatcg aacgcgcaga gctcgtgctc cgcctccgcc tcggcgatcg    1260

accccgcctc gacgacggcg tgcccgtggc gcgccaagag ccgccgcagc tccgcacgga    1320

tgacgatctc gtcctcgatc agcaggatcc ggctcatgct tccacctcgc gcccgcgccg    1380

cgccccggcc tcgcccgcca gcgggagccg cacgatcacc gtcgtcccct gccccaccgc    1440

gctccgcagc gccagcgcgc cgccgtgatc ctcgatgatc gagcgcgaga gcggcaggcc    1500

gagcccggtg ccgctcgggt cgcgcttcgt ggtcacgaac ggctccagca ccgcggagag    1560

gagctcctcg gggatgccgc tgccgtggtc ctcgacctcg acgacgatct ggcccgcctc    1620
```

-continued

```
gatccacccg cggacggcga cggtcgcgcc gggctcggac gcgtcgcggg cgttcgcgag   1680
caggttcacg aagacctgca cgagctcgcg ccggtcgccg atgacaacga gcgactccgg   1740
gcagtgctgc tccacccgca cgtgcggggc cgtgcggtcg agccggatca gccgatccgc   1800
ctcggccacc acctcggcga gcgacacgcg accgacccgc gcgcgcggga tctcgccggg   1860
cgacggcacg gcgccggtgc ggctgtgatc gagcagcgac cggaggatcg cctcgatgcg   1920
cgccgtctcg ccgaggatga ggcccgcccg cgcgcggatc tcgtcgctgt cggcctcggc   1980
ccggaggttc tgcgcgaggc aggcgatgcc ggtgagcggg ttgccgacct cgtgggccac   2040
gcccgcggcg agccgcccga tctgggccag gcggtcgcgg tgggcgagct gcgcctcgag   2100
cgcgcgctgc tcggtgcgat cctccacgag caggaccacg ccgcccgagg cggcccgcgc   2160
gtcgagcgga tcgagcgcgg cccggtgcac gcgcaggagg cgcgcccgcc cggccacgag   2220
cacctcgatc tcctcggcgc ccgcgccggc ctcgcccgcg gaggccgcgc gggccgcgcg   2280
ggcgaacagc tccgcgaacg gggccggcag ccggtcgagc ggcgccccga cgaggtcgcg   2340
ctcctcggcg ccgacgagcg cctcgaggcg ccggttgacg aggctgatcg cgccgtcgga   2400
gcccacggcg cagaccccga gagggagctg cgcgagcacc gagcgcagcc accgccgcag   2460
gagatcgagc tccctcgccg cgccgacgag ccgcgtctcg ccgcgcgcga ggcgccgctc   2520
cagccaccgg agctcctcgg tgagcgcgcc ggacgcgccg ccggacgcga ccggcgcgct   2580
cgcctccgcc tccgccgccg tcctcgcgag caccgggccg accagcggcg acaggttgcg   2640
gtgcagccgc tcctgcagcg cgtggagctc ggtgggccgc gtctcgtcgc gcgagatgtc   2700
gagctcgatc cgggcgcgcg tgacctcgat cgcggccgcc tcgcggccga gcagccgcgc   2760
gagcctgtcc tccagcgcgg ccacgctcga cgccacggtc gcgcgctcca ccgaggggcc   2820
gatctcgcgg cgcgtgcaca ggcgggccgc ctcgcgctcc tccctggccg gcgggcgcag   2880
cagcgagacg atcccgagcg tcgcgccgtt gacggcgagc gacacgaacg tcgggagcga   2940
ccacgggtcg atgggcgccg cgcccgccgg cgcgcccgcg cccccgcgca ggagcgcgag   3000
ccacgccgga tcgatcccgg gcacgccggg caggagcggc gcgaggcagg tggccgtcca   3060
ggtcgcgatg ccggcgagga gcccggccat gaaccccgcg cgcgtggcgc gctcccagaa   3120
gagcgcggcg agcaggcccg ggaggaactg cgcgaaggcg acgaacgaca cgatgccgct   3180
ctcgacgagc agcccgtggt gcggctgcgc gcggtggaag agccacccgc cgacgaggat   3240
ggccgcgagg agcacgcgcc ggagccacag cacgcgcgcg tacacgttgc ggcgcagcgt   3300
ccgccgcgcg agcggcagga gcaggtgcgt cgcgctgtcg ttcgcgaggg cgacggccgt   3360
gaccatggcc atggcgctcg ccgcggagat gccgccgatg aacgcggcga gcgcgagcca   3420
gcgctggccg agcagctgcg gcacgagcag cacgtagctg tcggcgggct cggccggggc   3480
gaggcgcgtc ccggcccaga ggacgggcag gacgggcagg ttgagcgcga gcaggaacag   3540
ggggaacgcc cacgccgccg tggcgagcgc gcggtccccg gcgccgctgg cgaacgccat   3600
gtgccactgc cgcggcagca ggaaggccgc ggcgaagctg atgacgagca tcgaggtcca   3660
gccgctgtcc tcccgcacgt ggcggccgag cgcctcgacc tcggcggcgt gctcgccgag   3720
ccagcccgcg agcccgccga gcccgccgaa cgccccgagc acggcggcga ggcccacggc   3780
cgcgagcacg gcgagcttcg ccgccgactc gaacgcgacg gccgccgcga ggccgtcctc   3840
gcgcccctgc tcggccgacg ggcgggcgcc gaagaaggcc gtgaagagcg cgagcagcgc   3900
gcagaagacg gcgcccacgg cctcctcgtg ccccggcccc gagagcacgc gcaccgactg   3960
```

-continued

```
cacggtcgcg cggaactgct gcgcgacgta gggcaggctc gccacgagcg cgaaggcggc   4020
gacgagcgcc ccggcggcgg ggctctggaa gcggaacgcg agcaggtcgg tgagcgacga   4080
gaggcgctgc tcgcgcgtga tgcgcagcac gcgcgcccag aggagcggcg tggccatgca   4140
cgcgagcgtc gggccgaggt acacagcgag gaagacgagc ccgtggcgct gcgcgaagcc   4200
gacgccgccg tagtacgtcc acgacgaggc gtagacgccg agcgagaggg cgagcacgag   4260
cgggctccgc gcgagcgcgc gcgggcgccg ggcgcgctgc gcggcgagcg cgatcgcggc   4320
gagcacgccg agccacgcca ccgtggcgaa caggaggacg cccacgtcga tcacggcggc   4380
ggctcccgct cgccgcggcc ggcgtcgccc cggtcggcgc gcgtcgcgag cgcggcgagc   4440
gcgatcagcg cgagccacac cgcgaagacg gccgccaccg cgagcgggcc gcgggcccag   4500
agcaagcgcg ccggcgacac gaggaggacc gcgcccagca gcacgagcac gagcgcgcga   4560
tccgccgcgc cggcctctgc gtcgcgtcct ccgcccatgg gcagaggcta ctcagggccg   4620
ccgcggctga atacgtgagg acgattgacg caatgcgtta ttgtggtctc aatcgcagcc   4680
gcggatcggc ggggcgggat ctgccgcgga tgggcagccg cgagccgccg atccgcctct   4740
tccgcggcgc gcgcgagcgc gggtgagcgc gcgcgatcac ccgcgctcgg ccgcgatcgt   4800
ggcgagcatg tcgcgcgcga gcgcgcgcga tcacccgctc tcggccgcga tcttctcgag   4860
gtgactgcgc gcgtgctcga tcacggcctc gttgcccatg tcgatccccc acttcgccgc   4920
gagcgcgggc cacgccgccc agcgctcggc ggcgtgggcc gcgaggccgg gccatgccgg   4980
accgccggcc gcctcgaagc gcgcgatgac cgcgtcgagc accgccttgc cgaaggcgcc   5040
ggcgaagagc gcgaagtcgc tcgagggatc gccgacgtgg gcctcggtcc agtcgaggat   5100
ccccgtcagg cggccgtcct cgcgcacgag catgtgcccg gggtggaggt cgccgtgcac   5160
cagggcgacg tggcgcggcc agcgcgcgtc gtccgcgagc cagcgctgcc accgcgccca   5220
cacggcctcg gggggcgaga gcgtcgagcg cgtctcgtcc atggcccgcg cgagggtcgc   5280
ccgctcgtcg tcgatggact tcacggggac gccggccgcc tcgatcgccg cggcgtcgat   5340
gcgctgcagc gccgcgaggg cgtccgccat cgagtcgatg aacgcggccg gcggcgccgc   5400
gggatcgacg tgattccagc ggacgcccgc ctcgggatcg aaggacaccg ccgggacgtc   5460
gccgagccgc ggataggcga tcacctggtc ggtgtgcacg cgccagtcgg gcacggccac   5520
gggcaggtgc ttgcgcacga gggccaagac gcgcgcctcg acgcgggccg ccttcaccac   5580
cgcgagccgg cgcggggtgc gcacgaccca cgggacgccc tcctcgtcgc gggcgtgcac   5640
gacgaggaag tcgagcccgc tctggtcgaa gtcggcgcgg ggcgcgacga tccggagccc   5700
ctcgcggcgc gcggcgtcga ggagcgcgcc gggggagtcg agcggcgcga agtcggagga   5760
ggcggtggag gaagcggtgg acgagagctc gtgatgttcg gtcatgatcg cggtcctctt   5820
cgcgcgccgc cggcagggcg gcgcgcgtgg aaaggggaag actcgcggcg cgagctcacg   5880
accgatcagg cgtgcatggc gtgcatcctc caggctgccg ggcgtgagtc gacgcgcccc   5940
gcgtcttcca cgtgtcgacg gaagacaggg cacggacagg cacccgcgcg ctcgccgcgc   6000
cgccccggcg gtgccgggga ggcggggagg acgaggatgc cgggctcagc gcagccggag   6060
aaatgccatg gcccgaggtt ctcacgcggc gtcccgcgcc gcaaccctct tcgcgcgcgt   6120
ggcgcggcgg cccgcggtga tagcatcgcc cgcatgggca tcgatgagga gctggcagag   6180
cagcgcatcg gtacgcggat cggcccgtgg tcggtggagc gcgtgctcgg ggtcggcggg   6240
atggcgagcg tctactactg ccgccgcgac gacgggtgcg tggcggcggt caagctcctg   6300
caccccgagc tcgccagcat cgaggaggtg cggaagcggt tcttgcgcga ggggccgatc   6360
```

-continued

```
ggcagcgcgc tcgccgccgt ggcgccgctc tgcgaggggc tgccgcaggt gatcgaggcg   6420
ggggaagcgg acggcgcggc ctacatggcc atggagatgc tcgaggggga gacggtcttc   6480
gatcgcatgg tgcggcacgg gacgctcccg gtcggccagg tgatcgcgct cgccgagcgg   6540
gtgctcgacg tgctggacgt ggcgcacgcc cacggcatcg tccaccgcga cctcaagccc   6600
gagaacctgc acatcggcaa cgacgggcgc gtgcgcgtgc tcgatttcgg cctcgcgcgc   6660
gtcctcgatc cgctgctcga ggacgtcgcc ggcgtgccgg agatgacgaa gaccagcacg   6720
ggcgtgtcga tcggcaccga cgattacatg gcccccgagc aggccctggg cctcatccgg   6780
gagatcgacg gccggacaga cctgttcggg ctgggagcca cgatgttccg cctgctcgcg   6840
ggccgcacga tccacggcaa cctggaggac gcgcacctgc tcatcgccgc cgccacggag   6900
aaggcgccgc cgctcgcgca gcacgccccc gccgcgccgc ccggcctgtg cgccgtcgtc   6960
gaccgcgccc tcgccttcct caagcaggag cgctaccccg acgcgcggac gatgcgcgcg   7020
gacctcgccg ccgtgcgcgc gggccgcgag ccgccgtatg cgacggccgc ggcgcggggg   7080
cgggcctagc gcgccggagt cctcggcggc ggaggcggcc cgccctcgtc ccgaggcggc   7140
tcgggtccgc tcggcgcgga gagggcgcgc ggagggcggc ggctctcgca ccccgccggg   7200
ctgcgcgagc ggctcagtgt tccacgcctc gaacgccgcc gttccataac gccgtctggc   7260
gttccgctgg gtgcggtcgc atgctccagc cgtggatcca ggcgtggcgc catcgccgcg   7320
gcgtccatcc tcgccgtgac ccgcgcccat gccggcgagc cgccatcgac gatgtcaggc   7380
tccgaggatc cggatccgga gctcgacggc tcgtcgcgcg gtgttgccct cgtgcgcggg   7440
ccgttacggc gcgccgacag gggcgatctc gtcggccatg cgacaaacag gtgacgggat   7500
gagctgacac cccgcagaaa ccggctcgaa acacgccccc ccaaaactcc ccccgaaaac   7560
aactacatct gtcaccgagc gtccgggcct catcgacgca acaaatatca cgtttcggac   7620
tggaccagca agcccgcata cgtcattgac agaatgtgga ctccccctat catatcgctc   7680
caatcgcccg gccgagctga agacagcggc gcagcgggcg cattgagcaa cagcccatcc   7740
aggtgaacga gcggagaccc gcgtccgaga cgcgccgact cgccgcatgt ggacagctcg   7800
gggtggcgtt cagccgcctg ccgtctccaa ggacggtccg ctgaacagat gccgcgcgct   7860
gcgctgtgga taacgggcgc gcgcgacgct ggagcgcctt caccgatcga agaggaagcc   7920
ccgccgaaaa gagttcgaaa aaaatgaagg atcgctcccc cgagcggcat ctacccgccc   7980
gcggcgcccg gatctcggcg tcgggcgatc gcttttgtgc gtagggtcga ggtgcgcccc   8040
tgccgtgtca gccattgaca tcgttgggcg ctgcctctgg tcccgtcgtc atggcctgct   8100
ggctgccgtg cagcggcgga cttgcatgga gaggatgatt ggaaatcgaa ggtccagtgg   8160
agcaggacgc cattgcgatc atcggcgtag cgtgccgatt tcccgggtct ccggactatg   8220
gccggtactg gcagctgctc gagcggggcg agcatgccat cctcgagatc ccacccggcc   8280
ggtgggatcc ccgggcccat tattcccctg acttcaataa gcctggcaag agcatcagca   8340
agtggtgcgg gctgatagac gacatcgcca gcttcgacca ccgcttcttc aacgtgtcgg   8400
agcgcgaggc gaagagcatg gaccctcagc agcgcctgct cctggaagag gcatggcgct   8460
gcatcgagga ctccggcgtg ccgctcgagc agctccgcgc ccggaagacg tccatctacg   8520
tgggcttcat ggcgacggat taccaccagg agtccgcggc cccgggccgc ccggtcgaca   8580
gctacgccgc cctggggagc tacggctcca tcctggccaa ccgcgtctcc tatacgctcg   8640
ggctgcgcgg cgcgagcatc gccatcgacg ccgcctgcgc ctcctccctc gtcgcgctcc   8700
```

-continued

```
acgaggccag gcgcgctctc cagcgaggtg aaagcgaatt tgcgctcgcc gccggcgtga   8760
gcctcaactt tcatccttgg aagtacgtct ccttctccaa gtcgcgcatg ctcagcccgg   8820
acgggctgtg caagacgttc gacgcggacg cgaacggcta cgtccccgga gacggggtgg   8880
gtgtcctctt gctgcacccc ctggccaagg ccatcgctgc gggatgccac gtctacggcg   8940
tcgtcgcggg ctccgcggtc aaccacaccg gcaccgcgcg ttccatcacc gcgccgcgcg   9000
tcgccgccca gcgggacgtc atcctcgagg cctacgagga cgcgggctgg aacccggaga   9060
cggtgacgta cgtggaggcc catggcaccg gcacctcgct gggggacccc atcgaggtgg   9120
aagcgctgac ccaggcgttc cgccgctaca cgaccgcgcg ccagcgctgc gcgatcgggt   9180
cggtgaaatc gaacatcggc cacctcgagg cagccgcggg cgtcgctggg gtcatcaagg   9240
tgctcatgat gctgaagcac cgcgtgatcc cgcggacgct gcatgtccag acgctcaacc   9300
cgctcatccg cttcgaggag acgcccttcg tggtcgccac ccgcgccatg gaatggcgcg   9360
cggaaggagg cgagcccctg cgcgcagggg tgagctcgtt cggcttcggt ggcgccaacg   9420
cccacgtcct gatatccgag cacggcggcg cgcgccgcga gccccgcccg cgaggcgagc   9480
tccgcggccc ccgcggcgca gccccgcggg gcgagacggc gggcgctcca gcggaggacg   9540
gcccgctggc ccgcgcggag gagctccctt cgcagcagga ggacgccgcg gcggacgagc   9600
gcgaaggcac cgtcttcctc ctctccgcca ggtccgcgtc gagcctgtcg agggccgtcc   9660
gacgctggga ggccttcgtc gacgatcccc tcgtgaaggc aggcctggcc acctcgctcc   9720
gcgatatctg cgcgaccctg gccgccggac ggcaaagctt cgagcaccgc cacggcttct   9780
acatcgacga cgagcgagac ctccggcgct tgctcaagga accgccggcg cgcctggaga   9840
agacccgacc tcctcgctgg gtgacgcggt tcggcgcgct cgccctcggg cagggcaggc   9900
ccgccgtccg tctgctcggc gcgcgccgcc tgctcgatcc tcaccttgac cgcatccgga   9960
ggtgcctcga ggagctgggg atcgagcacc aggatctccg gacgtaccgt caggacggcg  10020
atcccgggcg ccaggagctg ccctatgcgt tcctcttcgc tcacgcgtac gtctcggcgc  10080
tcgcggacct cggcttcacg ccgtacgcga ccagcggaga gggtcacggc atctggttgg  10140
cgctcgccca gagcggggtc ttgccgctga acgagatcgt gtcggtgctc tcgggggccg  10200
gagagctcca gaggctctcg ccccggcgtc ccaggctgcc gctcttcgat cccatccatt  10260
ccacctacct gatgccgtac ctcctggacg cgggctacgt ccgcgcgctc gtggagggcc  10320
tggcggttcc ggcagcgacg ctccgtgacc tcctcgcgag ggctcgactc ctgctccgcg  10380
cgcagttcac cttcaagaag ttcctgagcg agtggtcgcc ggccttgcag gccctgggca  10440
cgacgcctga gcgcctgctc gaggaggagc tccccgcgtc cgacgctcgc gcctcgctga  10500
tcgcgctcat cgcgcagagc tgcgtgcgca agctgaaccg caggtggcag ctcacggacg  10560
cgccctcctc gggagatccg cggttcgacg agctcgtcga cctggtggtc gacgggctcc  10620
tgccgcgcga ggcgctcgtg cagctcgccc tcggcgatcg ggcggacctc cacgagatcg  10680
ccggcaccct gcaccggcgt caggacctgc tcgatctcag ccagccgtac ggcatcctgc  10740
ggaggcgcag cgagcgcctg gacccgagcg agatcgacga tttttccggc tggatccggc  10800
agatcgcggg cctcgaagcg ccgggcctgc cgcccgaaga gggcgtcgcg ttcctggagc  10860
tcggcagggt ggcgaggcgc gcgcagcggg cgccggggcc agatctgagc gtcccagcgc  10920
tggacagccc gctgcagctc gtcgcgctgc gcctgtggct ggaggggact gacatccggt  10980
ggggagagct ctttccggag gggagcttcg cgaagatccc gctgcctggc tatgcgttcg  11040
atcaggcgca gttctggctg ccggcagcca gagaaggcac gtcccctccc gaggacgcgc  11100
```

-continued

```
gcgacgacgc cgacgcgcga cacgccgccg tcgcgccgca cggcgcggcg gaccgggctg  11160
aacgcccctc gatccccgtg gaccgcctga tcgccgatca cgtcatccag ggccgcgcca  11220
tcgtgcccgg cgccctcatg gtcgagatgg ccctggaggc gtcacagcgc gcccacgggc  11280
ggccggcggc ggtcctgaga gacatcgtgt tccagcgggc agttccgctc gacgcgcacg  11340
cgaacctcac gatcgatgtc gaccctgacg gcgggcgttt cgtggggaga gacggcgcgc  11400
agggggcatg ccgtggagcc tacgggagcg cgcccccctc tccgctggag cccctcgatg  11460
cgccggcccg cgacggcgac cgccgccgcg acgatagcct ctaccgcgac ctttcgcgcg  11520
tcgggtaccg ctacggcgag agcctgcagg tgatcgccgc gaccggtcgg gtcggctcgc  11580
gccatgtgtt cgagctccgc tccagcgtcg ctcgcacgac gcctgtcgcc ggcttcgacc  11640
cagcgctctt cgacgggctg ctccaggcgg cgctggtcgt ggggcagcgc ctcgggctgt  11700
tcggcggagg cggcgcgatc tatgtgcctc aagccatcgc gctcgtcgag cggctcgctc  11760
cggtggacgg gggctgcctg gtctgcatcg acgagcgcga tctctcgatc aaggagtacg  11820
gcctgaccgt cgacctgcgc gcctacgatc cgtcgggggc cggcctgctc cgggtagagg  11880
gcatcttctt tcgaaaggtg ctgccgggct tcgtcgagag ctcccctgcc agggtgaccg  11940
gcggcgccgc ggaggcgcca cgccgcgccg gagcggccgg agatcccgag tcggccgcgc  12000
cgcgagcagc gtgctatcag cccgtctggg agcgacggcc gctcccggat cgcggcgggg  12060
cacccccgcg tggtcgcgcg gtggcgatca tccgctccga ggcggactcc gcagcctggc  12120
tctcgcccct gcgagcgcgc tattcacagg tcacggtggc gcgcctcggc agcccgccgg  12180
gtgaggcggg cgaagatcgg ctcgtcctgg gcgacgatcg agaggagggc ttctccgagc  12240
tggtgcgccg ggcggagaga gcggccgccg gcgaggccgt cgacatctac ctcctggacg  12300
cgctgacgcc cgacgcccgc gtcccctcgc gcgcgcctgc ggcgctcgag ccggcgctgg  12360
gcccccgcga agaggccgcg gcgcgcagcg cgttcctgct ggccaaggcc ctggtgaaga  12420
gcgcggcgcc gtggcgcctg gtcatcggca cgcggcgctg ccaggccgtc gtgcccggag  12480
accggggcga agggttccgc cacggggtgc tcgccggcat ggcccggacc ctgacgcagg  12540
agaacccgcg ggttcaggtc cacctggtgg atttcgacgc cgctcctcca ctcgcatgcg  12600
ccggccacct cgtcgaggag tgcggtgtgc tcggcccggg ggactgggta gcctaccgcg  12660
acggcgcccg ttacgtccgc gcctttgcgc cggtcgagga gcccggcgcg acggccacgc  12720
cgccgttcca ggacggtcgc gtctatctgc tggtcggtgg cgccggcggg ctcggcctcg  12780
gcctcgcggg gcacatcgcc tcccgggcgc atgcgcgcct ggtcctgctc ggccgctctc  12840
cgctcggcca cgaggcggag cgccgcctgg cccgcctgcg cggcgacggc ggcgagactc  12900
tctacatcag cgcagatgtc agcgatccac agcagtgcga gcaggccctg gcggcggtcc  12960
gccagcgatt cggcgccatc cacggcgtgg tgcagatggc cggcgtggtc gaggacaagc  13020
tgatcgcagg caagacctgg gagtcggtcc gacgagagat ggcgcccaag gtgcagggga  13080
cctggctatt gcacgagctc acccggcgcg accctctcga cttcttcgtg accttctcct  13140
ccgtcgtctc cctgctggga aaccacggcc aggtgggcta cgcagcggcc aacgggttcc  13200
tcgacggctt catccaccac cgggcccgca ccggcgccgc gggcaggagc ctcggcgtga  13260
actggacgtt gtgggaggac ggcggcatgg gcgcggctcc cgggatcgtg cgccggttct  13320
cggcgcgcgg gctccctccc atccggcagc acgacgcctt cggcgcgctc gaacggttga  13380
tgaccggcgg acggtcgccg caggcgctcg tcctcgcaga gcccgcagag cacctcttcg  13440
```

-continued

```
cgagagcttc tacacgacct gctccccacg cggtcgctcc cgatccggag cgcggcgatc  13500
gcgagcaggc ccgagacaag gaacaggttc ggggagacgc gagcatgaca cgtactacgg  13560
ctaatcctca cgggacggcg cctgcagggg caggacagga cgggcggcgt atcgcccgga  13620
tcgaggagga tctccggcgg ctcgtctccg ccaggatcga ggctccgtcg caagcggtcg  13680
acgcggaaga gtccttcttt tcgctcgggg tcgactccgt ggctcttcaa gagatcacgg  13740
agacgctcga gcgcacctac ggctccctgc cgccgacgct gctcttcgag aatccgaaca  13800
tccgccagct ggcgcggtac ctcgcggagc gcgtccccgc gaggtcggca gcccccgcgg  13860
aggtggagcc ggcgcaggcg cccgccagcg ggcccgcaga ggcgccgcct gccgcccgag  13920
cggccgtgcc cctccccgcg ccggagccgc ctggcgaggc cgcctcccgc ggcgcgcggg  13980
tggctgccgt cgcggccggc caggagcacg acacgccggg cgcgccctcc acccgcgccg  14040
cgcgccgcga gagcccgtcc gatggccctg cgatcgcgat catcggcatg agcgcccgct  14100
tccccaagtc cccegatctg gacgcgttct ggcagaacct gctctcgggc cgggattgcg  14160
tcgacgagat ccccgccgag cgctgggacc accggcgcta cttcgccgag gcggcgcagc  14220
cccacaagac gtacgggcgg tggggcgggt tcatcgagga cgtcgaccgc ttcgacccga  14280
tgttcttcaa catctccccg cgcgaggcgg agcagatgga tccacagcag cgcctcttcc  14340
tggagtgcgc gtgggcgacg atggagcacg cgggatacgg cgacccgcgc gcgtacggcg  14400
accgcgccgt ggggttgttc gtcggggtga tgtggaacga atacagccgc atcggcagcc  14460
agctcaccct gcagaccgcg cgctacgcgg ggccgggctc gctctactgg gccatcgcca  14520
accgggtctc gtactggatg aacctcaccg gtccgagcct ggccatcgat acggcctgct  14580
cttcctcgct ggtcgccgtc catcaggcct gcatgagcat tcgcaacgga gagtgcgaca  14640
tggccatggc cggcgggatc aacctctcga tccaccccga caagtacctc tacctggcgc  14700
agtcgaagtt cttgtcgctc gacgggcgct gccgcagctt cggccagggt ggcaccggct  14760
acgtgcccgg cgagggcgtc ggcgccgtcc tcctcaagcc gctggagcag gcgctgcgtg  14820
acggcgatca cgtctacggc atcgtgcgcg gctccgcgat caaccacggc ggccgcgcca  14880
ccggcttcac ggtccccgat ccggaagccc aggcgaggct cgtgttcgac gccctgcgac  14940
gcgcgcgcgt gtcccccgat cagctgagct acatcgagtg ccacggcacg ggcacggcgc  15000
tcggagatcc cgtcgagatc gccggtctca gcaaggcgtt ccgcatggcg ggcgccaccc  15060
gcacgagcat ccccatcggc tccgtcaaat ccaacctggg ccacctggag gccgccgcgg  15120
ggatcgccgc gctcatcaag gtcctcctgt gcatgcagca ccaggcgatc ccgaagagcc  15180
tgcacagcga cgtcaagaac cccaacatcc gcttcgagga ggtcccgttc gaggtcgtga  15240
acgagacgcg ctcgtggcag ggggacggcg gggcgccccg ctttgccggc gtgagctcct  15300
tcggcgcggg cggctccaac gcccatgtca tcctcgagtc gtacgagcct catgtgcgcc  15360
tcagcgcggg cgacgacgcc gcggagggag gagccctcat cgtgctgtcc gcgaaggacc  15420
gcgagcgcct cgacgccctc gcgggacggc tgagggattt cctgcgcgag cgggcaggcc  15480
gcgccccctc gctgagcgac atcgcctaca cgctgcagct ggggcgccag cacatggatc  15540
atcggctggc gatcgtcgcc gccagccggg aggatctgct ggccaagctg gacgccgtgc  15600
tcgctggccg cggcgaggtg cccggcgcgt tccggggcga tgtccacggc gacaaggcgg  15660
cttccctcgc catggacggg gacgatcatg accgcgagta cctggagagg ctcgcccgcg  15720
accgcaggct ggacaggctc gctcgcctct ggctgctggg gctcagggtc ccgtgggagg  15780
agctccaccg agatcgcggc cgcaagcggg tcgccctgcc cacgtacccc ttcgcccgcg  15840
```

-continued

```
agcgttactg gctgcctgac gtggagagct cgatcaccgc cgcggcgccg gtcgaggccc  15900
ccgcgtcgga gcaggccccc gcgccccggg gggagaaggg ccttccggaa gacttcttct  15960
tccacgagca atggtccgtg gcgccgctgg atcctgcgac gggctcggac ggcgctgcgg  16020
tccggtccgc gctcgtgatc tacacgccgg agggtgaagc gctcgccgac gcgctgatcg  16080
cgaggcaccc cggcgctcgc gtcgcccgta ttctcctcgg cgccggccag gggggcgaagg  16140
ggcgccccgg cccggaggcc cgcgccgctc ggcttccccc cgcgcaggag gttcaggccg  16200
acgatcctgc cgccctcgag cgcgccctcc gcgagctggc cgccgccggc gtcgcgggcc  16260
tcgacgccat ctacttcctc ggcggtctgg ccgcacagga gcccgcggcg ggcgacctgg  16320
aggccgtgga gcgcgcccag cagcgtgggc tgctctcgct gtttcgcctg gcgaaggcgc  16380
tgggcgccct gggcctttcg tcgtcgccct gccagctgaa gatcatcacc aacgatgctt  16440
gctcggtgcg gaccggagat cccgagcgcc cgctcgccgc gggcctgtac ggcctggctc  16500
gatccatcgc caaggagtac ccgcgcctca acgtcagctg catcgacatc cagactcgag  16560
cgctgagcca cccggccgat gaggggctca tcagcgcggt gatcgccgag ccaggtcacc  16620
tccgcggccg agaggtggcg ctgcgggacg gcaagcgctt ccagcgcacg atggccgcct  16680
tgccgctgca gccgccggcg agggatcctt accgtccagg cggcgtgtac ctggtccttg  16740
gcggcgccgg tgggctcggc cacctgttca gccagcacct cgcagggacc taccgcgctc  16800
ggctcgtgtg gatcggccgg cgccccctcg aggccgacat ccggtcgcgc atcgccgacg  16860
tcgaggcgcg cggaggcgag gtcctctatc tccaggccga cgccggcgac ccgagctccc  16920
tgcgcgctgc cgtctcccgc gccaaggcgc gcttcggcgc gatccacggg gtcatccact  16980
ccgcggtcat cctcgggagc caccccatcg ccaccaccga cgaggccacg ttcgccgccg  17040
gagtccgcgc caagatcgcc ggcagcgtcg cgctccacca ggcggtcgcc gacgagcccc  17100
tcgatttctt gctctatttc ggatccatcg cctcctacct caacaacggc ggggccagcc  17160
cgtacgccgc cggctgcacg ttccaggaca ggtacgcggc attccagcgt tcccgcgtgc  17220
cctacccggt caagctcatc aactgggggt actggggcga cgtcggcgcg gtcgccggca  17280
acaccgagac tcatgaccag cagttcaacg ccatcggcgt cggggccatc gcgcccgagg  17340
acgggatgga ggcggcgcgc cgcgtcctcg cgcagcgcct gccccaggtg atcgcggcgc  17400
agctcacgcg cccgccccaa agcctcttcg gctacgacct gagccacgag gcgaccgtcc  17460
acccggagcg cttcgagccg ctgctcgagc ggagcgtgcc gcgcatccag cccggcctca  17520
gcgcggtccg cgagctcctg acgcatcagc ccgcgttcga cgcgctggag cgcttcagcg  17580
aggatctgct gctctgcatc ttccaggaca tgggcgcgtt ccagcgcgcc ggcagcgcgg  17640
aatcggcggc gaccctgcga gaacggctgg gcgtcgcggg ccgcttcggc cggctctacg  17700
actccctgct cgcgatcctc gagggggccg gttacctgcg catcgaagga gatcggctgt  17760
tcacgagcga acgggtgacg ccaaagaagc acgaggtgga acggcggatg cagcagctgg  17820
cggatctgcc ggcgatcgcg ccgtacgtcc gcttgctctg ggcgtgctat cggcggtacc  17880
ccgagctgct ccgcggtcag gtagccgcga cggacgtgct cttcccgcag ggctcgatgg  17940
atctgatggg gccgctctac aagggcaacg ccacggccga ccatttcaac gagctggtca  18000
tcaagagcct cctcgtgttc ctggacgccc gcgtcccgca cctgcgagag ggcgagaaga  18060
tcacgatcct ggaggtaggg gctgggacgg gcggcaccac cgcgtccgtg ctcgaggcgc  18120
tctcctccca tgcgcgccac ctcgagtact tctataccga catctctcac gccttcacgc  18180
```

-continued

```
gatacggcaa gcgccagtat ggcccgcgct accccttcgt caccttccag cccctcgacc  18240
tcgaggggga cgtggtggcg cagggcttct ccgcagagcg cttcgacgtg gtgctgggcg  18300
cgaacgtcgt gcacgcgaca aagaacctgc gcagcacgct gcagagcatc aagcggctcc  18360
tcaaggcgaa cggctggctc gtcctgaacg agatgacccg cgtcgttcac ttcctcacgc  18420
tctctgcggg tctcctggac ggctggtggc tcttcgaaga cgccgccgag cgcatgaaat  18480
ggtcccctct gctcagctcc ccgatgtgga agggcctgct ggaggaagag ggattccgcc  18540
gggtcgctcc tctccagcac agcgacggca cgtcctcctg gtcgatccag aacgtgatcc  18600
tcgccgagag cgacggcgtg agccgaagcc ggcggaccga gagcgccgct ccgcggccag  18660
cgccgtcggc cacgagcgcg gcggcggcgt ccgaagcgct cccgcccgcc ccgtccaccc  18720
ccgccgccga gccggtcgcc gcgttccggc cgatgtccct gcaggccgtc gaggacaaga  18780
tcatcgatag cctcgcgagc acgctgcaga tcgacaggtc caagctcagc tcggacgtgc  18840
cattcacgac gttcggggtc gattcgatct tcgccgtgga ggtcgccggc gtgatcgggc  18900
gcgagctgag catcgatctc aggaccacgg ccctgttcaa ctatcccacc gcgcgcgcgc  18960
tcgccgagca catcgccgcg acgttcgccc ccagcgaggc ggccccggcc agagcgcccg  19020
aaccggcggc gcagccgcgg gagcagctcc cctcgagccc gccgcagccg gcgccgggag  19080
cgccgccgcg gccagcgcag gccacgtcgc aggtccaggc gccggcgccg gagcgtccgc  19140
cggcgccgca gccggccggc gcccagcagc gggtccggca gctcgccctg ggtgccctcg  19200
ccgaggtgat ggcgatcgac gtgagggagc tcgatccgag cgcgaccctc gccgagtgcg  19260
gcatcgacgc tcagcaggcc gtcgtggtgg tgagccgcat gaaccaggcc ctcgggacga  19320
gcgccaccgc catggatctc ctccgatgcg ggaccctcgc ggacttcgtg gaccacctcc  19380
tcgcgtcctc gcccgcgccg cgcccggacg cggagacccg ccccggcacc gccgcggcgc  19440
tcccggcgcc cgcgccccct gcggcgatcg agcccaggtc cgcccggagc acggacatcg  19500
cggtggtggg catgtcctgc cggctgccgg gcgccgagac ggtcgccgac ttctggcgga  19560
atctctgcga gggtcataac gccatacggg agatcccgcc tgaccgctgg tccctcgatg  19620
ggttctacga tcccgacccc agcgtcgctg cccgcagcta cagcaagtgg ggtgggtttc  19680
tcgacaacat cggcgacttc gacccgctct tcttcggcat ctcaccgctg gaggcggagc  19740
tcacggatcc gcaacaacgc ctctttctcc aggaggcctg gaaggcgttc gaggacgccg  19800
ggtacagcgc cgaggcgctg agcgggcagc ggtgctgcgt gttcgtgggg tgcaaggacg  19860
gggattacgt ctacaagctc ggcccgtcgg cggacgcctc ctaccggctc atcgggaaca  19920
ccctgtccat cctcgcggcc cgcatctcct attttctcaa cctcaagggg ccgagcgtcc  19980
ctgtcgacac cgcttgctct tcctccttga tggcgatcca cctggcctgc cagagcctga  20040
tcagcgggtc cagcgacctc gccgtggccg gggcgtcgc cctgatgacc acgccggtga  20100
gccacatcat gctcagcaag acggggatgc tgtcgcccac ggggagctgc cgcacgttcg  20160
acgactccgc cgatgggctg gtccccgccg agggggtggc cgccgtcatc ctgaagccgc  20220
tcgacgccgc cctgcgcgat cgcaaccaca tctacggggt gatccgcggc tccgaggcga  20280
accaggacgg caagagcaac ggcatcacgg cgcccagcac cccctcgcag gccgccctgg  20340
aggtcgaggt ctaccgcaag ttcggggttc acccggagac catcggctac gtcgagaccc  20400
acggcaccgg caccaagctg gggacccca tcgagatcca cgcgctcacg gacgcgttcg  20460
ccgccttcac cgacaagaag ggttctgcc cggtcgggtc cgtgaagacg gggatcggcc  20520
acacgctggc agcgtccggg gccgcctccc tcatcaaggt gctctgctgc ctccagcacc  20580
```

-continued

```
gcacgctcgt gccgtcgctc cactatgacc ggcccaacag gcacatccac ttcgagaaca  20640
gcccgttcta cgtcaacacc gcccggaggc actgggcgca cgccggcgat ctcccgcgcc  20700
gggcggcgat cagctcgttc ggcatgagcg gcaccaacgt gcacctcatc gtcgaggagg  20760
cgcctccgga ggccgacgcc accgcgccca cggtggcccc ctataccctc atcccgatct  20820
cggcgaaggc gccggcgccg ctccatcgca gggtggcgga tctggccgcc tggctcgacg  20880
ccggcgggcg cgaccgcgag ctgggcgata tcgggtacac cctgggcgtc ggccggagcc  20940
attttcccct gcggctcgcc ttcgtcgcgc gcgacacgcg cgacctgcgc cgccagctgg  21000
cggcgtggct cgcgcgccac ccgaccgcgg acgacgtgcc ggcgccggcc gcgcggccgg  21060
agcccgcgct cggccagacg gcgggccgcc tggcgagcga gctccgcgac gcgccccccgc  21120
tcaccgccga cgcgtaccgt gagaagctgg aagccctggc ccacgcctat gtggcaaagc  21180
acgatcctga gtggcagtcc ctgttcgcgg gtcaggatcg acgcctgatc tcgctgccca  21240
cgtacccgtt caacaaccgc cggttctggg tggacgagcc ctcgcggtac gggctcgatc  21300
acgccgcgcc ggccgccagc gcggcgccgg cgccgcggcc ggagcccgcg ccggccgcgc  21360
gcctcgcggc gccggcggag cagccggggc acggagaccg gcgagcagat tcgctccttt  21420
atttcagatc ggcctgggaa accgcagagc acgaggctgc cgcgggccag ctccgcgctc  21480
cgatcctgct cttcgacgac ggcggcgccg tgcgcgagcg gctgctggac agcgaccgcc  21540
ccgtcatcgc cgtcacgccg ggccccgggt tccgcgagct gggaggcggc cgctacgagc  21600
tgaaccccgg cgacgcggcg gattacggcc gcctcgtcgc cgcctgcaag cagcggggcg  21660
cgctgccgcg cgaggtcgtg tacctgtggc cgctcgcgcg agctcaggcg caggcggagc  21720
cgacggcgcc cttcttccag gcgacctctc tgtgccgcgc gctcgccgac catcgccccg  21780
cgcacggcga ggctgtccgc atcctgtacg tctactggca ggacggggat cggctggacg  21840
ccagccatgc agccatgagc ggcctggccc gcagcctgca gctcgacctt ccgcacctcc  21900
actggaagac gctcggcctc gagccgcgga ccgccgacgg cgcgctgtgc gatctcgtcc  21960
tcgccgagct gctcgccccg ccgcagggcg cggtccgcta ccagcggggg caccggcaga  22020
tccagcggct ccagccgtgg cgccccgagg gcgaggcgag cgcgcccttc cgcagcaaag  22080
gggtctatct gatcaccggc ggcgccggtg ggctgggcgg cctgttcgcc gagcacctcg  22140
ctcgccgcca tcaagccagg ctggtcctgt gcgggcgctc tcccttgacg ccggccggcg  22200
acgacctcct ccgccgcctc gcccagctcg gcgcggaggc ggtctatgtg cgggccgacg  22260
tcgccgatcg cgaggacgtg ttcgcgctgc tcgggcgcgt cgaggcccgg ttcggcgcgc  22320
tccacggcgt cctccacagc gccggcgtca ccgccgacgc gagcttgcgc aacaagagcc  22380
gtgaccagat ggtcgccgtg ctcgcgccga aggtgctcgg caccctgcac ctcgacgacg  22440
ccacccgcca tcgagagctg gatttctttg ccctgttctc ctccgtcacc gcggtcatgg  22500
gcaacatggg gcagacggac tacggctacg ccaacagctt catggaccac ttcgcggcct  22560
ggcgcgaggc cgagcggcag agcggacgcc gcagcggaag gaccgtgtcg atcaactggc  22620
cgctctggcg agacggcggg atgagcgtct cgcaagagat gcagacgctg ctcacgtcca  22680
ccctcggcat gagcgcgctc tcgagcgacg cgggcatcca ggccttcgag cgcgccgtgg  22740
cctcggcgca cccccaggtc gtggtcctcg ccggtgacga ggccaagatc caggagagcc  22800
tcggcatcgc ggccccgacc ccgcccgccg gcgcgctccc ggggtcgcac ggcgcccctc  22860
ccgcggctcg cgcgaaggcg ccccccgcgc gcagcgcgct ggcaaagcag gtcgaggagc  22920
```

-continued

```
tcctgctgca ggcggtctcc ggggtgttga aggtcgctcg cgaagagctg aattacgatg  22980
cgccgctgag agattacggg ctggagtcca tcaacgtcat cgccctcacc aaccatctga  23040
accggaccta cgcgctcgac ctcaagccgg tgcggttctt cgagcacgag acgctcgccg  23100
cgctgggcgg ttggctatgc gaggagcgcg gggagcacct ggctcgacgc ttgggcccct  23160
cgcgcgcgcc cgaggccggg ctccccgctg cccccgcggc gccccccgag cccgcgcagg  23220
ccgccccggc gcagccggcg aaggagcccc cggcacggag cgcgcgggcc gccgagcgcg  23280
tcccgccgga ggcgccctcg gcccgggctg aacgggggat ggcggcccac gagcccatcg  23340
ccatcatcgg tatcggcggg gccctgccga agtccagcga cctgagcgcg ttctggcagc  23400
acctcgtgga cggccgctcc ctcgtctccg agctgcccgc cgatcgctgg gactggcgtg  23460
cttacgacaa cggcgacgcg aatcggaagg ggctgcgctg gggggagcttc tacgaggaca  23520
tggataagtt cgatccgatg ttcttcgggc tctccccgcg ggaggccgag ctgatggatc  23580
cccagcaccg cgtcttcctc gagaccgtgt ggaaggccat cgaggacgcc ggatacaggc  23640
cctccgatct ggcgaggagc aacaccggcg tcttcgtcgg cgcgtcgtcg ctcgactatc  23700
tcgagctgat gaacggacac cggacggagg cgtacgccct caccggcacg ccgcactcga  23760
tcctggcgaa ccggatctcg ttcttgctga acctgcacgg gcccagcgag cccatcaaca  23820
ccgcctgctc gagcgcgctg atcgccgtcc accgcgccgc ggagaccctc cgcagcggcg  23880
cctgcgatct ggccatcgcc ggcggggtca acgcgatcct cagccccgcg acggccctgg  23940
ccatcgcgaa ggcaggcatg ctgagcccgg acgggaagtg caagaccttc gatcggagcg  24000
cgaacggcta cgtccgcggc gagggggccg gcgcgctgct cctcaagccg ctccgccgcg  24060
cgctcgccga cggggatcac gtctatgcga tcctgcgcgg cagcgccgag aaccacggcg  24120
ggcgcgccaa ctcgctcacc gcccccaacc cgcgggccca ggcggatctc atcatcgcgg  24180
ccttccgcgc ggcgggcgtc gatccggcca ccgtgggcta catcgagacc cacggcacgg  24240
gcaccgccct cggcgatccc atcgagatca acggcctcaa gacggccttc gagcagatct  24300
acaaggatca tggccggccg ccgccgcagg cgccgcactg cgggctcggc tcggtcaaga  24360
ccaacgtcgg ccacctggag gcggccgccg ggatcccgag cctcttcaag gtcctcttgg  24420
cgatgaagca ccgcaagctg cccgggactc tccacctcca cgacctgaac ccctacatcg  24480
agctcgaggg cagccccttc tacatcgtca ccaggacgga ggactggaag cccgctctgg  24540
acgccgacgg ccgccccctc ccgctgcgcg ccgggatcag ctccttcggc gtcggcggct  24600
ccaacgccca cctggtcctc gaggagcacc acgacgagcg cgccgaggag ccgtccgcgg  24660
ccgaggtccg gcgcggccct catctgatcg tcctctccgc gaagagcgag gagcgcctcc  24720
acgcgtatgt agacgcgttg atcgcctacc tccgcgacac ggcgccggag cgccggccgt  24780
ccctcgggca catcgcgtat accctgctca ccggtcgtga cgtcatggac gcccgcctcg  24840
cctgcgtggc gaccgacacg gacgacctcg tcacccggct ctcccgttac cgggccggcg  24900
agagcgcggt ggacgggctg ttcaccggtc ggagcgacgg gagctccagc gcggcggccg  24960
tgctcatcga gggcgaagag ggccagcagt tcgtcgaggc gctcctccgc aaccgcaagt  25020
gggcccagat cgctcgcctg tgggtcgccg ggcgcacggg gatcgactgg tcctctctgt  25080
tcgacggcga gcgcgtgcgg cgcgtgccgc tgccgaccta cccccttcgcg cgggagcgat  25140
actgggtgcc tgacgagatc ggcaaggagc acgccgggaa cggcgcgccg cccgccgtca  25200
acggcaaggc gcacaacggt gccgccgagg gcggcgcccg tcccccggcc agcgcgggga  25260
gcacgctgcg cccgacgctc gacgctgcgc gctcgagccc cgagcggccc gtcttccaga  25320
```

-continued

```
aggagctgga ggccgacgcc ttttatctga gagatcacgt catcgccggc aacatcatcc  25380
ttccgggcgt ggggcacctg gagctcgctc gcgcggccgg tgagctcgcc ggcggacgac  25440
cggtgcgcgt catccgggac gtcctgtggg caaagcccat cctgctcgac ggaccgcggc  25500
tcgatgtgca ggtggcggtc agccatgacc gtcagggcgc cgagtaccag atccgccacg  25560
agggcgaggg ccgcgaggtc ctctactcgc gcggaaggct ggcctacgag ccggctccgc  25620
gccgcgacgg cgagccggag cgccgcgacg tgaaggcgat acggtctcga tgccacgacc  25680
gcaaagatca cgacacgttc taccgccggt atcgagaagc cgggttccgg tacggcccct  25740
ccttccgggt cgtccaggag gcctggggga acgagcgcga gtccttggga gcgctcgtcc  25800
tgccagacca cctgcgcgag gggttcccgc agttcggcct gcacccctgc ctgctggacg  25860
cctccctgca atccatcacc gggatgcagc tcgacgccgg ccgcgacgcg ccctccatga  25920
gcatcccctt cgccatgggc cagctggaga tcttcggccc gctgcctccc gtgtgctacg  25980
cgcacgcgac cctgggctcg cgccgcggcg aaggggcgcg cgagatcgtc aagtacaacg  26040
tcgcggtcct cgacgaggac ggcctcgtgc tggcgcgcat cacggacttc agcgcgcgcg  26100
ccttcacgaa cgaccagccg cgcagcccag ccgagcaggc cgctgcgccg ctcggctatt  26160
accaatcgac ctggaccaga agcgcgcttt gaacgtcggg gtaacctcat gtccagcact  26220
ctccgccaca cagacaccat cctcgtcctg ctgcccgcga gcgcggcgtt cagcgggctc  26280
gacgagcgcc tggtcgcgca ggtatccgat ccgcaacgcc tcgtcttcgt gcaggccggc  26340
gagcgcttcg cctcgatcga tccgcgacat taccgcgtcg atccggcgcg cccggaggat  26400
tacgtccggc tgttctcgga gctcgagcgc agcggcgcgc tgcccacgca tatcctccac  26460
gcgggcaact gcgtcggccc gagcgcgctg gggctggcg agcgcgacgc gttcgcgagc  26520
atccgcgagc ggctaggcca ggagctggag cgcggcctgt acgcgatcct ctcgctggtc  26580
caagccaagc tggccgtcaa ccccgctggc cccacccgct gcgtgttcgc gttcacgacc  26640
gacgaggccc acccgcgccc gcaccacgag gcggtgggcg gcctggcaaa ggccctcacg  26700
acggtcgatc atcgcttcca gctcgtcacc gtgcagatgg acgcgtgcga cgcggacacc  26760
gcggcgcgcc gcctcatcga ggagctgacc tcgcctcacc accagaatgg cggcgaggtg  26820
cgctacaggg gcggggagcg gttcgtacac gaggtgcagc ggctggagcc cgcgcccgag  26880
cggggagagc cgccggccgc gctcccgctg cgcgccggcg gcgtgtacct cgtgaccggc  26940
ggcggcggcg gcctggggat gctgttcgcc cggcacctgg ccgtgaagta cggcgcccgc  27000
ctggtcctca gcggccgcgc tccgctcgac gacgacaagc gcgcgaagct ccgcgagctc  27060
gaggcgctcg gcggccgcgc ggcgtacgtg cccgcggacg tgggcgacga ggccgagacg  27120
cggcgcctgc tctccgccgt ctccgcggag ttcggcgagc tccacggcat cttccactgc  27180
gctggagtgg ccgatcgcac gccgctcgcg agggccacga tcgcagattt cgagagggta  27240
ttgcgcccca aggtgcacgg cacgctccac ctcgacctgg agacccgcga ccgcgatctc  27300
gacgtcttcg tcctgttctc gtcgatctcg gcgctggtcg gcgacttcgg cgcgggcagc  27360
tactccgcgg cgaactgctt cctcgatcgc ttcgccgacg cccgcgagca gctgcgacgc  27420
agcggcctgc gccgcggcca gaccctgtcg gtcaactggc ccctctggca ggacgggggc  27480
atgaggatgc aagagcagga caaggccatg tacttccagt tctccggcat gggggccctg  27540
gaagcggccg agggcatcga ggccttcgag ggcgccctcc gggccgggcg gccccagctg  27600
ctcgtggtca ccggcgaccg caagaagatc gaccgcatcc tgcaggttcg cgagccgcgc  27660
```

-continued

```
tcggcggccg ctccacgcga agagccgcag cggcccgccg ccggaggcgc cgcgccgccg  27720
gccgcgagcc atccggggtc gagcgagggc cgaggcgcct ccgggggaga gcggtccagc  27780
tcagcgccgc agggctcgcc gcgcgcagcg acgcgaggcc cgctgccacg agagcagctc  27840
ctcgcgcagt gcagagacta cctgcgcaat ctgatcgccc aagccacaaa gctccccgtc  27900
gacaagatcc acgcggacag ggatctggag gactacggca tcaactccct catgatcatg  27960
gagctcaact ccatgctcga cagggatttc gacgcgctgc cgcgcaccct cttcttcgag  28020
tacaagaacg tcgccgagct cgccgccttc ttcgccgacg agcacgggtc gcggctgcag  28080
cagatcctcg cggggggcac ggactcgagc ccggacgcga cgccgccccc tgaggagcag  28140
ccgccggcgc cggagcccga cgcggcggcc gccctcgcgg cagcgccggc gcccgctccg  28200
cgcccgccgc ccgcagcgct ccgtcaggac gacgggcaca tcgccgtgat cgggtacggc  28260
ggccgcttcc ctaaggcgga cgatcccgag gcgttctgga ggatcctcaa ggaggggatc  28320
gactgcatca cggagatccc ccgcgagcgg tgggactggc gcgcgtacca cgacgacgtc  28380
ccggggacgc cggggaagat ctattgcaag tggggcggct tcatcaacga cttcgaccgc  28440
ttcgatccgc tcttcttccg cctctctccg cgcgcggcgc acagcatgga tccgcaggag  28500
cggctgttcc tgacggtcgc ctgggagacc ctggagcacg ctggctacac cctcgatcgc  28560
ctgaaccgcg ggtccgacgg gccccccggc ggcgcgggcc gccgcaaccg ggtcggcgtc  28620
ttcgcgggcg tcatgtggag cgactacggc aagcacgggc aggacgagct ccacaaggga  28680
aaccccgtga tcgcgagcgc cgattactcg tcgatcgcca accgggtgtc ctacgcgctc  28740
aacctgcacg gccccagcat cgcctccgac acggcctgct cgtcgtcgct cgtcgccatc  28800
cacctggcct gcgagagcct ccggcgaggc gagtgccact acgccatcgc cggcggggtg  28860
agcctctcgt tgcaccccgc caagtacctc cagatgagca acctgaaggc cctgtccgcc  28920
gagggcaagt gccgcagctt cggcgccggg ggcgccgggt acgtgcccgg cgagggcgcg  28980
ggcgcgctcc tcctcaagcc gctgcgtcag gccatcgccg acggcgacta catccacgcc  29040
gtcatcaggg gcaccgcggt caaccacgac ggcaagacca acgggtacac ggtcccgaac  29100
ccgaacgcgc aagccgacgt catctctcag gcgctgcggc aggccggcgt cgacgcgcgc  29160
acgatcagct acgtggaggc ccacgggaca ggcaccgagc ttggcgatcc gatcgaggtg  29220
accggcctgt ccaagagcta ccggaccgac accaaggaca ggcagttctg cgcgctggga  29280
tctgcgaagt ccaacgtcgg ccacctggaa ggcgcggccg gggtcgccgg cgtgatcaag  29340
gtgctcttgc agatgaagca caagcagatc gctccgtcgc tgcattcgcg ggagctgaac  29400
cccagcatcg atttcgcgag ctcgcccttc aaggtccctc aggagctcag cgcctgggag  29460
cgaccgcgcc tcgcgcggcc ggacggcgca ggagagatcc cgcgacgggc gggcgtcagc  29520
tccttcggcg ccggcgggac gaacgcgcac gtcatcctgg aggagttcga gaacgcgccg  29580
cgcgcgacat cgggtcggga ggacgtcctc gtggtgctct cggccaggag cgaggagcgc  29640
ctgcgcgcct acgcgggcaa gctcgccgcg tccttgcagc tgcggctcgc cggcgaggac  29700
gccgccgagc acctcgacct cgagcgcatc gcctacacgc tgcagaccgg gcgtgaggcg  29760
atggattcgc ggctcgccat catcgcctcc gatcctcgac agctcatcgc cgacctggag  29820
gcctacagcg aaggccgcct ggacgacaag ggccctcgct gcttctccgg cacggtcaag  29880
ccctatgagc tgccggagct cgaggcgacg caccaggccg ccatcgacga ggccgcggcg  29940
agctacgacc tgcgcgcgct cgcgcgacag tggatcgccg gatacgcgat cgactggccg  30000
aggctctatc cgtctccgcc gccctacccg ctggccctcc ccacgtatcc cttcgcgcga  30060
```

-continued

```
gaccgctact ggatccccgt cgccgcgcag gcgccggcgg tcgccgcggc ggcggcgaag  30120
ggcctccacc ccttcctgga cgccaacgta tccaccctgg aggagctggc gttcgagaag  30180
accttcgccc gcggcgacct cgtgctgcga gaccacgtga tcgccggtcg tccggtgctc  30240
cccgcggcgg tgtacctgga gatagcccgc gccgccggtc accacgcagg gccggggccg  30300
gtctccggcg tccaagacgc cacgtgggcg aggcccatcg tggccacggg cgactcggtc  30360
accttgcgcg tcagcctcgc ccgggagcgc cagtctgtca tttaccgtgt cacctcgcag  30420
cccgaagggc agccggtggt gcacgggtcc gggcacctca ccttcgcggc gcccgccgcc  30480
gcccccccgc cggcgtcgct ccgcgacatc atcgcccgct gcccgcggca gatctcggcc  30540
gacgaccttt atcgctcctt cgaggcgctg ggatccact atggccccgc gttccgcccc  30600
gttcaggcgc tccactgcgg ggagcgagag gccgtcgccg tcctgaggat gcccgatgcc  30660
gcgggcagcg gcgactacgc cctgaacccc tcgctgctgg acggcgccct gcaggcgatc  30720
gtccatatcg ggctcgacaa cgagctcgat ccgtcgctcc tgcgcctgcc cttcgccctc  30780
ggccggctcg tgatccggcg gcccctcgac gcgacgagct gccacgcgca cgcgatcctc  30840
acgcacgagt cgcgcgcagg cgaagaccgg gtgctgaaat accgcatcga cgtctatgac  30900
ggcgacggcg ctctccttgt cgagatcgtg gactacagcg tacgcgtcgt ggcgcgcgac  30960
gcgctcggcc ccgccggcgc ccgggcttcg caacccgcgc acacgctctg gtacgagccg  31020
cgctgggagg cgacgcccgc cgctccgggg cgcgcgtccg cggcgtggga tcggctgccc  31080
gagcggctcc tggtcttcgg ccgagacgac gagctcacgt cgcgccttgt cgaggcgctg  31140
agccggctcc ggcccacgcg gcggatcgtc ccgggcgcgg cgttcggcgc gctcgaccgg  31200
caaggctacc ggatcgatcc ggcggatccg agccactacc gccgcctctc ggaggagctg  31260
gatcgcgacg acccgtggtc gacgaggacc gtaggcgtca ttcacctctg gcgctatccg  31320
gccggcgccg agggcgctca cgcagggctc cactccctgc tctacctcgt ccagagcctc  31380
accgcccgca acgccgccca gcgcgtccgg tgcctcgtcg ccgtcggatc cacggacggc  31440
gccgccgatc cgcgcgacga ggcgctggcc ggcttcggcg ccgccctgtc ccctgtcaac  31500
cctcacctcg agctcatcac cctgcaagcc gacgcgacgc ggctcgacgc gcagcagatg  31560
gcgggcgtcc tgctccacga gctggccgcg tccgacaccg cccatggcag cgagatccgc  31620
tataccgacg ctgctgcccg gtggacacgc gcgttacggc ccctggagga cgggccgacg  31680
cggacagcgg acgcgccgcc gctgcggacg ggcggtgtgt acgtgatcac cggcgggagc  31740
ggctacctgg gctcgacctt cgcgcgccac ctcgccgggc ggtacggggc gcggctcgtc  31800
ctctgcggtc gatcctcgaa cgacgagcgc aaggaagccc tggtgcgcga gctccgcggc  31860
ctcggtggag aggcggtcta tgttcaagcg gacgtcagcg acgcaggcgc cgcgcagagg  31920
gtggtgcagg ccgcgcagca gcgcttcggg gcgctccacg gcatcctcca cgccgccggg  31980
accgacgagg cgccgccgct cgcgcgcgcc gacgccgcct ccttcgccaa ggtcctggac  32040
cccaaggtgc gcgggacgct gaacctggac gccgcgagcc gccaggtggt caccctggac  32100
ttcttcgcgc tcttctcgtc gatcgccgcg gtgatgggcg acctcggcgc cggctgctac  32160
gcgtacgcca acgcgttcat ggaccgcttc gccgccgctc gagagcggca gcgcgcgcaa  32220
ggtcgacgac acggcaagac gctggcgatc aactggcccc tgtgggccgg cgagggcatg  32280
agcctgcccg aagggcagca ggagctgtac gccggcatcg caggcatgcg cgcgctcgat  32340
ccggcgctgg gcctcgagct cttcgcgcgg gccctctcag ccccggcgcc gcagctgctc  32400
```

-continued

```
gtggtccacg gggatcccga gcggatgcgg cgggtcatcg agcggaggaa cccgcgcccg 32460
gcggcggctt catcgcatcc cgccgagccc gccgccagcg ccgcccccgg tgacgagcgc 32520
ctcgcccagg ccgtcgagga ttatctcaag ggccacttcg ccgcggtctt caagatggac 32580
gcggcgcaga tcgacccgca aaccagcttt gacgactacg gcatcgactc gctcgtgatc 32640
gtggagctcc acgcgcgcct cgacaaggac atgacgccgc tgccgcgcac gacgttcttc 32700
gagctccgga ccgtccgcgc ggtcgccgac cacctgctcg cgtctcgccg cgccgagctg 32760
cgccgggtcg tgggcctcga ccgggaggcc acggcgcccc ccgcgccgga ggccggcgag 32820
cccgcccggc gtggaggcgc ggaggccccc gcccacgcgg tggcccccggg cccggcggcc 32880
agcgcctcat cgaacgagca cgcgggcgcc ggagcgggcc gcgacgccgg cagccgagcg 32940
cccgcccggc ccggagcggc cctcgcggac gaaggcatcg cgatcatcgg catgagcggc 33000
cggtacccca tggcgcccga cctggacgcg ttctgggcca acctcaaggc cgggcgcgac 33060
tgcgtcgagg agatccccgc ggagcgatgg gaccaccggc ggtacttcga ccccgagccc 33120
gggaaggagg gcaagagcta ttgcgcgtgg ggtgggttca tcgaggacgt cgacaagttc 33180
gatccgctct tcttccagat ctcgcccaag caggtggcga cgatggaccc gcaggagcgg 33240
ctcttcctgg agaccgcgtg ggccacgctc gagcacggcg ggtacgggcg cgtgcaggaa 33300
gacgcggccc ggatagggtt gttcgcgggc gtgatgtggg acgattacgg cctgctcggg 33360
ctcgagcagg cggcgctcgg gaaccacgtg cccgccggct ccgatcacgc ctcgatcgcg 33420
aaccggatct cgttcgtgat gaacctgaga ggcccgagcc tcacggtctc cacggcgtgc 33480
tcctcgtcgc tcctggcggt gcacctggcg gtggagagcc tgaggcgagg cgagtgcgcc 33540
atggccatcg cgggaggcgt caacctgtcc atccacccga gcaagtacac ccgtctgtgc 33600
cagctccaga tgctcgcgcc ggacgggcgc tgccgcagct tcggcgccgg cggaaagggg 33660
tacgtgcccg gagagggcgt gggcgccgtg ctgctgaagc ccctgagcag ggccgaggcc 33720
gacggcgaca ccatctacgc cgtgatcaag ggcagcgccg tcaaccacgg gggcaagacc 33780
cacggataca cggtcccgag ccccaaggct caggccgacg tcatcgggcg cgccctcgag 33840
cgcgccggcg tccacgcgcg cacgatcagc tacgtggagg cccacggcac gggcaccgcg 33900
ctgggagatc ccatcgaggt cggcgggctg gaggagagct tcaggcgcga caccggcgac 33960
aggcagtact gcgcgctggg ctcggtgaaa tccaacatcg gccacctcga gagcgccgca 34020
gggatcgcgg ccctcacgaa ggtcgcgctg cagctgcacc accggcagat cgtgccgtct 34080
ctgcacgccg aggtgctcaa tccgaacatc catttcgaga gcacgccctt ctacgtccag 34140
cgaacgctcg acgcgtggcg ccagcccgag gtgcgcgagg gcggggtgac cgaggtccac 34200
ccgcgccgcg cgggcatcag ctccttcggc gccggtggga ccaacgtcca catggtcgtc 34260
gaggagtatc aggcttcgac tcctgccctc gagatcgcgg cggccgagcc tgagcttgtc 34320
gtgctctccg cgcacaccga agagcggctc cgcgctcacg ccgagcggct gctgcgcttc 34380
ttgcaaggct cgcggcctgg agggctcccc tcgcccagcg cgccgggccg gcgcctgccg 34440
gaggccgcgc agctccgcgc cgagctgcgg gacatcgtgg cgcgacgcct ggacgtcgcg 34500
ccgcgcgacg tcgacgagga cgccgagatc tgcgagctcg ggctcggcgc gctcgacgtg 34560
cgccgcctga ccgaagacat cgagcgccgc ttcggcctgc gggtgagccc cgaggacgtg 34620
accgagcgga cgacggtcgc aggcctcgca gggcgcctgc gacacctggc agcgccggac 34680
gccgatcggg acgacagcgc ggctcgtccc gccgtgcgct tgagcgatct cgcctatacc 34740
ctgcgcgccg gtcgcgatcc ccgccagcac cgcctcgcgc tgcacgtcgc cgatctggac 34800
```

-continued

```
gagctcatcg agcagctccg gcgctactgc gaggaaggcg cggccgacgg gtcgcgctgc  34860
ttcgccgggc aggcatccag gcgggccgga agcagcggat cgcgcaagga ggccatggcg  34920
gacgaggccc gggtgcgcgc cgccatcgcg gagcgagacc tggccacgct cggccggctc  34980
tgggtcgccg ggaccgacgt ggactgggag ccgctcgacg cgcgccgggc gcggcggcgc  35040
gtcccgctgc ccacgtaccc cttcgcccgc gagcgttact ggttctccag gagcggagac  35100
gccttcaccc tcggccaggc gggagagagg cgcttgcacc cgctcgtgca ggcgaacacc  35160
tccacgttcc acgcgcacac gtactccagc cggctccggg gcgacgcgtt ctacctcgcc  35220
gatcacctcg tgcacggcca gaagctcctc cccgcggcgg cgttcctgga gatggcccgc  35280
gccgccgggg agatggcgtc cgggcggccg gtccgcgaca tcctcgacgt cgtctggacc  35340
gcgcccgtcg tcgtgggcgc cgagccgcgc gagatcgaga taacgctccg gccggccgcc  35400
ggcgccatcg acttcgccgt gtcctccgcc gccgagcgcg cggtgatctc ccacgcgcag  35460
gggcggatgc gcctcgacga gggggatccc gccgaagagg cggcgccgcc cctcccgctc  35520
gatgacatcc tctcacgttg ctcgagggtc accggcggag acgcgtgcta ccgccgcctc  35580
cagcagctcg ggctgcacca cggcggcagc atgcgcgcgc tccacgagct gcgccgaggc  35640
gagggcgagg ccatcgcgga gattcgcctc ccggagcttc accacgtgga cttctccacc  35700
tttgccctcc atcccgccct gctcgacgct gccctgcaat gcacgctcgg gctgctggac  35760
gatgaggcgg cccgagcccc ctatcttcct ttcgccgtcg gccgggtcac gctgctccgc  35820
ccgctgccgg cgcggctctt cgcctatgcc acgccgtcgt ccgcgccgcc gggcacgaac  35880
gccagggcct ctcacgtcac gctggccgat cccgccggcc gggtgctcct cgagatgcgt  35940
gatttcaccg tccgcctcgc gacggcggac gtcgcgccca cccccgccca gcggctctat  36000
ttccggcctg gcttgcgccc tcagcgcgtc gaccgccccg ccggcgcgcg cgccccgcaa  36060
ggccccgtcc tgctcctcga caccgacgat gtcctctgga cggccgccag ggcgcgcctc  36120
caggcgccga tcggcctcgt ccttccaggg ccggagttcc aggcctcgag cgacgatcgg  36180
tatgtcatcg atccgagccg gccagagcac catcgacgcc tgctcgacgc gttcgtggcg  36240
cggcacggcg tgcctgcgtc ggtcttgtat ctccggtcgc tgcatgacga ccgggaggcc  36300
gccggcgaca cccgccacct cgacgcggtg ttgcacctct gccgcgcgct gcaggagcgg  36360
cgaggcgagc gatccgttcg cgtgctctac gtccacccga ccgagggcgg cgcggtcagc  36420
ccgcgccacg cggcgctggc tgccttcgcg cggagcgtgc gccgtgagga tcccaacctc  36480
ctgtgcagga ccgtggccgt gccgctcgac gtcggcccag gccgcctcgc cgacgcgttg  36540
ctcgccgagt gcagcccgga cgccgatcgc gcagatcccg ccgccgaggt gcattaccac  36600
gagggtcagc ggctcgtgcg ctgcttcgag cccttccagc ccgacgccag ccggcccgtg  36660
ccgctgcggg aggagggggt ctatgtcatc accggcggtg ccggcgggct ggggctcatc  36720
ctctccgacc acctggcccg gcggtaccgc gcgaagctcg tgctctgcgg tcgctctccg  36780
ctgtccgcgc agcaagcgtc gcgcgtccgc gccctcgaag cctcgggcgc cgaggtcctg  36840
gttctgcgcg ccgacgtgag ccagcgagac caggcgtccg ccgccctcca cgaggcccgg  36900
tctcggttcg ggcgaatcga cggcgtcgtg cacgccgcag gcgccttgcg ggacggcctg  36960
ctgtccaaga aggacccggc cgacgtcgac gccgtgatat ccgccaaggt gacaggcacg  37020
ctcctcctcg acgagctcac ccgggaggat catctcgact tcttcctgct gtgctcctcg  37080
gtcgccgcga tcctcggcag cgccggtcag gccgactatg cctacggcaa cgccttcatg  37140
```

-continued

```
gatgccttcg ccgccctccg cgaggagcaa cggcacagcg gccggcggcg cggggcgacc  37200
ctctcggtca actggccgct atggcaggaa ggcacgatga ggcccgacgc cgagtcgatc  37260
gcgtggatga cgcgggcgac cgggatggtg cccatggaca ccgagcaggg cctcgccgcc  37320
ctggaggact gcctgcgggc cggagggccg cagatcgccg tgctcgccgg cgatcccggc  37380
aagatccagg ctctgttcag cggagagcgc gccgcgccgg cggccggcgg ccccgccgcg  37440
ctcccgcccg tcgagcccgg cgcgtacgcg ccccgcgcgg tcggctttct caagcgcgtg  37500
ttctccgagc agtggcagct gccgatccac cgcatcgacg ccgagcagtc gctcgaccag  37560
tacgggctcg actcgatcat ggcgatgagc ctcacccgcc ggctggagac gttcttcggc  37620
gagctcccga agacgctgct cttcgagcac cagaccatcg ccgcgctggc tggctacctc  37680
gctcgccacc acgccgaggc gctccggcgc gtcgtcggcg acagcgcccc ggcggtcgct  37740
ccgccgcccc ggcccgatgc ggcccctccc ggcgcggcgc ccgcgcctcg cgagctctcc  37800
gcctcgcgcc tccctgcgcc gcagcccggg ggcctcgaca tcgccatcgt cgggctcagc  37860
gggcgctacc ccatggcgcc tgacctcgac gcgttctggg agaacctcgc ggccggccgc  37920
gactgcgtcg tggagatccc cgccgaccgc tgggaccacg ggcgctactt cgatccgaac  37980
ccgggcgcgg cgggcaagag ctacagcaaa tggggcggct tcctcgacga cgtcgatcgc  38040
ttcgatcccc tcttcttcaa catcgcgcct cgggaggcgg aggccatgga cccacaggag  38100
cgcgtgttcc tggaggtcgc gtggcacgcg ctggaagacg cgggctacgc gcgatcgccg  38160
ctggcgaacc gcgcgacagg cgtgttcgtg ggcgtcatgt acggtcacta tcagctcttc  38220
ggcgccgagg cgctggcgct ggatcggccc gtgtccgcgg gctcgtcctt cgcgtccatc  38280
gccaatcggg tgtcctattt cttcgacttc cgcggcccca gcgtcgcgct ggacaccatg  38340
tgctcctcct cgctgaccgc gatccacctg gcctgcgccg cccttcagcg aggcgagatc  38400
gagatggcgc tcgccggcgg cgtgaacctg tccctgcacc ctcagaagta catcctgctc  38460
agccgcggca agttcatggc caccgacggc cggtgccgca gcttcggcga gggcggcgac  38520
ggctatgtcc ccggcgaggg cgcgggggcc gtcgtgctca agcgcctgga ccgcgcgatc  38580
gccgacgggg atcgcatcca tggagtcgtc aaggcgagcg ccctcaacca cggcggcaag  38640
accagcggct acaccgtccc gaaccccagc gctcaggccg acgtcgtcgc cgccgcgctg  38700
gcgcagtccg gcgtcgatcc gcgcacgatc acctatgtcg aggcgcacgg gaccggcacc  38760
tcgctgggcg atcccatcga gatcgccgga ctcacaaggg ccttcgaggc ttccccgaag  38820
gagcgtccca cctgcgccat cgggtcggtc aagtcgaacg tggggcacct ggagtcggcc  38880
gcgggcgtcg ctggcctcac caaggtgctg ctgcagatgg cgcatgagca gctggtccct  38940
tcgatccacg cggatccccc caaccccaac atcaactttg ccgagtcgcc gttccgtgta  39000
cagcgggagc tcggtccctg gcgggctcct gtcgatgagc gcggccagcg gctccccctg  39060
cgggcgggcc tgagctcctt cggcgccggc ggcgccaacg cgcacctcgt gctggaggcc  39120
tacgtgccgg gcgacgaggc aggggccgcg gccgccgtga cggccgggag cgagcgcccg  39180
caggtgctcg tgctctcggc ccgcacgccc gagcgcttgc gcgtctccgc cgcgcggctg  39240
ctcgatcacc tccggacgcg cgcgcggggc acggcgctgg ccgatgtcgc gtacagcctg  39300
caagtcgggc gcgaggccat ggacgcgcgg ctggccctcg tggtcgacag cgcggagcag  39360
gccatcgcgc tgctcgagca ccacctcggc gaccgcgcgc ccgagggcgg ggcgccgcgc  39420
gcccaggaga cgcaggggct ggagcacatc cacgagggga gcgccagggc gggccacgtc  39480
cggcagctcg ttcacggccg ggcggccgca tctttcctgc aagccctcct cgatgaaggc  39540
```

-continued

```
gatctggaca ggatcgccgc gctctgggtg agcgggtgcg acgtcgactg ggcccgcctc  39600
cacgagggag cgaggccgcg ccgcgtcgct ctgcccgcct atcccttcgc gcgcgagcgc  39660
tgctggttcg ccgtgcccgc agaggaccgg cgcggcgggc tcccgacctc cgccgaggtc  39720
gcggcgacgg cgcggctgca cccgctcctg agccgcaaca cgtcgacgtt cagagagcag  39780
cggttcgcca cgaccttcac cggcgaggag atcctcctct cggaccaccg gatccgaggc  39840
cgcgccctgc tgccgggcac ggcttacctg gagatggcgc gtgtggccgg cgagctctcc  39900
gccgagggcc gcgtcggtcg tttcaccgag gtcacctggc tgcagccgat ccaggtcgat  39960
cgcggccccg tcgaggccac cctcgacctc cggccgaccg agacgggctg ccagtttcgc  40020
gtctgcacgc aggacggggc cctcgtccac gtgcgcggcc agctccacgt cgagccccag  40080
cccccgggag gcgagccgac ggtggacctg gcggccatca aggcgcgctg ccccgagcct  40140
ctcctgcggc aggactgcta tcgggccctg cgcgagcaag ggttcgagta tggccctgcg  40200
ttccaggtca tcgaggcctt ctacgacaac gacgaggagg ccctggccct gctcagcgtc  40260
gccgagcctg atttccaggg cttcgccggt gggctgcacc ccatgatcct ggacgcggcc  40320
ctccacgccg ggatgctgca caggcgagag ggcgcgaccg gcgacgtcac gccggtgccc  40380
ttctacctgg aagagctggt cgtccttcgc ccgctggagc gccgctgcta cgcgtatatg  40440
caggtgcggc gcctcgccgc aggagaagag cggagcgagg tcgccgtcat ggacgtgacc  40500
ctcgtggacg aggcgggctc gccgctcgtg cgcgtcaaag ggttcacggg gcggaagctc  40560
gtcgacgccg acgaggagcc ggagcaaaac gccgtcctct tcttcgggga cgcctggcag  40620
cccgccccgc tcccctcgcg tccgcccgcc ggcgcgccgc cggccagcgt cctcttgatc  40680
gccgaggaca ccgcccgggc gcgggcgttc gagcgcctgg tccgcgcgcg gggcggtcac  40740
ctgacgtggg tttgccctgt cgggtcgccc cgggcgcagg ccgagccgag cggcgcgccg  40800
agcgcggggt ccggcgatcg cggggctcca gggctcgcga tcgagccgcg ccccgtcgac  40860
gactaccgcg ggctgctcgc gacgttgaag gagcagggcc gcctgcccgg cgggatcatc  40920
cgcctgtggg acgcgccgag cctcgacacg gaagcgtctt cgcccgcgga gggaccggag  40980
agcgtcgagg agctgagaga gctcttccac ctcgtcgtcg cgctcgcgag cgcggtccct  41040
catccgaagg ctcgcctgat cctcgccttc cacggcgacc cggcgcccct cgccgtcgag  41100
gccacgtccg gcttctgcag gtccctcggg ctgctgctgc cgggcctgcg gtcgagcacg  41160
atccactgga cccaccgcga gcccgagcgc cacgccgagg acctctgggc cgagctcgcc  41220
gatcctgcga cgagggggat cggcgggagg aacggggcgg agatccgcta tcgcggtccg  41280
gaccggctcg cccgcaccgc ggcgcccgcc gcgctcgcgc ccgacgccgc gccggccccg  41340
ctccgccacg gaggggtcta cctcatcgcg ggaggcgccg gcgggctcgg gtacctggtc  41400
gcccagcacc tcgcccatcg ctaccgcgcg agcctcgtgc tcacgggccg ctcgcccctc  41460
gacgccggca aggagcggca gctcgccggg ctccgggacg ccggcggaca ggggctctat  41520
tgccaggcgg acgtcgcgga cgaggcggcc atggcggccg cggtgcgcct ggccaaggag  41580
cgattcggcg ccttgcacgg ggtgatccac gcggccggcg tgctcgacga gcgccccgtc  41640
gtcgagaaga cgtgggggga gttccacgag aacctgcggc ccaaggtcgc cggcagcgcg  41700
gtcctcgacc ggatcaccgc ggccgagccg ctcgacttct tcgcggtgtt ctcctccacg  41760
tcggccgtgc tcggagactt cggctcctgc gattacggaa gcggcaaccg gttccagatg  41820
gcctatggcg cccaccgcga gcggctgcgg cagcagggcc tccggcgcgg gatcaccgcc  41880
```

-continued

```
gtcatgaact ggccgctgtg gcgcgagggc ggcatgggcg gtcgcgccga gtgggagcaa  41940
acctacctga agacgagcgg cctggattac ctcgacacgg ccgccggtct ggaggcgttc  42000
gagcgcatcc tcggggcccg tcagtcgccc gtcacggtgt tctacggcaa gccgtcgcgt  42060
gtggcgaggg ccctcggcct cgacgcgccg ccgcccccgg cgggtcgcgg cgcggcggcc  42120
gcgccgctcc cgccggcgga ggcgccggcc gccgccccgg aggcggcggt ccgcgagagc  42180
gcggcgcgcg cgccgctgcg cgaggtgatc ctcgacgcga tcaccgaggt cctcaacgtc  42240
cggcgcggcg cgatcgcgcc ggacgtcaac atcgccgagt acggcttcga ctcggtgtcg  42300
cttgcgcagc tcgccgatca gctcggcgcg cgcctcgggt tgaagctggc gtcgctcgtg  42360
ttcttcgagc acacgacggt ggaagagatc gaggccttcc tggagcggaa gcacggcgcc  42420
gagctccgcg cgcggatgaa cggggcgcgg gagctccacg gccgcatgaa cgaggcgcga  42480
gagctccatg accgcatgaa cggggcgcga gagctccacg accgcatgaa cgaggcgcga  42540
gagctccacg accgcatgaa cggggctcga aaggaggctc cgcgcgcgaa ggagccggcg  42600
ccggccgacc cggctccgcc gccggcgcct cgcgagaacg gctcgcggct cgccggcgcg  42660
cctcgcgcga gcgcgccgcg caggccgcag gaaggcgcct cgcgcggcga catcgccatc  42720
atcggcgtca gcggccgcta cccgcaggcc gaggacctgc gcgcgctctg ggcgcggctc  42780
caggccggcg agagctgcat cgaggagatc cccgccgagc gctgggacaa ggatcgctac  42840
ttcgacccgc aaaagggccg gagcgggaag agcgagagca agtggggcgg cttcctccgc  42900
gacgtcgatc agttcgatcc gctgctcttc aacatccctc ccgcgcgggc tcggatcatg  42960
gatcccatgc agcggctctt cctggagagc gtctatgaga cgctcgagga cgccggctac  43020
acccgcgcca tgctgtcgaa ggacggcggc aaggtcgggg tgtacgtggg cgccatctac  43080
catcactacg ccatgctcgc cgcggacgag tcgacccgca gcctcctgct ctcggccttc  43140
ggcgcccaca tcgccaacca cgtgtcgcac ttcttcgatc tccacgggcc ctgcatggcg  43200
gtggacacga cctgcgcgtc gtcgctcacc gccatccacc tcgcgtgcga gggcctgctc  43260
ctcgggcgca cggatctcgc catcgccggc ggcgtcaacc tctccctcat cccggagaag  43320
tacctgggcc tgagccagct ccagttcatg agcggcgggg cgctcagccg cccccttcggc  43380
gacagcgacg gcatgatccc cggcgagggc gtcggcgccg tgctgctcaa gccgctggat  43440
cgcgcggtcc gcgatcgcga ccacatccac gcgatcatcc ggtccagcgc cgtcagccac  43500
ggcggcgcca gcacgggctt cacggcgccg aacctcaagg cccagtcgga catgttcgtg  43560
gaggcgatcg agagggcggg catcgaccca cgcacgatca gctacgtgga ggcggccgcc  43620
aacggcgctc cgctcggcga ccccatcgag gtcaacgcgc tgaccagggc gttccggcgc  43680
ttcaccgcgg acacgggctt ctgcgcgctc ggcaccgtca agtcgaacat cggtcatctg  43740
gaaggggcct ccggcgtctc ccagctcgcc aaggtgctgc tccagctccg gcacggcgcg  43800
ctggcgccga ccatcaacgc cgagccgagg aatccgaacc tgcacctcga cgacaccccg  43860
ttctacctcc aggagcgcct cgacgactgg cgtcgaccga tcatctccgg ccgcgaggtc  43920
ccgcgccgcg ccatgatcaa ctccttcggg gccggcgggg gatatgccac cctcgtggtg  43980
gaggagcacc gcccgccgcc gcgcgacgcc gcgccgggcc gctcgccctc cgggccgccc  44040
gagctgttcg tgctctccgc gaggagccgc aagagcctgc gcgagctggt cgtcaggatg  44100
cgcggcttcc tcgccgaggc gaccgacctg cgcctcgacg acgtggccta cacgctccag  44160
gtggggcgcg aggccctgga gctgcggctc gccgtggtgg cggacaccgt ggaggcgctc  44220
ctctcggcgc tggacggcta cctccgcgat cccgaggtcc ccgcgccggg cgtcttcacc  44280
```

-continued

```
ggccaggcgg atggcgacgc gtccagcggc gccgccgcgc ctcccgccca ggcgctccgc  44340
acgcccgagg aggcggcgcg ccggtgggtc gcgggcgccg cgatcgactg ggaggccctc  44400
tacccccctcc gcgacgcgcg gcgcatcccg ctgccgacct acccgttcga ccgccggcgg  44460
tgctggctgg atccggcgcc ctccgacgag gcctcgccga gccccgctgc gcccccgccc  44520
gaggcgcccc ggcccgccgc ggccccgccg gcgcccccca gcgcggaggc ccgcgcgctg  44580
gagggctacc tgtgcgcgcg gctggagtcc acgctgggcc tcgatcaggg cgagatctct  44640
gcccgcgcgt cgctgcggcg cctcggactg gactcgatcc tggccgccaa gctcaaggtc  44700
acgctggagg gagagctcgc catgaccatc cccatggagg tcctgagcgg cgacaagagc  44760
gtggcggagc tcggcgatta tctctctcga cggggagccc gcgcgccgga gagccgggcg  44820
aaggcgcgca gcggcgcggc cggggccgac ctgtccacct ccctcaaggc cctctcgggc  44880
gcggtgctgc gggaacagtt cctggcgttc gggcacgacc tggccggcgt accgggcgag  44940
gagctgactc ggctctacgc catcctgcaa gaggaatgat gacgatggaa agcgcgatga  45000
ccatccagga gtttgccaac ttgtctgcgg aggagaaggt gcaggtcctc ctgcgcttgc  45060
gggaccggcg cgcttcgtgg caggcggccc ccgagggccc cgcggccagc gctcagccct  45120
cgctccggcc cgtgatcacg gcccgcccgg gcgatcgctt cctccccttc ccgctgacgc  45180
cgatccagga gtccttcctg gtggccaagc aggtcgacag ggcgggcgat cacgtcggat  45240
gccacatcta cctggagatc gacgaggcgc gcctcgacgt ggcgcggctc gagcgcgcct  45300
tccaccggct cgtcgtccac cacgacatgc tccggaccgt cgttcgcgcc gacggcaccc  45360
agcaggtcca ggagcccggg cagccgcgca gctttccggt ggacgacctc cgcgggcgcc  45420
cgggcgcggc gctggacgcg cacctggaga gcgtgcgcgc gagcatgtcc caccgggtct  45480
acgcgccagg ggcctggccg ctccacgaga tccggatcac ccgctgcagc gacgagcgca  45540
gcgtcatcca cgtcagcatc gacgagtgga tcctggacgc cgccggcctc aacctcctgc  45600
tcacccagtg gtaccggctc tacagcgacc ctgacgcgac cctgcccgtc tgcgacctca  45660
gcttccgcga ttacgtcctg gcctcgaggg aattcgagcg ctcgccggcc taccaggggg  45720
atctcgccta ctggtgcgag aagctggccc agatgcccgg gggcccggcg ctgcctcgcg  45780
ccgagcagcc cgggaggccc gcgggccgcg cctgctaccc ccgtcgccgc gtccacgggc  45840
gcctggccga ggcgccgtgg cgcgcgctca aggacaaagc gcgggagctg gacgtctccc  45900
cgacggccct gctcctcacc ctcttcgccg aggccctcgc ctcccacagc gcgcccgggc  45960
cgttctccct cacgctcacg tacttcaacc gcccgccgat ccacccgcac atcgagcgcc  46020
tgctcggccc gctcatctcc acccaccgct tcctcgtcga gggagccacc gatctcacgc  46080
tgcaggagga ggtccagcgc agccagcgac agctctggcg cgacatggac cacgaccgcg  46140
ccgacagcat cctcgcgctc cgcgccctca gggcgaggcg cgcggcgccc cccgcgagca  46200
cggtcgtctt cacaagcgtc ctccacaacg tgagcagaga agcccggcag caggggcgga  46260
gcttcctcga tcaaatcacc tattcggtca cccagacccc gcaggtctac ctggaccacc  46320
aggtctacga gaaggacggc ggccttcatt tcacgtggga tgtcgtggac gccgtcttcg  46380
cgcccgggtg cgtcgacgcc ctcttcgaca cgtattcgcg gctcctcggg gcgctcgcgg  46440
cagagccctc gcgctggacg tcgccggggt ggcgcgagga gctcctgggc ccgcgccccc  46500
cgcgcggcgg cgggcccgac cggacctccg cggcgccggc cggcgagggt ctcgagatca  46560
tcgctcggcc ggaggagcgt caccagagat tccccctgtc cgatctgcag caggcctact  46620
```

-continued

```
tcgtcggccg caccgggttc gccgccaacg ggggcgtgag ctgccagatg taccaggaga  46680
tcgagctccg cgatccggac atcgtccgcc tcgatcgggc gtggcagcgc gtcatcgacg  46740
cccacgagat gctgcgcgcg gtcatccacg ccgacggcac ccagagcatc cgcgccgagg  46800
tcccgcgcta cgtcatcgag gtctcggacc tccgcgcggc gtcgcccgag gcccgcgcgg  46860
aggccctcgc tcggacgcgg gagaccatgg tcgccagggt attccccctg gatcagtggc  46920
ccttcttcga gctgcggctc tcgctcaccg agccgtcgag ggccgtcctc cacctgagca  46980
tggatctgct cctcgccgac gcgacgagca tccacctcgt cctgaagcag ctcttcgccc  47040
tgtacgagcg gcccgacggg ccgtgcgccg cgccgcggct ctccttccgc gactaccagc  47100
tcgcgctcaa ggaccacgag cgcgccgcgg gccacgccgt cggcgtcgcg tactggcgcc  47160
ggaggctcgc ggacctcccc ggcggccccg agctcggcat gcgcctgccc gacggccggg  47220
gcggccgcct gcggcgccgg cagttcgacg gcgtcctgga gcggtggtcg cgcctccagg  47280
agggcgccgc ggccctcggg gtctcggccg aggccgtgct gctgggcgtc tatttcgagg  47340
tcctggacgg ccgctccagc cggcgcccct tcaccgtggt cgtggcgcgc tgggaccggc  47400
cgccggtgca cccggagatc ggcgccgtgg tcggcgattt caccgcggtg agctggatcg  47460
tctcgccgcc gggcgagacc ttcgccgagc gcgtccggca cctggagcgc acgctctccg  47520
aggatcgcga gcaccgcctg gtcagcggct cccgggtgct gcagcagatg gccatcaagt  47580
cccggaacag gcagttcctc acgttcccgg tggtcttcac cggcctcggg cccagcctca  47640
agggcgacct ccccgacacc gtctctctcg gataccgcat cacccagacc ccccaggtct  47700
acctggacaa catcagcatg gaggccgacg acgccctgcg gctccactgg gactcggtcg  47760
agggcgtctt ccccgagggg ctcatcgagt cgatgttcgg cgcttactgc cgcatcctcg  47820
accggctggc ccgcgatcac gccgcctggc acgagggccg gctcgacgcg ccgcgcgccc  47880
ccgagggccc cgcgcccctg cccgcgccgg agggccgcga ccgcgcgccc ggcgccgccc  47940
ggcaccggac gaccctgcac cggctgatcg aggagcgcgc gagcctgtgc cccgaccatg  48000
tcgccctgat cgccgagcgc gagcagctca cgtaccggga gctcaaccgc cgggccaacc  48060
aggcggcgcg ccgcctgagg cggctcggcg tcgggcccga cgtcctcgtc ggcgtgctcg  48120
ccgaccgatc catcgagatg gtcgtcgccc tcctggccat cctcaaggcg ggcggggcgt  48180
acgtgccgat cgaccccacg taccccgcg agcggatcga cttcatcgcc gaggacgccg  48240
gcctctcggt cctcctcctc gcggaggagc gccgccggct cccgtcgttc cgcggcaccc  48300
agctgtgcct ctccaccgag cggcacctcc tggacggcga ggcggagcac gacctcggcc  48360
ccaccgccgg gccggatcac ctcgcttacg tcatctacac ctccgggtcc accggcaagc  48420
ccaaggggtg catgatccct catgacgcga tctgcaaccg gctgctctgg atgcaggacg  48480
agtaccggct ggcgccggac gatcgcgtcc tgcagaagac cccttatacg ttcgacgtct  48540
ccgtgtggga gttcttcctg cccctcatcg ccggcgcgac cctggtgatg gccaggccgg  48600
aggggcacaa ggacgtcgcc tacctggtcc gggtcatgga ggagcagcgg atcaccacgt  48660
gccacttcgt gccctccatg ctgaacttct tcctcaagga gccggcgctc ccaacgcacc  48720
tccgccaggt gttcacgagc ggcgaggccc tgtcctacga cgtcatggac acgttcctgc  48780
gccgctcccc ggccaggctc cacaacctct acggcccgac ggaggccgcg gtggacgtca  48840
cctactggcc gtgcgagcgc cggcccgatc gcaaggtgcc gatcggccgc gcgatctcga  48900
acgtcgagat ccacatcctc gacagcgcgc tcaggcccgt gcccgcgggc gccgagggcg  48960
atctctacat cggcggcgtc tgcctcgccc gcggctacct caaccggccc gagctctcgc  49020
```

-continued

```
gcgagcggtt cgtcccgagc cccttcgacc ccggcgcccg cctctacaac accggggatc  49080
gcgcgcgcac cctggacgac gggaacatcg agtacctggg ccggctcgac gcccaggtca  49140
agctgcgcgg gttccgcatc gagctcgggg agatcgaggc ggcgctgagc gcccacgagg  49200
ccgtgcagga cgccgtggtc gccgtgcagg acgcgcacac ggaggacccc aagctcgtcg  49260
cctacctggt cacgggcggc cggcccttcc cggcgcccgg cgccctcaag gcctatctca  49320
aggagcgctt gcccgactac atggttccga accgcttcgc gcccatcgcc cagatcccgg  49380
tgacggccca cggcaagctc gatcgcaagg ccctgccctg gccggtgccg gctccctcgg  49440
cccagccgga gcccccgccc gccggcgcgg ccgcggcgcc cccgggcgcc gcccaggccc  49500
ggcggccagc gggcgtctcc agggaggccg ccgaggaaga gctccagcgc atcctcggca  49560
aggcgctgca cctcacccgc ctcgatcccg gcgctgacct cttcgagctg ggcgccacct  49620
cgctcaccat cgtgcaggcg tcacagcaca tcgaggagcg cttcggcgtc gggctgccgg  49680
tcgaggtcgt cctggccgag ccgaccctcg acgccatcgc gcggcacgtc gccgagcgga  49740
cggcggctgg cgcgcccgag cccccggccc ccgggcccgc gctggacgcg cctcccgcgg  49800
cgcccgagcc cccggccgcc gccgccccg gcccgatcga tttcttctcc agggaagatc  49860
gggagcgctt caagcagcag cagctccacc tgcggcacgg cgtcgagggc ctcccgaccg  49920
tggatctggc cgacgctccc gcggccccgc gcctctaccg cgaccgcggg agccgccgcg  49980
actaccggcc cgagcccgtc tcgttcgacg acctctcgcg cctcctcgcc gtcctccggc  50040
ggtacccgag cggccagcag acccagctct gctatccctc ggccggcggc acctacgccg  50100
tgcagaccta tcttcacgtg aaggagggcg cggtcgagcg cctcccggcc gggatctact  50160
actaccaccc ggatcgcaac cagctggtgc tcatcaacga tcggcccgcc atccgccggg  50220
tgcaccactt ctattacaac cgcgagcact tcgaccgcgc cgggttcggg ctgttcttca  50280
tcgcccagac cgacgccatc cagcccatct acggcgatca gagcctcacc ttcgccgcga  50340
tcgaggcggg ggcgatgatc caggcgctca tgagccatca ggcggaggcg gacctgggcc  50400
tgtgcgccat gggagggctc gacttcgacg ccatccgcgc cgacttcaag ctcgggagcg  50460
ggcaccggta catcgtctgc atgctggggg gccgcgtcga tcgcgaaggc ggcgggcggc  50520
agggccgcgc gaggctcctc gagagcgcgg gggcggacgg ctcgtacggg gcggccgcgg  50580
cggaggccgc cgccccgcgc cgcgagcgcg aggctcccgc cggcgcgcgc gagatcgcgg  50640
tcatcggcct cgccggccgc taccccggcg cggacacgcc acgccagctg tggcgggcgc  50700
tccggagcgg ccagagcgcc gtgacccggc cgcccgccgg gcgcttcggc gcgagcgccc  50760
cgcagggcga cgagccccga ggcggcggag cctccccggg gtggggcggc tacctggagc  50820
ggctcgaccg cttcgacagc ctcttcttcg gcatctcgcc cgccgaggcg aagctcatgg  50880
atccccagga gcgcctgttc atcgaggtgg cctgggagtg cctggaggac gccgggtaca  50940
cccccgagga gctccgtcgc gccgccccc gggtgggcgt cttcgtcggc gccatgtgga  51000
gcgactacca gagcgtgggg ctggaggcgt ggcagcggga ccggcgcgcg aaggccgtgg  51060
cgttccactc ctccatcgcc aaccggatct cgtatctctt cgatctccac gggccgagcg  51120
tggccatcga cacctcctgc tcctcgggcc tgacagcgct gcacctggcg agccggagcc  51180
tccggctcgg cgagtgcgac gtggcccttg tcggcggggt caacctcctt ggtcacccgt  51240
tccaccccga cctgctcgag ggcctcaacc tcacgtcccg cgacgacaag acgcgcgcct  51300
tcggcgccgg gggcagcggc tgggtgcccg gcgagggcgt cggcgccgtg ctgctgcggc  51360
```

-continued

```
gcctgcccga ggccgaggag cgaggcgagc acatccgctg cgtcctcaag ggcacggcgc  51420
tcgcccacgc cggcaaggcg ccgcggtacg gcatgccgag cacgcgcgcc caggcgggct  51480
cgatccgtga cgccctcgcg gacggcgggg tcgccgcgtc ggagatcgat tacgtcgagt  51540
gcgccgccac cggctccggc atcgcggacg cctccgaggt cgacgcgctc aagcaggcgt  51600
tcgaggggcg gagccctgac ggcccgccgt gcctcctcgg gtcggtcaag ccgaacatcg  51660
gccacctcga gtccgcctcg gccttgtccc agctgaccaa ggtcatcctc cagctggagc  51720
acggcgagat cgccccgacg ctgcacacgg agccgcgcaa cccgctgatc cagctcgacg  51780
gcacgccctt ccggatcaac cgcgcgctgt ccccctggcc ccgggccgcc ggggcggacg  51840
cgcccccgcg gcgggcgctc atcaatgcgt tcggcgccac cggatcgtcc gcccacgccg  51900
tcgtggaaga gtaccggcct cgccgccggg cctcgacccc cgcggcggcc gtccccggcc  51960
tgttcgtctt cgtcctgtcc gcggacaccg ccgagcagct cgaggcctgc gcccgcgcgc  52020
tggcggagca cctgcgcgag cgctcgaccg cgcgtccgcg cgacgtcgcg ccgccggccg  52080
cggccgcaga cgtcgcgtac accctccagg tgggccgtcg cgcgatggac gagcgcctcg  52140
ccatcctcgc cggcgacctg gacgagctcg aggcccgcct gcgaggcttc ctcggcgggc  52200
gtggcgagga cgacggcgag cacctcttcc ggggtcgcgc ctcgtcgccg cgcgatcgag  52260
cgcccctgtc cccggaggcg ccgctccccg cgctggcgcg ggcctgggtg aacggagcat  52320
ccatcgcctg gcacgacctg tacaccgacg gatcgcggcg ccgggtgcct ctccccacct  52380
atcccttcgc ccgcccgtcc cactggctcg gtcggcccgc cggagacgcc gcggcgcctg  52440
ccgtcgcgcg cggcgagacc gccgaggagg cgccctcgcg cggcgagacc gccgaggagg  52500
cgccctcgcg cggcgagacc gccgaggagg cgccctcgcg cgagaccgcc gaggaggcgc  52560
ccgccgccct ggcgccggcg accgcggatc ccgcgctgcg caaggccacc ctcggcctgc  52620
tgtcctcctg cttcgccgag gtcgccgaga tcccgcgccg cagcctcgat cccgaggtcc  52680
ccctggaccg ctatggcctc aactcgatgc tgatcgccca gctctccgcg cgactcgagg  52740
cgctcctcgg cgagctgccg aagaccctcc tcttcgagca ccacaccctg gcagccctca  52800
ccgactggct ggtcgcccac cgcggcgacg cgctcctccg ccgcctcgac ctcccgcggc  52860
gggccgcggg gcccgcggcg tcccccggcg cgctccccgc ggcgcccgca gcccgccgcg  52920
ggccggcgag agagcgctcg gccgcggcct ctccggccct cgcgccggcc gcgcctctcg  52980
agagcgtcga catcgccatc gtcggcctga gcggccgcta tcccggggcc gacaccatcg  53040
acgccttctg gagcaacctg cgacaggggc gtgacagcgt caccgaggtg ccggccgatc  53100
gctgggacgc cgccgcgatc ttcgaccccg agggaggccc cggcaagacc cgccagcgct  53160
ggggtggctt cctcgatcgc gtcgatcgct tcgacgcgct cctcttcaac atctcaccgc  53220
gcgaggcggc gggcatggat ccccaggaga ggctgttcct ggagatcgcc tggtgcgcct  53280
tcgaggacgc ggtctatacc cgcgagcggc tcgccgaaga acaggcgcgc gccggggtgg  53340
gtgccggcgt gttcgtcggc agcatgtacc agcagtactc catgctcgcc cggacgcccg  53400
acgccggggc ctcgtcgtcc ttctggtcga tcgccaaccg ggtctcctac ttcttcgatc  53460
tgcgcgggcc gagcctcgcc gtggacaccg cgtgcgcctc gtccctcacc gcgctccacc  53520
tggcctgcga gagcctgcgc cggggggagt gctgcctcgc gctggctggc ggcgtcaacc  53580
tccacctcca cccgcacaag tacgtcgccc tcgatcgcct gggcctgctc gggagcggcg  53640
ccgccagcaa gagcctcggc gacggggacg gctacgtgcc cggcgaggcg gtcggcgccg  53700
tcgtcctcaa gccgctcgat cgcgccgtcg cggacaacga ccgcatctat ggcgtcatca  53760
```

-continued

```
aggggagctt cgccaaccac gccggcaaga ccgccgggta cggtgttccc agccccgccg  53820
cccaggccga cctgatcgcg gcggccctgc gccggacggg catcgatccc gagaccatcg  53880
gttatatcga ggtcgccgcc aacggctcct ccctgggcga cgcgatcgag ctcgcgggcc  53940
tcacgcaggc gttccgccgg ttcaccgccc ggaagcactt ctgcgccgtg ggctcggtca  54000
agtccaacat cggccatccg gaggccgcgt cgggtatcgc tcagctcacc aaggtgctcg  54060
gccagctcca tcaccggacg ctggtgccca cgctccacgc ggagccgcac aacccgaaca  54120
tcgacctgag ggacagcccg ttctatgtcc agcgagagct cggcccgtgg acggcgccga  54180
ccctcgccgg cgaggggggg accgcggagc tcccgcgccg cgccgcgatc agctcgttcg  54240
gggcgggcgg cgccaacacc catctcctcg tcgaggagta ctcgccccgc ccggacgacc  54300
ggggggacga gggcgcggtc cccggcgcgg tcatcgtccc gctgtccgcc cggaccgcgg  54360
ggcagctgcg cgcgtacgcc gcgacgctgg cggacgacct ggagcgccgc tcgcgcccgc  54420
gcggccacgg cgagcgggcg ctcgccgatc gcgacctgac cgccgtggca tataccctcc  54480
aggtcgggcg agaggccatg aacgagcgct cggccatcgt gaccgcgagc ctcggcgatc  54540
tcatcacgaa gctgaggcag ctcgccgcgg gccagacgga cgtcgacgat ctccatgtgg  54600
gcagcgccgc ggcgtcgctc tccgccctga tgctcgacgg ccgcgagggc caggcgttcc  54660
tctcgatcct cgtggaggac ggtcgccacg acaagctggc ccggctctgg gtgagcggcg  54720
cccggatcga ctggcggacg ctttacggcg gctcgacgcc gaggcccctg tcgctgcccc  54780
actacccctt tgccggcgac cgccactggc tcgacgacga ggcgctgccg catggcgccg  54840
cctggagcgc gaccgcggcg cctccggccc agaccgccgc ctggagcgcg accgcggcgc  54900
ctccggcccg cgccgcggat cctgggggtg cggcgccgcc cgaggggcca ggcggcgcgc  54960
ctccgggcgg cgcggcccgg cagcgcatcg cgcaggagct cacggcgatg gtctgcgatg  55020
tcctcaagat gcaggccagg gacgtcgacg gggacgaggc gctccgcaac tacggcatgg  55080
attcccgcct ctccgccgcc ttcatgcggt cggtgcagca gcggtacggg tcgagcgtgc  55140
cgctcagcgc cgcgcacacc catcccacct tgaaccagct cacggcccac attcatggcc  55200
tcctgagcag caacggcgca gcccggcacc cgtccgccgc gcccctcgcc gcgacctcgc  55260
cgtcgatcgc cacggccccg gcggcctccg cagccccggc ggcctccgcg gccccggcgg  55320
cctccgcagc ccccgcggcc tccgcagccc cggcggcctc cgcggccccc gcggcctccg  55380
cggcctccgc agtcccggcg gcgctccacg aggctccggc gcctgatccg cgcgcggggg  55440
acgcacggcc cggggcggac agcatcgccc cgcagcccga gccggggccc aaccccgacg  55500
agctcgtcgt catcaacccg cgcggctcac gcgggagctc gttctgggtg cacggcgcgc  55560
ctgggctcgc gcagccgctc tatcccctgt ctgccgcgct cggcacggat tacccgttct  55620
tcgccttcca ggcccggggc gtcgacgggc tcgccatgcc cttcacgagc atcgaggaga  55680
tcgcggccca ttacgtcgcc tgcctgcggc agcgtagtcc gagagggcct tacgtcgtgg  55740
gtgggctgtc ctccggcggc atcatcgcct tcgagatggc ccggcagctc ctctcgcaag  55800
gggagcgcgt ctcccggctg gtcatgctcg acacctatcc cgcggtcgcg ggcctcgcgc  55860
aggagacgcc gggcgacatc gacccgatcc tgccgctcct gctcatggcc aactccttca  55920
tcagcttcga tcgcgacgga gacacggcga tcaagcccga cgacctcgcc gggctccccc  55980
ccccgatgca gctcccgcgg gcggtgcagc tgatcaagga gcggagccgc accgcgctca  56040
gccgtgatca gatctacagg atgctgaacg ggaacatcgc tgtctacaag cacctcgacc  56100
```

-continued

```
tcgcgtgcag gaagtaccag cccggggtcc tcgacgccgt ggacgtcctg ttcttcaaag  56160
cggagaaagg cttcttcggc ggagcgaacc cgctggggct gcccatcctg gacgtgtttt  56220
cctcctatga ctatgtgacc ccgtggcgcc agtggatacg cggaggcctg caggtcgtgg  56280
agctgccttg cgcgcacgtc gacctcctgg agcccccggc gctccaccag gtggtcgcgc  56340
acgtccgcga ggcgctttca tgacaggtga gcggcgcgcg ggcgccgagc ccgcgggcgc  56400
cgagcccgcg ggcgccgagc ccgcgcgccg cattgcgttt gatatcgagc gatccgcatg  56460
atagacgacc ccgcgctgaa ccctacgtgg tctcgaccgc tgagccagcg attccgggga  56520
tcaagcgctc tcccggtggc agctcgcgcg tgtcgttgct ggagcgccga gccagaccgg  56580
accgagccag gcagccaggg agagcgcagc gctgcgcgac gaggtgccct ccttgcacag  56640
ggcgacgagg agcgacgacg cgatgcgccc gccctcggct gcgcggcgac gggaggtctt  56700
gagagaggcc ctctcgggcc cgatgacaga caatcagccg acaaggctct caacggacgg  56760
aaatttacat gacatcgatg gcgcgacacc tggacatcca cgaggagctc ccccagaccg  56820
ctccgctgcc gccacgcgcg atccagtggc gcaaggcgtt tcggctggcc aaggagctta  56880
cggagaagcc cttcaccgcc gagctctcct acgagctcat cttgtcgctc gacggcgggg  56940
cgaccgagcg catgtttcaa gacttcctcg ccgagccggg ggcgcgcgcg ctgatccaga  57000
agcggcccga cctggccgcg acgctgtccg acctggatct cctcggatcc atgccagagg  57060
gcagcttggg ccgcacctac aaggagatga cggagcggga cgggtacgct gtcaacggga  57120
tcatccatgt gatgaaggcg gtcccgacct tccaggaggt ggcgccggat ccccttcgcc  57180
agtggttcag cttccgcggc gcggtgctcc acgacgtcgc ccatgcgctc acggggtacg  57240
ggcgtgacct cgcgggcgag gtcgcgctcg gcctctacct cgcggcggtt tacccgccgt  57300
accggagcgg ggtcgtgtat tcgttcatca ccgcgctcgc gtcggtcacg gcgccgcagg  57360
accagaagct ccgcaaccta tcctacctgc gcgacgtgtg gatccgcggc cgccgctcgc  57420
gcatcccccct cagcgcgccc tgggaggacc tgctcccgct ccaggtggag gaggtgtgcc  57480
gtatgtacca ggtcccgctc gtgcgcgaga cgcacgcgga gggcatcctc cgcgatgcgt  57540
tcgagaaagg tccctggata ccgtcgttca aggcgcagag ctgggcatag ccggcccgcg  57600
cgccgaggcg agcccctggc gggcacgtcg tggcggcgcg cctcctcccc gcggcgcgac  57660
gggctccctc gcgccgcggg gaggaggcgc gcccgctctt ctgcatgacc cctgtgcaag  57720
aaccctgagg cggcctgggg gccgaggaag aaccgatgaa agcatacatg tttcccgggc  57780
aagggtctca ggcgaagggg atgggacggg cgctgttcga cgccttcccc gcgctcacgg  57840
ccagagcgga tggggtcctt ggctactcca tccgggcgct gtgccaggac gatcctgatc  57900
agcgcttgag ccagacccag ttcacccagc cggccctcta cgtggtcaac gccttgtcgt  57960
acctgaagag gcgcgaggag gaggctcccc ccgatttcct ggccggccac agcctgggcg  58020
agttcagcgc cctgttcgcc gcgggggtgt tcgacttcga gaccggcctc gcgctggtga  58080
agaagcgagg agagctgatg ggcgatgccc gcggcggcgg gatggccgcg gtcatcggtc  58140
tggacgagga gcgggttcgc gagctcctcg accagaacgg cgccacggcg gtcgacatcg  58200
ccaacctcaa cagcccatct caggtggtga tctcgggggc gaaggacgag atcgcccgcc  58260
tgcaggtccc cttcgaggcg gcaggggcga agaagtacac agtcctgcgc gtgagcgccg  58320
ctttccattc ccgcttcatg cgaccggcga tggtcgagtt cgggcggttc ctggagggct  58380
atgatttcgc gcctccgaag atcccggtga tctccaacgt gaccgcccgg ccctgcaagg  58440
ccgatggcat ccgcgcggcc ttgagcgagc agatcgccag tccggtccgg tggtgcgagt  58500
```

-continued

```
cgatacgtta cctgatgggc aggggcgtcg aggagttcgt ggagtgcggc cacggcatcg  58560
tcctgaccgg cctgtacgcc cagatccgtc gagacgccca gcccctcgtc gtcgacgagg  58620
gcgcggccgg gctcgaccgg cggggtccgc cggcggaggg ccggtcgccg gctgccttcg  58680
gctcatcgag gctggcggcg cccgcgcaga acggggcggc ggcgcccgcg cagaacgggg  58740
cggcggcgcc cgcgccggcg gcgcatgcgg ccgcggcgca tgcgcccgcg cagaacgggg  58800
cggcggcgcc cgcgcagaac ggggcagcgg cgcccgcgcc ggcggcgcgt gcggccgcgg  58860
cgcatgcggc ggcgccgaac ggggcggcgt cgccggagcc ggcggcgccc gcgccgaggg  58920
gggccaggcg gatctcgctc gaggtgctgg gcagcgccgc gttccgggag gactaccgct  58980
tgcgctacgc gtatgtcgcg ggctcgctgg tcgatgggat ctcctccaag gagatgatcg  59040
tgcgcatggg caaggcgggc ctgatcggct atctcgggac caagggggtg gcgctggacg  59100
ccgtcgaggc gtcgatcctc cacatccagc gcgagctccg cggtggtgag agctacgggg  59160
tgagcctgtg gtgcgacatg gacgactcgc acctcgaatg gcagagcgtc gcgctctacc  59220
tcaagcacga tattcggtac gtcgaggcgg tcgcctacat gcagataacg ccggcccttg  59280
tctgctatcg tctcaagggc gctcaccgcg atcaccgcgg cagggcagcc acgcctcggc  59340
gcgtgctcgc cagggtctcg aacctcgagg tcgcccgggc gttcatgagc cccgctgcgg  59400
atcacgtcct cgatcagctc gtgaaggacg ggcggctcac gcgcgaggag ggcgcgctcg  59460
gccgggagct ccccatcagc gacgacctgt gcgcgcacgc cgactccggc ggccccacgg  59520
acatggggac ggcagcggtg ctgatgccgg ccatggcgcg gctgcgcgac gacatgatga  59580
cgcggtacgg gtacgaaaag cggatccgcg tcggcatggc cggcggcctc ggcgccccgg  59640
aggcggtcgc gtccgcgttc atgctggggg ccgacttcat cgtcaccaac tccgtgaacc  59700
agtgctcgcc ggaggcgagc accagcgacc gggtcaagga catgctgcag gccgcgagcg  59760
tccacgacac cgcgtatgcg cccgccggcg acctgttcga gatgggagcc cgggtccagg  59820
tcctcaagcg tggcgtgctc ttccccgcgc gggccaaccg cctgtacgag ctctaccggc  59880
actacccgtc cctggacgcg ctcgacgcga ggaccaggga tcagctcgag aagcactatt  59940
tcaggcgcga tctcgacgat gtctggcggg atgcgctgtc tcgccggccg gggacgcgcc  60000
cggcggacgc ggccaggacg gagcgcgacc ccaagcacag gatgtccctc gtcttccggt  60060
ggtatttcgc ccactgctcg gagctggcgc ggcgagggga cgaggagaat cgggtgaact  60120
accaagtcca ctgcgggccg gccatgggcg ccttcaacca gtgggcgaag ggcacggatc  60180
tggaggactg gcgcaaccgc catgtcgatg tgatcgccga gcgcctgatg cgggcgtccg  60240
ccgatctcct cgatcaccgc atgcgcgcgc tctcgcggta gcgagctcga ggtgcatcgt  60300
acccttggag gcccatggct gctcgagaca gccgacgaag acgtaagggg cgagccgccc  60360
gccctcaccc gccccgcgtc ttctccgcct tctgccgccg caccatctcc gcgatccaga  60420
ccggcgcgaa cggcggcgtg cagcccggcg acgccggata gtctttgagc acctcgagcc  60480
gctcgccgat ggcgatggcg cgggcgcgca gcccggggtt gcggatgccg atctcggcga  60540
ggcagtggtt catcgaccac tgcttcgggc ccggcgccgt cttcatctcc gcctcgatct  60600
ggtcgagcag cgcggggaga tcgaggccgg cagggctctt cacgacgcgg tccgtcgtca  60660
ggctccatcc ggcgcgcccg accagctcgc tcgcggagtc cttccagcgg acacgcagct  60720
cctcggcgtg gcgcgacgcc ttcaccacgt tgacgatgaa ccagtcgagc agcttggggt  60780
agccgatctc ccggaccatc gcgtccagct cgtccgccga gaaggccttc ggcttgaaca  60840
```

-continued

```
cgagcgtcgc caggaggcgg gcgtcggggt ccccggtgcg ccacagctcg ccggccaggg  60900
cgtggtcgga cttcagctgc ttcgccagcg cgcggagctg ggtgaggttc acgccgtggg  60960
cgtctccggc gcgggcgttg acctcgcgca tcttctcgtt gcccagcgcg gcgagctccc  61020
gcatgacgtg ggtgacgttc atgggctcgg gctagccgta tccgcgggcg tcgtccagcg  61080
gcgcggcgtc gcgggggagg accagccgcg ttcctgggat ggatcgcggc cgtggctcgg  61140
ctgcgcgccc ggccgtcgat ccgccgcccc gctggcggat accgcccccct ggcgcggcgg  61200
acggcgcgcg ggcgctcagg gagcgggggt gaaggcgacg gtgagcgtgt aggggccggc  61260
gtccatcggc ctgtaggtgt cgacgacgac gaacaggggc tcaccgccgg tgacatcgat  61320
cacgagcgtc tcgtcatcgc cgcggccttc gtcgtcgacg cactcgatct cggcgtcgaa  61380
gtccgcgcag cgctcgcgca ggtagaagcc caagtcggtc tcggcggaca gcgtcagcgt  61440
gagcgtgccg tcgctcggcg gcgtgaaccg gtggatcgtc tccggcacgt cccatccgag  61500
gcagctgccc tcgaacgccg acgtagcggt cgccgtgttg cccgtgttct cgccgatggc  61560
gagctcggcc gcgccctcgc acagcacgtc gagctcgtag gcgcacgtgg cggagcatcc  61620
atcgccgctc gtggtgttgc cgtcgtcgca ctcctcgatc gcgtcgacgg ccccgtcgcc  61680
gcagacgatc ggcgcgaagc tgacgttcag cgtgtaggga ccggcctccc ccggctcgta  61740
ggagtcgacg acgatcggca cggtctggcc gtcgctcacg tagatctcga tccgctcttc  61800
gtcggggaag ccatcggagg ggtagctctc gtcggagcag tcgatctcgg agagcatgtc  61860
cgcgcacgag ctgcgggcgt agacgctatg atcggtcggc gactcgagct cgaccacgag  61920
cgtgccgac tgcccggcgg gcggcgtgaa caggtggatc tcttccggtc cgtgccccgt  61980
gttgccgagg tagcaggtcc cttccagcgc gctcgtgctc tccgacgtgt cgccgtggat  62040
cgtcgtcgag acgatgggtg tcgcgctcgc gcaggcggcc tcggcgatcg gggtgcaggt  62100
cgcggcgcag tcggtgtccg cgcaatcgta ggacccgtcc ccgtcgtcgt cctcgtagtt  62160
cgtgcagtcc gtctcgccga gcgtgcagac gccgctcagg gtgtcgcaca cgccgagcga  62220
ggggcactgc gcgttcgagg tgcacctcgg gacgcaggcc cggatgccgc cgccgatgtc  62280
ctcgcaggca taaccgtcgc ggcactccga cgacgcgctg cagagcgaaa ggcacgctcc  62340
cacgccgtcg aagagatcaa gacagacccc gccgtcgcac tctccgcccg gcgctggctc  62400
ggccgcggga tcacacaggt ccgagcagag ccccggatggg tatcccaatt cctcctcgga  62460
gaggcagatg tccccggtgc actcatcgtc cgtcgcgcag gcctcgtaca gcgcgcccgc  62520
cggcccgccg ccggtgccgg tgggctcgcc gccgccgccg ccgccgccgg taggctcgcc  62580
gccgccgccg ccgccggtag gctcgccgcc gccgccgccg ccggtgggct cgccgccgcc  62640
gccgccgccg ccgccggtag gctcgccgcc gccgccgccg ccggtgggct cgccgccgcc  62700
gccgccgccg gtgggctcgc cgccgccgcc gccgccggta ggctcgccgc cgccgccgcc  62760
gccgccggtg ggctcgccgc cgccgccgcc gccgccggtg ggctcgccgc cgccgccgcc  62820
gccgccggtg ggctcgccgc cgccgccgcc gccggtgggc tcgccgccgc cgccgccgcc  62880
ggtgggctcg ccgccgccgc cgccggtgcc agttccggtg ctcgtggcgt cgatgccgcc  62940
ggcaccgcca gcgccgccgg agccgccatg gccgccggcg ccgccctggc cgtcatcgtc  63000
tccgcatccc gcggctgccg acagcgccag cacgaaaaga cctgcaacga ttcgtacgtt  63060
catccacctg ctccaacgca agagagagtt gtcgtgacgc gaggtgcgcc tcaccccgcg  63120
gcgccgcgtg atgccatctt cggcgcaacc gctccgcctg ccaatccccc tttcatgggg  63180
gccgcctgcc tcggcgcgcg ccggtgtgcg cggtcgccgg atccgaccgg ggctgcgcat  63240
```

-continued

```
cgccatgaga atccgcgcgc ggagcacaca atgcgcctgc atcgtctgct gcgagggctg  63300
ctcttctttc atcgaacgtt ccgggctcgc ccttcgacga tactccaatg agggtcgttg  63360
tctcaggcac attggcacgg agggctccac agcccagcgg ggtgacctcc tggggtagct  63420
cgtgttgatc aggaagctcc atccggagag cctgccgcga atacctgggc gaaagcagga  63480
tcgggatccg agtcgagcga ccaggcgcgg ggccctatgc gctgtcgagc aggatggccc  63540
cgatcttcat gcgcaccgcc tccaggtgcg cctggcggcg acggccaacc acactctccc  63600
acttgaacgt gtcatcagca ctgcgttcgg ctcctcaggt tgtgtgaacg ttcacatttg  63660
gtctatcatg ccggcactcg aggcgcttga acgcgtcatc agcattttgt tcggctctcc  63720
aggttgtgtg aacgttcaca tttggtctat catgccggca ctcgaggcgc ttcgacaagg  63780
tgggccgatg tccgtttctc gccgcggagg aaatttatga tcaaaatggt caacggcgca  63840
gcgctgctcg ccgtgctcgc cgcagggtcc ctgacgctgg ccgcgtgcgg tcgcagcgac  63900
gacggcgcgt ccggcggcaa ggagctgcgg gtctggcact acgaggctcc cgagagcgcc  63960
atgggcgtgg cctggagcga ggccatcaag gagttcgagg cgacccatcc gggcgtgaag  64020
gtcaagctcg aggagaaggg cttcgagcag atccagaaga ccgcgcccat gatcatgaac  64080
tccaagagcg cccccgacgt catggagtac aacaagggca acgcgaccgc cgggctgctg  64140
tccaggcagg gcctgctcca ggacctcacc cccgaggcca ccaagcgcgg ctgggacaag  64200
ctgatcagcc ccggcgtgca ggtcgtcgcc aggtacgacg aaaagggcat catgggcggc  64260
gacacgtggt acggggtgcc caactacgcc gagtacgtgc aggtctacta caacaaggac  64320
ctgttcaaga agtacgacgt caaggtcccg accacgttcg acgagctcac cagggcgatg  64380
gacgcgttcg tcgccaaggg cgtgacgccg ctggccaacg ccggcgccga gtacatggcg  64440
cagcagtacg tctaccagct cgcgctggac aaggccgacc agccgtgggt gagcgcgttc  64500
cagcgctaca ccggcaagac cgacttcacc gacccggcat ggacgtacgg ggcgacgacg  64560
ttcgccgact gggtgacgaa gggctacatc gccaagagct cggtcagcac caaggccgag  64620
gatgccggcg tggcgttcat gagcggcaag atcccgatga tgttctccgg gagctggtgg  64680
ttcgggcgcg tggccaagga ggccaaattc gactgggata ccttcgtgtg gcccggcgcc  64740
aagatgaccc tcggatcggg cggcaacctg tgggtcgtcc cggcgggatc gaagaacaag  64800
cagctcgcct acgacttcat cgacatcacg ctgaagaaga agatccagaa catcctcggc  64860
aacgcgggcg gcgtcccggt ggcggccgac agctcggcca tcaccgagcc cagggccagg  64920
aagctcatcg acggcttcaa caccctcgcc cagtcgagcg gcctggcgta ctacccggac  64980
tggccggtcg cgggcttcta cgaccagtgg gtctcgcaga cccagaagct catgaacggc  65040
gatccgccgc ggtcggtgct cagcggcatc cagaagacct acgacagcgc cctgcccaag  65100
tgacgacacg cagctcgaca gggcgtgacc ggctcgccta ccttccctac ctgatccccg  65160
ggctgctgct gttcaccggg gtcatcgggg cgccgttcct gatgaacatc gggaccagct  65220
tcaccgactg ggccggcgtc ggcaccccga agtgggtggg gctggacaac taccgggagc  65280
tggcgaccga cggtgagttc tgggcgtcgt tccggaacaa cgtcctggtc atcgtcggga  65340
tggcgatcgt cccgacgatg atcgggctcg tgctggcctc cgccctgacc gacctgatcg  65400
accggcactt cggcccgcgc gccgccagcg tcctgcgcgc ctgcatctac ctgccgcagg  65460
tcctgccgat cgtcatcgcg ggcatcgtct ggagctggct gctcgccccc gagaacggcg  65520
cggtgaacga cctgctgggc gcgatcgggc tcggctcgct cgcgcacgac tggctcggcg  65580
```

-continued

```
atcccgccac cgcgctgtgg agcgtcatgg gggtcatggt ctggatccag atcggattcc 65640
ccctcgtgat cttcatgtcc gggctgcagc gcgtggaccc ctcactgtac gaggcggccg 65700
agatcgacgg cgcctcgtgg gcgcagcgct tctggcacgt cacgatcccg cagatcaggc 65760
ccgagctctt cgtggtgctg ctgtggacga cgatcgccgc gctcaaggcg ttcccgcaca 65820
tcttcgtgct cacgaggggc ggcccgggag gcgcgaccaa cgtgccgtcc tactactcct 65880
acgtcaattt cttcgagaag accgacgtcg gctacggctc ggcgatcgcc accgtgatga 65940
cgctgatcat cctcgcgctc accgtcgcct tcctgcggct gcagggccgt gagccggggg 66000
aagagcggtg accgtgacgc tggcccagag cccggggagc gcccccgcgc ggcgccggcc 66060
gcggcggcgc cgccggggtc cgtcggccta cgcggcgctg gtggcgctgg ccgcgctggc 66120
cgggatcatg ttgatcccct tcgccgtggt ggtcttcaac gcgctgaaga cgccggagga 66180
gtacaccgcc aacggcccgc tcgccccgcc ggagggaatc catctcgagg ggatcaagga 66240
cttctgggag cgcgtcggct tcggccatgt cctgttcaac agcctgctca tcagcggctc 66300
ggtggccgtg ctggcggtcc tgctgtcggt gctgaacgcc tacgcgctgg gcatcggccg 66360
gatcaagggc cggacgtggg tgcttgtcct gctgctgatg gccaacacgc tgccgcagga 66420
gtcgctggtc tacccgctgt actacctggc caacgagctc gggctctacg acacccggat 66480
cagcgtcatc ctcgtgttca ccgtcatcca gagcgcgttc ggcacctacc tgctgtcgtc 66540
ggtgatgtcg gcgttccccc ggccgctgct ggatgcggcg cagatagacg gcgccagccg 66600
gtggcagatc ctgtggcggg tggtcgtgcc ggtcgtgcgg cccacgctgg cggtgatgct 66660
cgtcttcttc ttcatctgga cctggaacga gttcctgatc cccctcgtct tcctcatctc 66720
caacgacaac cagacggtct cggtcgcgct cggcgtgctg caggggcagc ggctgatgga 66780
cgccaccatg tcgagcgccg ccgcgctgct cggcctgctg ccgaccgtcg tcttcttcct 66840
catcttccag cgcacgctat cgcgcggact cacagcagga gcgatcaagg aatgaagttc 66900
accgacggtt actggatgat gcgcaagggc gtgcacgcgg tttacccggc ggaggtcctc 66960
gacgtcgacg ccgggccggc gtcgttcgtc gtgcacgcgc ccgtccagcg gatccggcac 67020
cgcggcgacc tgctcaaggg cccggtggta accgtctcct gcgcgtcccc gatgccggac 67080
gtcatagccg tcaccatcac gcacttcgcg ggcgagcggc cccgcggccc ggcgttcgcg 67140
ctggccaccg acccgaccgg ggaggtgacg gtggacgagg acgcggccac gctgacctcc 67200
ggcgcgctgt cggtgcgggt cggcgcggc gaggggtgga ggctggactt cgtggccggg 67260
ggccgccgcc tcaccggcag cgcgcagaag gcgatggcga tcatcgacac cgacgacggc 67320
cgccactacg tgcgcgagca gctcgacctc ggcgtggacc acttcgtgta cggcctcggc 67380
gagcgcttcg ggccgctggt caagaacggc caggccgtcg acatctggaa cgccgacggc 67440
ggcacgtcca gcgagcaggc gtacaagaac gtgccgttct tcctcaccaa cgcgggctac 67500
ggcgtgttcg tcgaccatcc cgggcgcgtg tcgttcgagg tggcctccga ggcgatggcg 67560
cgggcgcagt tcagcgtcga gggccagtcg atgcgctact tcctcatcta cgggccgacg 67620
ccgagggaga tcctgcgcaa gtacaccgcg ctcaccgggc ggcccgcgcg ggtgccggtc 67680
tggtcgtacg ggctgtggct gtccacctcg ttcaccaccg agtacgacga ggcgaccgtc 67740
acctcgttca tcgacggaat ggccgagcgg ggcctgccgc tcagcgtctt ccacttcgac 67800
tgcttctgga tgcgcgagct ccagtggtgc gatttcgagt gggacccgcg cgtgttcccc 67860
gacccgcccg ggatgctgcg ccggctcagg gggcgcggcc tgcgcgtctg cgtctggatc 67920
aacccctaca tcgggcagcg ctcgccgctg ttcgaggagg gcagggcgcg cggctacctg 67980
```

-continued

```
ctgcggcggc cgaacggcga cgtgtggcag tgggacctgt ggcagccggg cctggccgtc  68040
gtcgacttca ccaaccccga ggcccgcgcc tggtacgccg ccaagctcga cgcgctgctc  68100
gacatgggcg tggactgctt caagaccgac ttcggcgagc gcatccccac cgacgtcgtc  68160
taccacgacg ggtccgaccc ggaacgcgcg cacaactact acgcctacct ctacaacaag  68220
acggtgttcg agctcttgcg cgagcggcgc ggcgagggcg aggcggtcgt gtttgcccgc  68280
tccgccacgg cgggcgggca gcagttcccg gtgcactggg gcggcgactg cgagtcgacg  68340
ttcgagggca tgggggagag cctgcgaggc ggcctgtcgc tgggcatgtc gggattcggc  68400
ttctggagcc acgacatcgg cgggttcgag ggcacccccg acccggcgct gttcaagcga  68460
tggatcgcgt tcgggctgct gtcgtcgcac agccggctgc acgggagccg ctcctaccgg  68520
gtgccatggc tgttcgacga cgaggcggtg gaggtgctgc ggcgcttcag ccggctgaag  68580
atgcggctga tgccctacct ggccggggcc gcgcggcagg cgtacgtcga gggcttgccg  68640
atgatgcgcg cgatggtcgt cgagttcccg gacgacccgg cctgcacgca cctggagcgg  68700
cagtacatgc tgggcggcga cctgctcgtg gcgcccgtct tctccgccga cggggagctc  68760
tcttattatg tgccgcgcgg cgtgtggacg cgctatctca ccggcgagcg cgtcgagggc  68820
ggccgctggg tgcgcgagcg ccacgggttc gacagcgcgc cgctgctcgt ccggccgggg  68880
gcggtgatcc ccgagggcgc ggtggaggac cgcccccgact acgaccacgc ggcgggtgtg  68940
acgctgcgcg tgtacgagcc ggcggacggc gcccgcgtca tgaccgtgat cccgggcgcg  69000
ggcggggacg cggtcacgac gttcaccacg tcacgggacg gcccggtggt gcgggtggag  69060
gccgcgggcg ccccaggtgc ctggaacgtt ctcctcgtca accgccgcgt cgtggccgtt  69120
gaaggcgggg agagcgcgga gcacccgcga ggagcgctgg tcagggcggc cggcggcgag  69180
ctggtcatca cgctggaggg ggagggctca accgcggcat ccgtccccag aggagacgac  69240
cgatgaagga ctgacgggcg cgccgcagag cacggcgcgc gcgccgtaga accgctctac  69300
gctgcccacg aagatgcgcg tcggcgcgct gaacagcgac gttgccgcga ggtccggagt  69360
ctgcgcgacg gagcgccggc cgcgcggcrg atcctcgtcg ccagccggcg atcgatcgcg  69420
ccgcaaattg cttgtatgcc tgctgttatc gacgagggag cgcgcctctc gatatagaat  69480
gacgtcacgc gctgtacgat cctgctcgac ggctgagcgc aatgggtttt accctgggct  69540
catgtccact tggtctagat ttcgccggat cgctgcctcc gcaccgctcg tcctcgcgct  69600
ggcgctccac ccctcgggtt cgagcgcgag tgacatgctg ccattccagg atcccggtct  69660
gtcgatcgag ctccgcgtcc gcgacctcct cgggcggctc acgctcgacg agaagctctc  69720
gctcctgcat cagttccagc ctgccattcc gcggctcggg attccggact tcaaggccgg  69780
caccgaggcg ctgcacggcg tggcctggtc gaccgatcgc gacaacggcg gcgccgtcgt  69840
gacggcgacc ggcacggtgt tcccgcaggc gatcggcctg gcgacgacct ggaacccgga  69900
tctcgtccgg caggtcggcg aggctgtcgg agacgaggtt cgcggctatc acgcgctcgc  69960
ccctcgcatc tggggtctgc aggtgtgggc gcccgtggtc aacctcctgc gcgacccgcg  70020
ctgggggcgc aacgaggagg gctactccga ggacccactc ctctccggtg tgatcgccgc  70080
cgcatacggg cgcggtctcg agggggacga cccgctctac ctgaagaccg cgccggtcat  70140
caaacactat ctcgccaaca acaacgagat ccatcgtgac accacgtcgt cgaacctgcg  70200
cccccgcgtg aagcacgagt acgacgagct ggccttcaag atgcccatcg ccgccgacgc  70260
cgtgaccggc gtcatgacat cctacaacct ggtcaacggc aggccggcca ccgtcaaccc  70320
```

-continued

```
ggatgtcggc gacgtcgtgc ggagttggac ggagaagacg ctctacaacg tgtccgacgc  70380
ctgggccccc tacaacttga ccggctccca gcggtacttc gccacgaacg aggaggcctt  70440
cgcggccacg ctcctggccg gagtggacag cttcaccgtc gacaacaacg acagcgcgcc  70500
caccatcgag attctccgct cggcgctcgc gcaagggctc ctcaccgagg aggacatcga  70560
cgcttccgtc gagcacgtcc tttccgtccg gctccggctc ggcgatttcg atccggacgg  70620
gggcccctac gccggtatcg ggcccgaggt catcgacagc ccggcgcacc gccagctggc  70680
ccgccgggcc gccggcgagg ccatggtgct gctcgagaac aggcgtcgcc tcctgccgct  70740
ggacccgtcg gccacgcggc ggatcgcggt cgtcgggccc ctctcggaca cgctctacac  70800
ggactggtac tccggggccc tcccgtaccg ggtcacgccc ctggacggca tccgcgagcg  70860
gctcagcggc gccacggtcc tctccagcga gggcgtggac cgcatcgtgc tgcgcgacgt  70920
cgcgagcggc cgctacgtga ccgccggcgc ggacgaggac ggggacgtcc tgcgcgtcag  70980
cgcggtcagc gcgggcccca ccgaggagtt cgacgtgttc gactgggggc agggcatcgt  71040
tacgctgcgc agcgcggcca acggcaaggt ggtcgaccgc ttcaacttcg gccccaactt  71100
cgcgaaccgc gccgcccagc cgtacgactg gttcgtccag cagcagctcg tcctcgagcc  71160
gcagagcgac ggcacgcacg tcatccgcta cgccggatac gagaaggcgt tcgactgggc  71220
cggacccgag gtctacctga ccatcgccga ggacggcgcg ctcgccttga ccgcgaccga  71280
cgcggccgac gcggcgcgct tcgaggtcga cgtggtccgg agcggcgtcg acgaagccgt  71340
gcgcgtggcg acaggcgccg acgccgccgt ggtcgtcgtc ggcagtatgc cgttcatcaa  71400
cgggcgggag gatcacgacc gcacgacgat ggcgctggcc gaggggcagt ccgccctggt  71460
acgggcggtg ctcgccgcca atccgcgcac catcctcgtg gtcgagacca gctatccgat  71520
gaccatgcca tgggagaagc tccacgtccc cgccatcctg tggaccaccc atgcgggcca  71580
ggagaccggc catgccatct ccgacgtcct cttcggcgac cacaatcccg ccgggcgact  71640
gacccagacc tggtaccgct cggcggacga cctgccggat atcctcgagt acgacatcat  71700
caaggcccgg cggacctatc tctacttcga cggtgagccg ctctatccgt tcgggtacgg  71760
gctgtcgtac tcgacctttg gctacgacaa cctccagctg agcgcccggt cggtccaggc  71820
cggcgacccg atctcggtgc gcgtcgacgt cacgaacacg agcccgcggg ccggcgacga  71880
ggtcgttcag ctctacagcc gccagccgtc gtcgcgcgat ccgcagcccg ccaagcagct  71940
gcgggcgttt cggcggatcc acctcgatcc gggcgagagg cggacggtcg agctcgattt  72000
cgccgcctcc gacctcgccc actgggacgt gacgcggagc cgctgggtcc tcgaggcgac  72060
tggcgtcgag ctgatggtcg gctcctcctc ggccgacatc cgccggcgca cgaccgtgcg  72120
cgtgcgcggc gagcgcatcc cggcgcgcga cctcgcccgc gagacgcgag cgctcgactt  72180
cgacgactac gccggcatcg agctggtcga cgagagcatg gagtggggcg atgccgtagg  72240
cgccaccgcg ggcggctggc tccgcttctc cgacgtggag ctgggcggcg gtgccagcca  72300
cttcagcggc gggttcgccc gcgccgaggc gggcgacgcg ctcgtcgaga tccggctcga  72360
cgatccggtc cgcggcaagg tggttgggac cgccgtcgtg ccgagcacgg gcgacgtgta  72420
cgcctacgcc accgtgaccg ccgagctcga cggcgctcgc gggcgacacg acgtctacct  72480
cgtgttccgt ggagccgccc gcctgtcgac cttcgcgatc gactgagggg cggttcgccc  72540
agcgcagggt caggcgcggc cggcgtggtg acggcagccg acctcgtgat gccctccctc  72600
ctgccccgcg ctcgagcgcg cagcggagct cttccgacgt gtccggtgcc cggccgcgcc  72660
ggagctgccc ccggcggcaa aacagcggaa gatgcgggaa tcgcagtgct ttctggcggg  72720
```

-continued

```
acctccgacg cgcgaaaccg gcccgcgcgg acggacgatg tcgcggcaat gatgcacaga  72780
gcctgttagg ctgcgcggca tgtcggatga gggtgcccgc cggcccgacg gatcctcggt  72840
gccatcgacg atggagagca gcgcgtccgt ggccccgagc cgcctcggcc ccggggacgt  72900
cgtgggccag cgctggcagc tcgacgagct cctcaagaaa gggggcatgg gccgggtgtt  72960
ccgggcgacg gacatccggc tcctcgagcc ggtggcgctc aagctgatgg atccggcgat  73020
cgtcgggacc gagcgggcgc gcgcccgctt cctccgcgag gcgcagaccg cggcgaagct  73080
gcggggcccg aacgtggtcc aggtcctcga cttcaacgtc gatgcggcca cgcaggtgcc  73140
ctacatcgcc atggagctgc tccgcggcga ggacctggcc gagcggatag cgcgcgggcc  73200
gctctcctac gacgagacgg tggcgatcct cgccggcgtc tgcagcgcga tcggccgggc  73260
ccaccgcatg gacatcttcc accgggacct caagccggcc aacgtcttcc tcgtcgagga  73320
cgacgacggc ccgctctgca aggtcctcga tttcggcatc gtcaagctcg cggacgtcgg  73380
gctcggccac caggggacgc cgcagaccga cgccggctcg acgctgggca cggtgagcta  73440
catgagcccg gagcagatcg ccgacgcccg gagggtcgat caccgcgcgg atctctgggc  73500
gctcggcgtg atcgcctacg agtgcatgac cgggcgccgg cccttccgcg gcgactcgct  73560
cttcgagctg gtccacgaga tctgctacgg cgtcccggtc gtgccgtcgc ggctggccga  73620
cgtcccgggc ggcttcgacg gctggttcgc gcgcgcgacc caccgcgatc gcgagcgccg  73680
cttcgcctcc gcccgcgagc tgctcgacgc gctccgcgcc ctcgccggcc gctccccgca  73740
gccggacgtg cgcatgagct ccgtcccccc gccgcccgac ccgtctcacg cccagagctg  73800
ggcctcggac gccaaccaga tcgacatcaa cgcgctcaag gacctgacct tcaagaacgc  73860
cgtggtccgc gagttcctcg acagcgccaa caagcacttc gtgtcgggga gcaaggggct  73920
cggcaagacc ctgttgctca cctacaagcg ctcggtcctc ggcgagatct acctcgcgtc  73980
gaacggccgc gagcgccgcc agtccgccgt gcagttcatc ccggaggggc ggccgtacct  74040
cgacctgatg ggcgacctcg gcagcgtcga tcagcacctg atcgacctca tgtcggggct  74100
ctacgagtgc aagcggctct ggagcttcag cttccgcctg tcgatcgtct cctaccagtc  74160
ggccctcgcc ggcgccggcg acgccagaga cctggcggcg ctcccgcggg gcctgcgcgg  74220
gctcctcgac ggccggcctg tcgagccgac catggtggtg aaggagctcc tgtcgatgac  74280
ggtcggcaag atcaaccagg tcatcgacgc catggagggc ccgctcgagc ggcggctccg  74340
ctcgctgcac agcggcgtct tcatcttcgt cgacaagctc gatcaggcgc tccggcggct  74400
gccgcgggcg gcctggatcc acatgcaagc ggggatgatc gaggccgcgt gggacctcat  74460
gaacgccaac cggcacgtga aggtcttcgc caccatccgc gaggaggcgt tctcggccta  74520
cgagtccgac atcaagacca acctcttcgg cgcgacgtcg acgctccgct acgcgaagca  74580
cgagctcttc gagctgctcg agaagctcac ctattattac gagcgactgc cgctccgcga  74640
gttcatccac ctcgacgtgg tgagcgcggg gcgctcggcg cgcggcgagg cgacgttcga  74700
cttcctctac cgccacaccc tcgggcggcc gcgcgacctc gtgatcctcg cgtcggagat  74760
ctcgcgcaac cgccgcgccc tcgacgagcg gaccttcacg cgcatcgtgc aggacacgag  74820
cgccggcctg ctggtggcca acgtcttcga cgagatgcgg gtcttcctcg aggtgctctg  74880
tcaccgcgac aagcgggctc gcttcctcgg cctcctgccg tccgacgtcc tcacccacga  74940
ggacctcgtc gacgtctggt gcggcttcca cggggtcgat cgcgcgtatt tcgacgctca  75000
cggccgggac gcggacgacg tctatcaccc gttccgcgag ctcttcgagt gcggcctgct  75060
```

-continued

```
cggggtgatc ggcggcgatc cggcggccga gcggaaggtg cagcgcttcc gccagccgca  75120

cgacgcggtc gtcggctcgc gccacgcgct gccgcgctcg ccctattacc tcctccaccc  75180

gtccctccgg gcgctcatcg agccgctccc cggcggcggc cggttccgcg cgatgcgcca  75240

cgtcgtcatc ggccacgggg agccctggcc gcgccactgg gatctcgtcg tcgacgtcca  75300

gcgcgagctc ttcaagcgcc cggacgccga cgaggagatc ggcgaggcgg tgttctccct  75360

cctcgaccac ctcgcggccg acgtcgccga cggcgagggc gagggcgccg cgcggcgggc  75420

gatcgccgcg tcacccaccc tcgcccgcct cggcgcccac ctcgatcgga tccgctggga  75480

cgatctccac ctcgccctcc tcgagctctt cccggccgcg cggcgggagg aggcggagcc  75540

gaccgatcgg gtcgaggtgg cgatgctcct catcgacatc gtgcggtcga cccacatgat  75600

cagcaagatc ggcgacacgc gcttcgtcgg ccacctccag cggctccgcc gcgtgctcct  75660

cgggtcgacg aacccccgcc tcttgaaggg gatcggcgac ggatacctcg cggtctatcc  75720

caccatgacg cgcgcgctcg acgcggcccg cgtgctccgc gacgcggtcg acgaccccgc  75780

cgagctccgc ctcgtcctgc actggggcgc ggtgcggatg agcgatcacg acgtgatcgg  75840

cagggaggtc caccggctct tccggatcga ggcggtcacc gaggaggatc gcgccgcgga  75900

gtcgagcgcc gggatcaccc tcgcgcagcc cggccgggtg aggctctcgc ggcccgcgct  75960

cgccgcgctg cccgacgccg agcgcgcggg cttccgccgg gcgggggcct tccggctgga  76020

ggggttcgac gagcccgagc cgatctgggt ggagatcggc gcgggccgct gaggtcgcgc  76080

gggctacggg gcgacgcgga gcgtccgcga ggcgacgagc gcccggcaga gggcgatccg  76140

gtcgtcgagg tcgaggccgg ggagctcgcg cacgtagaag atgccgtgcc gcgcgatgaa  76200

gcggagcgcg gcctcccccc gcagatcgac gcggacgagc acggcctcgc cgtcgacgag  76260

ctccgccttg ccgtccctca gccggaccga cgcctcgcga tcgcggatca cgcgccgcgg  76320

gccgcacacg gacgccgcgt cgctccacac cgcgggcggc ggctcgccgt agagggcgct  76380

gtacgcggcc acgagctcgt cccatgtcgc ctcgcggcgc gcgcccgcgg ccggcgcgtt  76440

gctcggcgcg tggtgcagga agcgcccgaa gaagcgccgg cagaactcgg cgtattcgag  76500

cgtgaagagg gcgaactggt gccaggcctc gtcgacgcgc agcgagaaca tcggataggc  76560

gcgggagcgg tcgatctcga cgagccagag atagcgcacg agctcccgga acagcgcctc  76620

tgcctcctcc cgggtggcca cggtcttgtt catgagcagc ttgtcgatca cgaagggcgc  76680

ccggtaagcg aagagatcag gcgtcctgcg ctgggtcgcg gtcacgatgt ccgtttgcat  76740

gggtcagttc tcctgggctt cgagcggctg aaaggtgccg tgatcgacga gcgcgcgggc  76800

gagcgcgagc tgctcggcct cggcgaggcc ggggatgtcg cgggggcgga gctcgcgggc  76860

ggcggcgagc gcgcggagcg cgggcgcggc ccacgcgtcg acgcggagca ggacctgggc  76920

gcgctcgccc gcgcgcgcga gcagctcggc gcggccggcg ctcgacgcca cgtcgaggtc  76980

cacgcccggc cagcggcgcg cgagggcggt ctgcgcgtcg aggtcctccg tccggccgag  77040

cgcgcgggcg gcgcgccgct tcgtcccggc gtcgccgcgg gcgtgcaggc gcgcgaggag  77100

cgcggcggcc cgcggccccc tccgctcgag ggcgtcgatc tgcgcccggc gcacgcgctc  77160

gcgggcgtgc gcgtggagcg cctcggacag cgcgtcctcg ggggcgggcg gcggcgcggc  77220

gccggtcagg ccgtcgatgg ggcccacctg cgcttccagg accggaccgt cgtgggggcc  77280

gagcaggtgc agcg                                                  77294
```

<210> SEQ ID NO 2
<211> LENGTH: 20

```
<212> TYPE: DNA
<213> ORGANISM: Artificial
<220> FEATURE:
<223> OTHER INFORMATION: Primer 66.2

<400> SEQUENCE: 2

ggacgggacg ctcctgcgcc                                                 20


<210> SEQ ID NO 3
<211> LENGTH: 20
<212> TYPE: DNA
<213> ORGANISM: Artificial
<220> FEATURE:
<223> OTHER INFORMATION: Primer 66.1

<400> SEQUENCE: 3

ctttagcagc ccttgcgccc                                                 20


<210> SEQ ID NO 4
<211> LENGTH: 18
<212> TYPE: DNA
<213> ORGANISM: Artificial
<220> FEATURE:
<223> OTHER INFORMATION: Primer 249-179.1

<400> SEQUENCE: 4

aggaagagct ccagcgca                                                   18


<210> SEQ ID NO 5
<211> LENGTH: 18
<212> TYPE: DNA
<213> ORGANISM: Artificial
<220> FEATURE:
<223> OTHER INFORMATION: Primer 249-179.3

<400> SEQUENCE: 5

atgaagctga tccagacc                                                   18


<210> SEQ ID NO 6
<211> LENGTH: 740
<212> TYPE: DNA
<213> ORGANISM: Artificial
<220> FEATURE:
<223> OTHER INFORMATION: Probe

<400> SEQUENCE: 6

aggaagagct ccagcgcatc ctcggcaagg cgctgcacct cacccgcctc gatcccggcg      60

ctgacctctt cgagctgggc gccacctcgc tcaccatcgt gcaggcgtca cagcacatcg     120

aggagcgctt cggcgtcggg ctgccggtcg aggtcgtcct ggccgagccg accctcgacg     180

ccatcgcgcg gcacgtcgcc gagcggacgg cggctggcgc gcccgagccc ccggcccccg     240

ggcccgcgct ggacgcgcct cccgcggcgc ccgagccccc ggccgccgcc gcccccggcc     300

cgatcgattt cttctccagg gaagatcggg agcgcttcaa gcagcagcag ctccacctgc     360

ggcacggcgt cgagggcctc ccgaccgtgg atctggccga cgctcccgcg gccccgcgcc     420

tctaccgcga ccgcgggagc cgccgcgact accggcccga gcccgtctcg ttcgacgacc     480

tctcgcgcct cctcgccgtc ctccggcggt acccgagcgg ccagcagacc cagctctgct     540

atccctcggc cggcggcacc tacgccgtgc agacctatct tcacgtgaag gagggcgcgg     600

tcgagcgcct cccggccggg atctactact accacccgga tcgcaaccag ctggtgctca     660

tcaacgatcg gcccgccatc cgccgggtgc accacttcta acaggttggc tgataagtcc     720
```

-continued

```
ccggtctgga tcagcttcat                                                740


<210> SEQ ID NO 7
<211> LENGTH: 37
<212> TYPE: DNA
<213> ORGANISM: Artificial
<220> FEATURE:
<223> OTHER INFORMATION: Table 7: 37 bp fragment adjacent to 43750-44079
      fragment found in version 3.

<400> SEQUENCE: 7

ggcccgacgg gccgtgcgcc gcgccgcggt tctcttt                             37


<210> SEQ ID NO 8
<211> LENGTH: 24
<212> TYPE: DNA
<213> ORGANISM: Artificial
<220> FEATURE:
<223> OTHER INFORMATION: Table 7:  51119-51137 version 2 fragment
      replaced.

<400> SEQUENCE: 8

atgaggcgac agcgccgttc tacc                                           24


<210> SEQ ID NO 9
<211> LENGTH: 19
<212> TYPE: DNA
<213> ORGANISM: Artificial
<220> FEATURE:
<223> OTHER INFORMATION: Table 7: version 3 replacment fragment for
      51119-51137.

<400> SEQUENCE: 9

tgagggacag cccgttcta                                                 19
```

POLYNUCLEOTIDES ENCODING DISORAZOLE POLYKETIDE SYNTHASE POLYPEPTIDES

RELATED APPLICATIONS

This application claims benefit of U.S. provisional patent applications Nos. 60/512,892 (filed Oct. 20, 2003), 60/484,934 (filed Jul. 2, 2003), 60/473,311 (filed May 22, 2003), 60/465,038 (filed Apr. 23, 2003), 60/455,521 (filed Mar. 17, 2003), and 60/431,272 (filed Dec. 6, 2002) each of which is incorporated by reference its entirety.

FIELD OF THE INVENTION

The invention relates to materials and methods for biosynthesis of disorazole, disorazole derivatives, and other useful polyketides. The invention finds application in the fields of molecular biology, chemistry, recombinant DNA technology, human and veterinary medicine, and agriculture.

BACKGROUND OF THE INVENTION

Polyketides are complex natural products that are produced by microorganisms such as fungi and mycelial bacteria. There are about 10,000 known polyketides, from which numerous pharmaceutical products in many therapeutic areas have been derived, including: adriamycin, epothilone, erythromycin, mevacor, rapamycin, tacrolimus, tetracycline, rapamycin, and many others. However, polyketides are made in very small amounts in microorganisms and are difficult to make or modify chemically. For this and other reasons, biosynthetic methods are preferred for production of therapeutically active polyketides. See PCT publication Nos. WO 93/13663; WO 95/08548; WO 96/40968; WO 97/02358; and WO 98/27203; U.S. Pat. Nos. 4,874,748; 5,063,155; 5,098,837; 5,149,639; 5,672,491; 5,712,146 and 6,410,301; Fu et al., 1994, *Biochemistry* 33:9321-26; McDaniel et al., 1993, *Science* 262: 1546-1550; Kao et al., 1994, *Science*, 265:509-12, and Rohr, 1995, *Angew. Chem. Int. Ed. Engl.* 34: 881-88, each of which is incorporated herein by reference.

Biosynthesis of polyketides may be accomplished by heterologous expression of Type I or modular polyketide synthase enzymes (PKSs). Type I PKSs are large multifunctional protein complexes, the protein components of which are encoded by multiple open reading frames (ORF) of PKS gene clusters. Each ORF of a Type I PKS gene cluster can encode one, two, or more modules of ketosynthase activity. Each module activates and incorporates a two-carbon (ketide) unit into the polyketide backbone. Each module also contains multiple ketide-modifying enzymatic activities, or domains. The number and order of modules, and the types of ketide-modifying domains within each module, determine the structure of the resulting product. Polyketide synthesis may also involve the activity of nonribosomal peptide synthetases (NRPSs) to catalyze incorporation of an amino acid-derived building block into the polyketide, as well as post-synthesis modification, or tailoring enzymes. The modification enzymes modify the polyketide by oxidation or reduction, addition of carbohydrate groups or methyl groups, or other modifications.

In PKS polypeptides, the regions that encode enzymatic activities (domains) are separated by linker regions. These regions collectively can be considered to define boundaries of the various domains. Generally, this organization permits PKS domains of different or identical substrate specificities to be substituted (usually at the level of encoding DNA) from other PKSs by various available methodologies. Using this method, new polyketide synthases (which produce novel polyketides) can be produced.

It will be recognized from the foregoing that genetic manipulation of PKS genes and heterologous expression of PKSs can be used for the efficient production of known polyketides, and for production of novel polyketides structurally related to, but distinct from, known polyketides (see references above, and Hutchinson, 1998, *Curr. Opin. Microbiol.* 1:319-29; Carreras and Santi, 1998, *Curr. Opin. Biotech.* 9:403-11; and U.S. Pat. Nos. 5,712,146 and 5,672,491, each of which is incorporated herein by reference).

One valuable class of polyketides are the disorazoles. Disorazoles are a family of complex 26-membered bislactone macrocycles having two oxazole rings, which were first detected in the So cel2 strain of *Sorangium cellulosum* (Irschik et al., 1995, *The Journal of Antibiotics*, 48:31-35). The So cel2 strain produces 29 congeners of disorazole compounds, with disorazole A (1) being the predominant product (see structure 1, below, and FIG. 1).

(1)

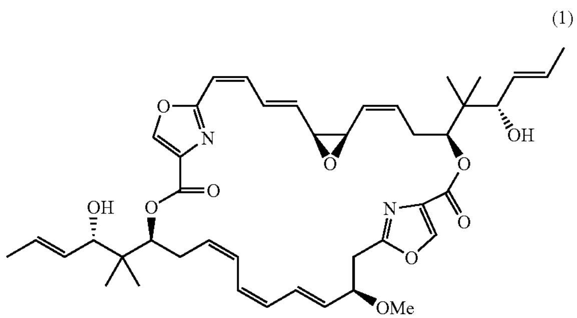

Disorazole A shows remarkable activity against eukaryotic cells, having high mammalian cell cytotoxic activity (MIC ~3-30 pg/ml) and activity against different fungi, including filamentous fungi belonging to the Ascomycetes, Basidiomycetes, Zygomycetes, Oomycetes, and Deuteromycetes families (MIC ~0.1-1 μg/ml). In contrast, the compound is not highly active against yeast and bacteria. Jansen et al., 1994, *Liebigs Ann. Chem.*, pp. 759-73.

The present invention provides polynucleotides and methods for biosynthesis of disorazoles, disorazole derivatives, and novel polyketides.

BRIEF SUMMARY OF THE INVENTION

In one aspect, the present invention provides a recombinant polynucleotide comprising a nucleic acid sequence that encodes a disorazole PKS domain or portion thereof. In one embodiment of the invention, the disorazole PKS domain is from *Sorangium cellulosum* (e.g., So cel2 strain). In one embodiment, a polynucleotide of the invention is expressed in a host cell under conditions in which one or more proteins encoded by a module of a disorazole PKS is produced. In one embodiment, disorazole or a disorazole-derivative is produced by the host cell upon expression of the polynucleotide of the invention. In an embodiment, the host cell is of a type that does not produce disorazole in the absence of expression of an exogenous polynucleotide, and in some embodiments the host cell does not produce any endogenous polyketide. One example of a suitable host cell is *Myxococcus xanthus*.

In another embodiment, a recombinant polynucleotides of the invention also comprises a coding sequence for one or more domains of non-disorazole polyketide synthase, to form a hybrid PKS. For example, a coding sequence for a module or domain (or portion thereof) of disorazole polyketide synthase may be combined with coding sequence from another PKS to form make a novel, hybrid or chimeric, PKS. Expression of such DNAs, in suitable host cells leads to the production of synthases capable of producing useful polyketides, such as a disorazole analog or a useful synthon thereof, or a novel polyketide.

In an aspect, the invention provides an isolated recombinant polynucleotide that comprises a nucleotide sequence encoding a disorazole polyketide synthase (PKS) protein or a fragment comprising at least one domain of said PKS. In an embodiment, the polynucleotide hydridizes under stringent hybridization conditions to a polynucleotide having the sequence of SEQ ID NO:1 or its complement. In an embodiment, the polynucleotide comprises a sequence encoding a disorazole polyketide synthase protein selected from the group consisting of DszA, DszB, DszC, and DszD; a disorazole polyketide synthase module selected from the group consisting of module 1, 2, 3, 4a, 4b, 5, 6, 7, or 8; or a domain selected from the group consisting of an AT domain, a KS domain, an ACP domain, a KR domain, a DH domain, and an ER domain. In an embodiment, the invention provides a recombinant DNA molecule comprising a sequence of at least about 200 basepairs with a sequence identical or substantially identical to a protein encoding region of SEQ ID NO:1.

The invention provides vectors, such as expression vectors, comprising an aforementioned polynucleotide. In a related aspect the invention provides a recombinant host cell comprising the vector. In an aspect the invention provides a recombinant host cell comprising an aforementioned polynucleotide integrated into the cell chromosomal DNA.

In an aspect, the invention provides an isolated polypeptide encoded by a recombinant polynucleotide of the invention. In an aspect, the invention provides a hybrid polyketide synthase comprising one or more polypeptides of a disorazole PKS and one or more polypeptides of a nondisorazole PKS.

In an aspect, the invention provides a method of producing a polyketide by growing the recombinant host cell under conditions whereby a polyketide synthesized by a PKS comprising a protein encoded by an aforementioned polynucleotide molecule is produced in the cell.

In an aspect, the invention provides a chimeric PKS that comprises at least one domain of a disorazole PKS, as well as a cell comprising such a chimeric PKS. A modified functional disorazole PKS that differs from the native disorazole PKS by the inactivation of at least one domain of the disorazole PKS and/or addition of at least one domain of a non-disorazole PKS is also provided, as well as a cell comprising the modified PKS.

The invention provides a recombinant expression system capable of producing a disorazole synthase domain in a host cell. The system comprises an encoding sequence for a disorazole polyketide synthase domain operably linked to control sequences effective in said cell to produce RNA that is translated into said domain. The invention provides a host cell modified to contain the recombinant expression system.

In an aspect, the invention provides a recombinant *Sorangium cellulosum* cell in which a dszA, dszB, dszC, or dszD gene is disrupted so as to reduce or eliminate production of disorazole.

DETAILED DESCRIPTION OF THE INVENTION

Disorazoles have been identified as inhibitors of tubulin polymerization, inducing decay of microtubules. Disorazoles are synthesized by the disorazole polyketide synthase (PKS) or "disorazole synthase." The disorazole synthase comprises four polypeptides, called DszA, DszB, DszC, and DszD, which are encoded by the dszA, dszB, dszC, and dszD genes, respectively. In the following discussion, it will be clear from context whether a polynucleotide or DNA sequence, or a polypeptide or amino acid sequence is being referred to. There terms "nucleic acid" and "polynucleotide" are used interchangeably below. Examples of polynucleotides are DNA and RNA.

Figure 1:
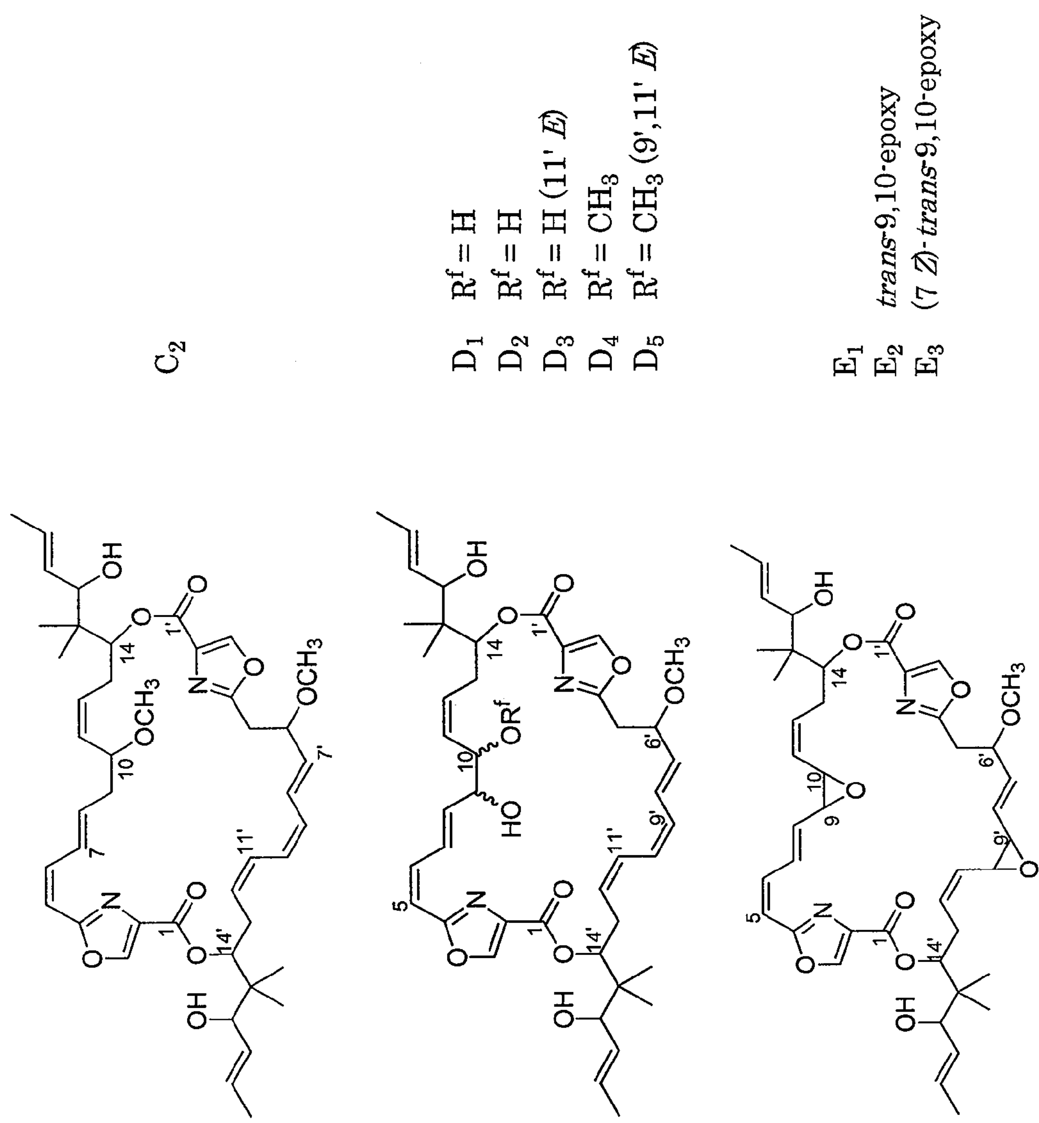
FIG. 1 shows the structures of disorazoles A, B, C, D, E, F, G, H and I.
Figure 1:
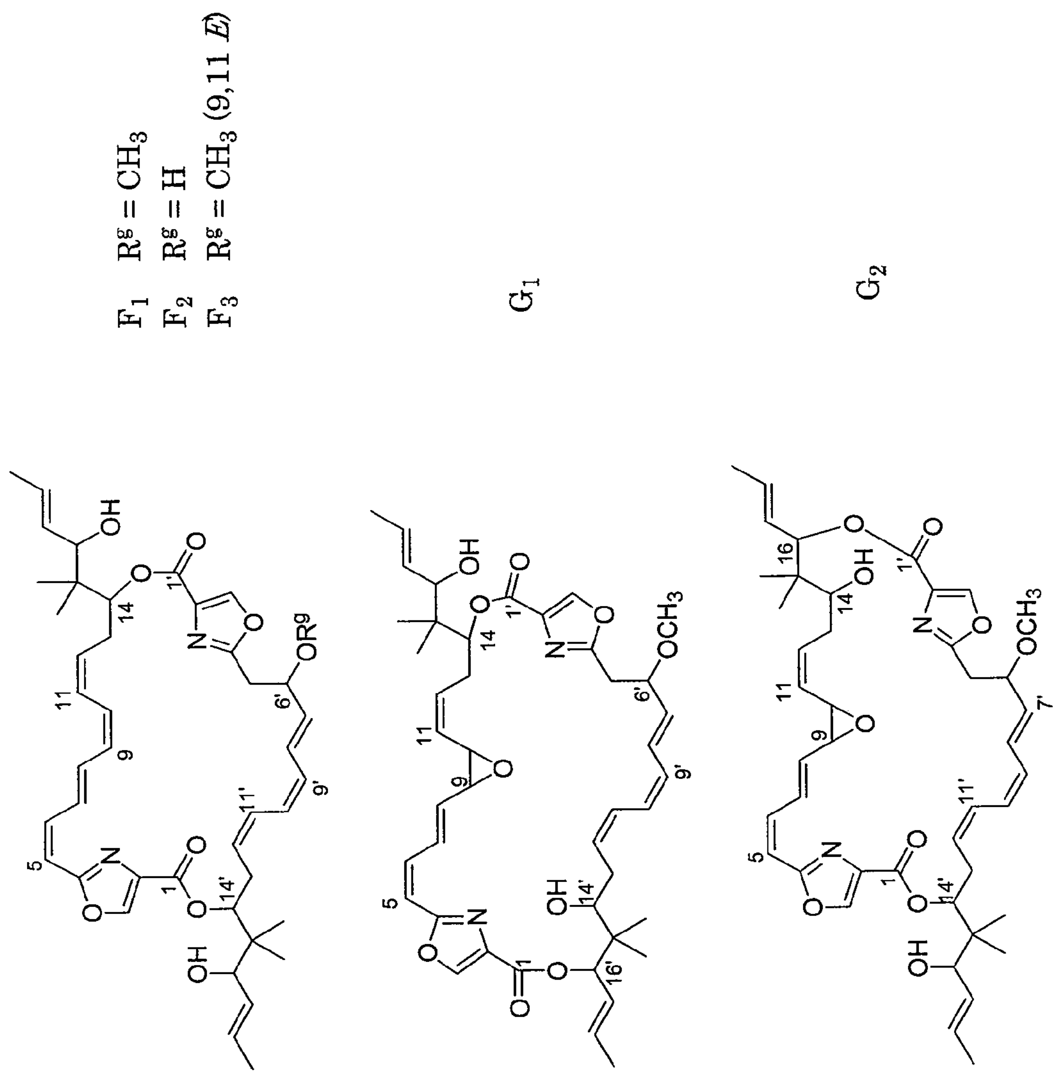
Figure 1:
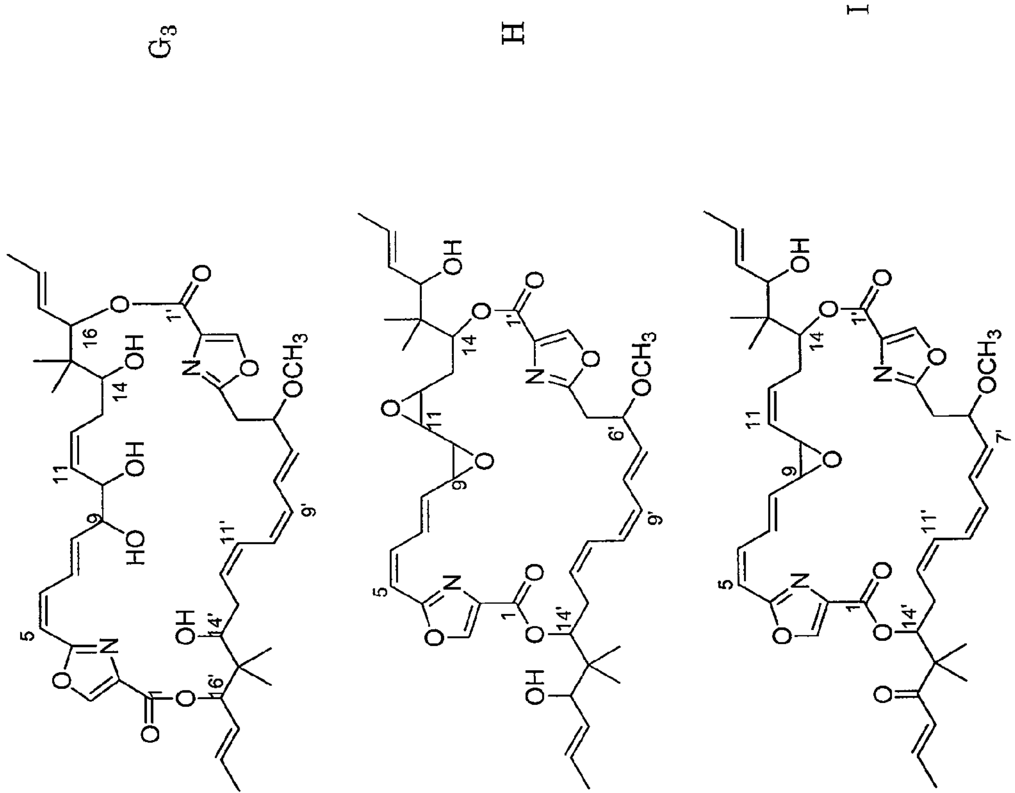
Figure 2:
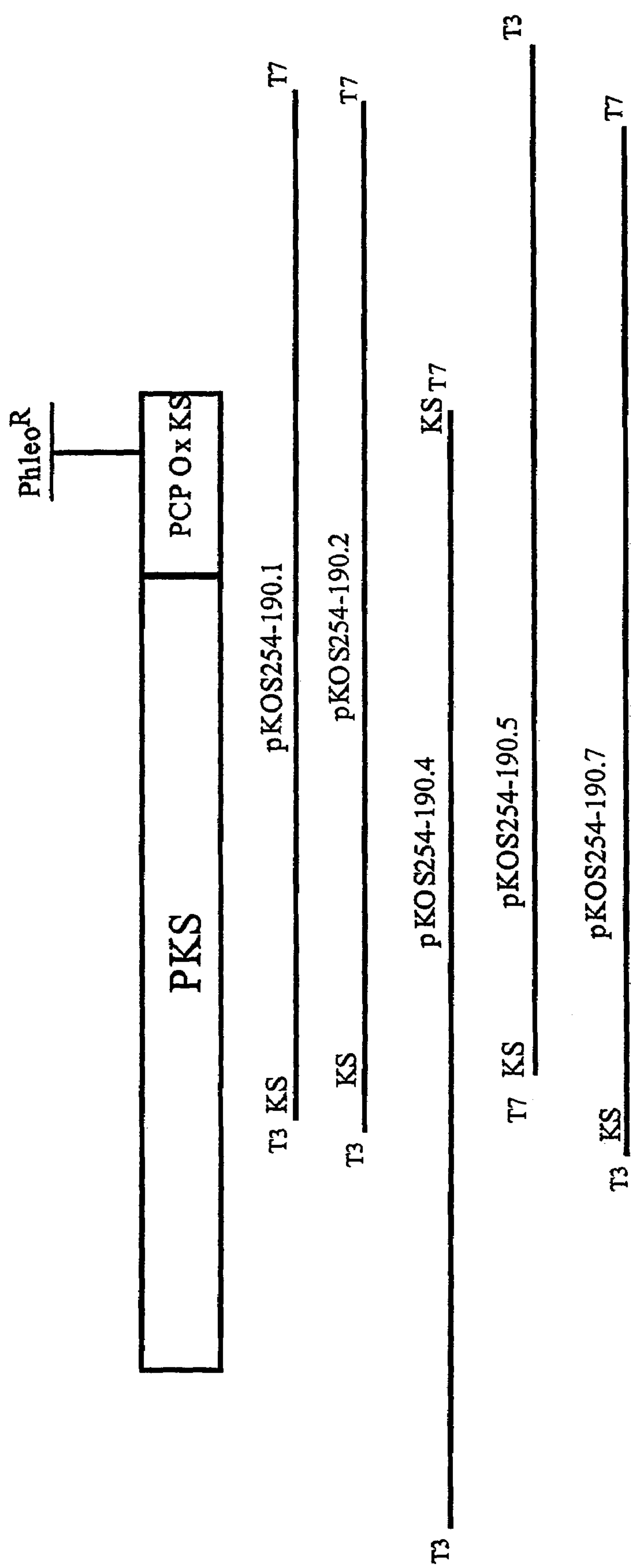
FIG. 2 is a cartoon showing the relationship between inserts of several cosmid clones comprising disorazole PKS genes. "Phleo$^R$" indicates the site of insertion of a phleomycin-containing transposon into the PKS gene cluster.

As described in the Examples below, recombinant DNAs encoding the disorazole biosynthetic genes have been cloned using a gene knockout strategy and characterized by sequencing. Seven cosmid clones (pKOS254-190.1, pKOS254-190.2, pKOS254-190.3, pKOS254-190.4, pKOS254-190.5, pKOS254-190.6, and pKOS254-190.7) containing disorazole PKS encoding sequences were identified. Cosmids pKOS254-190.1 and pKOS254-190.4 were deposited on Mar. 12, 2003, with the American Type Culture Collection (ATCC), Manassas, Va., USA, under the terms of the Budapest Treaty. Cosmid pKOS254-190.1 was deposited as K245-190.1 and assigned accession number PTA-5055. Cosmid pKOS254-190.4 was deposited as K245-190.4 and assigned accession number PTA-5056. Each of cosmids pKOS254-190.1 and pKOS254-190.4 contains most modules encoded in the disorazole PKS gene cluster, and the two cosmids together contain insert DNA that completely spans the disorazole PKS gene cluster. The relationships between the cosmid inserts are shown in FIG. 2.

Table 1 shows the sequence of the disorazole polyketide synthase gene cluster and flanking sequences, with reference to Seq. ID NO:1 (see TABLE 6). The boundaries of the DszA, DszB, DszC and DszD encoding sequences are shown, along with the approximate boundaries of modules, domains and scaffold and linker regions. In addition, sequences encoding additional ketide synthase modules (KS7.2x, ACP7.2x, KS1p, ACP1p, KS2p and ACP2p) are encoded. In addition, several open reading frames in the gene cluster or flanking regions are shown: ORFs 0, 1, 2, 3, A, 0r, 1r, 2r, 3r, 4r, 5r, and 6r lie in the flanking region and ORF x1 lies in the intervening region between dszC and dszD. Abbreviations are: ketoreductase (KR), dehydratase (DH), enoylreductase (ER), nonribosomal protein synthase (NRPS), methyltransferase (MT), acyl carrier protein (ACP), serine cyclization domain and/or condensation domain (Cy), adenylation domain (A), peptidyl carrier protein (PCP) or thiolation (T) domain, oxidase domain (Ox), thioesterase domain (TE), acyltransferase domain (AT).

TABLE 1

| DISORAZOLE POLYKETIDE SYNTHASE GENE CLUSTER AND FLANKING SEQUENCES | |
|---|---|
| ORF, Module and Domain Boundaries (with reference to SEQ ID NO: 1) | Description |
| >2 . . . 1357 (complement) | ORF0 (nter: 1-471 of 480 aa); homolog of ORF from Pseudomonas putida KT2440 [PP4696 (AAN70269)], putative nitrogen regulation protein NR(I) |
| 1354 . . . 4365(complement) | ORF1_dsz; homolog of HisK from Pseudomonas putida KT2440 [PP4695 (AAN70268)]; putative sensory box histidine kinase |
| 4831 . . . 5805(complement) | ORF2_dsz; homolog in family of known or putative phosphotransferases, including macrolide 2'-phosphotransferases: YcbJ_bacsu; MphB_bacha; MphB_pTZ3723-ecoli; MphBM_pSR1-staau |
| 5794 . . . 7089 | ORF3_dsz; homolog in family of known or putative Ser/Thr protein kinases |
| 8157 . . . 26192 | DszA; (modules 1-4a) |
| 8166 . . . 9440 | KS1 |
| 11100 . . . 11720 | DH1 |
| 12681 . . . 13520 | KR1 |
| 13620 . . . 13823 | ACP1 |
| 14067 . . . 15341 | KS2 |
| 16662 . . . 17540 | KR2 |
| 17829 . . . 18545 | MT2 (CMT) |
| 18768 . . . 18974 | ACP2 |
| 19173 . . . 19376 | ACP2bx |
| 19491 . . . 20759 | KS3 |
| 22020 . . . 22901 | KR3 |
| 22911 . . . 23120 | ACP3 |
| 23331 . . . 24626 | KS4 |
| 25251 . . . 26117 | DH4 |
| 26209 . . . 44979 | DszB; (modules 4b-7, together with an additional PKS module: 7.2x) |
| 26851 . . . 27693 | KR4 |
| 27850 . . . 28056 | ACP4 |
| 28234 . . . 29565 | KS5 |
| 30381 . . . 30948 | DH5 |
| 31651 . . . 32520 | KR5 |
| 32533 . . . 32739 | ACP5 |
| 32971 . . . 34266 | KS6 |
| 35119 . . . 35760 | DH6 |
| 36616 . . . 37479 | KR6 |
| 37480 . . . 37683 | ACP6 |
| 37834 . . . 39120 | KS7 |
| 39712 . . . 40377 | DH7 |
| 41293 . . . 42165 | KR7 |
| 42196 . . . 42405 | ACP7 |
| 42706 . . . 43986 | KS7.2x |
| 44542 . . . 44787 | ACP7.2x |
| 44976 . . . 56363 | DszC; DszC includes the NRPS (nonribosomal peptide synthase) module 8 and a thioesterase |
| 45039 . . . 46493 | Cy8#1 |
| 46530 . . . 47885 | Cy8#2 |
| 47895 . . . 49445 | A8 |
| 49530 . . . 49733 | T8; PCP |
| 49737 . . . 50492 | Ox8 |
| 50628 . . . 51911 | KS1p |
| 52608 . . . 52814 | ACP1p |
| 52986 . . . 54278 | KS2p |
| 54978 . . . 55235 | ACP2p |
| 55404 . . . 56360 | TE |
| 56371 . . . 56431 | probable hairpin terminator |
| 56769 . . . 57590 | ORFx1; compare ZP_00094564.1 (hypothetical protein [Novosphingobium aromaticivorans]) |
| 57756 . . . 60281 | DszD; AT/oxidoreductase; bidomain protein |
| 57756 . . . 58595 | AT |
| 58596 . . . 58931 | linker |
| 58932 . . . 60278 | Oxred |
| 60365 . . . 61042 (complement) | ORFA; homolog of *S. coelicolor* SCO1915 (& 1 each from 2 corynebacterial genomes); hypothetical protein |
| 63817 . . . 65103 | ORF0r; 0352/7408; probable solute-binding lipoprotein; ABC transporter, periplasmic binding-protein; homolog of *S. coelicolor* SCO7408 & others |

TABLE 1-continued

DISORAZOLE POLYKETIDE SYNTHASE GENE CLUSTER AND FLANKING SEQUENCES

| ORF, Module and Domain Boundaries (with reference to SEQ ID NO: 1) | Description |
|---|---|
| 65100 . . . 66011 | ORF1r; ABC permease unit |
| 66128 . . . 66895 | ORF2r; ABC permease unit; ORF1_brefu homolog |
| 66892 . . . 69246 | ORF3r; 1055; glycosyl hydrolase; homolog of S coelicolor SCO1055 |
| 69314 . . . 72526 | ORF4r; 5685; glycosyl hydrolase; homolog of S coelicolor SCO5685 |
| 69389 . . . 69389 | unclear sequence (1 bp) |
| 72800 . . . 76072 | ORF5r; 3820; serine-threonine protein kinase; homolog of *S. coelicolor* SCO3820 complement(76084 . . . 76740) ORF6r |
| 76084 . . . 76740 | ORF6r |

The organization of domains and modules of the disorazole PKS genes differs from that predicted based on the structure of disorazole and contains at least two unusual features. First, the sequenced disorazole biosynthetic gene cluster lacks a module that would load the acetate starter unit (loading module). Second, there are three modules, each consisting of only a KS and ACP domain, that are not predicted from the structure of disorazole. These are shown in Table 1 as KS7.2x-ACP7.2x, KS1p-ACP1p, and KS2p-ACP2p.

The absence of a loading module has not been previously reported for polyketide biosynthesis gene clusters. Possible explanations for its absence in the sequenced genes include (1) it lies in a region of the genome outside the disorazole gene cluster; and (2) the levels of acetyl-coA are high within the cell and permit the direct loading of the acetyl group onto the KS without the help of a loading domain. A situation similar to (2) occurs in the process of chemobiosynthesis also known as precursor directed biosynthesis (Jacobsen et al., 1997 "Precursor-directed biosynthesis of erythromycin analogs by an engineered polyketide synthase" *Science* 277:367-369). In precursor directed biosynthesis a mutation is introduced into the gene cluster that prevents the loading molecule from loading or being extended. A compound as an N-acetylcysteamine (SNAC) thioester is fed to the organism and becomes attached to the PKS enzyme. It then becomes extended by the PKS enzyme to make a variety of compounds depending on the SNAC that is fed to the organism. A third alternative is that module 1 functions as a loading and an extending module. In this case the AT loads the ACP of module 1. Since there is no starter unit, the KS functions to decarboxylate the malonate-ACP to give the acetyl-ACP. The acetyl group is then moved to the KS and is primed with the starter unit. The AT then loads another malonate group onto the ACP of module 1. Now in the presence of an acetyl starter unit attached to the KS, the KS can decarboxylate the malonate on the ACP and perform the condensation to give the appropriate molecule. This is then extended through the remaining PKS and NRPS modules.

The disorasole gene cluster encodes three modules, consisting of only a KS and ACP domain, that are not predicted from the structure of disorazole (shown in Table 1 as KS7.2x-ACP7.2x, KS1p-ACP1p, and KS2p-ACP2p. It is not clear whether or not these modules are required for biosynthesis of disorazole. Analysis of these domains revealed no obvious mutations that would indicate that they are inactive. It is possible that they are non-functional due to a (hypothetical) inability to interact with the AT domain. This could result in no extender unit being loaded, and the growing molecule would just be passed through these modules to either the NRPS or the TE. In certain embodiments of the invention, disorazole PKS polypeptides of the invention differ from native polypeptides by the deletion of all or part of these modules.

The invention provides purified, isolated and recombinant nucleic acid (e.g., DNA) molecules that encode a polypeptide or domain encoded in the disorazole PKS gene cluster and flanking regions, as well as recombinant nucleic acid molecules with the sequence of the reverse complement the polypeptide-encoding strand. The reverse complement of a nucleic acid sequence can be easily determined by well known methods. As used herein, unless otherwise stated or apparent from context, reference to disorazole "PKS" includes the NRPS module. In one embodiment of the invention, the PKS domains are derived from *Sorangium cellulosum*, for example, the So cel2 strain. The invention provides purified or recombinantly produced polypeptides encoded by an aforementioned DNA molecule or comprising a sequence encoded by an aforementioned DNA molecule (such as chimeric and fusion polypeptides).

In an aspect the invention provides purified and isolated DNA molecules that encode all or a portion of one or more modules of disorazole PKS. Examples of such encoded modules include the loading module, and module 1, 2, 3, 4 (including 4a and 4b individually), 5, 6, 7, or 8 of the disorazole PKS.

In an aspect the invention provides purified and isolated DNA molecules that encode all or a portion of one or more domains of disorazole PKS. Examples of such encoded domains include disorazole synthase ketoreductase (KR), dehydratase (DH), enoylreductase (ER), ketosynthase (KS), nonribosomal protein synthase (NRPS), methyltransferase (MT), acyl carrier protein (ACP), serine cyclization domain and/or condensation domain (Cy), adenylation domain (A), peptidyl carrier protein (PCP) or thiolation (T), oxidase domain (Ox), thioesterase (TE), and acyltransferase (AT) domains from any of modules 1-8 of the disorazole PKS.

In an aspect the invention provides purified and isolated DNA molecules that encode a disorazole post-synthesis modification enzyme and/or has the sequence of an ORF selected from ORFs 0, 1, 2, 3, A, 0r, 1r, 2r, 3r, 4r, 5r, 6r, and x1. Examples of such post-synthesis modification enzymes include a cytochrome P450-like epoxidation enzyme and an O-methyltransferase.

In an aspect the invention provides purified and isolated DNA molecules that encode a polyketide synthase domain encoded by KS7.2x, ACP7.2x, KS1p, ACP1p, KS2p, or ACP2p or module comprising an aforementioned domain.

In one embodiment, the invention provides a disorazole PKS domain or module (or portion thereof), or disorazole modification enzyme, or other PKS domain or ORF in the disorazole PKS gene cluster or flanking region as encoded by a polynucleotide insert of pKOS254-190.1, pKOS254-190.2, pKOS254-190.3, pKOS254-190.4, pKOS254-190.5, pKOS254-190.6, or pKOS254-190.7. In a preferred embodiment, the disorazole PKS domain or module or disorazole modification enzyme is encoded by a polynucleotide insert of pKOS254-190.1 or pKOS254-190.4.

Thus, as noted, in one aspect, the invention provides polynucleotides encoding a module or domain (or portion thereof) of a disorazole PKS biosynthetic enzyme, or disorazole modification enzyme. Accordingly, in a related aspect, the invention provides a recombinant polynucleotide encoding at least a fragment of a disorazole PKS protein comprising at least 10, 15, 20, or more consecutive amino acids of a protein encoded by the disorazole PKS gene cluster encoded by pKOS254-190.1 or pKOS254-190.4. In one embodiment, the polynucleotide encodes at least one complete domain of a disorazole polyketide synthase. In one embodiment, the polynucleotide encodes at least one complete ketosynthase, acyl carrier protein, ketoreductase, dehydratase, or acyltransferase domain of disorazole PKS. In a related aspect, a polynucleotide encodes at least one complete module of a disorazole polyketide synthase (selected from the modules 1-8 of disorazole PKS). In a related aspect, a polynucleotide encodes an acyltransferase activity.

In one aspect, the invention provides a polynucleotide comprising a sequence identical or substantially identical SEQ ID NO: 1 or its complement, or to a portion of SEQ ID NO: 1 or its complement encoding a domain, module, ORF, or region (e.g., as shown in Table 1). (Reference herein to SEQ ID NO:1 will be understood to refer also to the complementary nucleic acid sequence, except where clear from context that reference to a particular strand in intended.) In one aspect, the invention provides a polynucleotide comprising a sequence identical or substantially identical a fragment of SEQ ID NO:1 described in the Examples, infra, or a sequencing variant of SEQ ID NO: 1 described in the Examples, or a portion thereof encoding a domain, module, ORF, or region. As used in this context, two nucleic acid sequences (or two polypeptide sequences) are substantially identical if they have at least about 70% sequence identity, often at least about 80%, at least about 90%, at least about 95%, or even at least about 98% sequence identity. A degree of sequence identity can be determined by conventional methods, e.g., Smith and Waterman, 1981, *Adv. Appl. Math*. 2:482, by the search for similarity method of Pearson & Lipman, 1988, *Proc. Natl. Acad. Sci. USA* 85:2444, using the CLUSTAL W algorithm of Thompson et al., 1994, *Nucleic Acids Res* 22:467380, by computerized implementations of these algorithms (GAP, BESTFIT, FASTA, and TFASTA in the Wisconsin Genetics Software Package, Genetics Computer Group, 575 Science Dr., Madison, Wis. The BLAST algorithm (Altschul et al., 1990, *Mol. Biol.* 215:403-10) for which software may be obtained through the National Center for Biotechnology Information www.ncbi.nlm.nih.gov/) can also be used. When using any of the aforementioned algorithms, the default parameters for "Window" length. gap penalty, etc., are used. It will be appreciated that a reference to a DNA sequence is also a reference to the reverse complement of that sequence (e.g., the sequence of the complementary DNA strand).

Substantial sequence identity for nucleic acids can also be determined from the ability of the nucleic acids to hybridize with each other (or to the complementary sequence) under stringent hybridization conditions. "Stringent hybridization conditions" refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the $T_M$ of nucleic acids are well known in the art (see, e.g., Berger and Kimmel, 1987, Methods In Enzymology, Vol. 152: Guide To Molecular Cloning Techniques, San Diego: Academic Press, Inc. and Sambrook et al., 1989, Molecular Cloning: A Laboratory Manual, 2nd Ed., Vols. 1-3, Cold Spring Harbor Laboratory). Typically, stringent hybridization conditions are salt concentrations less than about 1.0 M sodium ion, typically about 0.01 to 1.0 M sodium ion at pH 7.0 to 8.3, and temperatures about 50° C., alternatively about 60° C. for probes greater than 50 nucleotides. As noted, stringent conditions may also be achieved with the addition of destabilizing agents such as formamide, in which case lower temperatures may be employed. As noted, stringent conditions may also be achieved with the addition of destabilizing agents such as formamide, in which case lower temperatures may be employed. Exemplary conditions include hybridization at 7% sodium dodecyl sulfate (SDS), 0.5 M $NaPO_4$ pH 7.0, 1 mM EDTA at 50° C. (or alternatively 65° C.); wash with 2×SSC, 1% SDS, at 50° C. (or alternatively 0.1-0.2×SSC, 1% SDS, at 50° C. or 65° C.). Other exemplary conditions for hybridization include (1) high stringency: 0.1×SSPE, 0.1% SDS, 65° C.; (2) medium stringency: 0.2×SSPE, 0.1% SDS, 50° C.; and (3) low stringency: 1.0×SSPE, 0.1% SDS, 50° C. Equivalent stringencies may be achieved using alternative buffers, salts and temperatures.

In an embodiment, a polynucleotide that is substantially identical to a region of SEQ ID NO:1 encodes a polypeptide with a biological activity (e.g., enzymatic activity) of the corresponding region of SEQ ID NO:1 (e.g., the enzymatic activity of a KS, AT, ACP, DH, KR, MT, Cy, TE, ACP, A, PCP, or Ox domain of a disorazole PKS).

In a related aspect, the invention provides a recombinant DNA molecule, comprising a sequence of at least about 200, optionally at least about 500, basepairs with a sequence identical or substantially identical to a protein encoding region of dszA, dszB, dszC or dszD. In an embodiment, the DNA molecule encodes a polypeptide, module or domain derived from a disorazole polyketide synthase (PKS) gene cluster.

The invention provides polypeptides comprising a sequence encoded by a polynucleotide disclosed herein. In an embodiment, the invention provides a recombinant protein comprising a module (e.g., a loading module, an acetyltransferase (AT) module, or module 1, 2, 3, 4, 5, 6, 7 or 8 of the disorazole PKS) or domain (e.g., KS, AT, ACP, DH, KR) of disorazole PKS. In one embodiment, the invention provides a recombinant PKS that produces a disorazole when expressed in a suitable cell (e.g., as described hereinbelow).

In one embodiment, the invention provides polynucleotides comprising at least about 12, 15, 25, 50, 75, 100, 500, or 1000 contiguous nucleotides as set forth in SEQ ID NO:

1, or a fragment thereof, or sequencing variant thereof. In an embodiment, the polynucleotide encodes a polypeptide with the biological activity (e.g., enzymatic activity) of the corresponding region of SEQ ID NO:1. In a related embodiment, the invention provides polynucleotides that encode a polypeptide that comprises at least 10, 15, 20, 30 or more contiguous amino acids encoded by SEQ ID NO: 1. Those of skill will recognize that, due to the degeneracy of the genetic code, a large number of DNA sequences encode the amino acid sequences of the domains, modules, and proteins of the disorazole PKS, the enzymes involved in disorazole modification and other polypeptides encoded by the genes of the disorazole biosynthetic gene cluster and flanking region. The present invention contemplates all such DNAs. For example, it may be advantageous to optimize sequence to account for the codon preference of a host organism. The invention also contemplates naturally occurring genes encoding the disorazole PKS and tailoring enzymes that are polymorphic or other variants. In addition, it will be appreciated that polypeptide, modules and domains of the invention may comprise one or more conservative amino acid substitutions relative to the polypeptides encoded by SEQ ID NO: 1. A conservative substitution is one that does not destroy the biological activity of the polypeptide, domain, or region; for example, conservative substitutions include aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

As used herein the term “recombinant” has its usual meaning in the art and refers to a polynucleotide synthesized or otherwise manipulated in vitro, or to methods of using recombinant polynucleotides to produce gene products in cells or other biological systems. Thus, a “recombinant” polynucleotide is defined either by its method of production or its structure. In reference to its method of production, the process is use of recombinant nucleic acid techniques, e.g., involving human intervention in the nucleotide sequence, typically selection or production. Alternatively, a recombinant polynucleotide can be a polynucleotide made by generating a sequence comprising fusion of two fragments which are not naturally contiguous to each other, but is meant to exclude products of nature. Thus, for example, products made by transforming cells with any non-naturally occurring vector is encompassed, as are polynucleotides comprising sequence derived using any synthetic oligonucleotide process, as are polynucleotides from which a region has been deleted. A recombinant polynucleotide can also be a coding sequence that has been modified in vivo using a recombinant oligo or polynucleotide (such as a PKS in which a domain is inactivated by homologous recombination using a recombinant polynucleotide). A “recombinant” polypeptide is one expressed from a recombinant polynucleotide.

The recombinant nucleic acids of the invention have a variety of uses, including use (1) for the synthesis of polyketides such as disorazoles and disorazole derivatives, (2) for production of chimeric and hybrid PKS proteins, which can be used for biosynthesis of novel polyketides, (3) for the generation of mutants of disorazole PKS proteins and domains, (4) in the design and synthesis of probes or primers for detection and manipulation of PKS genes and for amplification and analysis of PKS gene sequences, (5) for design and synthesis of peptides or polypeptides for generation of antibodies (e.g., for immunopurification of PKS proteins), (6) for preparation of vectors useful to knock-out an activity encoded by the disorazole PKS gene cluster (7) preparation of vectors useful for PKS domain substitutions or modification and (8) for other uses apparent to the ordinarily-skilled practitioner reading the present disclosure.

In one aspect of the invention, the PKS-domain encoding polynucleotides of the invention are operably linked to expression control sequences (e.g., promoter sequences) so that expression in host cells is effective. In an embodiment the control sequences are the same, or essentially the same, as those operably linked in the *S. cellulosum* (So cel2 strain) genome with the disorazole PKS sequences.

As noted, the present invention also provides polypeptides encoded by the above-described polynucleotides. Methods for conceptual translation and analysis of nucleotide sequences are well known, and those of skill reading this disclosure will be apprised of the sequence and characteristics of polypeptides encoded by the polynucleotides of the invention.

In an embodiment, the invention provides a polypeptide comprising at least 10, 15, 20, or more contiguous amino acids encoded by a polynucleotide described hereinabove. The invention also provides amino acid sequences that differ from the proteins of the disorazole PKS by insubstantial changes to the amino acid composition, i.e., by amino acid substitutions, but perform the same biosynthetic functions as the proteins herein disclosed.

In one aspect, the invention provides an isolated or recombinant DNA molecule comprising a nucleotide sequence that encodes at least one polypeptide, module or domain encoded by dszA, dszB, dszC or the disorazole PKS AT domain gene (dszD), e.g., a polypeptide, module or domain involved in the biosynthesis of a disorazole, wherein said nucleotide sequence comprises at least 20, 25, 30, 35, 40, 45, or 50 contiguous base pairs identical or substantially identical to dszA, dszB, dszC or dszD. In one aspect, the invention provides an isolated or recombinant DNA molecule comprising a nucleotide sequence that encodes at least one polypeptide, module or domain involved in the biosynthesis of a disorazole, wherein said polypeptide, module or domain comprises at least 10, 15, 20, 30, or 40 contiguous residues of a corresponding polypeptide, module or domain encoded by dszA, dszB, dszC or dszD.

The invention also provides cells comprising recombinant DNA molecules and vectors comprising recombinant DNA molecules that encode all or a portion of the disorazole PKS and are operably linked to expression control sequences that are effective in a suitable host cell. When such DNA molecules are introduced into a host cell and the host cell is cultured under conditions that lead to the expression of disorazole PKS proteins, disorazole and/or its analogs or derivatives may be produced. In one embodiment, the expression control sequences are those normally associated with a module of the *Sorangium cellulosum* disorazole polyketide synthase gene cluster.

In related embodiments, the invention provides a recombinant vector encoding a disorazole AT domain; (2) a cell in which a disorazole AT domain is modified or inactive; (3) a chimeric PKS comprising a disorazole PKS AT domain. In related embodiments, the invention provides a recombinant vector encoding (1) a recombinant vector encoding a disorazole dszA gene; (2) a cell in which a disorazole dszA gene is modified or inactive; (3) a chimeric PKS comprising a domain encoded by the dszA gene. In related embodiments, the invention provides (1) a recombinant vector encoding a disorazole dszB gene; (2) a cell in which a disorazole dszB gene is modified or inactive; (3) a chimeric PKS comprising a domain encoded by the dszB gene. In related embodiments, the invention provides (1) a recombinant vector encoding a disorazole dszC gene; (2) a cell in which a disorazole dszC gene is modified or inactive; (3) a chimeric PKS comprising a domain encoded by the dszC gene. In related embodiments, the invention provides (1) a recombinant vector encoding a disorazole dszD gene; (2) a cell in which a disorazole dszD gene is modified or inactive; (3) a chimeric PKS comprising a domain encoded by the dszD gene. In one embodiment, the invention provides a recombinant *Sorangium cellulosum* cell in which a dszA, dszB, dszC, or dszD gene is disrupted so as to reduce or eliminate production of disorazole. Guided by the present disclosure (including the sequence of the disorazole PKS genes) such disruption, or knockout, can be accomplished using routine methods.

In other related aspects, the invention provides (1) a PKS derived from the disorazole PKS by inactivation, addition or rearrangement of disorazole PKS domains or modules, and recombinant DNA molecules and vectors encoding such derivative PKSs; (2) chimeric or hybrid PKSs and recombinant DNA molecules and vectors encoding such chimeric or hybrid PKSs; and (3) PKS libraries comprising disorazole PKS domains. It will be understood by the reader that expression of such derivatives, hybrids, or libraries can be implemented in the same fashion (e.g., same hosts, control sequences, etc.) as is described in connection with production of disorazole PKSs.

It will be recognized by those of skill that recombinant polypeptides of the invention have a variety of uses, some of which are described in detail below, including but not limited to use as enzymes, or components of enzymes, useful for the synthesis or modification of polyketides. Recombinant polypeptides encoded by the disorazole PKS gene cluster are also useful as antigens for production of antibodies. Such antibodies find use for purification of bacterial (e.g., *Sorangium cellulosum*) proteins, detection and typing of bacteria, and particularly, as tools for strain improvement (e.g., to assay PKS protein levels to identify "up-regulated" strains in which levels of polyketide producing or modifying proteins are elevated) or assessment of efficiency of expression of recombinant proteins. Polyclonal and monoclonal antibodies can be made by well known and routine methods (see, e.g., Harlow and Lane, 1988, Antibodies: A Laboratory Manual, Cold Spring Harbor Laboratory, New York; Koehler and Milstein 1075, Nature 256: 495). In selecting polypeptide sequences for antibody production, it is not necessary to retain biological activity; however, the protein fragment must be immunogenic, and preferably antigenic (as can be determined by routine methods). Generally the protein fragment is produced by recombinant expression of a DNA comprising at least about 60, more often at least about 200, or even at least about 500 or more base pairs of protein coding sequence, such as a polypeptide, module or domain derived from a disorazole polyketide synthase (PKS) gene cluster. Methods for expression of recombinant proteins are well known. (See, e.g., Ausubel et al., 2002, Current Protocols In Molecular Biology, Greene Publishing and Wiley-Interscience, New York.)

Disorazole PKS Derivatives

In one aspect, the invention provides recombinant DNA molecules (and vectors comprising those recombinant DNA molecules) that encode all or a portion of the disorazole PKS and which, when transformed into a host cell and the host cell is cultured under conditions that lead to the expression of the disorazole PKS proteins and results in the production of disorazole, disorazole analogs or disorazole derivatives. In an embodiment, these recombinant DNA molecules can differ from a naturally occurring disorazole PKS gene cluster due to a mutation in a disorazole PKS domain-encoding sequence, resulting in deletion or inactivation of a PKS domain, or, alternatively, addition of a sequence encoding a domain of a disorazole or heterologous PKS domain to the disorazole PKS gene cluster, resulting in rearrangements of domains or modules of the disorazole PKS, or alternatively, gene modifications resulting in deletion or addition of a polyketide modifying enzyme (e.g., a methyltransferase, an oxidase or a glycosylation enzyme). It will be understood from this that the invention provides methods of making analogs of disorazole compounds by modifying the activity of the domains of the disorazole PKS. As noted above, modification of the domains of the disorazole PKS can be effected by, among other methods, deletion of the complete or partial coding sequence for a given domain resulting in inactivation of the domain, or by site-directed mutagenesis or point mutation that results in altered activity of the domains, and/or by addition or rearrangement of domains.

Mutations can be made to the native disorazole PKS sequences using any number of conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion (see, e.g., Kunkel, 1985, *Proc Natl Acad Sci USA* 82:448; and Geisselsoder et al., 1987, *BioTechniques* 5:786). Alternatively, the mutations can be effected using a mismatched primer (generally 10-20 nucleotides in length) which hybridizes to the native nucleotide sequence (generally cDNA corresponding to the RNA sequence) at a temperature below the melting temperature of the mismatched duplex. The primer can be made specific by keeping primer length and base composition within relatively narrow limits and by keeping the mutant base centrally located (see Zoller and Smith, 1983, *Methods in Enzymology* 100:468). Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations (see, e.g., Dalbie-McFarland et al. 1982, *Proc Natl Acad Sci USA* 79:6409). PCR mutagenesis can also be used for effecting the desired mutations. Many other suitable methods for manipulating PKS encoding sequences will be apparent.

In a related aspect, the invention provides a PKS derived from the disorazole PKS. A polyketide synthase may be considered "derived from" a naturally occurring PKS (e.g., disorazole) when it contains the scaffolding encoded by all the portion employed of the naturally occurring synthase gene, contains at least two modules that are functional, and contains mutations, deletions, or replacements of one or more of the activities of these fuinctional modules so that the nature of the resulting polyketide is altered. Particular embodiments include those wherein a KS, AT, KR, DH, NRPS, or ER has been deleted or replaced by a version of the activity from a different PKS or from another location within the same PKS. Also contemplated are derivatives where at least one noncondensation cycle enzymatic activity (KR, DH, or ER) has been deleted or where any of these activities has been mutated so as to change the ultimate polyketide synthesized. Regions encoding corresponding activities from different PKS synthases or from different locations in the same PKS synthase can be recovered, for example, using PCR techniques with appropriate primers. (By "corresponding" activity encoding regions is meant those regions encoding the same general type of activity, e.g., a ketoreductase activity in one location of a gene cluster would "correspond" to a ketoreductase-encoding activity in another location in the gene cluster or in a different gene cluster.)

If replacement of a particular target region in a host polyketide synthase is to be made, this replacement can be conducted in vitro using suitable restriction enzymes or can be effected in vivo using recombinant techniques involving homologous sequences framing the replacement gene. One such system involving plasmids of differing temperature sensitivities are described in PCT application WO 96/40968. Another useful method for modifying a PKS gene (e.g., making domain substitutions or "swaps") is a RED/ET cloning procedure developed for constructing domain swaps or modifications in an expression plasmid without first introducing restriction sites. The method is related to ET cloning methods (see, Datansko & Wanner, 2000, Proc. Natl. Acad. Sci. U.S.A. 97, 6640-45; Muyrers et al, 2000, Genetic Engineering 22:77-98). The RED/ET cloning procedure is used to introduce a unique restriction site in the recipient plasmid at the location of the targeted domain. This restriction site is used to subsequently linearize the recipient plasmid in a subsequent ET cloning step to introduce the modification. This linearization step is necessary in the absence of a selectable marker, which cannot be used for domain substitutions. An advantage of using this method for PKS engineering is that restriction sites do not have to be introduced in the recipient plasmid in order to construct the swap, which makes it faster and more powerfuil because boundary junctions can be altered more easily.

PKS Libraries

The disorazole PKS-encoding polynucleotides of the invention may also be used in the production of libraries of PKSs. The invention provides libraries of polyketides by generating modifications in, or using a portion of, the disorazole PKS so that the protein complexes produced by the cluster have altered activities in one or more respects, and thus produce polyketides other than the natural disorazole product of the PKS. Novel polyketides may thus be prepared, or polyketides in general prepared more readily, using this method. By providing a large number of different genes or gene clusters derived from a naturally occurring PKS gene cluster, each of which has been modified in a different way from the native PKS cluster, an effectively combinatorial library of polyketides can be produced as a result of the multiple variations in these activities. Expression vectors containing nucleotide sequences encoding a variety of PKS systems for the production of different polyketides can be transformed into the appropriate host cells to construct a polyketide library. In one approach, a mixture of such vectors is transformed into the selected host cells and the resulting cells plated into individual colonies and selected for successful transformants. Each individual colony has the ability to produce a particular PKS synthase and ultimately a particular polyketide. A variety of strategies can be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large. The polyketide producing colonies can be identified and isolated using known techniques and the produced polyketides further characterized. The polyketides produced by these colonies can be used collectively in a panel to represent a library or may be assessed individually for activity.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can be included.

Chimeric PKSs

In a further aspect, the invention provides methods for expressing chimeric or hybrid PKS encoding polynucleotides and products of such PKSs. As used herein, "chimeric" and "hybrid" are used interchangeably and include both (1) fusion proteins comprising regions encoded by the Disorazole PKS sequence and regions encoded by non-Disorazole PKS sequence and (2) PKS multiprotein complexes comprising polypeptide(s) encoded by dszA, B, C or D and polypeptides from non-Disorazole PKS(s). For example, the invention provides (1) encoding DNA for a chimeric PKS that is substantially patterned on a non-disorazole producing enzyme, but which includes one or more functional domains or modules of disorazole PKS; (2) encoding DNA for a chimeric PKS that is substantially patterned on the disorazole PKS, but which includes one or more functional domains or modules of another PKS or NRPS; and (3) methods for making disorazole analogs and derivatives.

With respect to item (1) above, in one embodiment, the invention provides chimeric PKS enzymes in which the genes for a non-disorazole PKS (e.g., the erythromycin PKS, epothilone PKS, rapamycin PKS) function as accepting genes, and one or more of the above-identified coding sequences for disorazole domains or modules are inserted as replacements for one or more domains or modules of comparable function. There are a wide variety of PKS genes that serve as readily available sources of DNA and sequence information for use in constructing the hybrid PKS-encoding DNA compounds of the invention. Methods for constructing hybrid PKS-encoding DNA compounds are described in U.S. Pat. Nos. 5,672,491; 5,712,146; and 6,509,455. A partial list of sources of PKS sequences for use in making chimeric molecules, for illustration and not limitation, includes Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FRO008) (Hu et al., 1994, *Mol. Micro-*

*biol*. 14:163-72); Epothilone (U.S. Pat. No. 6,303,342); Erythromycin (WO 93/13663; U.S. Pat. No. 5,824,513; Donadio et al., 1991, *Science* 252:675-79; Cortes et al., 1990, *Nature* 348:176-8); FK-506 (Motamedi et al., 1998, *Eur. J. Biochem*. 256:528-34; Motamedi et al., 1997, *Eur. J. Biochem*. 244:74-80); FK-520 (U.S. Pat. No. 6,503,737; see also Nielsen et al., 1991, *Biochem*. 30:5789-96); Lovastatin (U.S. Pat. No. 5,744,350); Nemadectin (MacNeil et al., 1993, supra); Niddamycin (Kakavas et al., 1997, *J. Bacteriol*. 179:7515-22); Oleandomycin (Swan et al., 1994, *Mol. Gen. Genet*. 242:358-62; U.S. Pat. No. 6,388,099; Olano et al., 1998, *Mol. Gen. Genet*. 259:299-308); Platenolide (EP Pat. App. 791,656); Rapamycin (Schwecke et al., 1995, *Proc. Natl. Acad. Sci. USA* 92:7839-43); Aparicio et al., 1996, *Gene* 169:9-16); Rifamycin (August et al., 1998, *Chemistry & Biology*, 5:69-79); Soraphen (U.S. Pat. No. 5,716,849; Schupp et al., 1995, *J. Bacteriology* 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences remain to be discovered and characterized, but will be available to those of skill (e.g., by reference to GenBank).

As noted, construction of such enzymes is most effectively achieved by construction of appropriate encoding polynucleotides. In this example of the invention, it is not necessary to replace an entire domain or module accepting of the PKS with an entire domain or module of disorazole PKS, rather peptide subsequences of a PKS domain or module that correspond to a peptide subsequence in an accepting domain or module, or which otherwise provide useful function, may be used as replacements. Accordingly, appropriate encoding DNAs for construction of such chimeric PKS include those that encode at least 10, 15, 20 or more amino acids of a selected disorazole domain or module.

The use of the appropriate interpolypeptide linkers directs the proper assembly of the PKS, thereby improving the catalytic activity of the resulting hybrid PKS. In one embodiment, the components of a chimeric PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication WO 00/47724.

Expression

The present invention provides recombinant DNA molecules and vectors comprising recombinant DNA molecules that encode all or a portion of the disorazole PKS and/or disorazole modification enzymes and that, when transformed into a host cell and the host cell is cultured under conditions that lead to the expression of said disorazole PKS and/or modification enzymes, results in the production of polyketides including but not limited to disorazole and/or analogs or derivatives thereof in useful quantities. The present invention also provides recombinant host cells comprising those recombinant vectors.

The DNA compounds of the invention can be expressed in host cells for production of known and novel compounds. A variety of hosts may be used for expression of disorazole PKS proteins. The various PKS nucleotide sequences, or a mixture of such sequences, can be cloned into one or more recombinant vectors as individual cassettes, with separate control elements or under the control of a single promoter. The encoding sequence for PKS subunits or components can include flanking restriction sites to allow for the easy deletion and insertion of other PKS subunits so that hybrid or chimeric PKSs can be generated. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include electroporation, conjugation, protoplast transformation, or the use of agents such as $CaCl_2$, lipofection, DMSO. Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity. In one embodiment the exogenous DNA sequence is integrated into the chromosomal DNA of the host cell.

Preferred hosts include fungal systems such as yeast and procaryotic hosts (e.g., *Streptomyces, E. coli*), Single cell cultures of mammalian cells can also be used. A variety of methods for heterologous expression of PKS genes and host cells suitable for expression of these genes and production of polyketides are described, for example, in U.S. Pat. Nos. 5,843,718 and 5,830,750; WO 01/31035, WO 01/27306, and WO 02/068613; and U.S. patent application Ser. No. 10/087,451 (published as US2002000087451); 60/355,211; and 60/396,513 (corresponding to published application 20020045220).

A particularly useful host cell is of genus *Myxococcus*, e.g., *Myxococcus xanthus*, the use of which is described in U.S. Pat. No. 6,410,301. In this respect, the inventors have discovered that *Sorangium cellulosum* expression control sequences (e.g., promoters) associated with polyketide synthase genes also drive transcription in *Myxococcus xanthus* host cells and it is expected that the disorazole PKS control sequences will function in *Myxococcus*. Accordingly, the *S. cellulosum* disorazole PKS control sequences are conveniently used for heterologous expression in *M. xanthus*.

As disclosed in U.S. Pat. No. 6,033,883 a wide variety of hosts can be used, even though some hosts natively do not contain the appropriate post-translational mechanisms to activate the acyl carrier proteins of the synthases. These hosts can be modified with the appropriate recombinant enzymes to effect these modifications. In one embodiment, the host lacks its own means for producing polyketides so that a more homogeneous product is obtained. In one embodiment, native modular PKS genes in the host cell have been deleted to produce a "clean host," as described in U.S. Pat. No. 5,672,491.

Appropriate host cells for the expression of PKS genes (including hybrid PKS) genes include those organisms capable of producing the needed precursors, such as malonyl-CoA, methylmalonyl-CoA, ethylmalonyl-CoA, and methoxymalonyl-ACP, and having phosphopantotheinylation systems capable of activating the ACP domains of modular PKSs. See, for example, U.S. Pat. No. 6,579,695. However, as disclosed in U.S. Pat. No. 6,033,883, a wide variety of hosts can be used, even though some hosts natively do not contain the appropriate post-translational mechanisms to activate the acyl carrier proteins of the synthases. Also see WO 97/13845 and WO 98/27203. The host cell may natively produce none, some, or all of the required polyketide precursors, and may be genetically engineered so as to produce the required polyketide precursors. Such hosts can be modified with the appropriate recombinant enzymes to effect these modifications. Suitable host cells include *Streptomyces, E. coli*, yeast, and other procaryotic hosts which use control sequences compatible with *Streptomyces* spp. Examples of suitable hosts that either natively produce modular polyketides or have been engineered so as to produce modular polyketides include but are not limited to actinomycetes such as *Streptomyces coelicolor, Streptomyces venezuelae, Streptomycesfradiae, Streptomyces ambofaciens*, and *Saccharopolyspora erythraea*, eubacteria such as *Escherichia coli*, myxobacteria such as *Myxococcus xanthus*, and yeasts such as *Saccharomyces cerevisiae*. In one embodiment, any native modular PKS genes in the host cell have been deleted or inactivated to produce a "clean host" (see U.S. Pat. No. 5,672,491).In some embodiments, the host cell expresses, or is engineered to express, a polyketide "tailoring" or "modifying" enzyme. Once a PKS product is released, it is subject to post-PKS tailoring reactions. These reactions are important for biological activity and for the diversity seen among macrolides. Tailoring enzymes normally associated with polyketide biosynthesis include oxygenases, glycosyl- and methyltransferases, acyltransferases, halogenases, cyclases, aminotransferases, and hydroxylases. Tailoring enzymes for modification of a product of the disorazole PKS, a non-disorazole PKS, or a chimeric PKS, can be those normally associated with disorazole biosynthesis or "heterologous" tailoring enzymes.

For purposes of the present invention, tailoring enzymes can be expressed in the organism in which they are naturally produced, or as recombinant proteins in heterologous hosts. In some cases, the structure produced by the heterologous or hybrid PKS may be modified with different efficiencies by post-PKS tailoring enzymes from different sources. In such cases, post-PKS tailoring enzymes can be recruited from other pathways to obtain the desired compound. Similarly, host cells can be selected, or engineered, for expression of a glycosylatation apparatus, amide synthases, (see, for example, U.S. patent publication 20020045220 "Biosynthesis of Polyketide Synthase Substrates"). For example and not limitation, the host cell can contain the desosamine, megosamine, and/or mycarose biosynthetic genes, corresponding glycosyl transferase genes, and hydroxylase genes (e.g., picK, megK, eryK, megF, and/or eryF). Methods for glycosylating polyketides are generally known in the art and can be applied in accordance with the methods of the present invention; the glycosylation may be effected intracellularly by providing the appropriate glycosylation enzymes or may be effected in vitro using chemical synthetic means as described herein and in PCT publication WO 98/49315. Glycosylation with desosamine, mycarose, and/or megosamine is effected in accordance with the methods of the invention in recombinant host cells provided by the invention. Alternatively and as noted, glycosylation may be effected intracellularly using endogenous or recombinantly produced intracellular glycosylases. In addition, synthetic chemical methods may be employed.

Alternatively, the aglycone compounds can be produced in the recombinant host cell, and the desired modification (e.g., glycosylation and hydroxylation) steps carried out in vitro (e.g., using purified enzymes, isolated from native sources or recombinantly produced) or in vivo in a converting cell different from the host cell (e.g., by supplying the converting cell with the aglycone).

Suitable control sequences for gene expression in various types of organisms are well known in the art. Control systems for expression in yeast are widely available and are routinely used. Control elements include promoters, optionally containing operator sequences, and other elements (such as ribosome binding sites) depending on the nature of the host. Particularly useful promoters for procaryotic hosts include those from PKS gene clusters which result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T7. In addition, synthetic promoters, such as the tac promoter can be used. Illustrative control sequences, vectors, and host cells of these types include the modified *S. coelicolor* CH999 and vectors described in PCT publication WO 96/40968 and similar strains of *S. lividans*. See U.S. Pat. Nos. 4,551,433, 5,672,491; 5,830,750, 5,843,718; and 6,177,262. The recombinant host cell can be cultured under conditions where a polyketide is produced by biosynthetic acitivity of a synthase comprising a protein comprising at least one domain (usually at least one module, or at least one polypeptide) encoded by a polynucleotide of the invention.

As discussed above, the sequenced region of the disorazole PKS gene cluster does not including a conventional loading module. If a separate loading module is used by *Sorangium cellulosum*, such that expression of dszA, dszB, dszC, and dszD would not result in the synthesis of disorazole if expressed in a heterologous host, such as *M. xanthus*, "SNAC feeding" can be used in the synthesis of polyketides (Jacobsen et al., 1997 "Precursor-directed biosynthesis of erythromycin analogs by an engineered polyketide synthase" *Science* 277:367-369). Alternatively, a recombinant loading module (e.g., from *Sorangium*) can be introduced into the cell or other methods for loading can be used.

Suitable culture conditions for production of polyketides using the cells of the invention will vary according to the host cell and the nature of the polyketide being produced, but will be know to those of skill in the art. See, for example, WO 98/27203 "Production of Polyketides in Bacteria and Yeast" and WO 01/83803 "Overproduction Hosts for Biosynthesis of Polyketides."

The polyketide product produced by host cells of the invention can be recovered (i.e., separated from the producing cells and at least partially purified) using routine techniques (e.g., extraction from broth followed by chromatography).

The compositions, cells and methods of the invention may be directed to the preparation of an individual polyketide or a number of polyketides. The polyketide may or may not be novel, but the method of preparation permits a more convenient or alternative method of preparing it. It will be understood that the resulting polyketides may be further modified to convert them to other useful compounds. For example, an ester linkage may be added to produce a "pharmaceutically acceptable ester" (i.e., an ester that hydrolyzes under physiologically relevant conditions to produce a compound or a salt thereof). Illustrative examples of suitable ester groups include but are not limited to formates, acetates, propionates, butyrates, succinates, and ethylsuccinates.

The polyketide product produced by recombinant cells can be chemically modified in a variety of ways (for example, a protecting group can be added to produce prodrug forms or for other purposes). A variety of protecting groups are disclosed, for example, in T. H. Greene and P. G. M. Wuts, Protective Groups in Organic Synthesis, Third Edition, John Wiley & Sons, New York (1999). Prodrugs are in general functional derivatives of the compounds that are readily convertible in vivo into the required compound. Conventional procedures for the selection and preparation of suitable prodrug derivatives are described, for example, in "Design of Prodrugs," H. Bundgaard ed., Elsevier, 1985.

Similarly, improvements in water solubility of a polyketide compound can be achieved by addition of groups containing solubilizing functionalities to the compound or by removal of hydrophobic groups from the compound, so as to decrease the lipophilicity of the compound. Typical groups containing solubilizing functionalities include, but are not limited to: 2-(dimethylaminoethyl)amino, piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl) ethyl, 2-(N-methylpyrrolidin-2-yl)ethyl, 2-(4-imidazolyl) ethyl, 2-(1-methyl-4-imidazolyl)ethyl, 2-(1-methyl-5-imidazolyl)ethyl, 2-(4-pyridyl)ethyl, and 3-(4-morpholino)-1-propyl.

In addition to post synthesis chemical or biosynthetic modifications, various polyketide forms or compositions can be produced, including but not limited to mixtures of polyketides, enantiomers, diastereomers, geometrical isomers, polymorphic crystalline forms and solvates, and combinations and mixtures thereof can be produced Many other modifications of polyketides produced according to the invention will be apparent to those of skill, and can be accomplished using techniques of pharmaceutical chemistry.

Prior to use the PKS product (whether modified or not) can be formulated for storage, stability or administration. For example, the polyketide products can be formulated as a "pharmaceutically acceptable salt." Suitable pharmaceutically acceptable salts of compounds include acid addition salts which may, for example, be formed by mixing a solution of the compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

Prior to administration to a mammal the PKS product will be formulated as a pharmaceutical composition according to methods well known in the art, e.g., combination with a pharmaceutically acceptable carrier. The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The composition may be administered in any suitable form such as solid, semisolid, or liquid form. See Pharmaceutical Dosage Forms and Drug Delivery Systems, $5^{th}$ edition, Lippicott Williams & Wilkins (1991). In an embodiment, for illustration and not limitation, the polyketide is combined in admixture with an organic or inorganic carrier or excipient suitable for external, internal, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

EXAMPLES

Example 1

Cloning and Characterization of Sorangium Cellulosum Disorazole Polyketide Synthase Gene Cluster This example describes the cloning of the disorazole PKS gene cluster using a knock-out approach. The strategy described in this example complements a related cloning effort described in U.S. provisional patent application No. 60/431,272, filed Dec. 6, 2002, and incorporated herein in its entirety.

I. Generating Transposon Insertions in *Sorangium cellulosum* So cel2

*Sorangium cellulosum* So cel2 was grown in SF medium to an $OD_{600}$ of 1.0. 10 ml of the culture was centrifuged to pellet the cells, and the cells were resuspended in approximately 0.5 ml of the same medium. The composition of SF medium is shown in Table 2.

The *E. coli* strain harboring the transposon (DH10B, pKOS111-47, pGZ119EH, pKOS249-52 (Phleomycin resistance) or pKOS249-123 (hygromycin resistance) was grown in 10 ml of LB incubated at 37° C. overnight without shaking. The overnight *E. coli* culture was centrifuged and the pelleted cells were mixed with the 0.5 ml of concentrated So cel2 cells. The mixed cells were spotted onto the center of an S42 plate and incubated at 30° C. overnight. The next day, the cells were scraped from the plates, resuspended in the fructose medium, and aliquots were plated in top agar on S42 plates containing kanamycin (100 μg/ml) and phleomycin (50 μg/ml) or hygromycin (100 μg/ml). The plates were incubated at 32° C. for 7-10 days.

II. Screening for Insertion Strains

Colonies that appeared on the plates were picked and inoculated into 2×96 well microtiter plates contain S42 agar medium. Of the two plates, one had a removable low protein-binding Nylon 66 membrane sealing the bottom (96 MicroWell™ plate with Low Protein Binding Nylon 66 Membrane, Loprodyne™ 1.2 um). Once the colonies had grown up on the "membrane bottom plate," the membrane was removed and the agar plugs containing the growing colonies were pushed into test tubes containing 4 ml of production media containing 2% cyclodextrin.

The cultures were grown at 30° C. for 14 days with shaking. A 1 ml aliquot of the supernatant was filtered through a 96-well glass fiber filter plate and a C18 column (96-well plate). 250 μl of 100% methanol was used to elute from the C18 column. To detect the presence of disorazole in the methanol eluted samples, 20 μl of the methanol extract was subjected to HPLC analysis using a Metachem Inertsil ODS-3 (5 μm, 4.6×150 mm) column and a linear gradient of 50-100% MeCN (0.1% HOAc) at 1 mL/min over 8 minutes. The retention time of the disorazole A peak is 8.3 min and has a characteristic UV maximum at 275 nm.

TABLE 2

| Liquid Medium (production media) | | SF Medium | |
|---|---|---|---|
| | Liter | | Liter |
| Potato starch | 8 g | Peptone | 1 g |
| Yeast extract | 2 g | $KNO_3$ | 2 g |
| Defatted soybean flour or meal | 2 g | $K_2HPO_4$ | 0.125 g |
| | | Fe(III)EDTA | 0.008 g |
| Fe(III)EDTA | 0.008 g | $MgSO_4 \cdot 7H_2O$ | 1.5 g |
| $MgSO_4 \cdot 7H_2O$ | 1 g | $CaCl_2 \cdot 2H_2O$ | 1 g |
| $CaCl_2 \cdot 2H_2O$ | 1 g | HEPES | 11 g |
| HEPES | 11.5 g | Fructose | 5 g |
| Glucose | 2 g | pH 7.4 | |
| pH medium with KOH to 7.4 | | | |

III. Cloning and Characterization of the Disorazole PKS Genes

Of approximately 600 drug resistant colonies screened, one showed no production of disorazole A and was grown up in SF medium. Chromosomal DNA was extracted according to published procedures (Jaoua et al., 1992, "Transfer of mobilizable plasmids to *Sorangium cellulosum* and evidence for their integration into the chromosome" *Plasmid* 28:157-65). The purified chromosomal DNA was subjected to partial SauIIIA digestion, ligated into the pKOS cosmid vector, and packaged into lambda heads using the Gigapack III XL packaging extracts (Stratagene).

To isolate cosmids containing the transposon (and the flanking chromosomal DNA), three tl of the packaged DNA was infected into XL1BlueMR, allowed to grow for an hour and then plated on LB plates containing phleomycin. Seven drug resistant colonies were isolated and cosmid DNA was isolated. Cosmid DNA was sequenced using primers that hybridize to the T3 and T7 promoter sequences present in the seven cosmid vectors at the sites immediately flanking the insertion, to obtain sequence at the ends of the inserts. Two of the cosmids, cosmids pKOS254-190.5 and pKOS254-190.6, had identical inserts. Table 3 summarizes the sequences obtained with reference to SEQ ID NO:1.

TABLE 3

| COSMID (and end sequenced) | Corresponding region of SEQ ID NO: 1 | |
|---|---|---|
| pKOS254-190.1 T7 end | 76928 | 77266 |
| pKOS254-190.1 T3 end (KS domain) | 34221 | 33420 |
| pKOS254-190.2 T7 end | 73132 | 73931 |
| pKOS254-190.4 T7 end (KS domain) | 51198 | 51460 |
| pKOS254-190.4 T3 end | 3007 | 3725 |
| pKOS254-190.7 T3 end (KS domain/DH domain) | 29496 | 30288 |
| pKOS254-190.5/pKOS254-190.6 T7 end (KS domain) | 43507 | 44330 |
| pKOS254-190.2 T3 end (KS domain) | 33426 | 33765 |

Cosmid pKOS254-190.2 contained an artifactual rearrangement at the T3 end. The "T3" ends of pKOS254-190.5/pKOS254-190.6 and pKOS254-190.3 and the "T7" end of pKOS254-190.7 T7 included sequence in the region flanking SEQ ID NO:1

The relationships of the clone inserts are shown in FIG. 2. Sequences characteristic of KS domains were identified in each of the clones, as indicated. The "CSSSL" (SEQ ID NO:10) motif characteristic of KS domains was found in the partially sequenced KS domains of pKOS254-190.1 and pKOS254-190.2. Interestingly, sequence analysis of pKOS254-190.7 revealed a ketosynthase (KS) domain adjacent to a dehydrogenase (DH) domain, with no intervening actyl transferase (AT) domain. This suggested that the AT activity is supplied by an AT encoded as a separate protein, rather than existing as domains in each of several modules.

The gene sequence flanking the transposon insertion site was also determined using primers 66.2 (GGACGGGACGCTCCTGCGCC [SEQ ID NO:2]) and 66.1 (CTTTAGCAGCCCTTGCGCCC [SEQ ID NO:3]). The site of insertion at the TA dinucleotide at bases 50,232 and 50,233 of SEQ ID NO:1. Based on sequence analysis, the site of insertion is an NRPS oxidation domain, which is bracketed by a KS domain and a PCP domain, as shown in FIG. 2.

Sequence of Cosmid pKOS254-190.4

Cosmid pKOS254-190.4 was partially sequenced and the sequence was assembled into 21 contigs. Table 4 summarizes the sequences obtained with reference to SEQ ID NO:1. Table 5 shows differences between the initial sequences (e.g., due to sequencing errors or gaps) and SEQ ID NO:1.

TABLE 4

| Contig | Corresponding region of SEQ ID NO: 1 | | Comment* |
|---|---|---|---|
| Fused M&T Contigs | 32774 | 34331 | 192 . . . 1490: predicted ketosynthase domain |
| Contig L | 38589 | 42122 | 2 . . . 532: predicted C-terminal region of a ketosynthase domain<br>1151 . . . 1624: predicted dehydratase domain"<br>2705 . . . 3481: predicted ketoreductase domain" |
| Contig I | 29496 | 31763 | 701 . . . 1108: predicted dehydratase domain" |

TABLE 4-continued

| Contig | Corresponding region of SEQ ID NO: 1 | | Comment* |
|---|---|---|---|
| Contig G | 22833 | 25082 | 106 . . . 288: ACP3; predicted acyl-carrier-protein domain<br>499 . . . 1794: KS4; predicted ketosynthase domain |
| Contig F | 17740 | 22733 | 90 . . . 806 (predicted S-adenosyl-methionine-dependent C-methyltransferase)<br>1029 . . . 1238 (predicted acyl-carrier-protein domain)<br>1752 . . . 3020 (KS3; predicted ketosynthase domain)<br>4290 . . . 4994 (KR3 (nter); predicted N-terminal region of a ketoreductase domain) |
| Contig E | 12912 | 17613 | 1 . . . 582 (predicted C-terminal region of a ketoreductase domain)<br>709 . . . 913 (ACP1; predicted acyl-carrier-protein domain"<br>1156 . . . 2430 (KS2; predicted ketosynthase domain)<br>3761 . . . 4702 (DszB (nter))<br>3803 . . . 4483 (KR2; predicted ketoreductase domain) |
| Contig D (Rev. Comp.) | 11008 | 12229 | 105 . . . 548 (DH1; predicted dehydratase domain) |
| Contig C | 8215 | 10980 | 98 . . . 1228 (KS(cter); predicted C-terminal region of a ketosynthase domain) |
| -"NRPS" Contig | 47894 | 51480 | |
| Contig A | 34422 | 37725 | |
| Contig B | 6941 | 8030 | |
| Contig J | 34422 | 35623 | |
| Contig OP | 43797 | 46757 | |
| Contig Q | 27043 | 28235 | |
| Contig R | 28472 | 29490 | |
| Contig 19 Ends | 42774 | 43658 | |
| Contig 20 Ends | 42332 | 42764 | |
| 45-20 | 25808 | 26716 | |
| 46-48 | 4301 | 5161 | |
| 4T3 | 3009 | 3754 | |

*The base pairs indicated in the comments correspond to the numbering of the original sequence obtained. For example, base pair 2 of Contig L is basepair 38591 of SEQ ID NO: 1.

TABLE 5

| DNA fragment | Seq ID No. | Nucleotide of SEQ ID NO: 1 | Nucleotide of DNA fragment | Change** |
|---|---|---|---|---|
| Contig B | 40 | 6941 | 1 | G -> C |
| | | 6945 | 5 | insert C |
| | | 6946 | 6 | G -> C |
| | | 6949 | 9 | A -> T |
| | | 6953-6954 | 14 | Remove G |
| | | 6956 | 17 | C -> T |
| | | 6957 | 18 | G -> C |
| | | 6958 | 19 | A -> G |
| | | 6961 | 22 | A -> G |
| | | 6962 | 23 | C -> A |
| | | 7914 | 975 | A -> G |
| | | 7962-7963 | 1024 | Remove A |
| Contig C | | 4242-8243 | 28 | Remove A |
| | | 8296-8297 | 83 | Remove N |
| | | 9925 | 1713 | C -> G |
| Contig D | 33 | 11086 | 79 | T -> C |
| Contig E | 30 | 16148 | 3237 | G -> C |
| | | 16150-16151 | 3240 | Remove C |
| | | 16157 | 3247 | A -> G |
| | | 16227 | 3317 | T -> C |
| Contig G | | 25057-25058 | 2226 | Remove G |
| 45-20 | 48 | 25808 | 1 | A -> C |
| | | 26688 | 881 | Insert A |
| Contig Q | 43 | 28221 | 1179 | T -> C |
| contigNOP | 42 | 44792 | 995-996 | Insert G |
| | | 44797 | 1000 | A -> G |
| | | 44808 | 1011 | C -> G |
| | | 44811 | 1014 | A -> G |
| | | 44816 | 1018-1019 | Insert G |

TABLE 5-continued

| DNA fragment | Seq ID No. | Nucleotide of SEQ ID NO: 1 | Nucleotide of DNA fragment | Change** |
|---|---|---|---|---|
| | | 44826 | 1027-1028 | Insert G |
| | | 44831 | 1033 | A -> G |
| | | 44855 | 1056-1057 | insert C |
| NRPS | 37 | 47898 | 5 | T -> C |
| | | 48780 | 887 | S -> C |
| | | 49515 | 1622 | C -> G |
| OX/KS | 18 | 50202-50231 | 1-30 | Remove bases Part of transposon |
| | | 51035 | 840 | N -> G |
| PCP/OX | 17 | 50234-50273 | 707-752 | Remove bases Part of transposon |
| 190.2T7 | 14 | 73207 | 76 | N -> C |
| 190.4T3 | 10 | 3007 | 1 | G -> C |
| 46-48 | 49 | 5130 | 821 | N -> G |
| | | 5139-5140 | 831 | Remove N |
| | | 5148 | 840 | A -> G |
| | | 5161 | 853 | A -> C |

**The base pairs indicated correspond to the numbering of the original sequence obtained. For example, base pair 1 of Contig B is basepair 6941 of SEQ ID NO: 1. The sequence resulting from the "change" corresponds to SEQ ID NO: 1 (e.g., nucleotide 6941 of SEQ ID NO: 1 is C).

The order of the contigs in the disorazole PKS is (in 5'->3' orientation) C-D-E-F-G-I-NRPS.

Example 2

Figure 3:
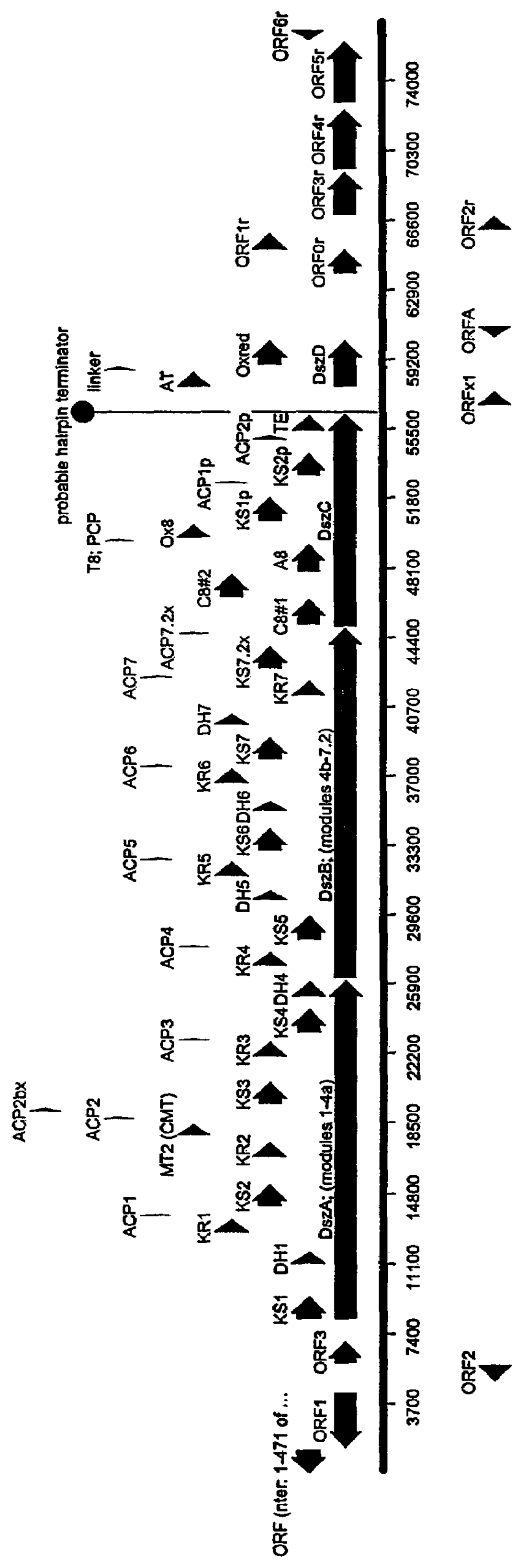
FIG. 3 shows the organization of the disorazole PKS genes dszA, dszB, and dszC.

Additional suquence analysis was carried out using the pKOS254-190.1 and pKOS254-190.4 resulting in the complete sequence of the disorazole synthase gene cluster and flanking regions as provided as SEQ ID NO:1 (Table 6). This 77,294 bp sequence includes the dszA, dszB, dsz C, dszD coding sequences and several other open reading frames. FIG. 3 shows the three proteins encoding modules 1-8 of the disorazole PKS gene cluster. dszA encodes modules 1, 2, 3 and part of module 4. dszB encodes the remainder of module 4 and modules 5, 6 and 7. dszC encodes module 8.

Figure 4:
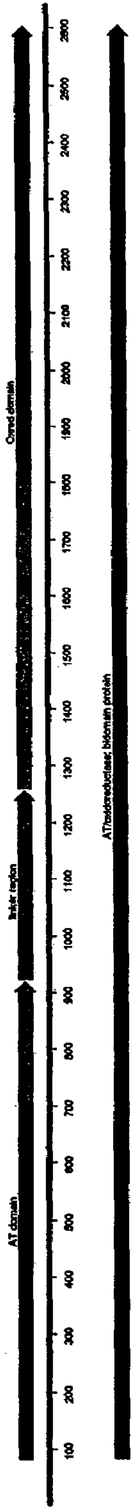
FIG. 4 shows the organization of the disorazole PKS gene dszD, encoding the AT/oxidoreductase bidomain protein.
Figure 5:
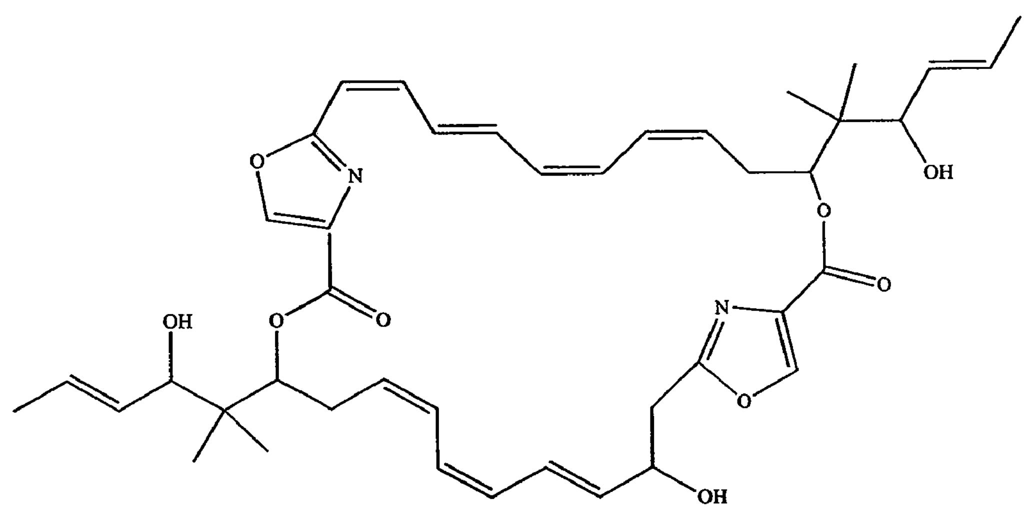
FIG. 5 shows the predicted product of the disorazole PKS (comprising the DszA, B, C and D proteins) in the absence of tailoring enzymes expressed in *Sorangium cellulosum.*

As is discussed above, the acyltransferase (AT) activity used in disorazole biosynthesis is not encoded by dszA, dszB and dszC, but instead is expressed as a distinct polypeptide, designated dszD. FIG. 4 shows the organization of the AT/oxidoreductase bidomain protein. The coding sequence for the AT/oxidoreductase bidomain is located downstream from dszC in pKOS254-190.1.

TABLE 6

Disorazole PKS

```
77294 BP SS-DNA
   1 TGGGTATCCC GAGCCGCTGG CGCCGTTCCC ACAAGGCCTT GCGGCTGATG CCGAGCCGAC
  61 GGGCAATCTC GGTCTCCGTC AGCTCGTCCT GGTGCTCCAG CACGAAGCGG CGGAAATAGC
 121 CCTCGAGCGA GTCCGAAGGC GGCGCCCCGT CGCGCAGCGA TGCGGAGGAG ACGGGCGGAG
 181 GCGGCCGCGG CGGGTCGTCG AGCCCGAGGT GGGCCCTCTC GATCGCGCTG CCCCCGGCGA
 241 GCACCACGGC GCGGTGAACG GCGTTCTCCA GCTCCCGGAC GTTGCCCGGC CACGGCGCCG
 301 CCGCGATGGC CGCGCGCGCC TCCGCCGACA GCGCGAGCGG CGCCTGCCCC ATCACCCGCG
 361 TCCGTCGCTT CAGCAGCGAC TCGGCGATGC GCACCGCGTC CCCGGGCCGC TCCCGCAGCG
 421 GCGGCAGCCG GATCTCCAGC ACCCGCAGCC GGAAATACAG GTCGCTCCGG AAGCTCCCCT
 481 CGCGCACCAT CGCCCCGAGA TCCCGGTGCG TCGCCGCGAT CAGCCGCACG TCCGCCCGCC
 541 GGGCGCGCGT CGACCCCACC CGCCGCACTT CGCCCGTCTG CAAAAAACGC AGCAGGCGCC
 601 CCTGCACCTT CATCGGCAGC TCGCCGACCT CGTCGAGCAG CAGCGTCCCG CCCTCCGCCG
 661 CCTCGCACAG CCCCGCCCGC GCCGCGAGCG CGCCCGCGGC CGCGCCGGCC TCGTACCCGA
 721 ACAGCTCGCC CTCGATCTGC GCATCGGGGA TCGCCGCGCA CTGCACGAGC ACGAACGGCT
 781 GCTGCCGCCG CGGGCTCAGC CGGTGCACCG CGCGCGCCAG CGTCTCCTTG CCCGTGCCCC
 841 CCTCGCCCAC CACCAGCAGC GTCGCCTCGC TCGGCGCCAC CTTGCGCACC TGCGCGAACA
 901 CCTCTCGCAT CGCCGCAGAG CCGCCCACCA TCCCCTCGAG CTCGTCGCCG TCCGGCGCCG
 961 GCGGCGCGGG CGGCGCGGCC AGAGGCGCGG GCGGCGCGGC CTCGGGGCGC ACGCTGGCGA
1021 GGTGGCGCTC GACAAGCGCG ACGAGCTCGT CGTGATCGAA CGGCTTCGAG AGGTAATCCG
1081 CCGCGCCCCG CTTCACGGCC TCCACCGCCG CCTTCACGGT CGCATAGCTC GTCATCAGCA
1141 CCACCGGCGC GCTCCCGCAC CGCCCCACGA GCTCCGTCCC CGGCGCGCCG GGCAAGCGCA
1201 CGTCCGCCAG CACCAGATCG AACGCGCAGA GCTCGTGCTC CGCCTCCGCC TCGGCGATCG
1261 ACCCCGCCTC GACGACGGCG TGCCCGTGGC GCGCCAAGAG CCGCCGCAGC TCCGCACGGA
1321 TGACGATCTC GTCCTCGATC AGCAGGATCC GGCTCATGCT TCCACCTCGC GCCCGCGCCG
1381 CGCCCCGGCC TCGCCCGCCA GCGGGAGCCG CACGATCACC GTCGTCCCCT GCCCCACCGC
1441 GCTCCGCAGC GCCAGCGCGC CGCCGTGATC CTCGATGATC GAGCGCGAGA GCGGCAGGCC
1501 GAGCCCGGTG CCGCTCGGGT CGCGCTTCGT GGTCACGAAC GGCTCCAGCA CCGCGGAGAG
1561 GAGCTCCTCG GGGATGCCGC TGCCGTGGTC CTCGACCTCG ACGACGATCT GGCCCGCCTC
1621 GATCCACCCG CGGACGGCGA CGGTCGCGCC GGGCTCGGAC GCGTCGCGGG CGTTCGCGAG
1681 CAGGTTCACG AAGACCTGCA CGAGCTCGCG CCGGTCGCCG ATGACAACGA GCGACTCCGG
1741 GCAGTGCTGC TCCACCCGCA CGTGCGGGGC CGTGCGGTCG AGCCGGATCA GCCGATCCGC
1801 CTCGGCCACC ACCTCGGCGA GCGACACGCG ACCGACCCGC GCGCGCGGGA TCTCGCCGGG
1861 CGACGGCACG GCGCCGGTGC GGCTGTGATC GAGCAGCGAC CGGAGGATCG CCTCGATGCG
1921 CGCCGTCTCG CCGAGGATGA GGCCCGCCCG CGCGCGGATC TCGTCGCTGT CGGCCTCGGC
1981 CCGGAGGTTC TGCGCGAGGC AGGCGATGCC GGTGAGCGGG TTGCCGACCT CGTGGGCCAC
2041 GCCCGCGGCG AGCCGCCCGA TCTGGGCCAG GCGGTCGCGG TGGGCGAGCT GCGCCTCGAG
2101 CGCGCGCTGC TCGGTGCGAT CCTCCACGAG CAGGACCACG CCGCCCGAGG CGGCCCGCGC
2161 GTCGAGCGGA TCGAGCGCGG CCCGGTGCAC GCGCAGGAGG CGCGCCCGCC CGGCCACGAG
2221 CACCTCGATC TCCTCGGCGC CCGCGCCGGC CTCGCCCGCG GAGGCCGCGC GGGCCGCGCG
2281 GGCGAACAGC TCCGCGAACG GGGCCGGCAG CCGGTCGAGC GGCGCCCCGA CGAGGTCGCG
2341 CTCCTCGGCG CCGACGAGCG CCTCGAGGCG CCGGTTGACG AGGCTGATCG CGCCGTCGGA
2401 GCCCACGGCG CAGACCCCGA GAGGGAGCTG CGCGAGCACC GAGCGCAGCC ACCGCCGCAG
2461 GAGATCGAGC TCCCTCGCCG CGCCGACGAG CCGCGTCTCG CCGCGCGCGA GGCGCCGCTC
2521 CAGCCACCGG AGCTCCTCGG TGAGCGCGCC GGACGCGCCG CCGGACGCGA CCGGCGCGCT
2581 CGCCTCCGCC TCCGCCGCCG TCCTCGCGAG CACCGGGCCG ACCAGCGGCG ACAGGTTGCG
2641 GTGCAGCCGC TCCTGCAGCG CGTGGAGCTC GGTGGGCCGC GTCTCGTCGC GCGAGATGTC
2701 GAGCTCGATC CGGGCGCGCG TGACCTCGAT CGCGGCCGCC TCGCGGCCGA GCAGCCGCGC
2761 GAGCCTGTCC TCCAGCGCGG CCACGCTCGA CGCCACGGTC GCGCGCTCCA CCGAGGGGCC
2821 GATCTCGCGG CGCGTGCACA GGCGGGCCGC CTCGCGCTCC TCCCTGGCCG GCGGGCGCAG
2881 CAGCGAGACG ATCCCGAGCG TCGCGCCGTT GACGGCGAGC GACACGAACG TCGGGAGCGA
2941 CCACGGGTCG ATGGGCGCCG CGCCCGCCGG CGCGCCCGCG CCCCCGCGCA GGAGCGCGAG
3001 CCACGCCGGA TCGATCCCGG GCACGCCGGG CAGGAGCGGC GCGAGGCAGG TGGCCGTCCA
3061 GGTCGCGATG CCGGCGAGGA GCCCGGCCAT GAACCCCGCG CGCGTGGCGC GCTCCCAGAA
3121 GAGCGCGGCG AGCAGGCCCG GGAGGAACTG CGCGAAGGCG ACGAACGACA CGATGCCGCT
3181 CTCGACGAGC AGCCCGTGGT GCGGCTGCGC GCGGTGGAAG AGCCACCCGC CGACGAGGAT
3241 GGCCGCGAGG AGCACGCGCC GGAGCCACAG CACGCGCGCG TACACGTTGC GGCGCAGCGT
3301 CCGCCGCGCG AGCGGCAGGA GCAGGTGCGT CGCGCTGTCG TTCGCGAGGG CGACGGCCGT
3361 GACCATGGCC ATGGCGCTCG CCGCGGAGAT GCCGCCGATG AACGCGGCGA GCGCGAGCCA
3421 GCGCTGGCCG AGCAGCTGCG GCACGAGCAG CACGTAGCTG TCGGCGGGCT CGGCCGGGGC
3481 GAGGCGCGTC CCGGCCCAGA GGACGGGCAG GACGGGCAGG TTGAGCGCGA GCAGGAACAG
3541 GGGGAACGCC CACGCCGCCG TGGCGAGCGC GCGGTCCCCG GCGCCGCTGG CGAACGCCAT
3601 GTGCCACTGC CGCGGCAGCA GGAAGGCCGC GGCGAAGCTG ATGACGAGCA TCGAGGTCCA
```

TABLE 6-continued

| Disorazole PKS | | | | | | |
|---|---|---|---|---|---|---|
| 3661 | GCCGCTGTCC | TCCCGCACGT | GGCGGCCGAG | CGCCTCGACC | TCGGCGGCGT | GCTCGCCGAG |
| 3721 | CCAGCCCGCG | AGCCCGCCGA | GCCCGCCGAA | CGCCCCGAGC | ACGGCGGCGA | GGCCCACGGC |
| 3781 | CGCGAGCACG | GCGAGCTTCG | CCGCCGACTC | GAACGCGACG | GCCGCCGCGA | GGCCGTCCTC |
| 3841 | GCGCCCCTGC | TCGGCCGACG | GGCGGGCGCC | GAAGAAGGCC | GTGAAGAGCG | CGAGCAGCGC |
| 3901 | GCAGAAGACG | GCGCCCACGG | CCTCCTCGTG | CCCCGGCCCC | GAGAGCACGC | GCACCGACTG |
| 3961 | CACGGTCGCG | CGGAACTGCT | GCGCGACGTA | GGGCAGGCTC | GCCACGAGCG | CGAAGGCGGC |
| 4021 | GACGAGCGCC | CCGGCGGCGG | GGCTCTGGAA | GCGGAACGCG | AGCAGGTCGG | TGAGCGACGA |
| 4081 | GAGGCGCTGC | TCGCGCGTGA | TGCGCAGCAC | GCGCGCCCAG | AGGAGCGGCG | TGGCCATGCA |
| 4141 | CGCGAGCGTC | GGGCCGAGGT | ACACAGCGAG | GAAGACGAGC | CCGTGGCGCT | GCGCGAAGCC |
| 4201 | GACGCCGCCG | TAGTACGTCC | ACGACGAGGC | GTAGACGCCG | AGCGAGAGGG | CGAGCACGAG |
| 4261 | CGGGCTCCGC | GCGAGCGCGC | GCGGGCGCCG | GGCGCGCTGC | GCGGCGAGCG | CGATCGCGGC |
| 4321 | GAGCACGCCG | AGCCACGCCA | CCGTGGCGAA | CAGGAGGACG | CCCACGTCGA | TCACGGCGGC |
| 4381 | GGCTCCCGCT | CGCCGCGGCC | GGCGTCGCCC | CGGTCGGCGC | GCGTCGCGAG | CGCGGCGAGC |
| 4441 | GCGATCAGCG | CGAGCCACAC | CGCGAAGACG | GCCGCCACCG | CGAGCGGGCC | GCGGGCCCAG |
| 4501 | AGCAAGCGCG | CCGGCGACAC | GAGGAGGACC | GCGCCCAGCA | GCACGAGCAC | GAGCGCGCGA |
| 4561 | TCCGCCGCGC | CGGCCTCTGC | GTCGCGTCCT | CCGCCCATGG | GCAGAGGCTA | CTCAGGGCCG |
| 4621 | CCGCGGCTGA | ATACGTGAGG | ACGATTGACG | CAATGCGTTA | TTGTGGTCTC | AATCGCAGCC |
| 4681 | GCGGATCGGC | GGGGCGGGAT | CTGCCGCGGA | TGGGCAGCCG | CGAGCCGCCG | ATCCGCCTCT |
| 4741 | TCCGCGGCGC | GCGCGAGCGC | GGGTGAGCGC | GCGCGATCAC | CCGCGCTCGG | CCGCGATCGT |
| 4801 | GGCGAGCATG | TCGCGCGCGA | GCGCGCGCGA | TCACCCGCTC | TCGGCCGCGA | TCTTCTCGAG |
| 4861 | GTGACTGCGC | GCGTGCTCGA | TCACGGCCTC | GTTGCCCATG | TCGATCCCCC | ACTTCGCCGC |
| 4921 | GAGCGCGGGC | CACGCCGCCC | AGCGCTCGGC | GGCGTGGGCC | GCGAGGCCGG | GCCATGCCGG |
| 4981 | ACCGCCGGCC | GCCTCGAAGC | GCGCGATGAC | CGCGTCGAGC | ACCGCCTTGC | CGAAGGCGCC |
| 5041 | GGCGAAGAGC | GCGAAGTCGC | TCGAGGGATC | GCCGACGTGG | GCCTCGGTCC | AGTCGAGGAT |
| 5101 | CCCCGTCAGG | CGGCCGTCCT | CGCGCACGAG | CATGTGCCCG | GGGTGGAGGT | CGCCGTGCAC |
| 5161 | CAGGGCGACG | TGGCGCGGCC | AGCGCGCGTC | GTCCGCGAGC | CAGCGCTGCC | ACCGCGCCCA |
| 5221 | CACGGCCTCG | GGGGGCGAGA | GCGTCGAGCG | CGTCTCGTCC | ATGGCCCGCG | CGAGGGTCGC |
| 5281 | CCGCTCGTCG | TCGATGGACT | TCACGGGGAC | GCCGGCCGCC | TCGATCGCCG | CGGCGTCGAT |
| 5341 | GCGCTGCAGC | GCCGCGAGGG | CGTCCGCCAT | CGAGTCGATG | AACGCGGCCG | GCGGCGCCGC |
| 5401 | GGGATCGACG | TGATTCCAGC | GGACGCCCGC | CTCGGGATCG | AAGGACACCG | CCGGGACGTC |
| 5461 | GCCGAGCCGC | GGATAGGCGA | TCACCTGGTC | GGTGTGCACG | CGCCAGTCGG | GCACGGCCAC |
| 5521 | GGGCAGGTGC | TTGCGCACGA | GGGCCAAGAC | GCGCGCCTCG | ACGCGGGCCG | CCTTCACCAC |
| 5581 | CGCGAGCCGG | CGCGGGGTGC | GCACGACCCA | CGGGACGCCC | TCCTCGTCGC | GGGCGTGCAC |
| 5641 | GACGAGGAAG | TCGAGCCCGC | TCTGGTCGAA | GTCGGCGCGG | GGCGCGACGA | TCCGGAGCCC |
| 5701 | CTCGCGGCGC | GCGGCGTCGA | GGAGCGCGCC | GGGGGAGTCG | AGCGGCGCGA | AGTCGGAGGA |
| 5761 | GGCGGTGGAG | GAAGCGGTGG | ACGAGAGCTC | GTGATGTTCG | GTCATGATCG | CGGTCCTCTT |
| 5821 | CGCGCGCCGC | CGGCAGGGCG | GCGCGCGTGG | AAAGGGGAAG | ACTCGCGGCG | CGAGCTCACG |
| 5881 | ACCGATCAGG | CGTGCATGGC | GTGCATCCTC | CAGGCTGCCG | GGCGTGAGTC | GACGCGCCCC |
| 5941 | GCGTCTTCCA | CGTGTCGACG | GAAGACAGGG | CACGGACAGG | CACCCGCGCG | CTCGCCGCGC |
| 6001 | CGCCCCGGCG | GTGCCGGGGA | GGCGGGGAGG | ACGAGGATGC | CGGGCTCAGC | GCAGCCGGAG |
| 6061 | AAATGCCATG | GCCCGAGGTT | CTCACGCGGC | GTCCCGCGCC | GCAACCCTCT | TCGCGCGCGT |
| 6121 | GGCGCGGCGG | CCCGCGGTGA | TAGCATCGCC | CGCATGGGCA | TCGATGAGGA | GCTGGCAGAG |
| 6181 | CAGCGCATCG | GTACGCGGAT | CGGCCCGTGG | TCGGTGGAGC | GCGTGCTCGG | GGTCGGCGGG |
| 6241 | ATGGCGAGCG | TCTACTACTG | CCGCCGCGAC | GACGGGTGCG | TGGCGGCGGT | CAAGCTCCTG |
| 6301 | CACCCCGAGC | TCGCCAGCAT | CGAGGAGGTG | CGGAAGCGGT | TCTTGCGCGA | GGGGCCGATC |
| 6361 | GGCAGCGCGC | TCGCCGCCGT | GGCGCCGCTC | TGCGAGGGGC | TGCCGCAGGT | GATCGAGGCG |
| 6421 | GGGGAAGCGG | ACGGCGCGGC | CTACATGGCC | ATGGAGATGC | TCGAGGGGGA | GACGGTCTTC |
| 6481 | GATCGCATGG | TGCGGCACGG | GACGCTCCCG | GTCGGCCAGG | TGATCGCGCT | CGCCGAGCGG |
| 6541 | GTGCTCGACG | TGCTGGACGT | GGCGCACGCC | CACGGCATCG | TCCACCGCGA | CCTCAAGCCC |
| 6601 | GAGAACCTGC | ACATCGGCAA | CGACGGGCGC | GTGCGCGTGC | TCGATTTCGG | CCTCGCGCGC |
| 6661 | GTCCTCGATC | CGCTGCTCGA | GGACGTCGCC | GGCGTGCCGG | AGATGACGAA | GACCAGCACG |
| 6721 | GGCGTGTCGA | TCGGCACCGA | CGATTACATG | GCCCCCGAGC | AGGCCCTGGG | CCTCATCCGG |
| 6781 | GAGATCGACG | GCCGGACAGA | CCTGTTCGGG | CTGGGAGCCA | CGATGTTCCG | CCTGCTCGCG |
| 6841 | GGCCGCACGA | TCCACGGCAA | CCTGGAGGAC | GCGCACCTGC | TCATCGCCGC | CGCCACGGAG |
| 6901 | AAGGCGCCGC | CGCTCGCGCA | GCACGCCCCC | GCCGCGCCGC | CCGGCCTGTG | CGCCGTCGTC |
| 6961 | GACCGCGCCC | TCGCCTTCCT | CAAGCAGGAG | CGCTACCCCG | ACGCGCGGAC | GATGCGCGCG |
| 7021 | GACCTCGCCG | CCGTGCGCGC | GGGCCGCGAG | CCGCCGTATG | CGACGGCCGC | GGCGCGGGGG |
| 7081 | CGGGCCTAGC | GCGCCGGAGT | CCTCGGCGGC | GGAGGCGGCC | CGCCCTCGTC | CCGAGGCGGC |
| 7141 | TCGGGTCCGC | TCGGCGCGGA | GAGGGCGCGC | GGAGGGCGGC | GGCTCTCGCA | CCCCGCCGGG |
| 7201 | CTGCGCGAGC | GGCTCAGTGT | TCCACGCCTC | GAACGCCGCC | GTTCCATAAC | GCCGTCTGGC |
| 7261 | GTTCCGCTGG | GTGCGGTCGC | ATGCTCCAGC | CGTGGATCCA | GGCGTGGCGC | CATCGCCGCG |
| 7321 | GCGTCCATCC | TCGCCGTGAC | CCGCGCCCAT | GCCGGCGAGC | CGCCATCGAC | GATGTCAGGC |
| 7381 | TCCGAGGATC | CGGATCCGGA | GCTCGACGGC | TCGTCGCGCG | GTGTTGCCCT | CGTGCGCGGG |
| 7441 | CCGTTACGGC | GCGCCGACAG | GGGCGATCTC | GTCGGCCATG | CGACAAACAG | GTGACGGGAT |
| 7501 | GAGCTGACAC | CCCGCAGAAA | CCGGCTCGAA | ACACGCCCCC | CCAAAACTCC | CCCCGAAAAC |
| 7561 | AACTACATCT | GTCACCGAGC | GTCCGGGCCT | CATCGACGCA | ACAAATATCA | CGTTTCGGAC |
| 7621 | TGGACCAGCA | AGCCCGCATA | CGTCATTGAC | AGAATGTGGA | CTCCCCCTAT | CATATCGCTC |
| 7681 | CAATCGCCCG | GCCGAGCTGA | AGACAGCGGC | GCAGCGGGCG | CATTGAGCAA | CAGCCCATCC |
| 7741 | AGGTGAACGA | GCGGAGACCC | GCGTCCGAGA | CGCGCCGACT | CGCCGCATGT | GGACAGCTCG |
| 7801 | GGGTGGCGTT | CAGCCGCCTG | CCGTCTCCAA | GGACGGTCCG | CTGAACAGAT | GCCGCGCGCT |
| 7861 | GCGCTGTGGA | TAACGGGCGC | GCGCGACGCT | GGAGCGCCTT | CACCGATCGA | AGAGGAAGCC |
| 7921 | CCGCCGAAAA | GAGTTCGAAA | AAAATGAAGG | ATCGCTCCCC | CGAGCGGCAT | CTACCCGCCC |
| 7981 | GCGGCGCCCG | GATCTCGGCG | TCGGGCGATC | GCTTTTGTGC | GTAGGGTCGA | GGTGCGCCCC |
| 8041 | TGCCGTGTCA | GCCATTGACA | TCGTTGGGCG | CTGCCTCTGG | TCCCGTCGTC | ATGGCCTGCT |
| 8101 | GGCTGCCGTG | CAGCGGCGGA | CTTGCATGGA | GAGGATGATT | GGAAATCGAA | GGTCCAGTGG |
| 8161 | AGCAGGACGC | CATTGCGATC | ATCGGCGTAG | CGTGCCGATT | TCCCGGGTCT | CCGGACTATG |
| 8221 | GCCGGTACTG | GCAGCTGCTC | GAGCGGGGCG | AGCATGCCAT | CCTCGAGATC | CCACCCGGCC |

TABLE 6-continued

| Disorazole PKS |
| --- |
| 8281 GGTGGGATCC CCGGGCCCAT TATTCCCCTG ACTTCAATAA GCCTGGCAAG AGCATCAGCA |
| 8341 AGTGGTGCGG GCTGATAGAC GACATCGCCA GCTTCGACCA CCGCTTCTTC AACGTGTCGG |
| 8401 AGCGCGAGGC GAAGAGCATG GACCCTCAGC AGCGCCTGCT CCTGGAAGAG GCATGGCGCT |
| 8461 GCATCGAGGA CTCCGGCGTG CCGCTCGAGC AGCTCCGCGC CCGGAAGACG TCCATCTACG |
| 8521 TGGGCTTCAT GGCGACGGAT TACCACCAGG AGTCCGCGGC CCCGGGCCGC CCGGTCGACA |
| 8581 GCTACGCCGC CCTGGGGAGC TACGGCTCCA TCCTGGCCAA CCGCGTCTCC TATACGCTCG |
| 8641 GGCTGCGCGG CGCGAGCATC GCCATCGACG CCGCCTGCGC CTCCTCCCTC GTCGCGCTCC |
| 8701 ACGAGGCCAG GCGCGCTCTC CAGCGAGGTG AAAGCGAATT TGCGCTCGCC GCCGGCGTGA |
| 8761 GCCTCAACTT TCATCCTTGG AAGTACGTCT CCTTCTCCAA GTCGCGCATG CTCAGCCCGG |
| 8821 ACGGGCTGTG CAAGACGTTC GACGCGGACG CGAACGGCTA CGTCCCCGGA GACGGGGTGG |
| 8881 GTGTCCTCTT GCTGCACCCC CTGGCCAAGG CCATCGCTGC GGGATGCCAC GTCTACGGCG |
| 8941 TCGTCGCGGG CTCCGCGGTC AACCACACCG GCACCGCGCG TTCCATCACC GCGCCGCGCG |
| 9001 TCGCCGCCCA GCGGGACGTC ATCCTCGAGG CCTACGAGGA CGCGGGCTGG AACCCGGAGA |
| 9061 CGGTGACGTA CGTGGAGGCC CATGGCACCG GCACCTCGCT GGGGGACCCC ATCGAGGTGG |
| 9121 AAGCGCTGAC CCAGGCGTTC CGCCGCTACA CGACCGCGCG CCAGCGCTGC GCGATCGGGT |
| 9181 CGGTGAAATC GAACATCGGC CACCTCGAGG CAGCCGCGGG CGTCGCTGGG GTCATCAAGG |
| 9241 TGCTCATGAT GCTGAAGCAC CGCGTGATCC CGCGGACGCT GCATGTCCAG ACGCTCAACC |
| 9301 CGCTCATCCG CTTCGAGGAG ACGCCCTTCG TGGTCGCCAC CCGCGCCATG GAATGGCGCG |
| 9361 CGGAAGGAGG CGAGCCCCTG CGCGCAGGGG TGAGCTCGTT CGGCTTCGGT GGCGCCAACG |
| 9421 CCCACGTCCT GATATCCGAG CACGGCGGCG CGCGCCGCGA GCCCCGCCCG CGAGGCGAGC |
| 9481 TCCGCGGCCC CCGCGGCGCA GCCCCGCGGG GCGAGACGGC GGGCGCTCCA GCGGAGGACG |
| 9541 GCCCGCTGGC CCGCGCGGAG GAGCTCCCTT CGCAGCAGGA GGACGCCGCG GCGGACGAGC |
| 9601 GCGAAGGCAC CGTCTTCCTC CTCTCCGCCA GGTCCGCGTC GAGCCTGTCG AGGGCCGTCC |
| 9661 GACGCTGGGA GGCCTTCGTC GACGATCCCC TCGTGAAGGC AGGCCTGGCC ACCTCGCTCC |
| 9721 GCGATATCTG CGCGACCCTG GCCGCCGGAC GGCAAAGCTT CGAGCACCGC CACGGCTTCT |
| 9781 ACATCGACGA CGAGCGAGAC CTCCGGCGCT TGCTCAAGGA ACCGCCGGCG CGCCTGGAGA |
| 9841 AGACCCGACC TCCTCGCTGG GTGACGCGGT TCGGCGCGCT CGCCCTCGGG CAGGGCAGGC |
| 9901 CCGCCGTCCG TCTGCTCGGC GCGCGCCGCC TGCTCGATCC TCACCTTGAC CGCATCCGGA |
| 9961 GGTGCCTCGA GGAGCTGGGG ATCGAGCACC AGGATCTCCG GACGTACCGT CAGGACGGCG |
| 10021 ATCCCGGGCG CCAGGAGCTG CCCTATGCGT TCCTCTTCGC TCACGCGTAC GTCTCGGCGC |
| 10081 TCGCGGACCT CGGCTTCACG CCGTACGCGA CCAGCGGAGA GGGTCACGGC ATCTGGTTGG |
| 10141 CGCTCGCCCA GAGCGGGGTC TTGCCGCTGA ACGAGATCGT GTCGGTGCTC TCGGGGGCCG |
| 10201 GAGAGCTCCA GAGGCTCTCG CCCCGGCGTC CCAGGCTGCC GCTCTTCGAT CCCATCCATT |
| 10261 CCACCTACCT GATGCCGTAC CTCCTGGACG CGGGCTACGT CCGCGCGCTC GTGGAGGGCC |
| 10321 TGGCGGTTCC GGCAGCGACG CTCCGTGACC TCCTCGCGAG GGCTCGACTC CTGCTCCGCG |
| 10381 CGCAGTTCAC CTTCAAGAAG TTCCTGAGCG AGTGGTCGCC GGCCTTGCAG GCCCTGGGCA |
| 10441 CGACGCCTGA GCGCCTGCTC GAGGAGGAGC TCCCCGCGTC CGACGCTCGC GCCTCGCTGA |
| 10501 TCGCGCTCAT CGCGCAGAGC TGCGTGCGCA AGCTGAACCG CAGGTGGCAG CTCACGGACG |
| 10561 CGCCCTCCTC GGGAGATCCG CGGTTCGACG AGCTCGTCGA CCTGGTGGTC GACGGGCTCC |
| 10621 TGCCGCGCGA GGCGCTCGTG CAGCTCGCCC TCGGCGATCG GGCGGACCTC CACGAGATCG |
| 10681 CCGGCACCCT GCACCGGCGT CAGGACCTGC TCGATCTCAG CCAGCCGTAC GGCATCCTGC |
| 10741 GGAGGCGCAG CGAGCGCCTG GACCCGAGCG AGATCGACGA TTTTTCCGGC TGGATCCGGC |
| 10801 AGATCGCGGG CCTCGAAGCG CCGGGCCTGC CGCCCGAAGA GGGCGTCGCG TTCCTGGAGC |
| 10861 TCGGCAGGGT GGCGAGGCGC GCGCAGCGGG CGCCGGGGCC AGATCTGAGC GTCCCAGCGC |
| 10921 TGGACAGCCC GCTGCAGCTC GTCGCGCTGC GCCTGTGGCT GGAGGGGACT GACATCCGGT |
| 10981 GGGGAGAGCT CTTTCCGGAG GGGAGCTTCG CGAAGATCCC GCTGCCTGGC TATGCGTTCG |
| 11041 ATCAGGCGCA GTTCTGGCTG CCGGCAGCCA GAGAAGGCAC GTCCCCTCCC GAGGACGCGC |
| 11101 GCGACGACGC CGACGCGCGA CACGCCGCCG TCGCGCCGCA CGGCGCGGCG GACCGGGCTG |
| 11161 AACGCCCCTC GATCCCCGTG GACCGCCTGA TCGCCGATCA CGTCATCCAG GGCCGCGCCA |
| 11221 TCGTGCCCGG CGCCCTCATG GTCGAGATGG CCCTGGAGGC GTCACAGCGC GCCCACGGGC |
| 11281 GGCCGGCGGC GGTCCTGAGA GACATCGTGT TCCAGCGGGC AGTTCCGCTC GACGCGCACG |
| 11341 CGAACCTCAC GATCGATGTC GACCCTGACG GCGGGCGTTT CGTGGGGAGA GACGGCGCGC |
| 11401 AGGGGGCATG CCGTGGAGCC TACGGGAGCG CGCCCCCCTC TCCGCTGGAG CCCCTCGATG |
| 11461 CGCCGGCCCG CGACGGCGAC CGCCGCCGCG ACGATAGCCT CTACCGCGAC CTTTCGCGCG |
| 11521 TCGGGTACCG CTACGGCGAG AGCCTGCAGG TGATCGCCGC GACCGGTCGG GTCGGCTCGC |
| 11581 GCCATGTGTT CGAGCTCCGC TCCAGCGTCG CTCGCACGAC GCCTGTCGCC GGCTTCGACC |
| 11641 CAGCGCTCTT CGACGGGCTG CTCCAGGCGG CGCTGGTCGT GGGGCAGCGC CTCGGGCTGT |
| 11701 TCGGCGGAGG CGGCGCGATC TATGTGCCTC AAGCCATCGC GCTCGTCGAG CGGCTCGCTC |
| 11761 CGGTGGACGG GGGCTGCCTG GTCTGCATCG ACGAGCGCGA TCTCTCGATC AAGGAGTACG |
| 11821 GCCTGACCGT CGACCTGCGC GCCTACGATC CGTCGGGGGC CGGCCTGCTC CGGGTAGAGG |
| 11881 GCATCTTCTT TCGAAAGGTG CTGCCGGGCT TCGTCGAGAG CTCCCCTGCC AGGGTGACCG |
| 11941 GCGGCGCCGC GGAGGCGCCA CGCCGCGCCG GAGCGGCCGG AGATCCCGAG TCGGCCGCGC |
| 12001 CGCGAGCAGC GTGCTATCAG CCCGTCTGGG AGCGACGGCC GCTCCCGGAT CGCGGCGGGG |
| 12061 CACCCCCGCG TGGTCGCGCG GTGGCGATCA TCCGCTCCGA GGCGGACTCC GCAGCCTGGC |
| 12121 TCTCGCCCCT GCGAGCGCGC TATTCACAGG TCACGGTGGC GCGCCTCGGC AGCCCGCCGG |
| 12181 GTGAGGCGGG CGAAGATCGG CTCGTCCTGG GCGACGATCG AGAGGAGGGC TTCTCCGAGC |
| 12241 TGGTGCGCCG GGCGGAGAGA GCGGCCGCCG GCGAGGCCGT CGACATCTAC CTCCTGGACG |
| 12301 CGCTGACGCC CGACGCCCGC GTCCCCTCGC GCGCGCCTGC GGCGCTCGAG CCGGCGCTGG |
| 12361 GCCCCCGCGA AGAGGCCGCG GCGCGCAGCG CGTTCCTGCT GGCCAAGGCC CTGGTGAAGA |
| 12421 GCGCGGCGCC GTGGCGCCTG GTCATCGGCA CGCGGCGCTG CCAGGCCGTC GTGCCCGGAG |
| 12481 ACCGGGGCGA AGGGTTCCGC CACGGGGTGC TCGCCGGCAT GGCCCGGACC CTGACGCAGG |
| 12541 AGAACCCGCG GGTTCAGGTC CACCTGGTGG ATTTCGACGC CGCTCCTCCA CTCGCATGCG |
| 12601 CCGGCCACCT CGTCGAGGAG TGCGGTGTGC TCGGCCCGGG GGACTGGGTA GCCTACCGCG |
| 12661 ACGGCGCCCG TTACGTCCGC GCCTTTGCGC CGGTCGAGGA GCCCGGCGCG ACGGCCACGC |
| 12721 CGCCGTTCCA GGACGGTCGC GTCTATCTGC TGGTCGGTGG CGCCGGCGGG CTCGGCCTCG |
| 12781 GCCTCGCGGG GCACATCGCC TCCCGGGCGC ATGCGCGCCT GGTCCTGCTC GGCCGCTCTC |
| 12841 CGCTCGGCCA CGAGGCGGAG CGCCGCCTGG CCCGCCTGCG CGGCGACGGC GGCGAGACTC |

TABLE 6-continued

| | Disorazole PKS |
|---|---|
| 12901 | TCTACATCAG CGCAGATGTC AGCGATCCAC AGCAGTGCGA GCAGGCCCTG GCGGCGGTCC |
| 12961 | GCCAGCGATT CGGCGCCATC CACGGCGTGG TGCAGATGGC CGGCGTGGTC GAGGACAAGC |
| 13021 | TGATCGCAGG CAAGACCTGG GAGTCGGTCC GACGAGAGAT GGCGCCCAAG GTGCAGGGGA |
| 13081 | CCTGGCTATT GCACGAGCTC ACCCGGCGCG ACCCTCTCGA CTTCTTCGTG ACCTTCTCCT |
| 13141 | CCGTCGTCTC CCTGCTGGGA AACCACGGCC AGGTGGGCTA CGCAGCGGCC AACGGGTTCC |
| 13201 | TCGACGGCTT CATCCACCAC CGGGCCCGCA CCGGCGCCGC GGGCAGGAGC CTCGGCGTGA |
| 13261 | ACTGGACGTT GTGGGAGGAC GGCGGCATGG GCGCGGCTCC CGGGATCGTG CGCCGGTTCT |
| 13321 | CGGCGCGCGG GCTCCCTCCC ATCCGGCAGC ACGACGCCTT CGGCGCGCTC GAACGGTTGA |
| 13381 | TGACCGGCGG ACGGTCGCCG CAGGCGCTCG TCCTCGCAGA GCCCGCAGAG CACCTCTTCG |
| 13441 | CGAGAGCTTC TACACGACCT GCTCCCCACG CGGTCGCTCC CGATCCGGAG CGCGGCGATC |
| 13501 | GCGAGCAGGC CCGAGACAAG GAACAGGTTC GGGGAGACGC GAGCATGACA CGTACTACGG |
| 13561 | CTAATCCTCA CGGGACGGCG CCTGCAGGGG CAGGACAGGA CGGGCGGCGT ATCGCCCGGA |
| 13621 | TCGAGGAGGA TCTCCGGCGG CTCGTCTCCG CCAGGATCGA GGCTCCGTCG CAAGCGGTCG |
| 13681 | ACGCGGAAGA GTCCTTCTTT TCGCTCGGGG TCGACTCCGT GGCTCTTCAA GAGATCACGG |
| 13741 | AGACGCTCGA GCGCACCTAC GGCTCCCTGC CGCCGACGCT GCTCTTCGAG AATCCGAACA |
| 13801 | TCCGCCAGCT GGCGCGGTAC CTCGCGGAGC GCGTCCCCGC GAGGTCGGCA GCCCCCGCGG |
| 13861 | AGGTGGAGCC GGCGCAGGCG CCCGCCAGCG GGCCCGCAGA GGCGCCGCCT GCCGCCCGAG |
| 13921 | CGGCCGTGCC CCTCCCCGCG CCGGAGCCGC CTGGCGAGGC CGCCTCCCGC GGCGCGCGGG |
| 13981 | TGGCTGCCGT CGCGGCCGGC CAGGAGCACG ACACGCCGGG CGCGCCCTCC ACCCGCGCCG |
| 14041 | CGCGCCGCGA GAGCCCGTCC GATGGCCCTG CGATCGCGAT CATCGGCATG AGCGCCCGCT |
| 14101 | TCCCCAAGTC CCCCGATCTG GACGCGTTCT GGCAGAACCT GCTCTCGGGC CGGGATTGCG |
| 14161 | TCGACGAGAT CCCCGCCGAG CGCTGGGACC ACCGGCGCTA CTTCGCCGAG GCGGCGCAGC |
| 14221 | CCCACAAGAC GTACGGGCGG TGGGGCGGGT TCATCGAGGA CGTCGACCGC TTCGACCCGA |
| 14281 | TGTTCTTCAA CATCTCCCCG CGCGAGGCGG AGCAGATGGA TCCACAGCAG CGCCTCTTCC |
| 14341 | TGGAGTGCGC GTGGGCGACG ATGGAGCACG CGGGATACGG CGACCCGCGC GCGTACGGCG |
| 14401 | ACCGCGCCGT GGGGTTGTTC GTCGGGGTGA TGTGGAACGA ATACAGCCGC ATCGGCAGCC |
| 14461 | AGCTCACCCT GCAGACCGCG CGCTACGCGG GGCCGGGCTC GCTCTACTGG GCCATCGCCA |
| 14521 | ACCGGGTCTC GTACTGGATG AACCTCACCG GTCCGAGCCT GGCCATCGAT ACGGCCTGCT |
| 14581 | CTTCCTCGCT GGTCGCCGTC CATCAGGCCT GCATGAGCAT TCGCAACGGA GAGTGCGACA |
| 14641 | TGGCCATGGC CGGCGGGATC AACCTCTCGA TCCACCCCGA CAAGTACCTC TACCTGGCGC |
| 14701 | AGTCGAAGTT CTTGTCGCTC GACGGGCGCT GCCGCAGCTT CGGCCAGGGT GGCACCGGCT |
| 14761 | ACGTGCCCGG CGAGGGCGTC GGCGCCGTCC TCCTCAAGCC GCTGGAGCAG GCGCTGCGTG |
| 14821 | ACGGCGATCA CGTCTACGGC ATCGTGCGCG GCTCCGCGAT CAACCACGGC GGCCGCGCCA |
| 14881 | CCGGCTTCAC GGTCCCCGAT CCGGAAGCCC AGGCGAGGCT CGTGTTCGAC GCCCTGCGAC |
| 14941 | GCGCGCGCGT GTCCCCCGAT CAGCTGAGCT ACATCGAGTG CCACGGCACG GGCACGGCGC |
| 15001 | TCGGAGATCC CGTCGAGATC GCCGGTCTCA GCAAGGCGTT CCGCATGGCG GGCGCCACCC |
| 15061 | GCACGAGCAT CCCCATCGGC TCCGTCAAAT CCAACCTGGG CCACCTGGAG GCCGCCGCGG |
| 15121 | GGATCGCCGC GCTCATCAAG GTCCTCCTGT GCATGCAGCA CCAGGCGATC CCGAAGAGCC |
| 15181 | TGCACAGCGA CGTCAAGAAC CCCAACATCC GCTTCGAGGA GGTCCCGTTC GAGGTCGTGA |
| 15241 | ACGAGACGCG CTCGTGGCAG GGGGACGGCG GGGCGCCCCG CTTTGCCGGC GTGAGCTCCT |
| 15301 | TCGGCGCGGG CGGCTCCAAC GCCCATGTCA TCCTCGAGTC GTACGAGCCT CATGTGCGCC |
| 15361 | TCAGCGCGGG CGACGACGCC GCGGAGGGAG GAGCCCTCAT CGTGCTGTCC GCGAAGGACC |
| 15421 | GCGAGCGCCT CGACGCCCTC GCGGGACGGC TGAGGGATTT CCTGCGCGAG CGGGCAGGCC |
| 15481 | GCGCCCCCTC GCTGAGCGAC ATCGCCTACA CGCTGCAGCT GGGGCGCCAG CACATGGATC |
| 15541 | ATCGGCTGGC GATCGTCGCC GCCAGCCGGG AGGATCTGCT GGCCAAGCTG GACGCCGTGC |
| 15601 | TCGCTGGCCG CGGCGAGGTG CCCGGCGCGT TCCGGGGCGA TGTCCACGGC GACAAGGCGG |
| 15661 | CTTCCCTCGC CATGGACGGG GACGATCATG ACCGCGAGTA CCTGGAGAGG CTCGCCCGCG |
| 15721 | ACCGCAGGCT GGACAGGCTC GCTCGCCTCT GGCTGCTGGG GCTCAGGGTC CCGTGGGAGG |
| 15781 | AGCTCCACCG AGATCGCGGC CGCAAGCGGG TCGCCCTGCC CACGTACCCC TTCGCCCGCG |
| 15841 | AGCGTTACTG GCTGCCTGAC GTGGAGAGCT CGATCACCGC CGCGGCGCCG GTCGAGGCCC |
| 15901 | CCGCGTCGGA GCAGGCCCCC GCGCCCCGGG GGGAGAAGGG CCTTCCGGAA GACTTCTTCT |
| 15961 | TCCACGAGCA ATGGTCCGTG GCGCCGCTGG ATCCTGCGAC GGGCTCGGAC GGCGCTGCGG |
| 16021 | TCCGGTCCGC GCTCGTGATC TACACGCCGG AGGGTGAAGC GCTCGCCGAC GCGCTGATCG |
| 16081 | CGAGGCACCC CGGCGCTCGC GTCGCCCGTA TTCTCCTCGG CGCCGGCCAG GGGGCGAAGG |
| 16141 | GGCGCCCCGG CCCGGAGGCC CGCGCCGCTC GGCTTCCCCC CGCGCAGGAG GTTCAGGCCG |
| 16201 | ACGATCCTGC CGCCCTCGAG CGCGCCCTCC GCGAGCTGGC CGCCGCCGGC GTCGCGGGCC |
| 16261 | TCGACGCCAT CTACTTCCTC GGCGGTCTGG CCGCACAGGA GCCCGCGGCG GGCGACCTGG |
| 16321 | AGGCCGTGGA GCGCGCCCAG CAGCGTGGGC TGCTCTCGCT GTTTCGCCTG GCGAAGGCGC |
| 16381 | TGGGCGCCCT GGGCCTTTCG TCGTCGCCCT GCCAGCTGAA GATCATCACC AACGATGCTT |
| 16441 | GCTCGGTGCG GACCGGAGAT CCCGAGCGCC CGCTCGCCGC GGGCCTGTAC GGCCTGGCTC |
| 16501 | GATCCATCGC CAAGGAGTAC CCGCGCCTCA ACGTCAGCTG CATCGACATC CAGACTCGAG |
| 16561 | CGCTGAGCCA CCCGGCCGAT GAGGGGCTCA TCAGCGCGGT GATCGCCGAG CCAGGTCACC |
| 16621 | TCCGCGGCCG AGAGGTGGCG CTGCGGGACG GCAAGCGCTT CCAGCGCACG ATGGCCGCCT |
| 16681 | TGCCGCTGCA GCCGCCGGCG AGGGATCCTT ACCGTCCAGG CGGCGTGTAC CTGGTCCTTG |
| 16741 | GCGGCGCCGG TGGGCTCGGC CACCTGTTCA GCCAGCACCT CGCAGGGACC TACCGCGCTC |
| 16801 | GGCTCGTGTG GATCGGCCGG CGCCCCCTCG AGGCCGACAT CCGGTCGCGC ATCGCCGACG |
| 16861 | TCGAGGCGCG CGGAGGCGAG GTCCTCTATC TCCAGGCCGA CGCCGGCGAC CCGAGCTCCC |
| 16921 | TGCGCGCTGC CGTCTCCCGC GCCAAGGCGC GCTTCGGCGC GATCCACGGG GTCATCCACT |
| 16981 | CCGCGGTCAT CCTCGGGAGC CACCCCATCG CCACCACCGA CGAGGCCACG TTCGCCGCCG |
| 17041 | GAGTCCGCGC CAAGATCGCC GGCAGCGTCG CGCTCCACCA GGCGGTCGCC GACGAGCCCC |
| 17101 | TCGATTTCTT GCTCTATTTC GGATCCATCG CCTCCTACCT CAACAACGGC GGGGCCAGCC |
| 17161 | CGTACGCCGC CGGCTGCACG TTCCAGGACA GGTACGCGGC ATTCCAGCGT TCCCGCGTGC |
| 17221 | CCTACCCGGT CAAGCTCATC AACTGGGGGT ACTGGGGCGA CGTCGGCGCG GTCGCCGGCA |
| 17281 | ACACCGAGAC TCATGACCAG CAGTTCAACG CCATCGGCGT CGGGGCCATC GCGCCCGAGG |
| 17341 | ACGGGATGGA GGCGGCGCGC CGCGTCCTCG CGCAGCGCCT GCCCCAGGTG ATCGCGGCGC |
| 17401 | AGCTCACGCG CCCGCCCCAA AGCCTCTTCG GCTACGACCT GAGCCACGAG GCGACCGTCC |
| 17461 | ACCCGGAGCG CTTCGAGCCG CTGCTCGAGC GGAGCGTGCC GCGCATCCAG CCCGGCCTCA |

TABLE 6-continued

| Disorazole PKS |
|---|
| 17521 GCGCGGTCCG CGAGCTCCTG ACGCATCAGC CCGCGTTCGA CGCGCTGGAG CGCTTCAGCG |
| 17581 AGGATCTGCT GCTCTGCATC TTCCAGGACA TGGGCGCGTT CCAGCGCGCC GGCAGCGCGG |
| 17641 AATCGGCGGC GACCCTGCGA GAACGGCTGG GCGTCGCGGG CCGCTTCGGC CGGCTCTACG |
| 17701 ACTCCCTGCT CGCGATCCTC GAGGGGGCCG GTTACCTGCG CATCGAAGGA GATCGGCTGT |
| 17761 TCACGAGCGA ACGGGTGACG CCAAAGAAGC ACGAGGTGGA ACGGCGGATG CAGCAGCTGG |
| 17821 CGGATCTGCC GGCGATCGCG CCGTACGTCC GCTTGCTCTG GGCGTGCTAT CGGCGGTACC |
| 17881 CCGAGCTGCT CCGCGGTCAG GTAGCCGCGA CGGACGTGCT CTTCCCGCAG GGCTCGATGG |
| 17941 ATCTGATGGG GCCGCTCTAC AAGGGCAACG CCACGGCCGA CCATTTCAAC GAGCTGGTCA |
| 18001 TCAAGAGCCT CCTCGTGTTC CTGGACGCCC GCGTCCCGCA CCTGCGAGAG GGCGAGAAGA |
| 18061 TCACGATCCT GGAGGTAGGG GCTGGGACGG GCGGCACCAC CGCGTCCGTG CTCGAGGCGC |
| 18121 TCTCCTCCCA TGCGCGCCAC CTCGAGTACT TCTATACCGA CATCTCTCAC GCCTTCACGC |
| 18181 GATACGGCAA GCGCCAGTAT GGCCCGCGCT ACCCCTTCGT CACCTTCCAG CCCCTCGACC |
| 18241 TCGAGGGGGA CGTGGTGGCG CAGGGCTTCT CCGCAGAGCG CTTCGACGTG GTGCTGGGCG |
| 18301 CGAACGTCGT GCACGCGACA AAGAACCTGC GCAGCACGCT GCAGAGCATC AAGCGGCTCC |
| 18361 TCAAGGCGAA CGGCTGGCTC GTCCTGAACG AGATGACCCG CGTCGTTCAC TTCCTCACGC |
| 18421 TCTCTGCGGG TCTCCTGGAC GGCTGGTGGC TCTTCGAAGA CGCCGCCGAG CGCATGAAAT |
| 18481 GGTCCCCTCT GCTCAGCTCC CCGATGTGGA AGGGCCTGCT GGAGGAAGAG GGATTCCGCC |
| 18541 GGGTCGCTCC TCTCCAGCAC AGCGACGGCA CGTCCTCCTG GTCGATCCAG AACGTGATCC |
| 18601 TCGCCGAGAG CGACGGCGTG AGCCGAAGCC GGCGGACCGA GAGCGCCGCT CCGCGGCCAG |
| 18661 CGCCGTCGGC CACGAGCGCG GCGGCGGCGT CCGAAGCGCT CCCGCCCGCC CCGTCCACCC |
| 18721 CCGCCGCCGA GCCGGTCGCC GCGTTCCGGC CGATGTCCCT GCAGGCCGTC GAGGACAAGA |
| 18781 TCATCGATAG CCTCGCGAGC ACGCTGCAGA TCGACAGGTC CAAGCTCAGC TCGGACGTGC |
| 18841 CATTCACGAC GTTCGGGGTC GATTCGATCT TCGCCGTGGA GGTCGCCGGC GTGATCGGGC |
| 18901 GCGAGCTGAG CATCGATCTC AGGACCACGG CCCTGTTCAA CTATCCCACC GCGCGCGCGC |
| 18961 TCGCCGAGCA CATCGCCGCG ACGTTCGCCC CCAGCGAGGC GGCCCCGGCC AGAGCGCCCG |
| 19021 AACCGGCGGC GCAGCCGCGG GAGCAGCTCC CCTCGAGCCC GCCGCAGCCG GCGCCGGGAG |
| 19081 CGCCGCCGCG GCCAGCGCAG GCCACGTCGC AGGTCCAGGC GCCGGCGCCG GAGCGTCCGC |
| 19141 CGGCGCCGCA GCCGGCCGGC GCCCAGCAGC GGGTCCGGCA GCTCGCCCTG GGTGCCCTCG |
| 19201 CCGAGGTGAT GGCGATCGAC GTGAGGGAGC TCGATCCGAG CGCGACCCTC GCCGAGTGCG |
| 19261 GCATCGACGC TCAGCAGGCC GTCGTGGTGG TGAGCCGCAT GAACCAGGCC CTCGGGACGA |
| 19321 GCGCCACCGC CATGGATCTC CTCCGATGCG GGACCCTCGC GGACTTCGTG GACCACCTCC |
| 19381 TCGCGTCCTC GCCCGCGCCG CGCCCGGACG CGGAGACCCG CCCCGGCACC GCCGCGGCGC |
| 19441 TCCCGGCGCC CGCGCCCCCT GCGGCGATCG AGCCCAGGTC CGCCCGGAGC ACGGACATCG |
| 19501 CGGTGGTGGG CATGTCCTGC CGGCTGCCGG GCGCCGAGAC GGTCGCCGAC TTCTGGCGGA |
| 19561 ATCTCTGCGA GGGTCATAAC GCCATACGGG AGATCCCGCC TGACCGCTGG TCCCTCGATG |
| 19621 GGTTCTACGA TCCCGACCCC AGCGTCGCTG CCCGCAGCTA CAGCAAGTGG GGTGGGTTTC |
| 19681 TCGACAACAT CGGCGACTTC GACCCGCTCT TCTTCGGCAT CTCACCGCTG GAGGCGGAGC |
| 19741 TCACGGATCC GCAACAACGC CTCTTTCTCC AGGAGGCCTG GAAGGCGTTC GAGGACGCCG |
| 19801 GGTACAGCGC CGAGGCGCTG AGCGGGCAGC GGTGCTGCGT GTTCGTGGGG TGCAAGGACG |
| 19861 GGGATTACGT CTACAAGCTC GGCCCGTCGG CGGACGCCTC CTACCGGCTC ATCGGGAACA |
| 19921 CCCTGTCCAT CCTCGCGGCC CGCATCTCCT ATTTTCTCAA CCTCAAGGGG CCGAGCGTCC |
| 19981 CTGTCGACAC CGCTTGCTCT TCCTCCTTGA TGGCGATCCA CCTGGCCTGC CAGAGCCTGA |
| 20041 TCAGCGGGTC CAGCGACCTC GCCGTGGCCG GGGGCGTCGC CCTGATGACC ACGCCGGTGA |
| 20101 GCCACATCAT GCTCAGCAAG ACGGGGATGC TGTCGCCCAC GGGGAGCTGC CGCACGTTCG |
| 20161 ACGACTCCGC CGATGGGCTG GTCCCCGCCG AGGGGGTGGC CGCCGTCATC CTGAAGCCGC |
| 20221 TCGACGCCGC CCTGCGCGAT CGCAACCACA TCTACGGGGT GATCCGCGGC TCCGAGGCGA |
| 20281 ACCAGGACGG CAAGAGCAAC GGCATCACGG CGCCCAGCAC CCCCTCGCAG GCCGCCCTGG |
| 20341 AGGTCGAGGT CTACCGCAAG TTCGGGGTTC ACCCGGAGAC CATCGGCTAC GTCGAGACCC |
| 20401 ACGGCACCGG CACCAAGCTG GGGGACCCCA TCGAGATCCA CGCGCTCACG GACGCGTTCG |
| 20461 CCGCCTTCAC CGACAAGAAG GGGTTCTGCC CGGTCGGGTC CGTGAAGACG GGGATCGGCC |
| 20521 ACACGCTGGC AGCGTCCGGG GCCGCCTCCC TCATCAAGGT GCTCTGCTGC CTCCAGCACC |
| 20581 GCACGCTCGT GCCGTCGCTC CACTATGACC GGCCCAACAG GCACATCCAC TTCGAGAACA |
| 20641 GCCCGTTCTA CGTCAACACC GCCCGGAGGC ACTGGGCGCA CGCCGGCGAT CTCCCGCGCC |
| 20701 GGGCGGCGAT CAGCTCGTTC GGCATGAGCG GCACCAACGT GCACCTCATC GTCGAGGAGG |
| 20761 CGCCTCCGGA GGCCGACGCC ACCGCGCCCA CGGTGGCCCC CTATACCCTC ATCCCGATCT |
| 20821 CGGCGAAGGC GCCGGCGCCG CTCCATCGCA GGGTGGCGGA TCTGGCCGCC TGGCTCGACG |
| 20881 CCGGCGGGCG CGACCGCGAG CTGGGCGATA TCGGGTACAC CCTGGGCGTC GGCCGGAGCC |
| 20941 ATTTTCCCCT GCGGCTCGCC TTCGTCGCGC GCGACACGCG CGACCTGCGC CGCCAGCTGG |
| 21001 CGGCGTGGCT CGCGCGCCAC CCGACCGCGG ACGACGTGCC GGCGCCGGCC GCGCGGCCGG |
| 21061 AGCCCGCGCT CGGCCAGACG GCGGGCCGCC TGGCGAGCGA GCTCCGCGAC GCGCCCCCGC |
| 21121 TCACCGCCGA CGCGTACCGT GAGAAGCTGG AAGCCCTGGC CCACGCCTAT GTGGCAAAGC |
| 21181 ACGATCCTGA GTGGCAGTCC CTGTTCGCGG GTCAGGATCG ACGCCTGATC TCGCTGCCCA |
| 21241 CGTACCCGTT CAACAACCGC CGGTTCTGGG TGGACGAGCC CTCGCGGTAC GGGCTCGATC |
| 21301 ACGCCGCGCC GGCCGCCAGC GCGGCGCCGG CGCCGCGGCC GGAGCCCGCG CCGGCCGCGC |
| 21361 GCCTCGCGGC GCCGGCGGAG CAGCCGGGGC ACGGAGACCG GCGAGCAGAT TCGCTCCTTT |
| 21421 ATTTCAGATC GGCCTGGGAA ACCGCAGAGC ACGAGGCTGC CGCGGGCCAG CTCCGCGCTC |
| 21481 CGATCCTGCT CTTCGACGAC GGCGGCGCCG TGCGCGAGCG GCTGCTGGAC AGCGACCGCC |
| 21541 CCGTCATCGC CGTCACGCCG GGCCCCGGGT TCCGCGAGCT GGGAGGCGGC CGCTACGAGC |
| 21601 TGAACCCCGG CGACGCGGCG GATTACGGCC GCCTCGTCGC CGCCTGCAAG CAGCGGGGCG |
| 21661 CGCTGCCGCG CGAGGTCGTG TACCTGTGGC CGCTCGCGCG AGCTCAGGCG CAGGCGGAGC |
| 21721 CGACGGCGCC CTTCTTCCAG GCGACCTCTC TGTGCCGCGC GCTCGCCGAC CATCGCCCCG |
| 21781 CGCACGGCGA GGCTGTCCGC ATCCTGTACG TCTACTGGCA GGACGGGGAT CGGCTGGACG |
| 21841 CCAGCCATGC AGCCATGAGC GGCCTGGCCC GCAGCCTGCA GCTCGACCTT CCGCACCTCC |
| 21901 ACTGGAAGAC GCTCGGCCTC GAGCCGCGGA CCGCCGACGG CGCGCTGTGC GATCTCGTCC |
| 21961 TCGCCGAGCT GCTCGCCCCG CCGCAGGGCG CGGTCCGCTA CCAGCGGGGG CACCGGCAGA |
| 22021 TCCAGCGGCT CCAGCCGTGG CGCCCCGAGG GCGAGGCGAG CGCGCCCTTC CGCAGCAAAG |
| 22081 GGGTCTATCT GATCACCGGC GGCGCCGGTG GGCTGGGCGG CCTGTTCGCC GAGCACCTCG |

TABLE 6-continued

| Disorazole PKS |
| --- |
| 22141 CTCGCCGCCA TCAAGCCAGG CTGGTCCTGT GCGGGCGCTC TCCCTTGACG CCGGCCGGCG |
| 22201 ACGACCTCCT CCGCCGCCTC GCCCAGCTCG GCGCGGAGGC GGTCTATGTG CGGGCCGACG |
| 22261 TCGCCGATCG CGAGGACGTG TTCGCGCTGC TCGGGCGCGT CGAGGCCCGG TTCGGCGCGC |
| 22321 TCCACGGCGT CCTCCACAGC GCCGGCGTCA CCGCCGACGC GAGCTTGCGC AACAAGAGCC |
| 22381 GTGACCAGAT GGTCGCCGTG CTCGCGCCGA AGGTGCTCGG CACCCTGCAC CTCGACGACG |
| 22441 CCACCCGCCA TCGAGAGCTG GATTTCTTTG CCCTGTTCTC CTCCGTCACC GCGGTCATGG |
| 22501 GCAACATGGG GCAGACGGAC TACGGCTACG CCAACAGCTT CATGGACCAC TTCGCGGCCT |
| 22561 GGCGCGAGGC CGAGCGGCAG AGCGGACGCC GCAGCGGAAG GACCGTGTCG ATCAACTGGC |
| 22621 CGCTCTGGCG AGACGGCGGG ATGAGCGTCT CGCAAGAGAT GCAGACGCTG CTCACGTCCA |
| 22681 CCCTCGGCAT GAGCGCGCTC TCGAGCGACG CGGGCATCCA GGCCTTCGAG CGCGCCGTGG |
| 22741 CCTCGGCGCA CCCCCAGGTC GTGGTCCTCG CCGGTGACGA GGCCAAGATC CAGGAGAGCC |
| 22801 TCGGCATCGC GGCCCCGACC CCGCCCGCCG GCGCGCTCCC GGGGTCGCAC GGCGCCCCTC |
| 22861 CCGCGGCTCG CGCGAAGGCG CCCCCCGCGC GCAGCGCGCT GGCAAAGCAG GTCGAGGAGC |
| 22921 TCCTGCTGCA GGCGGTCTCC GGGGTGTTGA AGGTCGCTCG CGAAGAGCTG AATTACGATG |
| 22981 CGCCGCTGAG AGATTACGGG CTGGAGTCCA TCAACGTCAT CGCCCTCACC AACCATCTGA |
| 23041 ACCGGACCTA CGCGCTCGAC CTCAAGCCGG TGCGGTTCTT CGAGCACGAG ACGCTCGCCG |
| 23101 CGCTGGGCGG TTGGCTATGC GAGGAGCGCG GGGAGCACCT GGCTCGACGC TTGGGCCCCT |
| 23161 CGCGCGCGCC CGAGGCCGGG CTCCCCGCTG CCCCCGCGGC GCCCCCCGAG CCCGCGCAGG |
| 23221 CCGCCCCGGC GCAGCCGGCG AAGGAGCCCC CGGCACGGAG CGCGCGGGCC GCCGAGCGCG |
| 23281 TCCCGCCGGA GGCGCCCTCG GCCCGGGCTG AACGGGGGAT GGCGGCCCAC GAGCCCATCG |
| 23341 CCATCATCGG TATCGGCGGG GCCCTGCCGA AGTCCAGCGA CCTGAGCGCG TTCTGGCAGC |
| 23401 ACCTCGTGGA CGGCCGCTCC CTCGTCTCCG AGCTGCCCGC CGATCGCTGG GACTGGCGTG |
| 23461 CTTACGACAA CGGCGACGCG AATCGGAAGG GGCTGCGCTG GGGGAGCTTC TACGAGGACA |
| 23521 TGGATAAGTT CGATCCGATG TTCTTCGGGC TCTCCCCGCG GGAGGCCGAG CTGATGGATC |
| 23581 CCCAGCACCG CGTCTTCCTC GAGACCGTGT GGAAGGCCAT CGAGGACGCC GGATACAGGC |
| 23641 CCTCCGATCT GGCGAGGAGC AACACCGGCG TCTTCGTCGG CGCGTCGTCG CTCGACTATC |
| 23701 TCGAGCTGAT GAACGGACAC CGGACGGAGG CGTACGCCCT CACCGGCACG CCGCACTCGA |
| 23761 TCCTGGCGAA CCGGATCTCG TTCTTGCTGA ACCTGCACGG GCCCAGCGAG CCCATCAACA |
| 23821 CCGCCTGCTC GAGCGCGCTG ATCGCCGTCC ACCGCGCCGC GGAGACCCTC CGCAGCGGCG |
| 23881 CCTGCGATCT GGCCATCGCC GGCGGGGTCA ACGCGATCCT CAGCCCCGCG ACGGCCCTGG |
| 23941 CCATCGCGAA GGCAGGCATG CTGAGCCCGG ACGGGAAGTG CAAGACCTTC GATCGGAGCG |
| 24001 CGAACGGCTA CGTCCGCGGC GAGGGGGCCG GCGCGCTGCT CCTCAAGCCG CTCCGCCGCG |
| 24061 CGCTCGCCGA CGGGGATCAC GTCTATGCGA TCCTGCGCGG CAGCGCCGAG AACCACGGCG |
| 24121 GGCGCGCCAA CTCGCTCACC GCCCCCAACC CGCGGGCCCA GGCGGATCTC ATCATCGCGG |
| 24181 CCTTCCGCGC GGCGGGCGTC GATCCGGCCA CCGTGGGCTA CATCGAGACC CACGGCACGG |
| 24241 GCACCGCCCT CGGCGATCCC ATCGAGATCA ACGGCCTCAA GACGGCCTTC GAGCAGATCT |
| 24301 ACAAGGATCA TGGCCGGCCG CCGCCGCAGG CGCCGCACTG CGGGCTCGGC TCGGTCAAGA |
| 24361 CCAACGTCGG CCACCTGGAG GCGGCCGCCG GGATCCCGAG CCTCTTCAAG GTCCTCTTGG |
| 24421 CGATGAAGCA CCGCAAGCTG CCCGGGACTC TCCACCTCCA CGACCTGAAC CCCTACATCG |
| 24481 AGCTCGAGGG CAGCCCCTTC TACATCGTCA CCAGGACGGA GGACTGGAAG CCCGCTCTGG |
| 24541 ACGCCGACGG CCGCCCCCTC CCGCTGCGCG CCGGGATCAG CTCCTTCGGC GTCGGCGGCT |
| 24601 CCAACGCCCA CCTGGTCCTC GAGGAGCACC ACGACGAGCG CGCCGAGGAG CCGTCCGCGG |
| 24661 CCGAGGTCCG GCGCGGCCCT CATCTGATCG TCCTCTCCGC GAAGAGCGAG GAGCGCCTCC |
| 24721 ACGCGTATGT AGACGCGTTG ATCGCCTACC TCCGCGACAC GGCGCCGGAG CGCCGGCCGT |
| 24781 CCCTCGGGCA CATCGCGTAT ACCCTGCTCA CCGGTCGTGA CGTCATGGAC GCCCGCCTCG |
| 24841 CCTGCGTGGC GACCGACACG GACGACCTCG TCACCCGGCT CTCCCGTTAC CGGGCCGGCG |
| 24901 AGAGCGCGGT GGACGGGCTG TTCACCGGTC GGAGCGACGG GAGCTCCAGC GCGGCGGCCG |
| 24961 TGCTCATCGA GGGCGAAGAG GGCCAGCAGT TCGTCGAGGC GCTCCTCCGC AACCGCAAGT |
| 25021 GGGCCCAGAT CGCTCGCCTG TGGGTCGCCG GGCGCACGGG GATCGACTGG TCCTCTCTGT |
| 25081 TCGACGGCGA GCGCGTGCGG CGCGTGCCGC TGCCGACCTA CCCCTTCGCG CGGGAGCGAT |
| 25141 ACTGGGTGCC TGACGAGATC GGCAAGGAGC ACGCCGGGAA CGGCGCGCCG CCCGCCGTCA |
| 25201 ACGGCAAGGC GCACAACGGT GCCGCCGAGG GCGGCGCCCG TCCCCCGGCC AGCGCGGGGA |
| 25261 GCACGCTGCG CCCGACGCTC GACGCTGCGC GCTCGAGCCC CGAGCGGCCC GTCTTCCAGA |
| 25321 AGGAGCTGGA GGCCGACGCC TTTTATCTGA GAGATCACGT CATCGCCGGC AACATCATCC |
| 25381 TTCCGGGCGT GGGGCACCTG GAGCTCGCTC GCGCGGCCGG TGAGCTCGCC GGCGGACGAC |
| 25441 CGGTGCGCGT CATCCGGGAC GTCCTGTGGG CAAAGCCCAT CCTGCTCGAC GGACCGCGGC |
| 25501 TCGATGTGCA GGTGGCGGTC AGCCATGACC GTCAGGGCGC CGAGTACCAG ATCCGCCACG |
| 25561 AGGGCGAGGG CCGCGAGGTC CTCTACTCGC GCGGAAGGCT GGCCTACGAG CCGGCTCCGC |
| 25621 GCCGCGACGG CGAGCCGGAG CGCCGCGACG TGAAGGCGAT ACGGTCTCGA TGCCACGACC |
| 25681 GCAAAGATCA CGACACGTTC TACCGCCGGT ATCGAGAAGC CGGGTTCCGG TACGGCCCCT |
| 25741 CCTTCCGGGT CGTCCAGGAG GCCTGGGGGA ACGAGCGCGA GTCCTTGGGA GCGCTCGTCC |
| 25801 TGCCAGACCA CCTGCGCGAG GGGTTCCCGC AGTTCGGCCT GCACCCCTGC CTGCTGGACG |
| 25861 CCTCCCTGCA ATCCATCACC GGGATGCAGC TCGACGCCGG CCGCGACGCG CCCTCCATGA |
| 25921 GCATCCCCTT CGCCATGGGC CAGCTGGAGA TCTTCGGCCC GCTGCCTCCC GTGTGCTACG |
| 25981 CGCACGCGAC CCTGGGCTCG CGCCGCGGCG AAGGGGCGCG CGAGATCGTC AAGTACAACG |
| 26041 TCGCGGTCCT CGACGAGGAC GGCCTCGTGC TGGCGCGCAT CACGGACTTC AGCGCGCGCG |
| 26101 CCTTCACGAA CGACCAGCCG CGCAGCCCAG CCGAGCAGGC CGCTGCGCCG CTCGGCTATT |
| 26161 ACCAATCGAC CTGGACCAGA AGCGCGCTTT GAACGTCGGG GTAACCTCAT GTCCAGCACT |
| 26221 CTCCGCCACA CAGACACCAT CCTCGTCCTG CTGCCCGCGA GCGCGGCGTT CAGCGGGCTC |
| 26281 GACGAGCGCC TGGTCGCGCA GGTATCCGAT CCGCAACGCC TCGTCTTCGT GCAGGCCGGC |
| 26341 GAGCGCTTCG CCTCGATCGA TCCGCGACAT TACCGCGTCG ATCCGGCGCG CCCGGAGGAT |
| 26401 TACGTCCGGC TGTTCTCGGA GCTCGAGCGC AGCGGCGCGC TGCCCACGCA TATCCTCCAC |
| 26461 GCGGGCAACT GCGTCGGCCC GAGCGCGCTG GGGGCTGGCG AGCGCGACGC GTTCGCGAGC |
| 26521 ATCCGCGAGC GGCTAGGCCA GGAGCTGGAG CGCGGCCTGT ACGCGATCCT CTCGCTGGTC |
| 26581 CAAGCCAAGC TGGCCGTCAA CCCCGCTGGC CCCACCCGCT GCGTGTTCGC GTTCACGACC |
| 26641 GACGAGGCCC ACCCGCGCCC GCACCACGAG GCGGTGGGCG GCCTGGCAAA GGCCCTCACG |
| 26701 ACGGTCGATC ATCGCTTCCA GCTCGTCACC GTGCAGATGG ACGCGTGCGA CGCGGACACC |

TABLE 6-continued

| Disorazole PKS | | | | | | |
|---|---|---|---|---|---|---|
| 26761 | GCGGCGCGCC | GCCTCATCGA | GGAGCTGACC | TCGCCTCACC | ACCAGAATGG | CGGCGAGGTG |
| 26821 | CGCTACAGGG | GCGGGGAGCG | GTTCGTACAC | GAGGTGCAGC | GGCTGGAGCC | CGCGCCCGAG |
| 26881 | CGGGGAGAGC | CGCCGGCCGC | GCTCCCGCTG | CGCGCCGGCG | GCGTGTACCT | CGTGACCGGC |
| 26941 | GGCGGCGGCG | GCCTGGGGAT | GCTGTTCGCC | CGGCACCTGG | CCGTGAAGTA | CGGCGCCCGC |
| 27001 | CTGGTCCTCA | GCGGCCGCGC | TCCGCTCGAC | GACGACAAGC | GCGCGAAGCT | CCGCGAGCTC |
| 27061 | GAGGCGCTCG | GCGGCCGCGC | GGCGTACGTG | CCCGCGGACG | TGGGCGACGA | GGCCGAGACG |
| 27121 | CGGCGCCTGC | TCTCCGCCGT | CTCCGCGGAG | TTCGGCGAGC | TCCACGGCAT | CTTCCACTGC |
| 27181 | GCTGGAGTGG | CCGATCGCAC | GCCGCTCGCG | AGGGCCACGA | TCGCAGATTT | CGAGAGGGTA |
| 27241 | TTGCGCCCCA | AGGTGCACGG | CACGCTCCAC | CTCGACCTGG | AGACCCGCGA | CCGCGATCTC |
| 27301 | GACGTCTTCG | TCCTGTTCTC | GTCGATCTCG | GCGCTGGTCG | GCGACTTCGG | CGCGGGCAGC |
| 27361 | TACTCCGCGG | CGAACTGCTT | CCTCGATCGC | TTCGCCGACG | CCCGCGAGCA | GCTGCGACGC |
| 27421 | AGCGGCCTGC | GCCGCGGCCA | GACCCTGTCG | GTCAACTGGC | CCCTCTGGCA | GGACGGGGGC |
| 27481 | ATGAGGATGC | AAGAGCAGGA | CAAGGCCATG | TACTTCCAGT | TCTCCGGCAT | GGGGGCCCTG |
| 27541 | GAAGCGGCCG | AGGGCATCGA | GGCCTTCGAG | GGCGCCCTCC | GGGCCGGGCG | GCCCCAGCTG |
| 27601 | CTCGTGGTCA | CCGGCGACCG | CAAGAAGATC | GACCGCATCC | TGCAGGTTCG | CGAGCCGCGC |
| 27661 | TCGGCGGCCG | CTCCACGCGA | AGAGCCGCAG | CGGCCCGCCG | CCGGAGGCGC | CGCGCCGCCG |
| 27721 | GCCGCGAGCC | ATCCGGGGTC | GAGCGAGGGC | CGAGGCGCCT | CCGGGGGAGA | GCGGTCCAGC |
| 27781 | TCAGCGCCGC | AGGGCTCGCC | GCGCGCAGCG | ACGCGAGGCC | CGCTGCCACG | AGAGCAGCTC |
| 27841 | CTCGCGCAGT | GCAGAGACTA | CCTGCGCAAT | CTGATCGCCC | AAGCCACAAA | GCTCCCCGTC |
| 27901 | GACAAGATCC | ACGCGGACAG | GGATCTGGAG | GACTACGGCA | TCAACTCCCT | CATGATCATG |
| 27961 | GAGCTCAACT | CCATGCTCGA | CAGGGATTTC | GACGCGCTGC | CGCGCACCCT | CTTCTTCGAG |
| 28021 | TACAAGAACG | TCGCCGAGCT | CGCCGCCTTC | TTCGCCGACG | AGCACGGGTC | GCGGCTGCAG |
| 28081 | CAGATCCTCG | CGGGGGGCAC | GGACTCGAGC | CCGGACGCGA | CGCCGCCCCC | TGAGGAGCAG |
| 28141 | CCGCCGGCGC | CGGAGCCCGA | CGCGGCGGCC | GCCCTCGCGG | CAGCGCCGGC | GCCCGCTCCG |
| 28201 | CGCCCGCCGC | CCGCAGCGCT | CCGTCAGGAC | GACGGGCACA | TCGCCGTGAT | CGGGTACGGC |
| 28261 | GGCCGCTTCC | CTAAGGCGGA | CGATCCCGAG | GCGTTCTGGA | GGATCCTCAA | GGAGGGGATC |
| 28321 | GACTGCATCA | CGGAGATCCC | CCGCGAGCGG | TGGGACTGGC | GCGCGTACCA | CGACGACGTC |
| 28381 | CCGGGGACGC | CGGGGAAGAT | CTATTGCAAG | TGGGGCGGCT | TCATCAACGA | CTTCGACCGC |
| 28441 | TTCGATCCGC | TCTTCTTCCG | CCTCTCTCCG | CGCGCGGCGC | ACAGCATGGA | TCCGCAGGAG |
| 28501 | CGGCTGTTCC | TGACGGTCGC | CTGGGAGACC | CTGGAGCACG | CTGGCTACAC | CCTCGATCGC |
| 28561 | CTGAACCGCG | GGTCCGACGG | GCCCCCCGGC | GGCGCGGGCC | GCCGCAACCG | GGTCGGCGTC |
| 28621 | TTCGCGGGCG | TCATGTGGAG | CGACTACGGC | AAGCACGGGC | AGGACGAGCT | CCACAAGGGA |
| 28681 | AACCCCGTGA | TCGCGAGCGC | CGATTACTCG | TCGATCGCCA | ACCGGGTGTC | CTACGCGCTC |
| 28741 | AACCTGCACG | GCCCCAGCAT | CGCCTCCGAC | ACGGCCTGCT | CGTCGTCGCT | CGTCGCCATC |
| 28801 | CACCTGGCCT | GCGAGAGCCT | CCGGCGAGGC | GAGTGCCACT | ACGCCATCGC | CGGCGGGGTG |
| 28861 | AGCCTCTCGT | TGCACCCCGC | CAAGTACCTC | CAGATGAGCA | ACCTGAAGGC | CCTGTCCGCC |
| 28921 | GAGGGCAAGT | GCCGCAGCTT | CGGCGCCGGG | GGCGCCGGGT | ACGTGCCCGG | CGAGGGCGCG |
| 28981 | GGCGCGCTCC | TCCTCAAGCC | GCTGCGTCAG | GCCATCGCCG | ACGGCGACTA | CATCCACGCC |
| 29041 | GTCATCAGGG | GCACCGCGGT | CAACCACGAC | GGCAAGACCA | ACGGGTACAC | GGTCCCGAAC |
| 29101 | CCGAACGCGC | AAGCCGACGT | CATCTCTCAG | GCGCTGCGGC | AGGCCGGCGT | CGACGCGCGC |
| 29161 | ACGATCAGCT | ACGTGGAGGC | CCACGGGACA | GGCACCGAGC | TTGGCGATCC | GATCGAGGTG |
| 29221 | ACCGGCCTGT | CCAAGAGCTA | CCGGACCGAC | ACCAAGGACA | GGCAGTTCTG | CGCGCTGGGA |
| 29281 | TCTGCGAAGT | CCAACGTCGG | CCACCTGGAA | GGCGCGGCCG | GGGTCGCCGG | CGTGATCAAG |
| 29341 | GTGCTCTTGC | AGATGAAGCA | CAAGCAGATC | GCTCCGTCGC | TGCATTCGCG | GGAGCTGAAC |
| 29401 | CCCAGCATCG | ATTTCGCGAG | CTCGCCCTTC | AAGGTCCCTC | AGGAGCTCAG | CGCCTGGGAG |
| 29461 | CGACCGCGCC | TCGCGCGGCC | GGACGGCGCA | GGAGAGATCC | CGCGACGGGC | GGGCGTCAGC |
| 29521 | TCCTTCGGCG | CCGGCGGGAC | GAACGCGCAC | GTCATCCTGG | AGGAGTTCGA | GAACGCGCCG |
| 29581 | CGCGCGACAT | CGGGTCGGGA | GGACGTCCTC | GTGGTGCTCT | CGGCCAGGAG | CGAGGAGCGC |
| 29641 | CTGCGCGCCT | ACGCGGGCAA | GCTCGCCGCG | TCCTTGCAGC | TGCGGCTCGC | CGGCGAGGAC |
| 29701 | GCCGCCGAGC | ACCTCGACCT | CGAGCGCATC | GCCTACACGC | TGCAGACCGG | GCGTGAGGCG |
| 29761 | ATGGATTCGC | GGCTCGCCAT | CATCGCCTCC | GATCCTCGAC | AGCTCATCGC | CGACCTGGAG |
| 29821 | GCCTACAGCG | AAGGCCGCCT | GGACGACAAG | GGCCCTCGCT | GCTTCTCCGG | CACGGTCAAG |
| 29881 | CCCTATGAGC | TGCCGGAGCT | CGAGGCGACG | CACCAGGCCG | CCATCGACGA | GGCCGCGGCG |
| 29941 | AGCTACGACC | TGCGCGCGCT | CGCGCGACAG | TGGATCGCCG | GATACGCGAT | CGACTGGCCG |
| 30001 | AGGCTCTATC | CGTCTCCGCC | GCCCTACCCG | CTGGCCCTCC | CCACGTATCC | CTTCGCGCGA |
| 30061 | GACCGCTACT | GGATCCCCGT | CGCCGCGCAG | GCGCCGGCGG | TCGCCGCGGC | GGCGGCGAAG |
| 30121 | GGCCTCCACC | CCTTCCTGGA | CGCCAACGTA | TCCACCCTGG | AGGAGCTGGC | GTTCGAGAAG |
| 30181 | ACCTTCGCCC | GCGGCGACCT | CGTGCTGCGA | GACCACGTGA | TCGCCGGTCG | TCCGGTGCTC |
| 30241 | CCCGCGGCGG | TGTACCTGGA | GATAGCCCGC | GCCGCCGGTC | ACCACGCAGG | GCCGGGGCCG |
| 30301 | GTCTCCGGCG | TCCAAGACGC | CACGTGGGCG | AGGCCCATCG | TGGCCACGGG | CGACTCGGTC |
| 30361 | ACCTTGCGCG | TCAGCCTCGC | CCGGGAGCGC | CAGTCTGTCA | TTTACCGTGT | CACCTCGCAG |
| 30421 | CCCGAAGGGC | AGCCGGTGGT | GCACGGGTCC | GGGCACCTCA | CCTTCGCGGC | GCCCGCCGCC |
| 30481 | GCCCCCCCGC | CGGCGTCGCT | CCGCGACATC | ATCGCCCGCT | GCCCGCGGCA | GATCTCGGCC |
| 30541 | GACGACCTTT | ATCGCTCCTT | CGAGGCGCTG | GGGATCCACT | ATGGCCCCGC | GTTCCGCCCC |
| 30601 | GTTCAGGCGC | TCCACTGCGG | GGAGCGAGAG | GCCGTCGCCG | TCCTGAGGAT | GCCCGATGCC |
| 30661 | GCGGGCAGCG | GCGACTACGC | CCTGAACCCC | TCGCTGCTGG | ACGGCGCCCT | GCAGGCGATC |
| 30721 | GTCCATATCG | GGCTCGACAA | CGAGCTCGAT | CCGTCGCTCC | TGCGCCTGCC | CTTCGCCCTC |
| 30781 | GGCCGGCTCG | TGATCCGGCG | GCCCCTCGAC | GCGACGAGCT | GCCACGCGCA | CGCGATCCTC |
| 30841 | ACGCACGAGT | CGCGCGCAGG | CGAAGACCGG | GTGCTGAAAT | ACCGCATCGA | CGTCTATGAC |
| 30901 | GGCGACGGCG | CTCTCCTTGT | CGAGATCGTG | GACTACAGCG | TACGCGTCGT | GGCGCGCGAC |
| 30961 | GCGCTCGGCC | CCGCCGGCGC | CCGGGCTTCG | CAACCCGCGC | ACACGCTCTG | GTACGAGCCG |
| 31021 | CGCTGGGAGG | CGACGCCCGC | CGCTCCGGGG | CGCGCGTCCG | CGGCGTGGGA | TCGGCTGCCC |
| 31081 | GAGCGGCTCC | TGGTCTTCGG | CCGAGACGAC | GAGCTCACGT | CGCGCCTTGT | CGAGGCGCTG |
| 31141 | AGCCGGCTCC | GGCCCACGCG | GCGGATCGTC | CCGGGCGCGG | CGTTCGGCGC | GCTCGACCGG |
| 31201 | CAAGGCTACC | GGATCGATCC | GGCGGATCCG | AGCCACTACC | GCCGCCTCTC | GGAGGAGCTG |
| 31261 | GATCGCGACG | ACCCGTGGTC | GACGAGGACC | GTAGGCGTCA | TTCACCTCTG | GCGCTATCCG |
| 31321 | GCCGGCGCCG | AGGGCGCTCA | CGCAGGGCTC | CACTCCCTGC | TCTACCTCGT | CCAGAGCCTC |

TABLE 6-continued

| Disorazole PKS |
|---|
| 31381 ACCGCCCGCA ACGCCGCCCA GCGCGTCCGG TGCCTCGTCG CCGTCGGATC CACGGACGGC |
| 31441 GCCGCCGATC CGCGCGACGA GGCGCTGGCC GGCTTCGGCG CCGCCCTGTC CCCTGTCAAC |
| 31501 CCTCACCTCG AGCTCATCAC CCTGCAAGCC GACGCGACGC GGCTCGACGC GCAGCAGATG |
| 31561 GCGGGCGTCC TGCTCCACGA GCTGGCCGCG TCCGACACCG CCCATGGCAG CGAGATCCGC |
| 31621 TATACCGACG CTGCTGCCCG GTGGACACGC GCGTTACGGC CCCTGGAGGA CGGGCCGACG |
| 31681 CGGACAGCGG ACGCGCCGCC GCTGCGGACG GGCGGTGTGT ACGTGATCAC CGGCGGGAGC |
| 31741 GGCTACCTGG GCTCGACCTT CGCGCGCCAC CTCGCCGGGC GGTACGGGGC GCGGCTCGTC |
| 31801 CTCTGCGGTC GATCCTCGAA CGACGAGCGC AAGGAAGCCC TGGTGCGCGA GCTCCGCGGC |
| 31861 CTCGGTGGAG AGGCGGTCTA TGTTCAAGCG GACGTCAGCG ACGCAGGCGC CGCGCAGAGG |
| 31921 GTGGTGCAGG CCGCGCAGCA GCGCTTCGGG GCGCTCCACG GCATCCTCCA CGCCGCCGGG |
| 31981 ACCGACGAGG CGCCGCCGCT CGCGCGCGCC GACGCCGCCT CCTTCGCCAA GGTCCTGGAC |
| 32041 CCCAAGGTGC GCGGGACGCT GAACCTGGAC GCCGCGAGCC GCCAGGTGGT CACCCTGGAC |
| 32101 TTCTTCGCGC TCTTCTCGTC GATCGCCGCG GTGATGGGCG ACCTCGGCGC CGGCTGCTAC |
| 32161 GCGTACGCCA ACGCGTTCAT GGACCGCTTC GCCGCCGCTC GAGAGCGGCA GCGCGCGCAA |
| 32221 GGTCGACGAC ACGGCAAGAC GCTGGCGATC AACTGGCCCC TGTGGGCCGG CGAGGGCATG |
| 32281 AGCCTGCCCG AAGGGCAGCA GGAGCTGTAC GCCGGCATCG CAGGCATGCG CGCGCTCGAT |
| 32341 CCGGCGCTGG GCCTCGAGCT CTTCGCGCGG GCCCTCTCAG CCCCGGCGCC GCAGCTGCTC |
| 32401 GTGGTCCACG GGGATCCCGA GCGGATGCGG CGGGTCATCG AGCGGAGGAA CCCGCGCCCG |
| 32461 GCGGCGGCTT CATCGCATCC CGCCGAGCCC GCCGCCAGCG CCGCCCCCGG TGACGAGCGC |
| 32521 CTCGCCCAGG CCGTCGAGGA TTATCTCAAG GGCCACTTCG CCGCGGTCTT CAAGATGGAC |
| 32581 GCGGCGCAGA TCGACCCGCA AACCAGCTTT GACGACTACG GCATCGACTC GCTCGTGATC |
| 32641 GTGGAGCTCC ACGCGCGCCT CAGAAAGGAC ATGACGCCGC TGCCGCGCAC GACGTTCTTC |
| 32701 GAGCTCCGGA CCGTCCGCGC GGTCGCCGAC CACCTGCTCG CGTCTCGCCG CGCCGAGCTG |
| 32761 CGCCGGGTCG TGGGCCTCGA CCGGGAGGCC ACGGCGCCCC CCGCGCCGGA GGCCGGCGAG |
| 32821 CCCGCCCGGC GTGGAGGCGC GGAGGCCCCC GCCCACGCGG TGGCCCCGGG CCCGGCGGCC |
| 32881 AGCGCCTCAT CGAACGAGCA CGCGGGCGCC GGAGCGGGCC GCGACGCCGG CAGCCGAGCG |
| 32941 CCCGCCCGGC CCGGAGCGGC CCTCGCGGAC GAAGGCATCG CGATCATCGG CATGAGCGGC |
| 33001 CGGTACCCCA TGGCGCCCGA CCTGGACGCG TTCTGGGCCA ACCTCAAGGC CGGGCGCGAC |
| 33061 TGCGTCGAGG AGATCCCCGC GGAGCGATGG GACCACCGGC GGTACTTCGA CCCCGAGCCC |
| 33121 GGGAAGGAGG GCAAGAGCTA TTGCGCGTGG GGTGGGTTCA TCGAGGACGT CGACAAGTTC |
| 33181 GATCCGCTCT TCTTCCAGAT CTCGCCCAAG CAGGTGGCGA CGATGGACCC GCAGGAGCGG |
| 33241 CTCTTCCTGG AGACCGCGTG GGCCACGCTC GAGCACGGCG GGTACGGGCG CGTGCAGGAA |
| 33301 GACGCGGCCC GGATAGGGGT GTTCGCGGGC GTGATGTGGG ACGATTACGG CCTGCTCGGG |
| 33361 CTCGAGCAGG CGGCGCTCGG GAACCACGTG CCCGCCGGCT CCGATCACGC CTCGATCGCG |
| 33421 AACCGGATCT CGTTCGTGAT GAACCTGAGA GGCCCGAGCC TCACGGTCTC CACGGCGTGC |
| 33481 TCCTCGTCGC TCCTGGCGGT GCACCTGGCG GTGGAGAGCC TGAGGCGAGG CGAGTGCGCC |
| 33541 ATGGCCATCG CGGGAGGCGT CAACCTGTCC ATCCACCCGA GCAAGTACAC CCGTCTGTGC |
| 33601 CAGCTCCAGA TGCTCGCGCC GGACGGGCGC TGCCGCAGCT TCGGCGCCGG CGGAAAGGGG |
| 33661 TACGTGCCCG GAGAGGGCGT GGGCGCCGTG CTGCTGAAGC CCCTGAGCAG GGCCGAGGCC |
| 33721 GACGGCGACA CCATCTACGC CGTGATCAAG GGCAGCGCCG TCAACCACGG GGGCAAGACC |
| 33781 CACGGATACA CGGTCCCGAG CCCCAAGGCT CAGGCCGACG TCATCGGGCG CGCCCTCGAG |
| 33841 CGCGCCGGCG TCCACGCGCG CACGATCAGC TACGTGGAGG CCCACGGCAC GGGCACCGCG |
| 33901 CTGGGAGATC CCATCGAGGT CGGCGGGCTG GAGGAGAGCT TCAGGCGCGA CACCGGCGAC |
| 33961 AGGCAGTACT GCGCGCTGGG CTCGGTGAAA TCCAACATCG GCCACCTCGA GAGCGCCGCA |
| 34021 GGGATCGCGG CCCTCACGAA GGTCGCGCTG CAGCTGCACC ACCGGCAGAT CGTGCCGTCT |
| 34081 CTGCACGCCG AGGTGCTCAA TCCGAACATC CATTTCGAGA GCACGCCCTT CTACGTCCAG |
| 34141 CGAACGCTCG ACGCGTGGCG CCAGCCCGAG GTGCGCGAGG GCGGGGTGAC CGAGGTCCAC |
| 34201 CCGCGCCGCG CGGGCATCAG CTCCTTCGGC GCCGGTGGGA CCAACGTCCA CATGGTCGTC |
| 34261 GAGGAGTATC AGGCTTCGAC TCCTGCCCTC GAGATCGCGG CGGCCGAGCC TGAGCTTGTC |
| 34321 GTGCTCTCCG CGCACACCGA AGAGCGGCTC CGCGCTCACG CCGAGCGGCT GCTGCGCTTC |
| 34381 TTGCAAGGCT CGCGGCCTGG AGGGCTCCCC TCGCCCAGCG CGCCGGGCCG GCGCCTGCCG |
| 34441 GAGGCCGCGC AGCTCCGCGC CGAGCTGCGG GACATCGTGG CGCGACGCCT GGACGTCGCG |
| 34501 CCGCGCGACG TCGACGAGGA CGCCGAGATC TGCGAGCTCG GGCTCGGCGC GCTCGACGTG |
| 34561 CGCCGCCTGA CCGAAGACAT CGAGCGCCGC TTCGGCCTGC GGGTGAGCCC CGAGGACGTG |
| 34621 ACCGAGCGGA CGACGGTCGC AGGCCTCGCA GGGCGCCTGC GACACCTGGC AGCGCCGGAC |
| 34681 GCCGATCGGG ACGACAGCGC GGCTCGTCCC GCCGTGCGCT TGAGCGATCT CGCCTATACC |
| 34741 CTGCGCGCCG GTCGCGATCC CCGCCAGCAC CGCCTCGCGC TGCACGTCGC CGATCTGGAC |
| 34801 GAGCTCATCG AGCAGCTCCG GCGCTACTGC GAGGAAGGCG CGGCCGACGG GTCGCGCTGC |
| 34861 TTCGCCGGGC AGGCATCCAG GCGGGCCGGA AGCAGCGGAT CGCGCAAGGA GGCCATGGCG |
| 34921 GACGAGGCCC GGGTGCGCGC CGCCATCGCG GAGCGAGACC TGGCCACGCT CGGCCGGCTC |
| 34981 TGGGTCGCCG GGACCGACGT GGACTGGGAG CCGCTCGACG CGCGCCGGGC GCGGCGGCGC |
| 35041 GTCCCGCTGC CCACGTACCC CTTCGCCCGC GAGCGTTACT GGTTCTCCAG GAGCGGAGAC |
| 35101 GCCTTCACCC TCGGCCAGGC GGGAGAGAGG CGCTTGCACC CGCTCGTGCA GGCGAACACC |
| 35161 TCCACGTTCC ACGCGCACAC GTACTCCAGC CGGCTCCGGG GCGACGCGTT CTACCTCGCC |
| 35221 GATCACCTCG TGCACGGCCA GAAGCTCCTC CCCGCGGCGG CGTTCCTGGA GATGGCCCGC |
| 35281 GCCGCCGGGG AGATGGCGTC CGGGCGGCCG GTCCGCGACA TCCTCGACGT CGTCTGGACC |
| 35341 GCGCCCGTCG TCGTGGGCGC CGAGCCGCGC GAGATCGAGA TAACGCTCCG GCCGGCCGCC |
| 35401 GGCGCCATCG ACTTCGCCGT GTCCTCCGCC GCCGAGCGCG CGGTGATCTC CCACGCGCAG |
| 35461 GGGCGGATGC GCCTCGACGA GGGGGATCCC GCCGAAGAGG CGGCGCCGCC CCTCCCGCTC |
| 35521 GATGACATCC TCTCACGTTG CTCGAGGGTC ACCGGCGGAG ACGCGTGCTA CCGCCGCCTC |
| 35581 CAGCAGCTCG GGCTGCACCA CGGCGGCAGC ATGCGCGCGC TCCACGAGCT GCGCCGAGGC |
| 35641 GAGGGCGAGG CCATCGCGGA GATTCGCCTC CCGGAGCTTC ACCACGTGGA CTTCTCCACC |
| 35701 TTTGCCCTCC ATCCCGCCCT GCTCGACGCT GCCCTGCAAT GCACGCTCGG GCTGCTGGAC |
| 35761 GATGAGGCGG CCCGAGCCCC CTATCTTCCT TTCGCCGTCG GCCGGGTCAC GCTGCTCCGC |
| 35821 CCGCTGCCGG CGCGGCTCTT CGCCTATGCC ACGCCGTCGT CCGCGCCGCC GGGCACGAAC |
| 35881 GCCAGGGCCT CTCACGTCAC GCTGGCCGAT CCCGCCGGCC GGGTGCTCCT CGAGATGCGT |
| 35941 GATTTCACCG TCCGCCTCGC GACGGCGGAC GTCGCGCCCA CCCCCGCCCA GCGGCTCTAT |

TABLE 6-continued

| Disorazole PKS |
| --- |
| 36001 TTCCGGCCTG GCTTGCGCCC TCAGCGCGTC GACCGCCCCG CCGGCGCGCG CGCCCCGCAA |
| 36061 GGCCCCGTCC TGCTCCTCGA CACCGACGAT GTCCTCTGGA CGGCCGCCAG GGCGCGCCTC |
| 36121 CAGGCGCCGA TCGGCCTCGT CCTTCCAGGG CCGGAGTTCC AGGCCTCGAG CGACGATCGG |
| 36181 TATGTCATCG ATCCGAGCCG GCCAGAGCAC CATCGACGCC TGCTCGACGC GTTCGTGGCG |
| 36241 CGGCACGGCG TGCCTGCGTC GGTCTTGTAT CTCCGGTCGC TGCATGACGA CCGGGAGGCC |
| 36301 GCCGGCGACA CCCGCCACCT CGACGCGGTG TTGCACCTCT GCCGCGCGCT GCAGGAGCGG |
| 36361 CGAGGCGAGC GATCCGTTCG CGTGCTCTAC GTCCACCCGA CCGAGGGCGG CGCGGTCAGC |
| 36421 CCGCGCCACG CGGCGCTGGC TGCCTTCGCG CGGAGCGTGC GCCGTGAGGA TCCCAACCTC |
| 36481 CTGTGCAGGA CCGTGGCCGT GCCGCTCGAC GTCGGCCCAG GCCGCCTCGC CGACGCGTTG |
| 36541 CTCGCCGAGT GCAGCCCGGA CGCCGATCGC GCAGATCCCG CCGCCGAGGT GCATTACCAC |
| 36601 GAGGGTCAGC GGCTCGTGCG CTGCTTCGAG CCCTTCCAGC CCGACGCCAG CCGGCCCGTG |
| 36661 CCGCTGCGGG AGGAGGGGGT CTATGTCATC ACCGGCGGTG CCGGCGGGCT GGGGCTCATC |
| 36721 CTCTCCGACC ACCTGGCCCG GCGGTACCGC GCGAAGCTCG TGCTCTGCGG TCGCTCTCCG |
| 36781 CTGTCCGCGC AGCAAGCGTC GCGCGTCCGC GCCCTCGAAG CCTCGGGCGC CGAGGTCCTG |
| 36841 GTTCTGCGCG CCGACGTGAG CCAGCGAGAC CAGGCGTCCG CCGCCCTCCA CGAGGCCCGG |
| 36901 TCTCGGTTCG GGCGAATCGA CGGCGTCGTG CACGCCGCAG GCGCCTTGCG GGACGGCCTG |
| 36961 CTGTCCAAGA AGGACCCGGC CGACGTCGAC GCCGTGATAT CCGCCAAGGT GACAGGCACG |
| 37021 CTCCTCCTCG ACGAGCTCAC CCGGGAGGAT CATCTCGACT TCTTCCTGCT GTGCTCCTCG |
| 37081 GTCGCCGCGA TCCTCGGCAG CGCCGGTCAG GCCGACTATG CCTACGGCAA CGCCTTCATG |
| 37141 GATGCCTTCG CCGCCCTCCG CGAGGAGCAA CGGCACAGCG GCCGGCGGCG CGGGGCGACC |
| 37201 CTCTCGGTCA ACTGGCCGCT ATGGCAGGAA GGCACGATGA GGCCCGACGC CGAGTCGATC |
| 37261 GCGTGGATGA CGCGGGCGAC CGGGATGGTG CCCATGGACA CCGAGCAGGG CCTCGCCGCC |
| 37321 CTGGAGGACT GCCTGCGGGC CGGAGGGCCG CAGATCGCCG TGCTCGCCGG CGATCCCGGC |
| 37381 AAGATCCAGG CTCTGTTCAG CGGAGAGCGC GCCGCGCCGG CGGCCGGCGG CCCCGCCGCG |
| 37441 CTCCCGCCCG TCGAGCCCGG CGCGTACGCG CCCCGCGCGG TCGGCTTTCT CAAGCGCGTG |
| 37501 TTCTCCGAGC AGTGGCAGCT GCCGATCCAC CGCATCGACG CCGAGCAGTC GCTCGACCAG |
| 37561 TACGGGCTCG ACTCGATCAT GGCGATGAGC CTCACCCGCC GGCTGGAGAC GTTCTTCGGC |
| 37621 GAGCTCCCGA AGACGCTGCT CTTCGAGCAC CAGACCATCG CCGCGCTGGC TGGCTACCTC |
| 37681 GCTCGCCACC ACGCCGAGGC GCTCCGGCGC GTCGTCGGCG ACAGCGCCCC GGCGGTCGCT |
| 37741 CCGCCGCCCC GGCCCGATGC GGCCCCTCCC GGCGCGGCGC CCGCGCCTCG CGAGCTCTCC |
| 37801 GCCTCGCGCC TCCCTGCGCC GCAGCCCGGG GGCCTCGACA TCGCCATCGT CGGGCTCAGC |
| 37861 GGGCGCTACC CCATGGCGCC TGACCTCGAC GCGTTCTGGG AGAACCTCGC GGCCGGCCGC |
| 37921 GACTGCGTCG TGGAGATCCC CGCCGACCGC TGGGACCACG GGCGCTACTT CGATCCGAAC |
| 37981 CCGGGCGCGG CGGGCAAGAG CTACAGCAAA TGGGGCGGCT TCCTCGACGA CGTCGATCGC |
| 38041 TTCGATCCCC TCTTCTTCAA CATCGCGCCT CGGGAGGCGG AGGCCATGGA CCCACAGGAG |
| 38101 CGCGTGTTCC TGGAGGTCGC GTGGCACGCG CTGGAAGACG CGGGCTACGC GCGATCGCCG |
| 38161 CTGGCGAACC GCGCGACAGG CGTGTTCGTG GGCGTCATGT ACGGTCACTA TCAGCTCTTC |
| 38221 GGCGCCGAGG CGCTGGCGCT GGATCGGCCC GTGTCCGCGG GCTCGTCCTT CGCGTCCATC |
| 38281 GCCAATCGGG TGTCCTATTT CTTCGACTTC CGCGGCCCCA GCGTCGCGCT GGACACCATG |
| 38341 TGCTCCTCCT CGCTGACCGC GATCCACCTG GCCTGCGCCG CCCTTCAGCG AGGCGAGATC |
| 38401 GAGATGGCGC TCGCCGGCGG CGTGAACCTG TCCCTGCACC CTCAGAAGTA CATCCTGCTC |
| 38461 AGCCGCGGCA AGTTCATGGC CACCGACGGC CGGTGCCGCA GCTTCGGCGA GGGCGGCGAC |
| 38521 GGCTATGTCC CCGGCGAGGG CGCGGGGGCC GTCGTGCTCA AGCGCCTGGA CCGCGCGATC |
| 38581 GCCGACGGGG ATCGCATCCA TGGAGTCGTC AAGGCGAGCG CCCTCAACCA CGGCGGCAAG |
| 38641 ACCAGCGGCT ACACCGTCCC GAACCCCAGC GCTCAGGCCG ACGTCGTCGC CGCCGCGCTG |
| 38701 GCGCAGTCCG GCGTCGATCC GCGCACGATC ACCTATGTCG AGGCGCACGG GACCGGCACC |
| 38761 TCGCTGGGCG ATCCCATCGA GATCGCCGGA CTCACAAGGG CCTTCGAGGC TTCCCCGAAG |
| 38821 GAGCGTCCCA CCTGCGCCAT CGGGTCGGTC AAGTCGAACG TGGGGCACCT GGAGTCGGCC |
| 38881 GCGGGCGTCG CTGGCCTCAC CAAGGTGCTG CTGCAGATGG CGCATGAGCA GCTGGTCCCT |
| 38941 TCGATCCACG CGGATCCCCC CAACCCCAAC ATCAACTTTG CCGAGTCGCC GTTCCGTGTA |
| 39001 CAGCGGGAGC TCGGTCCCTG GCGGGCTCCT GTCGATGAGC GCGGCCAGCG GCTCCCCCTG |
| 39061 CGGGCGGGCC TGAGCTCCTT CGGCGCCGGC GGCGCCAACG CGCACCTCGT GCTGGAGGCC |
| 39121 TACGTGCCGG GCGACGAGGC AGGGGCCGCG GCCGCCGTGA CGGCCGGGAG CGAGCGCCCG |
| 39181 CAGGTGCTCG TGCTCTCGGC CCGCACGCCC GAGCGCTTGC GCGTCTCCGC CGCGCGGCTG |
| 39241 CTCGATCACC TCCGGACGCG CGCGCGGGGC ACGGCGCTGG CCGATGTCGC GTACAGCCTG |
| 39301 CAAGTCGGGC GCGAGGCCAT GGACGCGCGG CTGGCCCTCG TGGTCGACAG CGCGGAGCAG |
| 39361 GCCATCGCGC TGCTCGAGCA CCACCTCGGC GACCGCGCGC CCGAGGGCGG GGCGCCGCGC |
| 39421 GCCCAGGAGA CGCAGGGGCT GGAGCACATC CACGAGGGGA GCGCCAGGGC GGGCCACGTC |
| 39481 CGGCAGCTCG TTCACGGCCG GGCGGCCGCA TCTTTCCTGC AAGCCCTCCT CGATGAAGGC |
| 39541 GATCTGGACA GGATCGCCGC GCTCTGGGTG AGCGGGTGCG ACGTCGACTG GGCCCGCCTC |
| 39601 CACGAGGGAG CGAGGCCGCG CCGCGTCGCT CTGCCCGCCT ATCCCTTCGC GCGCGAGCGC |
| 39661 TGCTGGTTCG CCGTGCCCGC AGAGGACCGG CGCGGCGGGC TCCCGACCTC CGCCGAGGTC |
| 39721 GCGGCGACGG CGCGGCTGCA CCCGCTCCTG AGCCGCAACA CGTCGACGTT CAGAGAGCAG |
| 39781 CGGTTCGCCA CGACCTTCAC CGGCGAGGAG ATCCTCCTCT CGGACCACCG GATCCGAGGC |
| 39841 CGCGCCCTGC TGCCGGGCAC GGCTTACCTG GAGATGGCGC GTGTGGCCGG CGAGCTCTCC |
| 39901 GCCGAGGGCC GCGTCGGTCG TTTCACCGAG GTCACCTGGC TGCAGCCGAT CCAGGTCGAT |
| 39961 CGCGGCCCCG TCGAGGCCAC CCTCGACCTC CGGCCGACCG AGACGGGCTG CCAGTTTCGC |
| 40021 GTCTGCACGC AGGACGGGGC CCTCGTCCAC GTGCGCGGCC AGCTCCACGT CGAGCCCCAG |
| 40081 CCCCCGGGAG GCGAGCCGAC GGTGGACCTG GCGGCCATCA AGGCGCGCTG CCCCGAGCCT |
| 40141 CTCCTGCGGC AGGACTGCTA TCGGGCCCTG CGCGAGCAAG GGTTCGAGTA TGGCCCTGCG |
| 40201 TTCCAGGTCA TCGAGGCCTT CTACGACAAC GACGAGGAGG CCCTGGCCCT GCTCAGCGTC |
| 40261 GCCGAGCCTG ATTTCCAGGG CTTCGCCGGT GGGCTGCACC CCATGATCCT GGACGCGGCC |
| 40321 CTCCACGCCG GGATGCTGCA CAGGCGAGAG GGCGCGACCG GCGACGTCAC GCCGGTGCCC |
| 40381 TTCTACCTGG AAGAGCTGGT CGTCCTTCGC CCGCTGGAGC GCCGCTGCTA CGCGTATATG |
| 40441 CAGGTGCGGC GCCTCGCCGC AGGAGAAGAG CGGAGCGAGG TCGCCGTCAT GGACGTGACC |
| 40501 CTCGTGGACG AGGCGGGCTC GCCGCTCGTG CGCGTCAAAG GGTTCACGGG GCGGAAGCTC |
| 40561 GTCGACGCCG ACGAGGAGCC GGAGCAAAAC GCCGTCCTCT TCTTCGGGGA CGCCTGGCAG |

TABLE 6-continued

| Disorazole PKS |
|---|
| 40621 CCCGCCCCGC TCCCCTCGCG TCCGCCCGCC GGCGCGCCGC CGGCCAGCGT CCTCTTGATC |
| 40681 GCCGAGGACA CCGCCCGGGC GCGGGCGTTC GAGCGCCTGG TCCGCGCGCG GGGCGGTCAC |
| 40741 CTGACGTGGG TTTGCCCTGT CGGGTCGCCC CGGGCGCAGG CCGAGCCGAG CGGCGCGCCG |
| 40801 AGCGCGGGGT CCGGCGATCG CGGGGCTCCA GGGCTCGCGA TCGAGCCGCG CCCCGTCGAC |
| 40861 GACTACCGCG GGCTGCTCGC GACGTTGAAG GAGCAGGGCC GCCTGCCCGG CGGGATCATC |
| 40921 CGCCTGTGGG ACGCGCCGAG CCTCGACACG GAAGCGTCTT CGCCCGCGGA GGGACCGGAG |
| 40981 AGCGTCGAGG AGCTGAGAGA GCTCTTCCAC CTCGTCGTCG CGCTCGCGAG CGCGGTCCCT |
| 41041 CATCCGAAGG CTCGCCTGAT CCTCGCCTTC CACGGCGACC CGGCGCCCCT CGCCGTCGAG |
| 41101 GCCACGTCCG GCTTCTGCAG GTCCCTCGGG CTGCTGCTGC CGGGCCTGCG GTCGAGCACG |
| 41161 ATCCACTGGA CCCACCGCGA GCCCGAGCGC CACGCCGAGG ACCTCTGGGC CGAGCTCGCC |
| 41221 GATCCTGCGA CGAGGGGGAT CGGCGGGAGG AACGGGGCGG AGATCCGCTA TCGCGGTCCG |
| 41281 GACCGGCTCG CCCGCACCGC GGCGCCCGCC GCGCTCGCGC CCGACGCCGC GCCGGCCCCG |
| 41341 CTCCGCCACG GAGGGGTCTA CCTCATCGCG GGAGGCGCCG GCGGGCTCGG GTACCTGGTC |
| 41401 GCCCAGCACC TCGCCCATCG CTACCGCGCG AGCCTCGTGC TCACGGGCCG CTCGCCCCTC |
| 41461 GACGCCGGCA AGGAGCGGCA GCTCGCCGGG CTCCGGGACG CCGGCGGACA GGGGCTCTAT |
| 41521 TGCCAGGCGG ACGTCGCGGA CGAGGCGGCC ATGGCGGCCG CGGTGCGCCT GGCCAAGGAG |
| 41581 CGATTCGGCG CCTTGCACGG GGTGATCCAC GCGGCCGGCG TGCTCGACGA GCGCCCCGTC |
| 41641 GTCGAGAAGA CGTGGGGGGA GTTCCACGAG AACCTGCGGC CCAAGGTCGC CGGCAGCGCG |
| 41701 GTCCTCGACC GGATCACCGC GGCCGAGCCG CTCGACTTCT TCGCGGTGTT CTCCTCCACG |
| 41761 TCGGCCGTGC TCGGAGACTT CGGCTCCTGC GATTACGGAA GCGGCAACCG GTTCCAGATG |
| 41821 GCCTATGGCG CCCACCGCGA GCGGCTGCGG CAGCAGGGCC TCCGGCGCGG GATCACCGCC |
| 41881 GTCATGAACT GGCCGCTGTG GCGCGAGGGC GGCATGGGCG GTCGCGCCGA GTGGGAGCAA |
| 41941 ACCTACCTGA AGACGAGCGG CCTGGATTAC CTCGACACGG CCGCCGGTCT GGAGGCGTTC |
| 42001 GAGCGCATCC TCGGGGCCCG TCAGTCGCCC GTCACGGTGT TCTACGGCAA GCCGTCGCGT |
| 42061 GTGGCGAGGG CCCTCGGCCT CGACGCGCCG CCGCCCCCGG CGGGTCGCGG CGCGGCGGCC |
| 42121 GCGCCGCTCC CGCCGGCGGA GGCGCCGGCC GCCGCCCCGG AGGCGGCGGT CCGCGAGAGC |
| 42181 GCGGCGCGCG CGCCGCTGCG CGAGGTGATC CTCGACGCGA TCACCGAGGT CCTCAACGTC |
| 42241 CGGCGCGGCG CGATCGCGCC GGACGTCAAC ATCGCCGAGT ACGGCTTCGA CTCGGTGTCG |
| 42301 CTTGCGCAGC TCGCCGATCA GCTCGGCGCG CGCCTCGGGT TGAAGCTGGC GTCGCTCGTG |
| 42361 TTCTTCGAGC ACACGACGGT GGAAGAGATC GAGGCCTTCC TGGAGCGGAA GCACGGCGCC |
| 42421 GAGCTCCGCG CGCGGATGAA CGGGGCGCGG GAGCTCCACG GCCGCATGAA CGAGGCGCGA |
| 42481 GAGCTCCATG ACCGCATGAA CGGGGCGCGA GAGCTCCACG ACCGCATGAA CGAGGCGCGA |
| 42541 GAGCTCCACG ACCGCATGAA CGGGGCTCGA AAGGAGGCTC CGCGCGCGAA GGAGCCGGCG |
| 42601 CCGGCCGACC CGGCTCCGCC GCCGGCGCCT CGCGAGAACG GCTCGCGGCT CGCCGGCGCG |
| 42661 CCTCGCGCGA GCGCGCCGCG CAGGCCGCAG GAAGGCGCCT CGCGCGGCGA CATCGCCATC |
| 42721 ATCGGCGTCA GCGGCCGCTA CCCGCAGGCC GAGGACCTGC GCGCGCTCTG GGCGCGGCTC |
| 42781 CAGGCCGGCG AGAGCTGCAT CGAGGAGATC CCCGCCGAGC GCTGGGACAA GGATCGCTAC |
| 42841 TTCGACCCGC AAAAGGGCCG GAGCGGGAAG AGCGAGAGCA AGTGGGGCGG CTTCCTCCGC |
| 42901 GACGTCGATC AGTTCGATCC GCTGCTCTTC AACATCCCTC CCGCGCGGGC TCGGATCATG |
| 42961 GATCCCATGC AGCGGCTCTT CCTGGAGAGC GTCTATGAGA CGCTCGAGGA CGCCGGCTAC |
| 43021 ACCCGCGCCA TGCTGTCGAA GGACGGCGGC AAGGTCGGGG TGTACGTGGG CGCCATCTAC |
| 43081 CATCACTACG CCATGCTCGC CGCGGACGAG TCGACCCGCA GCCTCCTGCT CTCGGCCTTC |
| 43141 GGCGCCCACA TCGCCAACCA CGTGTCGCAC TTCTTCGATC TCCACGGGCC CTGCATGGCG |
| 43201 GTGGACACGA CCTGCGCGTC GTCGCTCACC GCCATCCACC TCGCGTGCGA GGGCCTGCTC |
| 43261 CTCGGGCGCA CGGATCTCGC CATCGCCGGC GGCGTCAACC TCTCCCTCAT CCCGGAGAAG |
| 43321 TACCTGGGCC TGAGCCAGCT CCAGTTCATG AGCGGCGGGG CGCTCAGCCG CCCCTTCGGC |
| 43381 GACAGCGACG GCATGATCCC CGGCGAGGGC GTCGGCGCCG TGCTGCTCAA GCCGCTGGAT |
| 43441 CGCGCGGTCC GCGATCGCGA CCACATCCAC GCGATCATCC GGTCCAGCGC CGTCAGCCAC |
| 43501 GGCGGCGCCA GCACGGGCTT CACGGCGCCG AACCTCAAGG CCCAGTCGGA CATGTTCGTG |
| 43561 GAGGCGATCG AGAGGGCGGG CATCGACCCA CGCACGATCA GCTACGTGGA GGCGGCCGCC |
| 43621 AACGGCGCTC CGCTCGGCGA CCCCATCGAG GTCAACGCGC TGACCAGGGC GTTCCGGCGC |
| 43681 TTCACCGCGG ACACGGGCTT CTGCGCGCTC GGCACCGTCA AGTCGAACAT CGGTCATCTG |
| 43741 GAAGGGGCCT CCGGCGTCTC CCAGCTCGCC AAGGTGCTGC TCCAGCTCCG GCACGGCGCG |
| 43801 CTGGCGCCGA CCATCAACGC CGAGCCGAGG AATCCGAACC TGCACCTCGA CGACACCCCG |
| 43861 TTCTACCTCC AGGAGCGCCT CGACGACTGG CGTCGACCGA TCATCTCCGG CCGCGAGGTC |
| 43921 CCGCGCCGCG CCATGATCAA CTCCTTCGGG GCCGGCGGGG GATATGCCAC CCTCGTGGTG |
| 43981 GAGGAGCACC GCCCGCCGCC GCGCGACGCC GCGCCGGGCC GCTCGCCCTC CGGGCCGCCC |
| 44041 GAGCTGTTCG TGCTCTCCGC GAGGAGCCGC AAGAGCCTGC GCGAGCTGGT CGTCAGGATG |
| 44101 CGCGGCTTCC TCGCCGAGGC GACCGACCTG CGCCTCGACG ACGTGGCCTA CACGCTCCAG |
| 44161 GTGGGGCGCG AGGCCCTGGA GCTGCGGCTC GCCGTGGTGG CGGACACCGT GGAGGCGCTC |
| 44221 CTCTCGGCGC TGGACGGCTA CCTCCGCGAT CCCGAGGTCC CCGCGCCGGG CGTCTTCACC |
| 44281 GGCCAGGCGG ATGGCGACGC GTCCAGCGGC GCCGCCGCGC CTCCCGCCCA GGCGCTCCGC |
| 44341 ACGCCCGAGG AGGCGGCGCG CCGGTGGGTC GCGGGCGCCG CGATCGACTG GGAGGCCCTC |
| 44401 TACCCCCTCC GCGACGCGCG GCGCATCCCG CTGCCGACCT ACCCGTTCGA CCGCCGGCGG |
| 44461 TGCTGGCTGG ATCCGGCGCC CTCCGACGAG GCCTCGCCGA GCCCCGCTGC GCCCCCGCCC |
| 44521 GAGGCGCCCC GGCCGCCGC GGCCCCGCCG GCGCCCCCCA GCGCGGAGGC CCGCGCGCTG |
| 44581 GAGGGCTACC TGTGCGCGCG GCTGGAGTCC ACGCTGGGCC TCGATCAGGG CGAGATCTCT |
| 44641 GCCCGCGCGT CGCTGCGGCG CCTCGGACTG GACTCGATCC TGGCCGCCAA GCTCAAGGTC |
| 44701 ACGCTGGAGG GAGAGCTCGC CATGACCATC CCCATGGAGG TCCTGAGCGG CGACAAGAGC |
| 44761 GTGGCGGAGC TCGGCGATTA TCTCTCTCGA CGGGGAGCCC GCGCGCCGGA GAGCCGGGCG |
| 44821 AAGGCGCGCA GCGGCGCGGC CGGGGCCGAC CTGTCCACCT CCCTCAAGGC CCTCTCGGGC |
| 44881 GCGGTGCTGC GGGAACAGTT CCTGGCGTTC GGGCACGACC TGGCCGGCGT ACCGGGCGAG |
| 44941 GAGCTGACTC GGCTCTACGC CATCCTGCAA GAGGAATGAT GACGATGGAA AGCGCGATGA |
| 45001 CCATCCAGGA GTTTGCCAAC TTGTCTGCGG AGGAGAAGGT GCAGGTCCTC CTGCGCTTGC |
| 45061 GGGACCGGCG CGCTTCGTGG CAGGCGGCCC CCGAGGGCCC CGCGGCCAGC GCTCAGCCCT |
| 45121 CGCTCCGGCC CGTGATCACG GCCCGCCCGG GCGATCGCTT CCTCCCCTTC CCGCTGACGC |
| 45181 CGATCCAGGA GTCCTTCCTG GTGGCCAAGC AGGTCGACAG GGCGGGCGAT CACGTCGGAT |

TABLE 6-continued

| Disorazole PKS | | | | | | |
|---|---|---|---|---|---|---|
| 45241 | GCCACATCTA | CCTGGAGATC | GACGAGGCGC | GCCTCGACGT | GGCGCGGCTC | GAGCGCGCCT |
| 45301 | TCCACCGGCT | CGTCGTCCAC | CACGACATGC | TCCGGACCGT | CGTTCGCGCC | GACGGCACCC |
| 45361 | AGCAGGTCCA | GGAGCCCGGG | CAGCCGCGCA | GCTTTCCGGT | GGACGACCTC | CGCGGGCGCC |
| 45421 | CGGGCGCGGC | GCTGGACGCG | CACCTGGAGA | GCGTGCGCGC | GAGCATGTCC | CACCGGGTCT |
| 45481 | ACGCGCCAGG | GGCCTGGCCG | CTCCACGAGA | TCCGGATCAC | CCGCTGCAGC | GACGAGCGCA |
| 45541 | GCGTCATCCA | CGTCAGCATC | GACGAGTGGA | TCCTGGACGC | CGCCGGCCTC | AACCTCCTGC |
| 45601 | TCACCCAGTG | GTACCGGCTC | TACAGCGACC | CTGACGCGAC | CCTGCCCGTC | TGCGACCTCA |
| 45661 | GCTTCCGCGA | TTACGTCCTG | GCCTCGAGGG | AATTCGAGCG | CTCGCCGGCC | TACCAGGGGG |
| 45721 | ATCTCGCCTA | CTGGTGCGAG | AAGCTGGCCC | AGATGCCCGG | GGGCCCGGCG | CTGCCTCGCG |
| 45781 | CCGAGCAGCC | CGGGAGGCCC | GCGGGCCGCG | CCTGCTACCC | CCGTCGCCGC | GTCCACGGGC |
| 45841 | GCCTGGCCGA | GGCGCCGTGG | CGCGCGCTCA | AGGACAAAGC | GCGGGAGCTG | GACGTCTCCC |
| 45901 | CGACGGCCCT | GCTCCTCACC | CTCTTCGCCG | AGGCCCTCGC | CTCCCACAGC | GCGCCCGGGC |
| 45961 | CGTTCTCCCT | CACGCTCACG | TACTTCAACC | GCCCGCCGAT | CCACCCGCAC | ATCGAGCGCC |
| 46021 | TGCTCGGCCC | GCTCATCTCC | ACCCACCGCT | TCCTCGTCGA | GGGAGCCACC | GATCTCACGC |
| 46081 | TGCAGGAGGA | GGTCCAGCGC | AGCCAGCGAC | AGCTCTGGCG | CGACATGGAC | CACGACCGCG |
| 46141 | CCGACAGCAT | CCTCGCGCTC | CGCGCCCTCA | GGGCGAGGCG | CGCGGCGCCC | CCCGCGAGCA |
| 46201 | CGGTCGTCTT | CACAAGCGTC | CTCCACAACG | TGAGCAGAGA | AGCCCGGCAG | CAGGGGCGGA |
| 46261 | GCTTCCTCGA | TCAAATCACC | TATTCGGTCA | CCCAGACCCC | GCAGGTCTAC | CTGGACCACC |
| 46321 | AGGTCTACGA | GAAGGACGGC | GGCCTTCATT | TCACGTGGGA | TGTCGTGGAC | GCCGTCTTCG |
| 46381 | CGCCCGGGTG | CGTCGACGCC | CTCTTCGACA | CGTATTCGCG | GCTCCTCGGG | GCGCTCGCGG |
| 46441 | CAGAGCCCTC | GCGCTGGACG | TCGCCGGGGT | GGCGCGAGGA | GCTCCTGGGC | CCGCGCCCCC |
| 46501 | CGCGCGGCGG | CGGGCCCGAC | CGGACCTCCG | CGGCGCCGGC | CGGCGAGGGT | CTCGAGATCA |
| 46561 | TCGCTCGGCC | GGAGGAGCGT | CACCAGAGAT | TCCCCCTGTC | CGATCTGCAG | CAGGCCTACT |
| 46621 | TCGTCGGCCG | CACCGGGTTC | GCCGCCAACG | GGGGCGTGAG | CTGCCAGATG | TACCAGGAGA |
| 46681 | TCGAGCTCCG | CGATCCGGAC | ATCGTCCGCC | TCGATCGGGC | GTGGCAGCGC | GTCATCGACG |
| 46741 | CCCACGAGAT | GCTGCGCGCG | GTCATCCACG | CCGACGGCAC | CCAGAGCATC | CGCGCCGAGG |
| 46801 | TCCCGCGCTA | CGTCATCGAG | GTCTCGGACC | TCCGCGCGGC | GTCGCCCGAG | GCCCGCGCGG |
| 46861 | AGGCCCTCGC | TCGGACGCGG | GAGACCATGG | TCGCCAGGGT | ATTCCCCCTG | GATCAGTGGC |
| 46921 | CCTTCTTCGA | GCTGCGGCTC | TCGCTCACCG | AGCCGTCGAG | GGCCGTCCTC | CACCTGAGCA |
| 46981 | TGGATCTGCT | CCTCGCCGAC | GCGACGAGCA | TCCACCTCGT | CCTGAAGCAG | CTCTTCGCCC |
| 47041 | TGTACGAGCG | GCCCGACGGG | CCGTGCGCCG | CGCCGCGGCT | CTCCTTCCGC | GACTACCAGC |
| 47101 | TCGCGCTCAA | GGACCACGAG | CGCGCCGCGG | GCCACGCCGT | CGGCGTCGCG | TACTGGCGCC |
| 47161 | GGAGGCTCGC | GGACCTCCCC | GGCGGCCCCG | AGCTCGGCAT | GCGCCTGCCC | GACGGCCGGG |
| 47221 | GCGGCCGCCT | GCGGCGCCGG | CAGTTCGACG | GCGTCCTGGA | GCGGTGGTCG | CGCCTCCAGG |
| 47281 | AGGGCGCCGC | GGCCCTCGGG | GTCTCGGCCG | AGGCCGTGCT | GCTGGGCGTC | TATTTCGAGG |
| 47341 | TCCTGGACGG | CCGCTCCAGC | CGGCGCCCCT | TCACCGTGGT | CGTGGCGCGC | TGGGACCGGC |
| 47401 | CGCCGGTGCA | CCCGGAGATC | GGCGCCGTGG | TCGGCGATTT | CACCGCGGTG | AGCTGGATCG |
| 47461 | TCTCGCCGCC | GGGCGAGACC | TTCGCCGAGC | GCGTCCGGCA | CCTGGAGCGC | ACGCTCTCCG |
| 47521 | AGGATCGCGA | GCACCGCCTG | GTCAGCGGCT | CCCGGGTGCT | GCAGCAGATG | GCCATCAAGT |
| 47581 | CCCGGAACAG | GCAGTTCCTC | ACGTTCCCGG | TGGTCTTCAC | CGGCCTCGGG | CCCAGCCTCA |
| 47641 | AGGGCGACCT | CCCCGACACC | GTCTCTCTCG | GATACCGCAT | CACCCAGACC | CCCCAGGTCT |
| 47701 | ACCTGGACAA | CATCAGCATG | GAGGCCGACG | ACGCCCTGCG | GCTCCACTGG | GACTCGGTCG |
| 47761 | AGGGCGTCTT | CCCCGAGGGG | CTCATCGAGT | CGATGTTCGG | CGCTTACTGC | CGCATCCTCG |
| 47821 | ACCGGCTGGC | CCGCGATCAC | GCCGCCTGGC | ACGAGGGCCG | GCTCGACGCG | CCGCGCGCCC |
| 47881 | CCGAGGGCCC | CGCGCCCCTG | CCCGCGCCGG | AGGGCCGCGA | CCGCGCGCCC | GGCGCCGCCC |
| 47941 | GGCACCGGAC | GACCCTGCAC | CGGCTGATCG | AGGAGCGCGC | GAGCCTGTGC | CCCGACCATG |
| 48001 | TCGCCCTGAT | CGCCGAGCGC | GAGCAGCTCA | CGTACCGGGA | GCTCAACCGC | CGGGCCAACC |
| 48061 | AGGCGGCGCG | CCGCCTGAGG | CGGCTCGGCG | TCGGGCCCGA | CGTCCTCGTC | GGCGTGCTCG |
| 48121 | CCGACCGATC | CATCGAGATG | GTCGTCGCCC | TCCTGGCCAT | CCTCAAGGCG | GGCGGGGCGT |
| 48181 | ACGTGCCGAT | CGACCCCACG | TACCCCCGCG | AGCGGATCGA | CTTCATCGCC | GAGGACGCCG |
| 48241 | GCCTCTCGGT | CCTCCTCCTC | GCGGAGGAGC | GCCGCCGGCT | CCCGTCGTTC | CGCGGCACCC |
| 48301 | AGCTGTGCCT | CTCCACCGAG | CGGCACCTCC | TGGACGGCGA | GGCGGAGCAC | GACCTCGGCC |
| 48361 | CCACCGCCGG | GCCGGATCAC | CTCGCTTACG | TCATCTACAC | CTCCGGGTCC | ACCGGCAAGC |
| 48421 | CCAAGGGGTG | CATGATCCCT | CATGACGCGA | TCTGCAACCG | GCTGCTCTGG | ATGCAGGACG |
| 48481 | AGTACCGGCT | GGCGCCGGAC | GATCGCGTCC | TGCAGAAGAC | CCCTTATACG | TTCGACGTCT |
| 48541 | CCGTGTGGGA | GTTCTTCCTG | CCCCTCATCG | CCGGCGCGAC | CCTGGTGATG | GCCAGGCCGG |
| 48601 | AGGGGCACAA | GGACGTCGCC | TACCTGGTCC | GGGTCATGGA | GGAGCAGCGG | ATCACCACGT |
| 48661 | GCCACTTCGT | GCCCTCCATG | CTGAACTTCT | TCCTCAAGGA | GCCGGCGCTC | CCAACGCACC |
| 48721 | TCCGCCAGGT | GTTCACGAGC | GGCGAGGCCC | TGTCCTACGA | CGTCATGGAC | ACGTTCCTGC |
| 48781 | GCCGCTCCCC | GGCCAGGCTC | CACAACCTCT | ACGGCCCGAC | GGAGGCCGCG | GTGGACGTCA |
| 48841 | CCTACTGGCC | GTGCGAGCGC | CGGCCCGATC | GCAAGGTGCC | GATCGGCCGC | GCGATCTCGA |
| 48901 | ACGTCGAGAT | CCACATCCTC | GACAGCGCGC | TCAGGCCCGT | GCCCGCGGGC | GCCGAGGGCG |
| 48961 | ATCTCTACAT | CGGCGGCGTC | TGCCTCGCCC | GCGGCTACCT | CAACCGGCCC | GAGCTCTCGC |
| 49021 | GCGAGCGGTT | CGTCCCGAGC | CCCTTCGACC | CCGGCGCCCG | CCTCTACAAC | ACCGGGGATC |
| 49081 | GCGCGCGCAC | CCTGGACGAC | GGGAACATCG | AGTACCTGGG | CCGGCTCGAC | GCCCAGGTCA |
| 49141 | AGCTGCGCGG | GTTCCGCATC | GAGCTCGGGG | AGATCGAGGC | GGCGCTGAGC | GCCCACGAGG |
| 49201 | CCGTGCAGGA | CGCCGTGGTC | GCCGTGCAGG | ACGCGCACAC | GGAGGACCCC | AAGCTCGTCG |
| 49261 | CCTACCTGGT | CACGGGCGGC | CGGCCCTTCC | CGGCGCCCGG | CGCCCTCAAG | GCCTATCTCA |
| 49321 | AGGAGCGCTT | GCCCGACTAC | ATGGTTCCGA | ACCGCTTCGC | GCCCATCGCC | CAGATCCCGG |
| 49381 | TGACGGCCCA | CGGCAAGCTC | GATCGCAAGG | CCCTGCCCTG | GCCGGTGCCG | GCTCCCTCGG |
| 49441 | CCCAGCCGGA | GCCCCCGCCC | GCCGGCGCGG | CCGCGGCGCC | CCCGGGCGCC | GCCCAGGCCC |
| 49501 | GGCGGCCAGC | GGGCGTCTCC | AGGGAGGCCG | CCGAGGAAGA | GCTCCAGCGC | ATCCTCGGCA |
| 49561 | AGGCGCTGCA | CCTCACCCGC | CTCGATCCCG | GCGCTGACCT | CTTCGAGCTG | GGCGCCACCT |
| 49621 | CGCTCACCAT | CGTGCAGGCG | TCACAGCACA | TCGAGGAGCG | CTTCGGCGTC | GGGCTGCCGG |
| 49681 | TCGAGGTCGT | CCTGGCCGAG | CCGACCCTCG | ACGCCATCGC | GCGGCACGTC | GCCGAGCGGA |
| 49741 | CGGCGGCTGG | CGCGCCCGAG | CCCCCGGCCC | CCGGGCCCGC | GCTGGACGCG | CCTCCCGCGG |
| 49801 | CGCCCGAGCC | CCCGGCCGCC | GCCGCCCCCG | GCCCGATCGA | TTTCTTCTCC | AGGGAAGATC |

TABLE 6-continued

| Disorazole PKS |
|---|
| 49861 GGGAGCGCTT CAAGCAGCAG CAGCTCCACC TGCGGCACGG CGTCGAGGGC CTCCCGACCG |
| 49921 TGGATCTGGC CGACGCTCCC GCGGCCCCGC GCCTCTACCG CGACCGCGGG AGCCGCCGCG |
| 49981 ACTACCGGCC CGAGCCCGTC TCGTTCGACG ACCTCTCGCG CCTCCTCGCC GTCCTCCGGC |
| 50041 GGTACCCGAG CGGCCAGCAG ACCCAGCTCT GCTATCCCTC GGCCGGCGGC ACCTACGCCG |
| 50101 TGCAGACCTA TCTTCACGTG AAGGAGGGCG CGGTCGAGCG CCTCCCGGCC GGGATCTACT |
| 50161 ACTACCACCC GGATCGCAAC CAGCTGGTGC TCATCAACGA TCGGCCCGCC ATCCGCCGGG |
| 50221 TGCACCACTT CTATTACAAC CGCGAGCACT TCGACCGCGC CGGGTTCGGG CTGTTCTTCA |
| 50281 TCGCCCAGAC CGACGCCATC CAGCCCATCT ACGGCGATCA GAGCCTCACC TTCGCCGCGA |
| 50341 TCGAGGCGGG GGCGATGATC CAGGCGCTCA TGAGCCATCA GGCGGAGGCG GACCTGGGCC |
| 50401 TGTGCGCCAT GGGAGGGCTC GACTTCGACG CCATCCGCGC CGACTTCAAG CTCGGGAGCG |
| 50461 GGCACCGGTA CATCGTCTGC ATGCTGGGGG GCCGCGTCGA TCGCGAAGGC GGCGGGCGGC |
| 50521 AGGGCCGCGC GAGGCTCCTC GAGAGCGCGG GGGCGGACGG CTCGTACGGG GCGGCCGCGG |
| 50581 CGGAGGCCGC CGCCCCGCGC CGCGAGCGCG AGGCTCCCGC CGGCGCGCGC GAGATCGCGG |
| 50641 TCATCGGCCT CGCCGGCCGC TACCCCGGCG CGGACACGCC ACGCCAGCTG TGGCGGGCGC |
| 50701 TCCGGAGCGG CCAGAGCGCC GTGACCCGGC CGCCCGCCGG GCGCTTCGGC GCGAGCGCCC |
| 50761 CGCAGGGCGA CGAGCCCCGA GGCGGCGGAG CCTCCCCGGG GTGGGGCGGC TACCTGGAGC |
| 50821 GGCTCGACCG CTTCGACAGC CTCTTCTTCG GCATCTCGCC CGCCGAGGCG AAGCTCATGG |
| 50881 ATCCCCAGGA GCGCCTGTTC ATCGAGGTGG CCTGGGAGTG CCTGGAGGAC GCCGGGTACA |
| 50941 CCCCCGAGGA GCTCCGTCGC GCCGCCCCCC GGGTGGGCGT CTTCGTCGGC GCCATGTGGA |
| 51001 GCGACTACCA GAGCGTGGGG CTGGAGGCGT GGCAGCGGGA CCGGCGCGCG AAGGCCGTGG |
| 51061 CGTTCCACTC CTCCATCGCC AACCGGATCT CGTATCTCTT CGATCTCCAC GGGCCGAGCG |
| 51121 TGGCCATCGA CACCTCCTGC TCCTCGGGCC TGACAGCGCT GCACCTGGCG AGCCGGAGCC |
| 51181 TCCGGCTCGG CGAGTGCGAC GTGCCCCTTG TCGGCGGGGT CAACCTCCTT GGTCACCCGT |
| 51241 TCCACCCCGA CCTGCTCGAG GGCCTCAACC TCACGTCCCG CGACGACAAG ACGCGCGCCT |
| 51301 TCGGCGCCGG GGGCAGCGGC TGGGTGCCCG GCGAGGGCGT CGGCGCCGTG CTGCTGCGGC |
| 51361 GCCTGCCCGA GGCCGAGGAG CGAGGCGAGC ACATCCGCTG CGTCCTCAAG GGCACGGCGC |
| 51421 TCGCCCACGC CGGCAAGGCG CCGCGGTACG GCATGCCGAG CACGCGCGCC CAGGCGGGCT |
| 51481 CGATCCGTGA CGCCCTCGCG GACGGCGGGG TCGCCGCGTC GGAGATCGAT TACGTCGAGT |
| 51541 GCGCCGCCAC CGGCTCCGGC ATCGCGGACG CCTCCGAGGT CGACGCGCTC AAGCAGGCGT |
| 51601 TCGAGGGGCG GAGCCCTGAC GGCCCGCCGT GCCTCCTCGG GTCGGTCAAG CCGAACATCG |
| 51661 GCCACCTCGA GTCCGCCTCG GCCTTGTCCC AGCTGACCAA GGTCATCCTC CAGCTGGAGC |
| 51721 ACGGCGAGAT CGCCCCGACG CTGCACACGG AGCCGCGCAA CCCGCTGATC CAGCTCGACG |
| 51781 GCACGCCCTT CCGGATCAAC CGCGCGCTGT CCCCCTGGCC CCGGGCCGCC GGGGCGGACG |
| 51841 CGCCCCCGCG GCGGGCGCTC ATCAATGCGT TCGGCGCCAC CGGATCGTCC GCCCACGCCG |
| 51901 TCGTGGAAGA GTACCGGCCT CGCCGCCGGG CCTCGACCCC CGCGGCGGCC GTCCCCGGCC |
| 51961 TGTTCGTCTT CGTCCTGTCC GCGGACACCG CCGAGCAGCT CGAGGCCTGC GCCCGCGCGC |
| 52021 TGGCGGAGCA CCTGCGCGAG CGCTCGACCG CGCGTCCGCG CGACGTCGCG CCGCCGGCCG |
| 52081 CGGCCGCAGA CGTCGCGTAC ACCCTCCAGG TGGGCCGTCG CGCGATGGAC GAGCGCCTCG |
| 52141 CCATCCTCGC CGGCGACCTG GACGAGCTCG AGGCCCGCCT GCGAGGCTTC CTCGGCGGGC |
| 52201 GTGGCGAGGA CGACGGCGAG CACCTCTTCC GGGGTCGCGC CTCGTCGCCG CGCGATCGAG |
| 52261 CGCCCCTGTC CCCGGAGGCG CCGCTCCCCG CGCTGGCGCG GGCCTGGGTG AACGGAGCAT |
| 52321 CCATCGCCTG GCACGACCTG TACACCGACG GATCGCGGCG CCGGGTGCCT CTCCCCACCT |
| 52381 ATCCCTTCGC CCGCCCGTCC CACTGGCTCG GTCGGCCCGC CGGAGACGCC GCGGCGCCTG |
| 52441 CCGTCGCGCG CGGCGAGACC GCCGAGGAGG CGCCCTCGCG CGGCGAGACC GCCGAGGAGG |
| 52501 CGCCCTCGCG CGGCGAGACC GCCGAGGAGG CGCCCTCGCG CGAGACCGCC GAGGAGGCGC |
| 52561 CCGCCGCCCT GGCGCCGGCG ACCGCGGATC CCGCGCTGCG CAAGGCCACC CTCGGCCTGC |
| 52621 TGTCCTCCTG CTTCGCCGAG GTCGCCGAGA TCCCGCGCCG CAGCCTCGAT CCCGAGGTCC |
| 52681 CCCTGGACCG CTATGGCCTC AACTCGATGC TGATCGCCCA GCTCTCCGCG CGACTCGAGG |
| 52741 CGCTCCTCGG CGAGCTGCCG AAGACCCTCC TCTTCGAGCA CCACACCCTG GCAGCCCTCA |
| 52801 CCGACTGGCT GGTCGCCCAC CGCGGCGACG CGCTCCTCCG CCGCCTCGAC CTCCCGCGGC |
| 52861 GGGCCGCGGG GCCCGCGGCG TCCCCCGGCG CGCTCCCCGC GGCGCCCGCA GCCCGCCGCG |
| 52921 GGCCGGCGAG AGAGCGCTCG GCCGCGGCCT CTCCGGCCCT CGCGCCGGCC GCGCCTCTCG |
| 52981 AGAGCGTCGA CATCGCCATC GTCGGCCTGA GCGGCCGCTA TCCCGGGGCC GACACCATCG |
| 53041 ACGCCTTCTG GAGCAACCTG CGACAGGGGC GTGACAGCGT CACCGAGGTG CCGGCCGATC |
| 53101 GCTGGGACGC CGCCGCGATC TTCGACCCCG AGGGAGGCCC CGGCAAGACC CGCCAGCGCT |
| 53161 GGGGTGGCTT CCTCGATCGC GTCGATCGCT TCGACGCGCT CCTCTTCAAC ATCTCACCGC |
| 53221 GCGAGGCGGC GGGCATGGAT CCCCAGGAGA GGCTGTTCCT GGAGATCGCC TGGTGCGCCT |
| 53281 TCGAGGACGC GGTCTATACC CGCGAGCGGC TCGCCGAAGA ACAGGCGCGC GCCGGGGTGG |
| 53341 GTGCCGGCGT GTTCGTCGGC AGCATGTACC AGCAGTACTC CATGCTCGCC CGGACGCCCG |
| 53401 ACGCCGGGGC CTCGTCGTCC TTCTGGTCGA TCGCCAACCG GGTCTCCTAC TTCTTCGATC |
| 53461 TGCGCGGGCC GAGCCTCGCC GTGGACACCG CGTGCGCCTC GTCCCTCACC GCGCTCCACC |
| 53521 TGGCCTGCGA GAGCCTGCGC CGGGGGGAGT GCTGCCTCGC GCTGGCTGGC GGCGTCAACC |
| 53581 TCCACCTCCA CCCGCACAAG TACGTCGCCC TCGATCGCCT GGGCCTGCTC GGGAGCGGCG |
| 53641 CCGCCAGCAA GAGCCTCGGC GACGGGGACG GCTACGTGCC CGGCGAGGCG GTCGGCGCCG |
| 53701 TCGTCCTCAA GCCGCTCGAT CGCGCCGTCG CGGACAACGA CCGCATCTAT GGCGTCATCA |
| 53761 AGGGGAGCTT CGCCAACCAC GCCGGCAAGA CCGCCGGGTA CGGTGTTCCC AGCCCCGCCG |
| 53821 CCCAGGCCGA CCTGATCGCG GCGGCCCTGC GCCGGACGGG CATCGATCCC GAGACCATCG |
| 53881 GTTATATCGA GGTCGCCGCC AACGGCTCCT CCCTGGGCGA CGCGATCGAG CTCGCGGGCC |
| 53941 TCACGCAGGC GTTCCGCCGG TTCACCGCCC GGAAGCACTT CTGCGCCGTG GGCTCGGTCA |
| 54001 AGTCCAACAT CGGCCATCCG GAGGCCGCGT CGGGTATCGC TCAGCTCACC AAGGTGCTCG |
| 54061 GCCAGCTCCA TCACCGGACG CTGGTGCCCA CGCTCCACGC GGAGCCGCAC AACCCGAACA |
| 54121 TCGACCTGAG GGACAGCCCG TTCTATGTCC AGCGAGAGCT CGGCCCGTGG ACGGCGCCGA |
| 54181 CCCTCGCCGG CGAGGGGGGG ACCGCGGAGC TCCCGCGCCG CGCCGCGATC AGCTCGTTCG |
| 54241 GGGCGGGCGG CGCCAACACC CATCTCCTCG TCGAGGAGTA CTCGCCCCGC CCGGACGACC |
| 54301 GGGGGGACGA GGGCGCGGTC CCCGGCGCGG TCATCGTCCC GCTGTCCGCC CGGACCGCGG |
| 54361 GGCAGCTGCG CGCGTACGCC GCGACGCTGG CGGACGACCT GGAGCGCCGC TCGCGCCCGC |
| 54421 GCGGCCACGG CGAGCGGGCG CTCGCCGATC GCGACCTGAC CGCCGTGGCA TATACCCTCC |

TABLE 6-continued

| Disorazole PKS | | | | | | |
|---|---|---|---|---|---|---|
| 54481 | AGGTCGGGCG | AGAGGCCATG | AACGAGCGCT | CGGCCATCGT | GACCGCGAGC | CTCGGCGATC |
| 54541 | TCATCACGAA | GCTGAGGCAG | CTCGCCGCGG | GCCAGACGGA | CGTCGACGAT | CTCCATGTGG |
| 54601 | GCAGCGCCGC | GGCGTCGCTC | TCCGCCCTGA | TGCTCGACGG | CCGCGAGGGC | CAGGCGTTCC |
| 54661 | TCTCGATCCT | CGTGGAGGAC | GGTCGCCACG | ACAAGCTGGC | CCGGCTCTGG | GTGAGCGGCG |
| 54721 | CCCGGATCGA | CTGGCGGACG | CTTTACGGCG | GCTCGACGCC | GAGGCCCCTG | TCGCTGCCCC |
| 54781 | ACTACCCCTT | TGCCGGCGAC | CGCCACTGGC | TCGACGACGA | GGCGCTGCCG | CATGGCGCCG |
| 54841 | CCTGGAGCGC | GACCGCGGCG | CCTCCGGCCC | AGACCGCCGC | CTGGAGCGCG | ACCGCGGCGC |
| 54901 | CTCCGGCCCG | CGCCGCGGAT | CCTGGGGGTG | CGGCGCCGCC | CGAGGGGCCA | GGCGGCGCGC |
| 54961 | CTCCGGGCGG | CGCGGCCCGG | CAGCGCATCG | CGCAGGAGCT | CACGGCGATG | GTCTGCGATG |
| 55021 | TCCTCAAGAT | GCAGGCCAGG | GACGTCGACG | GGGACGAGGC | GCTCCGCAAC | TACGGCATGG |
| 55081 | ATTCCCGCCT | CTCCGCCGCC | TTCATGCGGT | CGGTGCAGCA | GCGGTACGGG | TCGAGCGTGC |
| 55141 | CGCTCAGCGC | CGCGCACACC | CATCCCACCT | TGAACCAGCT | CACGGCCCAC | ATTCATGGCC |
| 55201 | TCCTGAGCAG | CAACGGCGCA | GCCCGGCACC | CGTCCGCCGC | GCCCCTCGCC | GCGACCTCGC |
| 55261 | CGTCGATCGC | CACGGCCCCG | GCGGCCTCCG | CAGCCCCGGC | GGCCTCCGCG | GCCCCGGCGG |
| 55321 | CCTCCGCAGC | CCCCGCGGCC | TCCGCAGCCC | CCCCGGCCTC | CGCGGCCCCC | GCGGCCTCCG |
| 55381 | CGGCCTCCGC | AGTCCCGGCG | GCGCTCCACG | AGGCTCCGGC | GCCTGATCCG | CGCGCGGGGG |
| 55441 | ACGCACGGCC | CGGGGCGGAC | AGCATCGCCC | CGCAGCCCGA | GCCGGGGCCC | AACCCCGACG |
| 55501 | AGCTCGTCGT | CATCAACCCG | CGCGGCTCAC | GCGGGAGCTC | GTTCTGGGTG | CACGGCGCGC |
| 55561 | CTGGGCTCGC | GCAGCCGCTC | TATCCCCTGT | CTGCCGCGCT | CGGCACGGAT | TACCCGTTCT |
| 55621 | TCGCCTTCCA | GGCCCGGGGC | GTCGACGGGC | TCGCCATGCC | CTTCACGAGC | ATCGAGGAGA |
| 55681 | TCGCGGCCCA | TTACGTCGCC | TGCCTGCGGC | AGCGTAGTCC | GAGAGGGCCT | TACGTCGTGG |
| 55741 | GTGGGCTGTC | CTCCGGCGGC | ATCATCGCCT | TCGAGATGGC | CCGGCAGCTC | CTCTCGCAAG |
| 55801 | GGGAGCGCGT | CTCCCGGCTG | GTCATGCTCG | ACACCTATCC | CGCGGTCGCG | GGCCTCGCGC |
| 55861 | AGGAGACGCC | GGGCGACATC | GACCCGATCC | TGCCGCTCCT | GCTCATGGCC | AACTCCTTCA |
| 55921 | TCAGCTTCGA | TCGCGACGGA | GACACGGCGA | TCAAGCCCGA | CGACCTCGCC | GGGCTCCCCC |
| 55981 | CCCCGATGCA | GCTCCCGCGG | GCGGTGCAGC | TGATCAAGGA | GCGGAGCCGC | ACCGCGCTCA |
| 56041 | GCCGTGATCA | GATCTACAGG | ATGCTGAACG | GGAACATCGC | TGTCTACAAG | CACCTCGACC |
| 56101 | TCGCGTGCAG | GAAGTACCAG | CCCGGGGTCC | TCGACGCCGT | GGACGTCCTG | TTCTTCAAAG |
| 56161 | CGGAGAAAGG | CTTCTTCGGC | GGAGCGAACC | CGCTGGGGCT | GCCCATCCTG | GACGTGTTTT |
| 56221 | CCTCCTATGA | CTATGTGACC | CCGTGGCGCC | AGTGGATACG | CGGAGGCCTG | CAGGTCGTGG |
| 56281 | AGCTGCCTTG | CGCGCACGTC | GACCTCCTGG | AGCCCCCGGC | GCTCCACCAG | GTGGTCGCGC |
| 56341 | ACGTCCGCGA | GGCGCTTTCA | TGACAGGTGA | GCGGCGCGCG | GGCGCCGAGC | CCGCGGGCGC |
| 56401 | CGAGCCCGCG | GGCGCCGAGC | CCGCGCGCCG | CATTGCGTTT | GATATCGAGC | GATCCGCATG |
| 56461 | ATAGACGACC | CCGCGCTGAA | CCCTACGTGG | TCTCGACCGC | TGAGCCAGCG | ATTCCGGGGA |
| 56521 | TCAAGCGCTC | TCCCGGTGGC | AGCTCGCGCG | TGTCGTTGCT | GGAGCGCCGA | GCCAGACCGG |
| 56581 | ACCGAGCCAG | GCAGCCAGGG | AGAGCGCAGC | GCTGCGCGAC | GAGGTGCCCT | CCTTGCACAG |
| 56641 | GGCGACGAGG | AGCGACGACG | CGATGCGCCC | GCCCTCGGCT | GCGCGGCGAC | GGGAGGTCTT |
| 56701 | GAGAGAGGCC | CTCTCGGGCC | CGATGACAGA | CAATCAGCCG | ACAAGGCTCT | CAACGGACGG |
| 56761 | AAATTTACAT | GACATCGATG | GCGCGACACC | TGGACATCCA | CGAGGAGCTC | CCCCAGACCG |
| 56821 | CTCCGCTGCC | GCCACGCGCG | ATCCAGTGGC | GCAAGGCGTT | TCGGCTGGCC | AAGGAGCTTA |
| 56881 | CGGAGAAGCC | CTTCACCGCC | GAGCTCTCCT | ACGAGCTCAT | CTTGTCGCTC | GACGGCGGGG |
| 56941 | CGACCGAGCG | CATGTTTCAA | GACTTCCTCG | CCGAGCCGGG | GGCGCGCGCG | CTGATCCAGA |
| 57001 | AGCGGCCCGA | CCTGGCCGCG | ACGCTGTCCG | ACCTGGATCT | CCTCGGATCC | ATGCCAGAGG |
| 57061 | GCAGCTTGGG | CCGCACCTAC | AAGGAGATGA | CGGAGCGGGA | CGGGTACGCT | GTCAACGGGA |
| 57121 | TCATCCATGT | GATGAAGGCG | GTCCCGACCT | TCCAGGAGGT | GGCGCCGGAT | CCCCTTCGCC |
| 57181 | AGTGGTTCAG | CTTCCGCGGC | GCGGTGCTCC | ACGACGTCGC | CCATGCGCTC | ACGGGGTACG |
| 57241 | GGCGTGACCT | CGCGGGCGAG | GTCGCGCTCG | GCCTCTACCT | CGCGGCGGTT | TACCCGCCGT |
| 57301 | ACCGGAGCGG | GGTCGTGTAT | TCGTTCATCA | CCGCGCTCGC | GTCGGTCACG | GCGCCGCAGG |
| 57361 | ACCAGAAGCT | CCGCAACCTA | TCCTACCTGC | GCGACGTGTG | GATCCGCGGC | CGCCGCTCGC |
| 57421 | GCATCCCCCT | CAGCGCGCCC | TGGGAGGACC | TGCTCCCGCT | CCAGGTGGAG | GAGGTGTGCC |
| 57481 | GTATGTACCA | GGTCCCGCTC | GTGCGCGAGA | CGCACGCGGA | GGGCATCCTC | CGCGATGCGT |
| 57541 | TCGAGAAAGG | TCCCTGGATA | CCGTCGTTCA | AGGCGCAGAG | CTGGGCATAG | CCGGCCCGCG |
| 57601 | CGCCGAGGCG | AGCCCCTGGC | GGGCACGTCG | TGGCGGCGCG | CCTCCTCCCC | GCGGCGCGAC |
| 57661 | GGGCTCCCTC | GCGCCGCGGG | GAGGAGGCGC | GCCCGCTCTT | CTGCATGACC | CCTGTGCAAG |
| 57721 | AACCCTGAGG | CGGCCTGGGG | GCCGAGGAAG | AACCGATGAA | AGCATACATG | TTTCCCGGGC |
| 57781 | AAGGGTCTCA | GGCGAAGGGG | ATGGGACGGG | CGCTGTTCGA | CGCCTTCCCC | GCGCTCACGG |
| 57841 | CCAGAGCGGA | TGGGGTCCTT | GGCTACTCCA | TCCGGGCGCT | GTGCCAGGAC | GATCCTGATC |
| 57901 | AGCGCTTGAG | CCAGACCCAG | TTCACCCAGC | CGGCCCTCTA | CGTGGTCAAC | GCCTTGTCGT |
| 57961 | ACCTGAAGAG | GCGCGAGGAG | GAGGCTCCCC | CCGATTTCCT | GGCCGGCCAC | AGCCTGGGCG |
| 58021 | AGTTCAGCGC | CCTGTTCGCC | GCGGGGGTGT | TCGACTTCGA | GACCGGCCTC | GCGCTGGTGA |
| 58081 | AGAAGCGAGG | AGAGCTGATG | GGCGATGCCC | GCGGCGGCGG | GATGGCCGCG | GTCATCGGTC |
| 58141 | TGGACGAGGA | GCGGGTTCGC | GAGCTCCTCG | ACCAGAACGG | CGCCACGGCG | GTCGACATCG |
| 58201 | CCAACCTCAA | CAGCCCATCT | CAGGTGGTGA | TCTCGGGGGC | GAAGGACGAG | ATCGCCCGCC |
| 58261 | TGCAGGTCCC | CTTCGAGGCG | GCAGGGGCGA | AGAAGTACAC | AGTCCTGCGC | GTGAGCGCCG |
| 58321 | CTTTCCATTC | CCGCTTCATG | CGACCGGCGA | TGGTCGAGTT | CGGGCGGTTC | CTGGAGGGCT |
| 58381 | ATGATTTCGC | GCCTCCGAAG | ATCCCGGTGA | TCTCCAACGT | GACCGCCCGG | CCCTGCAAGG |
| 58441 | CCGATGGCAT | CCGCGCGGCC | TTGAGCGAGC | AGATCGCCAG | TCCGGTCCGG | TGGTGCGAGT |
| 58501 | CGATACGTTA | CCTGATGGGC | AGGGGCGTCG | AGGAGTTCGT | GGAGTGCGGC | CACGGCATCG |
| 58561 | TCCTGACCGG | CCTGTACGCC | CAGATCCGTC | GAGACGCCCA | GCCCCTCGTC | GTCGACGAGG |
| 58621 | GCGCGGCCGG | GCTCGACCGG | CGGGGTCCGC | CGGCGGAGGG | CCGGTCGCCG | GCTGCCTTCG |
| 58681 | GCTCATCGAG | GCTGGCGGCG | CCCGCGCAGA | ACGGGGCGGC | GGCGCCCGCG | CAGAACGGGG |
| 58741 | CGGCGGCGCC | CGCGCCGGCG | GCGCATGCGG | CCGCGGCGCA | TGCGCCCGCG | CAGAACGGGG |
| 58801 | CGGCGGCGCC | CGCGCAGAAC | GGGGCAGCGG | CGCCCGCGCC | GGCGGCGCGT | GCGGCCGCGG |
| 58861 | CGCATGCGGC | GGCGCCGAAC | GGGGCGGCGT | CGCCGGAGCC | GGCGGCGCCC | GCGCCGAGGG |
| 58921 | GGGCCAGGCG | GATCTCGCTC | GAGGTGCTGG | GCAGCGCCGC | GTTCCGGGAG | GACTACCGCT |
| 58981 | TGCGCTACGC | GTATGTCGCG | GGCTCGCTGG | TCGATGGGAT | CTCCTCCAAG | GAGATGATCG |
| 59041 | TGCGCATGGG | CAAGGCGGGC | CTGATCGGCT | ATCTCGGGAC | CAAGGGGGTG | GCGCTGGACG |

TABLE 6-continued

| Disorazole PKS | | | | | | |
|---|---|---|---|---|---|---|
| 59101 | CCGTCGAGGC | GTCGATCCTC | CACATCCAGC | GCGAGCTCCG | CGGTGGTGAG | AGCTACGGGG |
| 59161 | TGAGCCTGTG | GTGCGACATG | GACGACTCGC | ACCTCGAATG | GCAGAGCGTC | GCGCTCTACC |
| 59221 | TCAAGCACGA | TATTCGGTAC | GTCGAGGCGG | TCGCCTACAT | GCAGATAACG | CCGGCCCTTG |
| 59281 | TCTGCTATCG | TCTCAAGGGC | GCTCACCGCG | ATCACCGCGG | CAGGGCAGCC | ACGCCTCGGC |
| 59341 | GCGTGCTCGC | CAGGGTCTCG | AACCTCGAGG | TCGCCCGGGC | GTTCATGAGC | CCCGCTGCGG |
| 59401 | ATCACGTCCT | CGATCAGCTC | GTGAAGGACG | GGCGGCTCAC | GCGCGAGGAG | GGCGCGCTCG |
| 59461 | GCCGGGAGCT | CCCCATCAGC | GACGACCTGT | GCGCGCACGC | CGACTCCGGC | GGCCCCACGG |
| 59521 | ACATGGGGAC | GGCAGCGGTG | CTGATGCCGG | CCATGGCGCG | GCTGCGCGAC | GACATGATGA |
| 59581 | CGCGGTACGG | GTACGAAAAG | CGGATCCGCG | TCGGCATGGC | CGGCGGCCTC | GGCGCCCCGG |
| 59641 | AGGCGGTCGC | GTCCGCGTTC | ATGCTGGGGG | CCGACTTCAT | CGTCACCAAC | TCCGTGAACC |
| 59701 | AGTGCTCGCC | GGAGGCGAGC | ACCAGCGACC | GGGTCAAGGA | CATGCTGCAG | GCCGCGAGCG |
| 59761 | TCCACGACAC | CGCGTATGCG | CCCGCCGGCG | ACCTGTTCGA | GATGGGAGCC | CGGGTCCAGG |
| 59821 | TCCTCAAGCG | TGGCGTGCTC | TTCCCCGCGC | GGGCCAACCG | CCTGTACGAG | CTCTACCGGC |
| 59881 | ACTACCCGTC | CCTGGACGCG | CTCGACGCGA | GGACCAGGGA | TCAGCTCGAG | AAGCACTATT |
| 59941 | TCAGGCGCGA | TCTCGACGAT | GTCTGGCGGG | ATGCGCTGTC | TCGCCGGCCG | GGGACGCGCC |
| 60001 | CGGCGGACGC | GGCCAGGACG | GAGCGCGACC | CCAAGCACAG | GATGTCCCTC | GTCTTCCGGT |
| 60061 | GGTATTTCGC | CCACTGCTCG | GAGCTGGCGC | GGCGAGGGGA | CGAGGAGAAT | CGGGTGAACT |
| 60121 | ACCAAGTCCA | CTGCGGGCCG | GCCATGGGCG | CCTTCAACCA | GTGGGCGAAG | GGCACGGATC |
| 60181 | TGGAGGACTG | GCGCAACCGC | CATGTCGATG | TGATCGCCGA | GCGCCTGATG | CGGGCGTCCG |
| 60241 | CCGATCTCCT | CGATCACCGC | ATGCGCGCGC | TCTCGCGGTA | GCGAGCTCGA | GGTGCATCGT |
| 60301 | ACCCTTGGAG | GCCCATGGCT | GCTCGAGACA | GCCGACGAAG | ACGTAAGGGG | CGAGCCGCCC |
| 60361 | GCCCTCACCC | GCCCCGCGTC | TTCTCCGCCT | TCTGCCGCCG | CACCATCTCC | GCGATCCAGA |
| 60421 | CCGGCGCGAA | CGGCGGCGTG | CAGCCCGGCG | ACGCCGGATA | GTCTTTGAGC | ACCTCGAGCC |
| 60481 | GCTCGCCGAT | GGCGATGGCG | CGGGCGCGCA | GCCCGGGGTT | GCGGATGCCG | ATCTCGGCGA |
| 60541 | GGCAGTGGTT | CATCGACCAC | TGCTTCGGGC | CCGGCGCCGT | CTTCATCTCC | GCCTCGATCT |
| 60601 | GGTCGAGCAG | CGCGGGGAGA | TCGAGGCCGG | CAGGGCTCTT | CACGACGCGG | TCCGTCGTCA |
| 60661 | GGCTCCATCC | GGCGCGCCCG | ACCAGCTCGC | TCGCGGAGTC | CTTCCAGCGG | ACACGCAGCT |
| 60721 | CCTCGGCGTG | GCGCGACGCC | TTCACCACGT | TGACGATGAA | CCAGTCGAGC | AGCTTGGGGT |
| 60781 | AGCCGATCTC | CCGGACCATC | GCGTCCAGCT | CGTCCGCCGA | GAAGGCCTTC | GGCTTGAACA |
| 60841 | CGAGCGTCGC | CAGGAGGCGG | GCGTCGGGGT | CCCCGGTGCG | CCACAGCTCG | CCGGCCAGGG |
| 60901 | CGTGGTCGGA | CTTCAGCTGC | TTCGCCAGCG | CGCGGAGCTG | GGTGAGGTTC | ACGCCGTGGG |
| 60961 | CGTCTCCGGC | GCGGGCGTTG | ACCTCGCGCA | TCTTCTCGTT | GCCCAGCGCG | GCGAGCTCCC |
| 61021 | GCATGACGTG | GGTGACGTTC | ATGGGCTCGG | GCTAGCCGTA | TCCGCGGGCG | TCGTCCAGCG |
| 61081 | GCGCGGCGTC | GCGGGGGAGG | ACCAGCCGCG | TTCCTGGGAT | GGATCGCGGC | CGTGGCTCGG |
| 61141 | CTGCGCGCCC | GGCCGTCGAT | CCGCCGCCCC | GCTGGCGGAT | ACCGCCCCCT | GGCGCGGCGG |
| 61201 | ACGGCGCGCG | GGCGCTCAGG | GAGCGGGGGT | GAAGGCGACG | GTGAGCGTGT | AGGGGCCGGC |
| 61261 | GTCCATCGGC | CTGTAGGTGT | CGACGACGAC | GAACAGGGGC | TCACCGCCGG | TGACATCGAT |
| 61321 | CACGAGCGTC | TCGTCATCGC | CGCGGCCTTC | GTCGTCGACG | CACTCGATCT | CGGCGTCGAA |
| 61381 | GTCCGCGCAG | CGCTCGCGCA | GGTAGAAGCC | CAAGTCGGTC | TCGGCGGACA | GCGTCAGCGT |
| 61441 | GAGCGTGCCG | TCGCTCGGCG | GCGTGAACCG | GTGGATCGTC | TCCGGCACGT | CCCATCCGAG |
| 61501 | GCAGCTGCCC | TCGAACGCCG | ACGTAGCGGT | CGCCGTGTTG | CCCGTGTTCT | CGCCGATGGC |
| 61561 | GAGCTCGGCC | GCGCCCTCGC | ACAGCACGTC | GAGCTCGTAG | GCGCACGTGG | CGGAGCATCC |
| 61621 | ATCGCCGCTC | GTGGTGTTGC | CGTCGTCGCA | CTCCTCGATC | GCGTCGACGG | CCCCGTCCCC |
| 61681 | GCAGACGATC | GGCGCGAAGC | TGACGTTCAG | CGTGTAGGGA | CCGGCCTCCC | CCGGCTCGTA |
| 61741 | GGAGTCGACG | ACGATCGGCA | CGGTCTGGCC | GTCGCTCACG | TAGATCTCGA | TCCGCTCTTC |
| 61801 | GTCGGGGAAG | CCATCGGAGG | GGTAGCTCTC | GTCGGAGCAG | TCGATCTCGG | AGAGCATGTC |
| 61861 | CGCGCACGAG | CTGCGGGCGT | AGACGCTATG | ATCGGTCGGC | GACTCGAGCT | CGACCACGAG |
| 61921 | CGTGCCCGAC | TGCCCGGCGG | GCGGCGTGAA | CAGGTGGATC | TCTTCCGGTC | CGTGCCCCGT |
| 61981 | GTTGCCGAGG | TAGCAGGTCC | CTTCCAGCGC | GCTCGTGCTC | TCCGACGTGT | CGCCGTGGAT |
| 62041 | CGTCGTCGAG | ACGATGGGTG | TCGCGCTCGC | GCAGGCGGCC | TCGGCGATCG | GCGTGCAGGT |
| 62101 | CGCGGCGCAG | TCGGTGTCCG | CGCAATCGTA | GGACCCGTCC | CCGTCGTCGT | CCTCGTAGTT |
| 62161 | CGTGCAGTCC | GTCTCGCCGA | GCGTGCAGAC | GCCGCTCAGG | GTGTCGCACA | CGCCGAGCGA |
| 62221 | GGGGCACTGC | GCGTTCGAGG | TGCACCTCGG | GACGCAGGCC | CGGATGCCGC | CGCCGATGTC |
| 62281 | CTCGCAGGCA | TAACCGTCGC | GGCACTCCGA | CGACGCGCTG | CAGAGCGAAA | GGCACGCTCC |
| 62341 | CACGCCGTCG | AAGAGATCAA | GACAGACCCC | GCCGTCGCAC | TCTCCGCCCG | GCGCTGGCTC |
| 62401 | GGCCGCGGGA | TCACACAGGT | CCGAGCAGAG | CCCGGATGGG | TATCCCAATT | CCTCCTCGGA |
| 62461 | GAGGCAGATG | TCCCCGGTGC | ACTCATCGTC | CGTCGCGCAG | GCCTCGTACA | GCGCGCCCGC |
| 62521 | CGGCCCGCCG | CCGGTGCCGG | TGGGCTCGCC | GCCGCCGCCG | CCGCCGCCGG | TAGGCTCGCC |
| 62581 | GCCGCCGCCG | CCGCCGGTAG | GCTCGCCGCC | GCCGCCGCCG | CCGGTGGGCT | CGCCGCCGCC |
| 62641 | GCCGCCGCCG | CCGCCGGTAG | GCTCGCCGCC | GCCGCCGCCG | CCGGTGGGCT | CGCCGCCGCC |
| 62701 | GCCGCCGCCG | GTGGGCTCGC | CGCCGCCGCC | GCCGCCGGTA | GGCTCGCCGC | CGCCGCCGCC |
| 62761 | GCCGCCGGTG | GGCTCGCCGC | CGCCGCCGCC | GCCGCCGGTG | GGCTCGCCGC | CGCCGCCGCC |
| 62821 | GCCGCCGGTG | GGCTCGCCGC | CGCCGCCGCC | GCCGGTGGGC | TCGCCGCCGC | CGCCGCCGCC |
| 62881 | GGTGGGCTCG | CCGCCGCCGC | CGCCGGTGCC | AGTTCCGGTG | CTCGTGGCGT | CGATGCCGCC |
| 62941 | GGCACCGCCA | GCGCCGCCGG | AGCCGCCATG | GCCGCCGGCG | CCGCCCTGGC | CGTCATCGTC |
| 63001 | TCCGCATCCC | GCGGCTGCCG | ACAGCGCCAG | CACGAAAAGA | CCTGCAACGA | TTCGTACGTT |
| 63061 | CATCCACCTG | CTCCAACGCA | AGAGAGAGTT | GTCGTGACGC | GAGGTGCGCC | TCACCCCGCG |
| 63121 | GCGCCGCGTG | ATGCCATCTT | CGGCGCAACC | GCTCCGCCTG | CCAATCCCCC | TTTCATGGGG |
| 63181 | GCCGCCTGCC | TCGGCGCGCG | CCGGTGTGCG | CGGTCGCCGG | ATCCGACCGG | GGCTGCGCAT |
| 63241 | CGCCATGAGA | ATCCGCGCGC | GGAGCACACA | ATGCGCCTGC | ATCGTCTGCT | GCGAGGGCTG |
| 63301 | CTCTTCTTTC | ATCGAACGTT | CCGGGCTCGC | CCTTCGACGA | TACTCCAATG | AGGGTCGTTG |
| 63361 | TCTCAGGCAC | ATTGGCACGG | AGGGCTCCAC | AGCCCAGCGG | GGTGACCTCC | TGGGGTAGCT |
| 63421 | CGTGTTGATC | AGGAAGCTCC | ATCCGGAGAG | CCTGCCGCGA | ATACCTGGGC | GAAAGCAGGA |
| 63481 | TCGGGATCCG | AGTCGAGCGA | CCAGGCGCGG | GGCCCTATGC | GCTGTCGAGC | AGGATGGCCC |
| 63541 | CGATCTTCAT | GCGCACCGCC | TCCAGGTGCG | CCTGGCGGCG | ACGGCCAACC | ACACTCTCCC |
| 63601 | ACTTGAACGT | GTCATCAGCA | CTGCGTTCGG | CTCCTCAGGT | TGTGTGAACG | TTCACATTTG |
| 63661 | GTCTATCATG | CCGGCACTCG | AGGCGCTTGA | ACGCGTCATC | AGCATTTTGT | TCGGCTCTCC |

TABLE 6-continued

Disorazole PKS

```
63721 AGGTTGTGTG AACGTTCACA TTTGGTCTAT CATGCCGGCA CTCGAGGCGC TTCGACAAGG
63781 TGGGCCGATG TCCGTTTCTC GCCGCGGAGG AAATTTATGA TCAAAATGGT CAACGGCGCA
63841 GCGCTGCTCG CCGTGCTCGC CGCAGGGTCC CTGACGCTGG CCGCGTGCGG TCGCAGCGAC
63901 GACGGCGCGT CCGGCGGCAA GGAGCTGCGG GTCTGGCACT ACGAGGCTCC CGAGAGCGCC
63961 ATGGGCGTGG CCTGGAGCGA GGCCATCAAG GAGTTCGAGG CGACCCATCC GGGCGTGAAG
64021 GTCAAGCTCG AGGAGAAGGG CTTCGAGCAG ATCCAGAAGA CCGCGCCCAT GATCATGAAC
64081 TCCAAGAGCG CCCCCGACGT CATGGAGTAC AACAAGGGCA ACGCGACCGC CGGGCTGCTG
64141 TCCAGGCAGG GCCTGCTCCA GGACCTCACC CCCGAGGCCA CCAAGCGCGG CTGGGACAAG
64201 CTGATCAGCC CCGGCGTGCA GGTCGTCGCC AGGTACGACG AAAAGGGCAT CATGGGCGGC
64261 GACACGTGGT ACGGGGTGCC CAACTACGCC GAGTACGTGC AGGTCTACTA CAACAAGGAC
64321 CTGTTCAAGA AGTACGACGT CAAGGTCCCG ACCACGTTCG ACGAGCTCAC CAGGGCGATG
64381 GACGCGTTCG TCGCCAAGGG CGTGACGCCG CTGGCCAACG CCGGCGCCGA GTACATGGCG
64441 CAGCAGTACG TCTACCAGCT CGCGCTGGAC AAGGCCGACC AGCCGTGGGT GAGCGCGTTC
64501 CAGCGCTACA CCGGCAAGAC CGACTTCACC GACCCGGCAT GGACGTACGG GGCGACGACG
64561 TTCGCCGACT GGGTGACGAA GGGCTACATC GCCAAGAGCT CGGTCAGCAC CAAGGCCGAG
64621 GATGCCGGCG TGGCGTTCAT GAGCGGCAAG ATCCCGATGA TGTTCTCCGG GAGCTGGTGG
64681 TTCGGGCGCG TGGCCAAGGA GGCCAAATTC GACTGGGATA CCTTCGTGTG GCCCGGCGCC
64741 AAGATGACCC TCGGATCGGG CGGCAACCTG TGGGTCGTCC CGGCGGGATC GAAGAACAAG
64801 CAGCTCGCCT ACGACTTCAT CGACATCACG CTGAAGAAGA AGATCCAGAA CATCCTCGGC
64861 AACGCGGGCG GCGTCCCGGT GGCGGCCGAC AGCTCGGCCA TCACCGAGCC CAGGGCCAGG
64921 AAGCTCATCG ACGGCTTCAA CACCCTCGCC CAGTCGAGCC GCCTGGCGTA CTACCCGGAC
64981 TGGCCGGTCG CGGGCTTCTA CGACCAGTGG GTCTCGCAGA CCCAGAAGCT CATGAACGGC
65041 GATCCGCCGC GGTCGGTGCT CAGCGGCATC CACAAGACCT ACGACAGCGC CCTGCCCAAG
65101 TGACGACACG CAGCTCGACA GGGCGTGACC GGCTCGCCTA CCTTCCCTAC CTGATCCCCG
65161 GGCTGCTGCT GTTCACCGGG GTCATCGGGG CGCCGTTCCT GATGAACATC GGGACCAGCT
65221 TCACCGACTG GCCCGGCGTC GGCACCCCGA AGTGGGTGGG GCTGGACAAC TACCGGGAGC
65281 TGGCGACCGA CGGTGAGTTC TGGGCGTCGT TCCGGAACAA CGTCCTGGTC ATCGTCGGGA
65341 TGGCGATCGT CCCGACGATG ATCGGGCTCG TGCTGGCCTC CGCCCTGACC GACCTGATCG
65401 ACCGGCACTT CGGCCCGCGC GCCGCCAGCG TCCTGCGCGC CTGCATCTAC CTGCCGCAGG
65461 TCCTGCCGAT CGTCATCGCG GGCATCGTCT GGAGCTGGCT GCTCCCCCCC GAGAACGGCG
65521 CGGTGAACGA CCTGCTGGGC GCGATCGGGC TCGGCTCGCT CGCGCACGAC TGGCTCCGCG
65581 ATCCCGCCAC CGCGCTGTGG AGCGTCATGG GGGTCATGGT CTGGATCCAG ATCGGATTCC
65641 CCCTCGTGAT CTTCATGTCC GGGCTGCAGC GCGTGGACCC CTCACTGTAC GAGGCGGCCG
65701 AGATCGACGG CGCCTCGTGG GCGCAGCGCT TCTGGCACGT CACGATCCCG CAGATCAGGC
65761 CCGAGCTCTT CGTGGTGCTG CTGTGGACGA CGATCGCCGC GCTCAAGGCG TTCCCGCACA
65821 TCTTCGTGCT CACGAGGGGC GGCCCGGGAG GCGCGACCAA CGTGCCGTCC TACTACTCCT
65881 ACGTCAATTT CTTCGAGAAG ACCGACGTCG GCTACGGCTC GGCGATCGCC ACCGTGATGA
65941 CGCTGATCAT CCTCGCGCTC ACCGTCGCCT TCCTGCGGCT GCAGGGCCGT GAGCCGGGGG
66001 AAGAGCGGTG ACCGTGACGC TGGCCCAGAG CCCGGGGAGC GCCCCCGCGC GGCGCCGGCC
66061 GCGGCGGCGC CGCCGGGGTC CGTCGGCCTA CGCGGCGCTG GTGGCGCTGG CCGCGCTGGC
66121 CGGGATCATG TTGATCCCCT TCGCCGTGGT GGTCTTCAAC GCGCTGAAGA CGCCGGAGGA
66181 GTACACCGCC AACGGCCCGC TCGCCCCGCC GGAGGGAATC CATCTCGAGG GGATCAAGGA
66241 CTTCTGGGAG CGCGTCGGCT TCGGCCATGT CCTGTTCAAC AGCCTGCTCA TCAGCGGCTC
66301 GGTGGCCGTG CTGGCGGTCC TGCTGTCGGT GCTGAACGCC TACGCGCTGG GCATCGGCCG
66361 GATCAAGGGC CGGACGTGGG TGCTTGTCCT GCTGCTGATG GCCAACACGC TGCCGCAGGA
66421 GTCGCTGGTC TACCCGCTGT ACTACCTGGC CAACGAGCTC GGGCTCTACG ACACCCGGAT
66481 CAGCGTCATC CTCGTGTTCA CCGTCATCCA GAGCGCGTTC GGCACCTACC TGCTGTCGTC
66541 GGTGATGTCG GCGTTCCCCC GGCCGCTGCT GGATGCGGCG CAGATAGACG GCGCCAGCCG
66601 GTGGCAGATC CTGTGGCGGG TGGTCGTGCC GGTCGTGCGG CCCACGCTGG CGGTGATGCT
66661 CGTCTTCTTC TTCATCTGGA CCTGGAACGA GTTCCTGATC CCCCTCGTCT TCCTCATCTC
66721 CAACGACAAC CAGACGGTCT CGGTCGCGCT CGGCGTGCTG CAGGGGCAGC GGCTGATGGA
66781 CGCCACCATG TCGAGCGCCG CCGCGCTGCT CGGCCTGCTG CCGACCGTCG TCTTCTTCCT
66841 CATCTTCCAG CGCACGCTAT CGCGCGGACT CACAGCAGGA GCGATCAAGG AATGAAGTTC
66901 ACCGACGGTT ACTGGATGAT GCGCAAGGGC GTGCACGCGG TTTACCCGGC GGAGGTCCTC
66961 GACGTCGACG CCGGGCCGGC GTCGTTCGTC GTGCACGCGC CCGTCCAGCG GATCCGGCAC
67021 CGCGGCGACC TGCTCAAGGG CCCGGTGGTA ACCGTCTCCT GCGCGTCCCC GATGCCGGAC
67081 GTCATAGCCG TCACCATCAC GCACTTCGCG GGCGAGCGGC CCCGCGGCCC GGCGTTCGCG
67141 CTGGCCACCG ACCCGACCGG GGAGGTGACG GTGGACGAGG ACGCGGCCAC GCTGACCTCC
67201 GGCGCGCTGT CGGTGCGGGT CGGGCGCGGC GAGGGGTGGA GGCTGGACTT CGTGGCCGGG
67261 GGCCGCCGCC TCACCGGCAG CGCGCAGAAG GCGATGGCGA TCATCGACAC CGACGACGGC
67321 CGCCACTACG TGCGCGAGCA GCTCGACCTC GGCGTGGACC ACTTCGTGTA CGGCCTCGGC
67381 GAGCGCTTCG GGCCGCTGGT CAAGAACGGC CAGGCCGTCG ACATCTGGAA CGCCGACGGC
67441 GGCACGTCCA GCGAGCAGGC GTACAAGAAC GTGCCGTTCT TCCTCACCAA CGCGGGCTAC
67501 GGCGTGTTCG TCGACCATCC CGGGCGCGTG TCGTTCGAGG TGGCCTCCGA GGCGATGGCG
67561 CGGGCGCAGT TCAGCGTCGA GGGCCAGTCG ATGCGCTACT TCCTCATCTA CGGGCCGACG
67621 CCGAGGGAGA TCCTGCGCAA GTACACCGCG CTCACCGGGC GGCCCGCGCG GGTGCCGGTC
67681 TGGTCGTACG GGCTGTGGCT GTCCACCTCG TTCACCACCG AGTACGACGA GGCGACCGTC
67741 ACCTCGTTCA TCGACGGAAT GGCCGAGCGG GGCCTGCCGC TCAGCGTCTT CCACTTCGAC
67801 TGCTTCTGGA TGCGCGAGCT CCAGTGGTGC GATTTCGAGT GGGACCCGCG CGTGTTCCCC
67861 GACCCGCCCG GGATGCTGCG CCGGCTCAGG GGGCGCGGCC TGCGCGTCTG CGTCTGGATC
67921 AACCCCTACA TCGGGCAGCG CTCGCCGCTG TTCGAGGAGG GCAGGGCGCG CGGCTACCTG
67981 CTGCGGCGGC CGAACGGCGA CGTGTGGCAG TGGGACCTGT GGCAGCCGGG CCTGGCCGTC
68041 GTCGACTTCA CCAACCCCGA GGCCCGCGCC TGGTACGCCG CCAAGCTCGA CGCGCTGCTC
68101 GACATGGGCG TGGACTGCTT CAAGACCGAC TTCGGCGAGC GCATCCCCAC CGACGTCGTC
68161 TACCACGACG GGTCCGACCC GGAACGCGCG CACAACTACT ACGCCTACCT CTACAACAAG
68221 ACGGTGTTCG AGCTCTTGCG CGAGCGGCGC GGCGAGGGCG AGGCGGTCGT GTTTGCCCGC
68281 TCCGCCACGG CGGGCGGGCA GCAGTTCCCG GTGCACTGGG GCGGCGACTG CGAGTCGACG
```

TABLE 6-continued

| Disorazole PKS |
|---|
| 68341 TTCGAGGGCA TGGGGGAGAG CCTGCGAGGC GGCCTGTCGC TGGGCATGTC GGGATTCGGC |
| 68401 TTCTGGAGCC ACGACATCGG CGGGTTCGAG GGCACCCCCG ACCCGGCGCT GTTCAAGCGA |
| 68461 TGGATCGCGT TCGGGCTGCT GTCGTCGCAC AGCCGGCTGC ACGGGAGCCG CTCCTACCGG |
| 68521 GTGCCATGGC TGTTCGACGA CGAGGCGGTG GAGGTGCTGC GGCGCTTCAG CCGGCTGAAG |
| 68581 ATGCGGCTGA TGCCCTACCT GGCCGGGGCC GCGCGGCAGG CGTACGTCGA GGGCTTGCCG |
| 68641 ATGATGCGCG CGATGGTCGT CGAGTTCCCG GACGACCCGG CCTGCACGCA CCTGGAGCGG |
| 68701 CAGTACATGC TGGGCGGCGA CCTGCTCGTG GCGCCCGTCT TCTCCGCCGA CGGGGAGCTC |
| 68761 TCTTATTATG TGCCGCGCGG CGTGTGGACG CGCTATCTCA CCGGCGAGCG CGTCGAGGGC |
| 68821 GGCCGCTGGG TGCGCGAGCG CCACGGGTTC GACAGCGCGC CGCTGCTCGT CCGGCCGGGG |
| 68881 GCGGTGATCC CCGAGGGCGC GGTGGAGGAC CGCCCCGACT ACGACCACGC GGCGGGTGTG |
| 68941 ACGCTGCGCG TGTACGAGCC GGCGGACGGC GCCCGCGTCA TGACCGTGAT CCCGGGCGCG |
| 69001 GGCGGGGACG CGGTCACGAC GTTCACCACG TCACGGGACG GCCCGGTGGT GCGGGTGGAG |
| 69061 GCCGCGGGCG CCCCAGGTGC CTGGAACGTT CTCCTCGTCA ACCGCCGCGT CGTGGCCGTT |
| 69121 GAAGGCGGGG AGAGCGCGGA GCACCCGCGA GGAGCGCTGG TCAGGGCGGC CGGCGGCGAG |
| 69181 CTGGTCATCA CGCTGGAGGG GGAGGGCTCA ACCGCGGCAT CCGTCCCCAG AGGAGACGAC |
| 69241 CGATGAAGGA CTGACGGGCG CGCCGCAGAG CACGGCGCGC GCGCCGTAGA ACCGCTCTAC |
| 69301 GCTGCCCACG AAGATGCGCG TCGGCGCGCT GAACAGCGAC GTTGCCGCGA GGTCCGGAGT |
| 69361 CTGCGCGACG GAGCGCCGGC CGCGCGGCRG ATCCTCGTCG CCAGCCGGCG ATCGATCGCG |
| 69421 CCGCAAATTG CTTGTATGCC TGCTGTTATC GACGAGGGAG CGCGCCTCTC GATATAGAAT |
| 69481 GACGTCACGC GCTGTACGAT CCTGCTCGAC GGCTGAGCGC AATGGGTTTT ACCCTGGGCT |
| 69541 CATGTCCACT TGGTCTAGAT TTCGCCGGAT CGCTGCCTCC GCACCGCTCG TCCTCGCGCT |
| 69601 GGCGCTCCAC CCCTCGGGTT CGAGCGCGAG TGACATGCTG CCATTCCAGG ATCCCGGTCT |
| 69661 GTCGATCGAG CTCCGCGTCC GCGACCTCCT CGGGCGGCTC ACGCTCGACG AGAAGCTCTC |
| 69721 GCTCCTGCAT CAGTTCCAGC CTGCCATTCC GCGGCTCGGG ATTCCGGACT TCAAGGCCGG |
| 69781 CACCGAGGCG CTGCACGGCG TGGCCTGGTC GACCGATCGC GACAACGGCG GCGCCGTCGT |
| 69841 GACGGCGACC GGCACGGTGT TCCCGCAGGC GATCGGCCTG GCGACGACCT GGAACCCGGA |
| 69901 TCTCGTCCGG CAGGTCGGCG AGGCTGTCGG AGACGAGGTT CGCGGCTATC ACGCGCTCGC |
| 69961 CCCTCGCATC TGGGGTCTGC AGGTGTGGGC GCCCGTGGTC AACCTCCTGC GCGACCCGCG |
| 70021 CTGGGGGCGC AACGAGGAGG GCTACTCCGA GGACCCACTC CTCTCCGGTG TGATCGCCGC |
| 70081 CGCATACGGG CGCGGTCTCG AGGGGGACGA CCCGCTCTAC CTGAAGACCG CGCCGGTCAT |
| 70141 CAAACACTAT CTCGCCAACA ACAACGAGAT CCATCGTGAC ACCACGTCGT CGAACCTGCG |
| 70201 CCCCCGCGTG AAGCACGAGT ACGACGAGCT GGCCTTCAAG ATGCCCATCG CCGCCGACGC |
| 70261 CGTGACCGGC GTCATGACAT CCTACAACCT GGTCAACGGC AGGCCGGCCA CCGTCAACCC |
| 70321 GGATGTCGGC GACGTCGTGC GGAGTTGGAC GGAGAAGACG CTCTACAACG TGTCCGACGC |
| 70381 CTGGGCCCCC TACAACTTGA CCGGCTCCCA GCGGTACTTC GCCACGAACG AGGAGGCCTT |
| 70441 CGCGGCCACG CTCCTGGCCG GAGTGGACAG CTTCACCGTC GACAACAACG ACAGCGCGCC |
| 70501 CACCATCGAG ATTCTCCGCT CGGCGCTCGC GCAAGGGCTC CTCACCGAGG AGGACATCGA |
| 70561 CGCTTCCGTC GAGCACGTCC TTTCCGTCCG GCTCCGGCTC GGCGATTTCG ATCCGGACGG |
| 70621 GGGCCCCTAC GCCGGTATCG GGCCCGAGGT CATCGACAGC CCGGCGCACC GCCAGCTGGC |
| 70681 CCGCCGGGCC GCCGGCGAGG CCATGGTGCT GCTCGAGAAC AGGCGTCGCC TCCTGCCGCT |
| 70741 GGACCCGTCG GCCACGCGGC GGATCGCGGT CGTCGGGCCC CTCTCGGACA CGCTCTACAC |
| 70801 GGACTGGTAC TCCGGGGCCC TCCCGTACCG GGTCACGCCC CTGGACGGCA TCCGCGAGCG |
| 70861 GCTCAGCGGC GCCACGGTCC TCTCCAGCGA GGGCGTGGAC CGCATCGTGC TGCGCGACGT |
| 70921 CGCGAGCGGC CGCTACGTGA CCGCCGGCGC GGACGAGGAC GGGGACGTCC TGCGCGTCAG |
| 70981 CGCGGTCAGC GCGGGCCCCA CCGAGGAGTT CGACGTGTTC GACTGGGGGC AGGGCATCGT |
| 71041 TACGCTGCGC AGCGCGGCCA ACGGCAAGGT GGTCGACCGC TTCAACTTCG GCCCCAACTT |
| 71101 CGCGAACCGC GCCGCCCAGC CGTACGACTG GTTCGTCCAG CAGCAGCTCG TCCTCGAGCC |
| 71161 GCAGAGCGAC GGCACGCACG TCATCCGCTA CGCCGGATAC GAGAAGGCGT TCGACTGGGC |
| 71221 CGGACCCGAG GTCTACCTGA CCATCGCCGA GGACGGCGCG CTCGCCTTGA CCGCGACCGA |
| 71281 CGCGGCCGAC GCGGCGCGCT TCGAGGTCGA CGTGGTCCGG AGCGGCGTCG ACGAAGCCGT |
| 71341 GCGCGTGGCG ACAGGCGCCG ACGCCGCCGT GGTCGTCGTC GGCAGTATGC CGTTCATCAA |
| 71401 CGGGCGGGAG GATCACGACC GCACGACGAT GGCGCTGGCC GAGGGGCAGT CCGCCCTGGT |
| 71461 ACGGGCGGTG CTCGCCGCCA ATCCGCGCAC CATCCTCGTG GTCGAGACCA GCTATCCGAT |
| 71521 GACCATGCCA TGGGAGAAGC TCCACGTCCC CGCCATCCTG TGGACCACCC ATGCGGGCCA |
| 71581 GGAGACCGGC CATGCCATCT CCGACGTCCT CTTCGGCGAC CACAATCCCG CCGGGCGACT |
| 71641 GACCCAGACC TGGTACCGCT CGGCGGACGA CCTGCCGGAT ATCCTCGAGT ACGACATCAT |
| 71701 CAAGGCCCGG CGGACCTATC TCTACTTCGA CGGTGAGCCG CTCTATCCGT TCGGGTACGG |
| 71761 GCTGTCGTAC TCGACCTTTG GCTACGACAA CCTCCAGCTG AGCGCCCGGT CGGTCCACGC |
| 71821 CGGCGACCCG ATCTCGGTGC GCGTCGACGT CACGAACACG AGCCCGCGGG CCGGCGACGA |
| 71881 GGTCGTTCAG CTCTACAGCC GCCAGCCGTC GTCGCGCGAT CCGCAGCCCG CCAAGCAGCT |
| 71941 GCGGGCGTTT CGGCGGATCC ACCTCGATCC GGGCGAGAGG CGGACGGTCG AGCTCGATTT |
| 72001 CGCCGCCTCC GACCTCGCCC ACTGGGACGT GACGCGGAGC CGCTGGGTCC TCGAGGCGAC |
| 72061 TGGCGTCGAG CTGATGGTCG GCTCCTCCTC GGCCGACATC CGCCGGCGCA CGACCGTGCG |
| 72121 CGTGCGCGGC GAGCGCATCC CGGCGCGCGA CCTCGCCCGC GAGACGCGAG CGCTCGACTT |
| 72181 CGACGACTAC GCCGGCATCG AGCTGGTCGA CGAGAGCATG GAGTGGGGCG ATGCCGTAGG |
| 72241 CGCCACCGCG GGCGGCTGGC TCCGCTTCTC CGACGTGGAG CTGGGCGGCG GTGCCAGCCA |
| 72301 CTTCAGCGGC GGGTTCGCCC GCGCCGAGGC CGGCGACGCC CTCGTCGAGA TCCGGCTCGA |
| 72361 CGATCCGGTC CGCGGCAAGG TGGTTGGGAC CGCCGTCGTG CCGAGCACGG GCGACGTGTA |
| 72421 CGCCTACGCC ACCGTGACCG CCGAGCTCGA CGGCGCTCGC GGGCGACACG ACGTCTACCT |
| 72481 CGTGTTCCGT GGAGCCGCCC GCCTGTCGAC CTTCGCGATC GACTGAGGGG CGGTTCGCCC |
| 72541 AGCGCAGGGT CAGGCGCGGC CGGCGTGGTG ACGGCAGCCG ACCTCGTGAT GCCCTCCCTC |
| 72601 CTGCCCCGCG CTCGAGCGCG CAGCGGAGCT CTTCCGACGT GTCCGGTGCC CGGCCGCGCC |
| 72661 GGAGCTGCCC CCGGCGGCAA AACAGCGGAA GATGCGGGAA TCGCAGTGCT TTCTGGCGGG |
| 72721 ACCTCCGACG CGCGAAACCG GCCCGCGCGG ACGGACGATG TCGCGGCAAT GATGCACAGA |
| 72781 GCCTGTTAGG CTGCGCGGCA TGTCGGATGA GGGTGCCCGC CGGCCCGACG GATCCTCGGT |
| 72841 GCCATCGACG ATGGAGAGCA GCGCGTCCGT GGCCCCGAGC CGCCTCGGCC CCGGGGACGT |
| 72901 CGTGGGCCAG CGCTGGCAGC TCGACGAGCT CCTCAAGAAA GGGGGCATGG GCCGGGTGTT |

TABLE 6-continued

| Disorazole PKS |
|---|
| 72961 CCGGGCGACG GACATCCGGC TCCTCGAGCC GGTGGCGCTC AAGCTGATGG ATCCGGCGAT |
| 73021 CGTCGGGACC GAGCGGGCGC GCGCCCGCTT CCTCCGCGAG GCGCAGACCG CGGCGAAGCT |
| 73081 GCGGGGCCCG AACGTGGTCC AGGTCCTCGA CTTCAACGTC GATGCGGCCA CGCAGGTGCC |
| 73141 CTACATCGCC ATGGAGCTGC TCCGCGGCGA GGACCTGGCC GAGCGGATAG CGCGCGGGCC |
| 73201 GCTCTCCTAC GACGAGACGG TGGCGATCCT CGCCGGCGTC TGCAGCGCGA TCGGCCGGGC |
| 73261 CCACCGCATG GACATCTTCC ACCGGGACCT CAAGCCGGCC AACGTCTTCC TCGTCGAGGA |
| 73321 CGACGACGGC CCGCTCTGCA AGGTCCTCGA TTTCGGCATC GTCAAGCTCG CGGACGTCGG |
| 73381 GCTCGGCCAC CAGGGGACGC CGCAGACCGA CGCCGGCTCG ACGCTGGGCA CGGTGAGCTA |
| 73441 CATGAGCCCG GAGCAGATCG CCGACGCCCG GAGGGTCGAT CACCGCGCGG ATCTCTGGGC |
| 73501 GCTCGGCGTG ATCGCCTACG AGTGCATGAC CGGGCGCCGG CCCTTCCGCG GCGACTCGCT |
| 73561 CTTCGAGCTG GTCCACGAGA TCTGCTACGG CGTCCCGGTC GTGCCGTCGC GGCTGGCCGA |
| 73621 CGTCCCGGGC GGCTTCGACG GCTGGTTCGC GCGCGCGACC CACCGCGATC GCGAGCGCCG |
| 73681 CTTCGCCTCC GCCCGCGAGC TGCTCGACGC GCTCCGCGCC CTCGCCGGCC GCTCCCCGCA |
| 73741 GCCGGACGTG CGCATGAGCT CCGTCCCCCC GCCGCCCGAC CCGTCTCACG CCCAGAGCTG |
| 73801 GGCCTCGGAC GCCAACCAGA TCGACATCAA CGCGCTCAAG GACCTGACCT TCAAGAACGC |
| 73861 CGTGGTCCGC GAGTTCCTCG ACAGCGCCAA CAAGCACTTC GTGTCGGGGA GCAAGGGGCT |
| 73921 CGGCAAGACC CTGTTGCTCA CCTACAAGCG CTCGGTCCTC GGCGAGATCT ACCTCGCGTC |
| 73981 GAACGGCCGC GAGCGCCGCC AGTCCGCCGT GCAGTTCATC CCGGAGGGGC GGCCGTACCT |
| 74041 CGACCTGATG GGCGACCTCG GCAGCGTCGA TCAGCACCTG ATCGACCTCA TGTCGGGGCT |
| 74101 CTACGAGTGC AAGCGGCTCT GGAGCTTCAG CTTCCGCCTG TCGATCGTCT CCTACCAGTC |
| 74161 GGCCCTCGCC GGCGCCGGCG ACGCCAGAGA CCTGGCGGCG CTCCCGCGGG GCCTGCGCGG |
| 74221 GCTCCTCGAC GGCCGGCCTG TCGAGCCGAC CATGGTGGTG AAGGAGCTCC TGTCGATGAC |
| 74281 GGTCGGCAAG ATCAACCAGG TCATCGACGC CATGGAGGGC CCGCTCGAGC GGCGGCTCCG |
| 74341 CTCGCTGCAC AGCGGCGTCT TCATCTTCGT CGACAAGCTC GATCAGGCGC TCCGGCGGCT |
| 74401 GCCGCGGGCG GCCTGGATCC ACATGCAAGC GGGGATGATC GAGGCCGCGT GGGACCTCAT |
| 74461 GAACGCCAAC CGGCACGTGA AGGTCTTCGC CACCATCCGC GAGGAGGCGT TCTCGGCCTA |
| 74521 CGAGTCCGAC ATCAAGACCA ACCTCTTCGG CGCGACGTCG ACGCTCCGCT ACGCGAAGCA |
| 74581 CGAGCTCTTC GAGCTGCTCG AGAAGCTCAC CTATTATTAC GAGCGACTGC CGCTCCGCGA |
| 74641 GTTCATCCAC CTCGACGTGG TGAGCGCGGG GCGCTCGGCG CGCGGCGAGG CGACGTTCGA |
| 74701 CTTCCTCTAC CGCCACACCC TCGGGCGGCC GCGCGACCTC GTGATCCTCG CGTCGGAGAT |
| 74761 CTCGCGCAAC CGCCGCGCCC TCGACGAGCG GACCTTCACG CGCATCGTGC AGGACACGAG |
| 74821 CGCCGGCCTG CTGGTGGCCA ACGTCTTCGA CGAGATGCGG GTCTTCCTCG AGGTGCTCTG |
| 74881 TCACCGCGAC AAGCGGGCTC GCTTCCTCGG CCTCCTGCCG TCCGACGTCC TCACCCACGA |
| 74941 GGACCTCGTC GACGTCTGGT GCGGCTTCCA CGGGGTCGAT CGCGCGTATT TCGACGCTCA |
| 75001 CGGCCGGGAC GCGGACGACG TCTATCACCC GTTCCGCGAG CTCTTCGAGT GCGGCCTGCT |
| 75061 CGGGGTGATC GGCGGCGATC CGGCGGCCGA GCGGAAGGTG CAGCGCTTCC GCCAGCCGCA |
| 75121 CGACGCGGTC GTCGGCTCGC GCCACGCGCT GCCGCGCTCG CCCTATTACC TCCTCCACCC |
| 75181 GTCCCTCCGG GCGCTCATCG AGCCGCTCCC CGGCGGCGGC CGGTTCCGCG CGATGCGCCA |
| 75241 CGTCGTCATC GGCCACGGGG AGCCCTGGCC GCGCCACTGG GATCTCGTCG TCGACGTCCA |
| 75301 GCGCGAGCTC TTCAAGCGCC CGGACGCCGA CGAGGAGATC GGCGAGGCGG TGTTCTCCCT |
| 75361 CCTCGACCAC CTCGCGGCCG ACGTCGCCGA CGGCGAGGGC GAGGGCGCCG CGCGGCGGGC |
| 75421 GATCGCCGCG TCACCCACCC TCGCCCGCCT CGGCGCCCAC CTCGATCGGA TCCGCTGGGA |
| 75481 CGATCTCCAC CTCGCCCTCC TCGAGCTCTT CCCGGCCGCG CGGCGGGAGG AGGCGGAGCC |
| 75541 GACCGATCGG GTCGAGGTGG CGATGCTCCT CATCGACATC GTGCGGTCGA CCCACATGAT |
| 75601 CAGCAAGATC GGCGACACGC GCTTCGTCGG CCACCTCCAG CGGCTCCGCC GCGTGCTCCT |
| 75661 CGGGTCGACG AACCCCCGCC TCTTGAAGGG GATCGGCGAC GGATACCTCG CGGTCTATCC |
| 75721 CACCATGACG CGCGCGCTCG ACGCGGCCCG CGTGCTCCGC GACGCGGTCG ACGACCCCCC |
| 75781 CGAGCTCCGC CTCGTCCTGC ACTGGGGCGC GGTGCGGATG AGCGATCACG ACGTGATCGG |
| 75841 CAGGGAGGTC CACCGGCTCT TCCGGATCGA GGCGGTCACC GAGGAGGATC GCGCCGCGGA |
| 75901 GTCGAGCGCC GGGATCACCC TCGCGCAGCC CGGCCGGGTG AGGCTCTCGC GGCCCGCGCT |
| 75961 CGCCGCGCTG CCCGACGCCG AGCGCGCGGG CTTCCGCCGG GCGGGGGCCT TCCGGCTGGA |
| 76021 GGGGTTCGAC GAGCCCGAGC CGATCTGGGT GGAGATCGGC GCGGGCCGCT GAGGTCGCGC |
| 76081 GGGCTACGGG GCGACGCGGA GCGTCCGCGA GGCGACGAGC GCCCGGCAGA GGGCGATCCG |
| 76141 GTCGTCGAGG TCGAGGCCGG GGAGCTCGCG CACGTAGAAG ATGCCGTGCC GCGCGATGAA |
| 76201 GCGGAGCGCG GCCTCCCCCC GCAGATCGAC GCGGACGAGC ACGGCCTCGC CGTCGACGAG |
| 76261 CTCCGCCTTG CCGTCCCTCA GCCGGACCGA CGCCTCGCGA TCGCGGATCA CGCGCCGCGG |
| 76321 GCCGCACACG GACGCCGCGT CGCTCCACAC CGCGGGCGGC GGCTCGCCGT AGAGGGCGCT |
| 76381 GTACGCGGCC ACGAGCTCGT CCCATGTCGC CTCGCGGCGC GCGCCCGCGG CCGGCGCGTT |
| 76441 GCTCGGCGCG TGGTGCAGGA AGCGCCCGAA GAAGCGCCGG CAGAACTCGG CGTATTCGAG |
| 76501 CGTGAAGAGG GCGAACTGGT GCCAGGCCTC GTCGACGCGC AGCGAGAACA TCGGATAGGC |
| 76561 GCGGGAGCGG TCGATCTCGA CGAGCCAGAG ATAGCGCACG AGCTCCCGGA ACAGCGCCTC |
| 76621 TGCCTCCTCC CGGGTGGCCA CGGTCTTGTT CATGAGCAGC TTGTCGATCA CGAAGGGCGC |
| 76681 CCGGTAAGCG AAGAGATCAG GCGTCCTGCG CTGGGTCGCG GTCACGATGT CCGTTTGCAT |
| 76741 GGGTCAGTTC TCCTGGGCTT CGAGCGGCTG AAAGGTGCCG TGATCGACGA GCGCGCGGGC |
| 76801 GAGCGCGAGC TGCTCGGCCT CGGCGAGGCC GGGGATGTCG CGGGGGCGGA GCTCGCGGGC |
| 76861 GGCGGCGAGC GCGCGGAGCG CGGGCGCGGC CCACGCGTCG ACGCGGAGCA GGACCTGGGC |
| 76921 GCGCTCGCCC GCGCGCGCGA GCAGCTCGGC GCGGCCGGCG CTCGACGCCA CGTCGAGGTC |
| 76981 CACGCCCGGC CAGCGGCGCG CGAGGGCGGT CTGCGCGTCG AGGTCCTCCG TCCGGCCGAG |
| 77041 CGCGCGGGCG GCGCGCCGCT TCGTCCCGGC GTCGCCGCGG GCGTGCAGGC GCGCGAGGAG |
| 77101 CGCGGCGGCC CGCGGCCCCC TCCGCTCGAG GGCGTCGATC TGCGCCCGGC GCACGCGCTC |
| 77161 GCGGGCGTGC GCGTGGAGCG CCTCGGACAG CGCGTCCTCG GGGGCGGGCG GCGGCGCGGC |
| 77221 GCCGGTCAGG CCGTCGATGG GGCCCACCTG CGCTTCCAGG ACCGGACCGT CGTGGGGGCC |
| 77281 GAGCAGGTGC AGCG |

Earlier versions of the sequence of dszA, B, C and D differed from SEQ ID NO:1 due to minor sequencing errors and/or small gaps in sequence. SEQ ID NO:1 (“version 1”) is 77,294 bp in length. “Version 2” was 53,366 bp in length and corresponded to basepairs 3009 to 56,374 of SEQ ID NO:1. (The version 2 sequence differed from SEQ ID NO:1 at position 9925/6920 which was C.) “Version 3” was 53,784 bp in length and corresponded to basepairs 3009 to 56374 of SEQ ID NO:1. Version 2 differed from version 3 as shown in Table 7.

The invention provides polynucleotides having the sequence each of the DNA sequences disclosed herein, including the version 1, 2, and 3 sequences, fragments (such as described in Table 4).

TABLE 7

| Seq ID NO:1 nucleotide no. | Change |
|---|---|
| 28756 . . . 29032 | “gap #1 in ver. 3 (ver. 3 estimate: approx. 300 bp; length found: 277 bp)” |
| 42790 . . . 42790 | “G->C; (ver. 3 G->ver. 2 C)” |
| 43750 . . . 44079 | “gap #2 in ver. 3 (ver. 3 estimate: approx. 300 bp), together with ver. 3 adjacent 37 bp: [GGCCCGACGGGCCGTGCGCCGCGCCGCGGTTCTCTTT] (SEQ ID NO:7), replaced here by a total of 330 bp” |
| 44092 . . . 44092 | “T->C; (ver. 3 T->ver. 2 C)” |
| 44166 . . . 44167 | “C->CC; (ver. 3 C->ver. 2 CC)” |
| 44169 . . . 44169 | “T->C; (ver. 3 T->ver. 2 C)” |
| 49623 . . . 49623 | “T->C; (ver. 3 T->ver. 2 C)” |
| 49690 . . . 49691 | “GG->CT; (ver. 3 GG->ver. 2 CT)” |
| 49702 . . . 49702 | “A->C; (ver. 3 A->ver. 2 C)” |
| 50603 . . . 50603 | “TT->T; (ver. 3 TT->ver. 2 T)” |
| 50694 . . . 50694 | “G->C; (ver. 3 G->ver. 2 C)” |
| 50719 . . . 50719 | “GG->G; (ver. 3 GG->ver. 2 G)” |
| 50739 . . . 50739 | “T->C; (ver. 3 T->ver. 2 C)” |
| 50760 . . . 50760 | “N->C; (ver. 3 N->ver. 2 C)” |
| 50773 . . . 50773 | “GG->G; (ver. 3 GG->ver. 2 G)” |
| 50829 . . . 50829 | “N->C; (ver. 3 N->ver. 2 C)” |
| 50956 . . . 50956 | “N->A; (ver. 3 N->ver. 2 A)” |
| 50973 . . . 50974 | “TC->CT; (ver. 3 TC->ver. 2 CT)” |
| 51005 . . . 51005 | “N->G; (ver. 3 N->ver. 2 G)” |
| 51043 . . . 51043 | “C->A; (ver. 3 C->ver. 2 A)” |
| 51050 . . . 51050 | “C->T; (ver. 3 C->ver. 2 T)” |
| 51066 . . . 51066 | “GC->C; (ver. 3 GC->ver. 2 C)” |
| 51070 . . . 51070 | “C->A; (ver. 3 C->ver. 2 A)” |
| 51119 . . . 51137 | “24 bp->19 bp; (ver. 3 24 bp: ATGAGGCGACAGCGCCGTTCTACC (SEQ ID NOL:8), replaced by 19 bp: TGAGGGACAGCCCGTTCTA(SEQ ID NO:9))” |
| 51160 . . . 51160 | “C->T; (ver. 3 C->ver. 2 T)” |
| 51208 . . . 51208 | “CC->C; (ver. 3 CC->ver. 2 C)” |
| 52170 . . . 52170 | “T->G; (ver. 3 T->ver. 2 G)” |
| 53366 . . . 53366 | “truncation; in the ver. 3 sequence, this base was followed by an additional 379 |

Example 3

*Mysococcus Xanthus* Host Cell Expressing the Disorazole PKS and Capable of Producing Disorazole This example describes creation of a *Myxococcus xanthus* host cell expressing the disorazole PKS and capable of producing disorazole. Briefly, a *Sorangium cellulosum* genomic library is screened using probes from the *S. cellulosum* disorazole NRPS oxidation domain coding sequence of pKOS254-190.4. A genomic clone encoding the complete NRPS oxidation domain plus those disorazole PKS modules and accessory proteins not encoded by pKOS254-190.1, is selected and referred to as pKOS254-190.8. pKOS254-190.4 and pKOS254-190.8 are introduced into *M. xanthus* by homologous recombination using established methods, resulting in a complete PKS gene cluster. The host cells are fermented and produce disorazole.

To obtain pKOS254-190.8, a cosmid library is screened using a $^{32}P$-labeled probe generated by PCR amplification of pKOS254-190.4 using primers 249-179.1 [5'-AGGAAGAGCTCCAGCGCA-3'; SEQ ID NO:4] and 249-179.3 [5'-ATGAAGCTGATCCAGACC-3'; SEQ ID NO:5]. The probe has the sequence

```
5'-AGGAAGAGCTCCAGCGCATCCTCGGCAAGGCGCTGCACCTCACCCGCCTCGATCCCGGCGCTGACCTCTTCGAGCTG  [SEQ ID NO:6]

GGCGCCACCTCGCTCACCATCGTGCAGGCGTCACAGCACATCGAGGAGCGCTTCGGCGTCGGGCTGCCGGTCGAGGT

CGTCCTGGCCGAGCCGACCCTCGACGCCATCGCGCGGCACGTCGCCGAGCGGACGGCGGCTGGCGCGCCCGAGCCCC

CGGCCCCCGGGCCCGCGCTGGACGCGCCTCCCGCGGCGCCCGAGCCCCCGGCCGCCGCCGCCCCCGGCCCGATCGAT

TTCTTCTCCAGGGAAGATCGGGAGCGCTTCAAGCAGCAGCAGCTCCACCTGCGGCACGGCGTCGAGGGCCTCCCGAC

CGTGGATCTGGCCGACGCTCCCGCGGCCCCGCGCCTCTACCGCGACCGCGGGAGCCGCCGCGACTACCGGCCCGAGC

CCGTCTCGTTCGACGACCTCTCGCGCCTCCTCGCCGTCCTCCGGCGGTACCCGAGCGGCCAGCAGACCCAGCTCTGC

TATCCCTCGGCCGGCGGCACCTACGCCGTGCAGACCTATCTTCACGTGAAGGAGGGCGCGGTCGAGCGCCTCCCGGC

CGGGATCTACTACTACCACCCGGATCGCAACCAGCTGGTGCTCATCAACGATCGGCCCGCCATCCGCCGGGTGCACC

ACTTCTAACAGGTTGGCTGATAAGTCCCCGGTCTGGATCAGCTTCAT.
```

A cosmid library was made from So cel2 chromosomal DNA following the manufacturer's protocol (Stratagene, Inc., La Jolla, Calif.). To obtain *Sorangium cellulosum* genomic DNA, *S. cellulosum* So cel2 cells were grown in a fructose based medium to obtain dispersed growth of the strain. The dispersed-growth medium composition used is: $MgSO_4.7H_2O$, 015%; $CaCl_2.2H_2O$, 0.1%, $KNO_3$, 0.2%; $K_2HPO_4$, 0.0125%, fructose, 0.5%, Na—Fe-III-EDTA, 8 mg/L, peptone from casein, tryptically digested, 0.1%, HEPES, 1.1%. The medium was adjusted to pH 7.4 with KOH. Chromosomal DNA was isolated from 5 ml of So cel2 culture in stationary phase. The cells were pelleted and resuspended in 1 ml of STE buffer (25% sucrose, 10 mM Tris pH8.0, 1 mM EDTA) and lysed with 200 μl of rapid lysis mix RLM (5% SDS, 0.5 M Tris pH7.6, 125 mM EDTA), mixed by inverting the tube several times, and then incubated at 65-70° C. for 30 minutes or until the mixture cleared. The mixture was then neutralized with 200 μl of 5 M potassium acetate and vortexed until thoroughly mixed. The tube was centrifuged for 10 minutes and the supernatant was removed. The mixture was then extracted with 500 μl of TE-saturated phenol, and the solution vortexed several seconds. The tube was centrifuged and the bottom DNA-containing layer was removed. Two volumes of 100% ethanol were added and the tube was inverted several times until the DNA precipitate was visible. The DNA was pelleted and then washed with 70% ethanol. The DNA was resuspended in TE.

A cosmid containing the complete oxidation domain and those disorazole genes absent from pKOS254-190.4 is isolated and called pKOS254-190.8. pKOS254-190.8 and pKOS254-190.4 are recombined into the *M. Xanthus* chromosome using regions of homology from these cosmids to reconstruct the disorazole gene cluster, analogous to the method described (for the epothilone PKS gene cluster) by Julien and Shah, 2002, "Heterologous expression of epothilone biosynthetic genes in *Myxococcus xanthus*" *Antimicrob Agents Chemother*. 46:2772-8, incorporated herein by reference. Also see U.S. Pat. No. 6,410,301, incorporated herein by reference.

Example 4

*Myxococcus Xanthus* Host Cell Expressing a Disorazole PKS Obtained by BAC Cloning This example describes cloning of a bacterial artificial chromosome (BAC) encoding the complete disorazole gene cluster. The BAC is introduced into *M. xanthus* by conjugation, for integration into the *M. xanthus* chromosome.

A *S. cellulosum* bacterial artificial chromosome (BAC) library containing an average insert size of 100 kb was prepared by standard methods (Amplicon) and Probe 249-179 (Example 2) is used to screen for a BAC containing the complete disorazole gene cluster. The BAC, referred to as pKOS254-190.9 is integrated into a phage attachment site using integration functions from myxophage Mx9. A transposon is constructed that contains the attP site from Mx9 along with the tetracycline gene from pACYC184. The necessary integration genes are supplied by a *M. xanthus* strain that expresses the integrase gene from the mgl (constitutive) promoter (see Magrini et al., 1999, *J. Bact*. 181: 4062-70). Once the transposon is constructed, it is transposed onto pKOS254-190.9 to create pKOS254-190.10. This BAC is conjugated into *M. xanthus*. This resulting host contains all the disorazole genes as and corresponding *Sorangium cellulosum* PKS gene promoters (which have been discovered to be active in *Myxococcus*). This strain is fermented and tested for the production of disorazole A.

Although the present invention has been described in detail with reference to specific embodiments, those of skill in the art will recognize that modifications and improvements are within the scope and spirit of the invention, as set forth in the claims, which follow. All publications and patent documents cited are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

We claim:

1. An isolated recombinant polynucleotide that comprising a nucleotide sequence that encodes a disorazole polyketide synthase (PKS) protein, wherein said polynucleotide encodes a polypeptide having at least 98% sequence identity to the amino acid sequence of a domain of the disorazole polyketide synthase encoded by SEQ ID NO:1, wherein said domain is required for the biosynthesis of disorazole.

2. The polynucleotide of claim 1, wherein said polynucleotide encodes a domain having 100% sequence identity to the amino acid sequence of said domain of the disorazole polyketide synthase encoded by SEQ ID NO:1.

3. An isolated recombinant polynucleotide comprising a nucleotide sequence that encodes a PKS domain having at least 98% sequence identity to the amino acid sequence of a domain encoded in bases 8157-26117 (DszA); 26209-44787(DszB); 44976-56431 (DszC); or 57756-60278 (DszD) of SEQ ID NO:1, wherein said domain is required for the biosynthesis of disorazole.

4. The polynucleotide of claim 3, comprising a nucleotide sequence that encodes a PKS domain having 100% sequence identity to the amino acid sequence of a domain encoded in bases 8157-26117 (DszA); 26209-44787(DszB); 44976-56431 (DszC); or 57756-60278 (DszD) of SEQ ID NO:1.

5. The polynucleotide of claim 1, wherein said polynucleotide encodes a polypeptide having at least 98% sequence identity to the amino acid sequence of a module of the disorazole polyketide synthase encoded by SEQ ID NO:1 bases 8166-13823 (module 1), 14067-19376 (module 2), 19491-23120 (module 3), 23331-26117 (module 4a), 26209-28056 (module 4b), 28234-29565 (module 5), 32971-37683 (module 6), 37834-4205 (module 7), or 42706-44787(module 8), wherein said module is required for the biosynthesis of disorazole.

6. A vector that comprises a polynucleotide of claim 1.

7. The vector of claim 6 that is an expression vector.

8. An isolated recombinant host cell comprising the vector of claim 7.

9. An isolated recombinant host cell comprising a polynucleotide of claim 1 integrated into the cell chromosomal DNA.

10. A method of producing a polyketide, which method comprises growing the recombinant host cell of claim 8 under conditions whereby a polyketide synthesized by a PKS comprising a protein encoded by said polynucleotide molecule is produced in the cell.

11. The polynucleotide of claim 1 that encodes a chimeric PKS polypeptide that comprises at least one domain of a disorazole PKS.

12. An isolated recombinant host cell comprising the chimeric PKS polynucleotide of claim 11.

13. The polynucleotide of claim 5, wherein said polypeptide has 100% sequence identity to said module of the disorazole polyketide synthase encoded by SEQ ID NO:1.

* * * * *